(12) United States Patent
Novobrantseva et al.

(10) Patent No.: US 9,127,275 B2
(45) Date of Patent: Sep. 8, 2015

(54) COMPOSITIONS AND METHODS FOR INHIBITING EXPRESSION OF KLF-1 AND BCL11A GENES

(75) Inventors: Tatiana Novobrantseva, Cambridge, MA (US); Brian Bettencourt, Cambridge, MA (US); Stuart Milstein, Cambridge, MA (US); Anna Borodovsky, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/992,669

(22) PCT Filed: Dec. 9, 2011

(86) PCT No.: PCT/US2011/064275
§ 371 (c)(1),
(2), (4) Date: Oct. 1, 2013

(87) PCT Pub. No.: WO2012/079046
PCT Pub. Date: Jun. 14, 2012

(65) Prior Publication Data
US 2014/0018410 A1 Jan. 16, 2014

Related U.S. Application Data

(60) Provisional application No. 61/422,049, filed on Dec. 10, 2010.

(51) Int. Cl.
*C12N 15/11* (2006.01)
*C12N 15/113* (2010.01)

(52) U.S. Cl.
CPC .......... *C12N 15/113* (2013.01); *C12N 2310/14* (2013.01); *C12N 2310/344* (2013.01)

(58) Field of Classification Search
CPC .. C12N 15/113; C12N 2310/14; C12N 15/86; C12N 2310/321; C12N 2310/344; A61K 35/28
See application file for complete search history.

(56) References Cited

U.S. PATENT DOCUMENTS

| | | | |
|---|---|---|---|
| 2005/0246794 A1* | 11/2005 | Khvorova et al. | 800/286 |
| 2005/0255487 A1* | 11/2005 | Khvorova et al. | 435/6 |
| 2007/0287681 A1* | 12/2007 | Jeong et al. | 514/44 |
| 2008/0039413 A1 | 2/2008 | Morris et al. | |
| 2010/0120893 A1* | 5/2010 | Sah et al. | 514/44 A |

FOREIGN PATENT DOCUMENTS

| | | |
|---|---|---|
| WO | 0185765 A2 | 11/2001 |
| WO | 2010030963 A2 | 3/2010 |

OTHER PUBLICATIONS

Zhou et al, KLF1 regulates BCL11A expression and y- to β-globin gene switching, published online Aug. 2010, Nature Genetics, vol. 42, 9: 742-744.*
Abnova. H00053335-R01. Homo sapiens B-cell CLL/lymphoma 11A (zinc finger protein) (BCL11A) transcript variant 2, mRNA. Feb. 2010 [Retrieved from the Internet Jun. 30, 2012; <https://abnova.com/de/products_detail.asp?Catalog_id=H00053335-R01>].
Basu et al. "EKLF amd KLF2 have compensatory roles in embryonic beta-globin gene expression and primitive erthropoiesis" Blood (2007) 110(9):3417-25.
Borg et al. "Haploinsufficiency for the erythroid transcription factor KLF1 causes hereditary persistence of fetal hemoglobin" Nat Genet. (2010) 42(9):801-5.
European Search Report for European Application No. 11847400.6 dated Apr. 10, 2014.
GenBank Direct Submisison NM_138559.1 GI: 20336312 "Homo sapiens B-cell CIL/lymphoma 11 A (zinc finger protein) (BCI 11 A), transcript variant 3, mRNA" [Retrieved Dec. 8, 2010 ,http://ww.ncbi.nlm.nih.gov/nuccore/20336312>].
GenBank Direct Submission AY692278. Homo sapiens B-cell lymphoma/leukaemia 11A extra-short form (BCL11A).mRNA, complete cds, alternatively spliced. Aug. 25, 2004 [Retrrieved from the Internet Jun. 30, 2012: <http:www.ncbi.nlm.nih.giv/nuccore/AY692278>] nucleotides 179-197.
GenBank Direct Submission DQ039554. Homo sapiens BCL11A gene, Virtual Transcript, partial sequence, genomic survey sequence. May 19, 2010 [Retrrieved from the Internet Jun. 30, 2012: <http:www.ncbi.nlm.nih.giv/nucgss/DQ039554>] nucleotides 150-152.
GenBank Direct Submission NM 022893.3 GI: 148539885 "Homo sapiens B-cell CIL/lymphoma 11A (zinc finger protein) (BCI11A)" [Retrieved Dec. 8, 2010 <http://ww.ncbi.nlm.nih.gov/nuccore/148539885>].
GenBank Direct Submission NM-006563.3 GI: 156071501 "Homo sapiens Kruppel-like factor 1 (erythroid) (KLF1), mRNA" [Retrieved Dec. 8, 2010 <http://ww.ncbi.nlm.nih.gov/nuccore/156071501>].
GenBank Direct Submission NM_018014.3 GI: 148539884 "Homo sapiens B-cell CIL/lymphoma 11A (zinc finger protein) (BCI11A), transcript variant 2, mRNA" [Retrieved Dec. 8, 2010 <http://ww.ncbi.nlm.nih.gov/nuccore/148539884>.
International Search Report and Written Opinion for International Application No. PCT/US2011064275 dated Jul. 12, 2012.
Lettre et al. "DNA polymorphisms at the BCL11A, HBS1L-MYB, and beta-globin loci associate with fetal hemoglobin levels and pain crises in sickle cell disease" Proc Natl Acad Sci U S A. (2008) 105(33):11869-74.
Novel treatment for sickle cell disease and beta-thalassemia. Newsletter from Technology & Innovation Development Office of Children's Hospital Boston, printed on Dec. 8, 2010.
Orkin et al. "Sickle Cell Disease at 100 Years". Science (2010) vol. 329, pp. 291-292.
Sankaran "Targeted theapeutic strategies for fetal hemoglobin induction" Hematology (Am. Soc. Hematol. Educ. Program) (2011) 2011:459-65.

(Continued)

*Primary Examiner* — Tracy Vivlemore
*Assistant Examiner* — Kate Poliakova
(74) *Attorney, Agent, or Firm* — Lando & Anastasi, LLP

(57) ABSTRACT

The invention relates to double-stranded ribonucleic acid (dsRNA) compositions targeting the KLF1 gene and the BCL11A gene, and methods of using such dsRNA compositions to inhibit expression of KLF1 and BCL11 A, respectively.

44 Claims, 22 Drawing Sheets

(56) References Cited

OTHER PUBLICATIONS

Sankaran et al. "Human Fetal Hemoglobin Expression is Regulated by the Developmental Stage-Specific Repressor BCL11A" Science (2008) vol. 322, pp. 1839-1842.

Sripichal et al. "HbF-Inducing Cytokines and BCL11A shRNA Have Combined Effects Upon Globin Gene Reprogramming in Adult Human Erythroblasts" Blood (ASH Annual Meeting Abstracts) (2010) vol. 116, No. 21, pp. 861.

Xu et al "Transcriptional silencing of ?-globin by BCL11A involves long-range interactions and cooperation with SOX6" Genes Dev. (2010) 24(8): 783-798.

* cited by examiner

FIG. 1

```
   1 tcagagttca cgaggcagcc gaggaagagg aggcttgagg cccagggtgg gcaccagcca
  61 gccatggcca cagccgagac cgccttgccc tccatcagca cactgaccgc cctgggcccc
 121 ttcccggaca cacaggatga cttcctcaag tggtggcgct ccgaagaggc gcaggacatg
 181 ggcccgggtc ctcctgaccc cacggagccg cccctccacg tgaagtctga ggaccagccc
 241 ggggaggaag aggacgatga gaggggcgcg gacgccacct gggacctgga tctcctcctc
 301 accaacttct cgggcccgga gccggtggc gcgcccaga cctgcgctct ggcgcccagc
 361 gaggcctccg gggcgcaata tccgccgccg cccgagactc tgggcgcata tgctggcggc
 421 ccggggctgg tggctgggct tttggggttcg gaggatcact cgggttgggt gcgccctgcc
 481 ctgcgagccc gggctcccga cgccttcgtg ggcccagccc tggctccagc cccggccccc
 541 gagcccaagg cgctggcgct gcaaccggtg tacccggggc ccggcgccgg ctcctcgggt
 601 ggctacttcc cgcggaccgg gctttcagtg cctgcggcgt cgggcgcccc ctacgggcta
 661 ctgtccgggt accccgcgat gtaccggcg cctcagtacc aagggcactt ccagctcttc
 721 cgcgggctcc agggacccgc gcccggtccc gccacgtccc cctccttcct gagttgtttg
 781 ggacccggga cggtgggcac tggactcggg gggactgcag aggatccagg tgtgatagcc
 841 gagaccgcgc catccaagcg aggccgacgt tcgtgggcgc gcaagaggca ggcagcgcac
 901 acgtgcgcgc acccgggttg cggcaagagc tacaccaaga gctcccacct gaaggcgcat
 961 ctgcgcacgc acacagggga gaagccatac gcctgcacgt gggaaggctg cggctggaga
1021 ttcgcgcgct cggacgagct gacccgccac taccggaaac acacggggca gcgcccttc
1081 cgctgccagc tctgcccacg tgcttttcg cgctctgacc acctggcctt gcacatgaag
1141 cgccaccttt gagccctgcc ctggcacttg gactctccta gtgactgggg atgggacaag
1201 aagcctgttt ggtggtctct tcacacggac gcgcgtgaca caatgctggg tggttttccc
1261 acgaatggac cctctcctgg actcgcgttc ccaagatcc acccaaatat caaacacgga
1321 cccatagaca gccctggggg agcctcttac ggaaaatccg acaagccttc agccacaggg
1381 agccacacag agatgtccaa actgtcgtgc aaacccagtg agacagaccg ccaaataaac
1441 ggactcagtg gacactcaga ccagctccca gatggccctg gacagcagga gagggtgtgg
1501 gatgaggctt cccagagacc ctgggtctag aaagcggctc ctgaaggtcc cttattgtgg
1561 ctgatattaa ctgtcaatgg ttatgggtcc tataaaaatg cccctcccag ataaa
        (SEQ ID NO:1)
```

FIG 2.

```
   1 gtgggcagac aggagccctc caagaaactt tcctagcctc atagcccatg aggcagaaga
  61 gagagaggag gcctgaggtc cagggtggac accagccagc catggcctca gctgagactg
 121 tcttaccctc catcagtaca ctcaccaccc tgggacagtt cctggacacc caggaggact
 181 tcctcaagtg gtggcggtct gaggagacgc aggatttggg gccggggccc ccgaatccca
 241 cggggccgtc ccatacgtg agtctgaaat cggaggaccc ttccggagag gacgatgaga
 301 gggacgtgac ctgtgcgtgg gacccggatc ttttccttac aaactttcca ggttccgagt
 361 ctcccggcac ttcccggacc tgtgccctgg cgcccagcgt ggggccagtg gcacagttcg
 421 agccgcctga gtctctgggc gcctatgcgg gtggcccagg gttggtgact gggcctttgg
 481 gctccgagga gcacacaagc tgggcgcacc cgactccgag accccagcc cctgaaccct
 541 tcgtggcccc tgccctggcc ccgggactcg ctcccaaggc tcagccctcg tactccgact
 601 cgcgagcggg ctccgtaggg ggcttcttcc cgcgggcggg gcttgcggtg cccgcagctc
 661 caggcgcccc ctatggggctg ctgtcgggat accccgcgct gtaccccgcg ccacagtacc
 721 aaggccactt ccagctcttt cgcgggctcg cggcgccttc tgctggtccc acggcgcccc
 781 cttccttctt gaattgtctg ggacctggga ctgtggccac agaactcggg gccactgcga
 841 tcgccggaga cgcaggcttg tccccgggaa ctgcgccgcc caaacgcagc cggcgaactt
 901 tggcacctaa gaggcaggcg gcacatacgt gcgggcacga aggctgcggg aagagctaca
 961 ccaagagctc gcacctcaag gcgcacctgc gcacgcacac gggagagaag ccttatgcct
1021 gctcctggga cggctgtgac tggaggttcg ctcgctcaga cgaactgacg cgccactacc
1081 ggaagcacac tggacatcgt cccttctgct gtggcctctg cccacgtgct ttttcacgct
1141 ctgaccactt agctctgcac atgaagcgtc acctctgagt gatcctgcac aaggactggg
1201 gatgaaataa gagtggatcc aaggaccgta tcccaaaaga tgggccatta tatagtccta
1261 cccagatcaa aaactgacca gaagaccata caaaggagcc ttcaggacaa acctcacatg
1321 tcctcaggga gccccacaca tggccccaca gacccagcaa tatagaccac cagataaatc
1381 aactcaaatg gaccccctaga ccagaggagt gaccctgtgt cctggacgca gatggactgg
1441 ggtgagattt cctaagatct agaagggagc ttcacactgt gcccatctgc taggattgtt
1501 gtcgttacta taaaaatttc ccatataaaa ccag (SEQ ID NO:2)
```

FIG. 3A

```
   1  tttttttttt  tttttttgctt  aaaaaaaagc  catgacggct  ctcccacaat  tcatcttccc
  61  tgcgccatct  ttgtattatt  tctaatttat  tttggatgtc  aaaaggcact  gatgaagata
 121  ttttctctgg  agtctccttc  tttctaaccc  ggctctcccg  atgtgaaccg  agccgtcgtc
 181  cgcccgccgc  cgccgccgcc  gccgccgccg  cccgccccgc  agcccaccat  gtctcgccgc
 241  aagcaaggca  aaccccagca  cttaagcaaa  cggaattct  cgcccgagcc  tcttgaagcc
 301  attcttacag  atgatgaacc  agaccacggc  ccgttgggag  ctccagaagg  ggatcatgac
 361  ctcctcacct  gtgggcagtg  ccagatgaac  ttcccattgg  gggacattct  tatttttatc
 421  gagcacaaac  ggaaacaatg  caatggcagc  ctctgcttag  aaaaagctgt  ggataagcca
 481  ccttccccctt  caccaatcga  gatgaaaaaa  gcatccaatc  ccgtggaggt  tggcatccag
 541  gtcacgccag  aggatgacga  ttgtttatca  acgtcatcta  gaggaatttg  ccccaaacag
 601  gaacacatag  cagataaact  tctgcactgg  aggggcctct  cctcccctcg  ttctgcacat
 661  ggagctctaa  tccccacgcc  tgggatgagt  gcagaatatg  ccccgcaggg  tatttgtaaa
 721  gatgagccca  gcagctacac  atgtacaact  tgcaaacagc  cattcaccag  tgcatggttt
 781  ctcttgcaac  acgcacagaa  cactcatgga  ttaagaatct  acttagaaag  cgaacacgga
 841  agtcccctga  ccccgcgggt  tggtatccct  tcaggactag  gtgcagaatg  tccttcccag
 901  ccacctctcc  atgggattca  tattgcagac  aataacccct  ttaacctgct  aagaatacca
 961  ggatcagtat  cgagagaggc  ttccggcctg  gcagaagggc  gctttccacc  cactccccc
1021  ctgtttagtc  caccaccgag  acatcacttg  gaccccacc   gcatagagcg  cctgggggcg
1081  gaagagatgg  ccctggccac  ccatcacccg  agtgcctttg  acagggtgct  gcggttgaat
1141  ccaatggcta  tggagcctcc  cgccatggat  ttctctagga  gacttagaga  gctggcaggg
1201  aacacgtcta  gcccaccgct  gtccccaggc  cggcccagcc  ctatgcaaag  gttactgcaa
1261  ccattccagc  caggtagcaa  gccgcccttc  ctggcgacgc  ccccccctccc  tcctctgcaa
1321  tccgcccctc  ctccctccca  gccccggtc   aagtccaagt  catgcgagtt  ctgcggcaag
1381  acgttcaaat  ttcagagcaa  cctggtggtg  caccggcgca  gccacacggg  cgagaagccc
1441  tacaagtgca  acctgtgcga  ccacgcgtgc  acccaggcca  gcaagctgaa  cgccacatg
1501  aagacgcaca  tgcacaaatc  gtcccccatg  acggtcaagt  ccgacgacgg  tctctccacc
1561  gccagctccc  cggaacccgg  caccagcgac  ttggtgggca  gcgccagcag  cgcgctcaag
1621  tccgtggtgg  ccaagttcaa  gagcgagaac  gaccccaacc  tgatcccgga  aacggggac
1681  gaggaggaag  aggaggacga  cgaggaagag  gaagaagagg  aggaagagga  ggaggaggag
1741  ctgacggaga  gcgagagggt  ggactacggc  ttcgggctga  gcctggaggc  ggcgcgccac
1801  cacgagaaca  gctcgcgggg  cgcggtcgtg  ggcgtgggcg  acgagagccg  cgccctgccc
1861  gacgtcatgc  agggcatggt  gctcagctcc  atgcagcact  tcagcgaggc  cttccaccag
1921  gtcctgggcg  agaagcataa  gcgcggccac  ctggccgagg  ccgagggcca  cagggacact
1981  tgcgacgaag  actcggtggc  cggcgagtcg  gaccgcatag  acgatggcac  tgttaatggc
2041  cgcggctgct  ccccgggcga  gtcggcctcg  ggggcctgt   ccaaaaagct  gctgctgggc
```

FIG. 3B

```
2101 agccccagct cgctgagccc cttctctaag cgcatcaagc tcgagaagga gttcgacctg
2161 cccccggccg cgatgcccaa cacggagaac gtgtactcgc agtggctcgc cggctacgcg
2221 gcctccaggc agctcaaaga tcccttcctt agcttcggag actccagaca tcgccttttt
2281 gcctcctcgt cggagcactc ctcggagaac gggagtttgc gcttctccac accgcccggg
2341 gagctggacg gagggatctc ggggcgcagc ggcacgggaa gtggagggag cacgccccat
2401 attagtggtc cgggcccggg caggcccagc tcaaaagagg gcagacgcag cgacacttgt
2461 gagtactgtg ggaaagtctt caagaactgt agcaatctca ctgtccacag gagaagccac
2521 acgggcgaaa ggccttataa atgcgagctg tgcaactatg cctgtgccca gagtagcaag
2581 ctcaccaggc acatgaaaac gcatggccag gtggggaagg acgtttacaa atgtgaaatt
2641 tgtaagatgc cttttagcgt gtacagtacc ctggagaaac acatgaaaaa atggcacagt
2701 gatcgagtgt tgaataatga tataaaaact gaatagaggt atattaatac ccctccctca
2761 ctcccacctg acacccccttt tttcaccact ccccttcccc atcgccctcc agccccactc
2821 cctgtaggat ttttttctag tcccatgtga tttaaacaaa caaacaaaca aacagaagta
2881 acgaagctaa gaatatgaga gtgcttgtca ccagcacacc tgtttttttt cttttcttt
2941 ttctttttc ttttcctttt ttttttttt tcctttatgt tctcaccgtt tgaatgcatg
3001 atctgtatgg ggcaatacta ttgcatttta cgcaaacttt gagcctttct cttgtgcaat
3061 aatttacatg ttgtgtatgt ttttttttaa acttagacag catgtatggt atgttatggc
3121 tattttaaat tgtccctaat tcgttgctga gcaaacatgt tgctgtttcc agttccgttc
3181 tgagagaaaa agagagagag agagaaaaag accatgctgc atacattctg taatacatat
3241 catgtacagt tttatttat aacgtgagga ggaaaaacag tctttggatt aaccctctat
3301 agacagaata gatagcactg aaaaaaaatc tctatgagct aaatgtctgt ctctaaaggg
3361 ttaaatgtat caattggaaa ggaagaaaaa aggccttgaa ttgacaaatt aacagaaaaa
3421 cagaacaagt ttattctatc atttggtttt aaaatatgag tgccttggat ctattaaaac
3481 cacatcgatg gttctttcta cttgttataa acttgtagct taattcagca ttgggtgagg
3541 taataaacct taggaactag catataattc tatattgtat ttctcacaac aatggctacc
3601 taaaagatg acccattatg tcctagttaa tcatcatttt tcctttagtt taattttata
3661 aacaaaactg attataccag tataaaagct actttgctcc tggtgagagc ttaaaagaaa
3721 tgggctgttt tgcccaaagt tttattttt ttaaacaatg attaaattga atgtgtaatg
3781 tgcaaaagcc ctggaacgca attaaataca ctagtaagga gttcatttta tgaagatatt
3841 tgctttaata atgtcttttt aaaaatactg gcaccaaaag aaatagatcc agatctactt
3901 ggttgtcaag tggacaatca aatgataaac tttaagacct tgtataccat attgaaagga
3961 agaggctgac aataaggttt gacagagggg aacagaagaa aataatatga tttattagca
4021 caacgtggta ctatttgcca tttaaaacta gaacaggtat ataagctaat attgatacaa
4081 tgatgattaa ctatgaattc ttaagacttg catttaaatg tgacattctt aaaaaagaa
4141 gagaaagaat tttaagagta gcagtatata tgtctgtgct ccctaaaagt tgtacttcat
```

FIG. 3C

```
4201 ttcttttcca tacactgtgt gctatttgtg ttaacatgga agaggattca ttgttttat
4261 ttttatttt ttaattttt ctttttatt aagctagcat ctgccccagt tggtgttcaa
4321 atagcacttg actctgcctg tgatatctgt atcttttctc taatcagaga tacagaggtt
4381 gagtataaaa taaacctgct cagataggac aattaagtgc actgtacaat tttcccagtt
4441 tacaggtcta tacttaaggg aaaagttgca agaatgctga aaaaaattg aacacaatct
4501 cattgaggag catttttaa aaactaaaaa aaaaaaact tgccagcca tttacttgac
4561 tattgagctt acttacttgg acgcaacatt gcaagcgctg tgaatggaaa cagaatacac
4621 ttaacataga aatgaatgat tgctttcgct tctacagtgc aaggattttt ttgtacaaaa
4681 cttttttaaa tataaatgtt aagaaaaatt tttttaaaa aacacttcat tatgtttagg
4741 ggggaactgc atttagggt tccattgtct tggtggtgtt acaagacttg ttatccattt
4801 aaaaatggta gtggaaattc tatgccttgg atacacaccg ctcttcaggt tgtaaaaaaa
4861 aaaaacatac attggggaaa ggtttaagat tatatagtac ttaaatatag gaaaatgcac
4921 actcatgttg attcctatgc taaaatacat ttatggtctt ttttctgtat ttctagaatg
4981 gtatttgaat taaatgttca tctagtgtta ggcactatag tatttatatt gaagcttgta
5041 tttttaactg ttgcttgttc tcttaaaagg tatcaatgta cctttttgg tagtggaaaa
5101 aaaaaagaca ggctgccaca gtatatttt ttaatttggc aggataatat agtgcaaatt
5161 atttgtatgc ttcaaaaaaa aaaaaagag agaaacaaaa aagtgtgaca ttacagatga
5221 gaagccatat aatggcggtt tgggggagcc tgctagaatg tcacatggat ggctgtcata
5281 ggggttgtac atatccttt ttgttccttt ttcctgctgc catactgtat gcagtactgc
5341 aagctaataa cgttggtttg ttatgtagtg tgctttttgt ccctttcctt ctatcaccct
5401 acattccagc atcttacctt catatgcagt aaagaaaga aagaaaaaaa aaggaaaaaa
5461 aaaaaaaaac caatgttttg cagttttttt cattgccaaa aactaaatgg tgctttatat
5521 ttagattgga aagaatttca tatgcaaagc atattaaaga gaagcccgc tttagtcaat
5581 actttttgt aaatggcaat gcagaatatt ttgttattgg ccttttctat tcctgtaatg
5641 aaagctgttt gtcgtaactt gaaattttat cttttactat gggagtcact atttattatt
5701 gcttatgtgc cctgttcaaa acagaggcac ttaatttgat cttttatttt tctttgtttt
5761 tattttttt tttatttaga tgaccaaagg tcattacaac ctggctttt attgtatttg
5821 tttctggtct ttgttaagtt ctattggaaa aaccactgtc tgtgttttt tggcagttgt
5881 ctgcattaac ctgttcatac acccatttg tccctttatt gaaaaaataa aaaaaattaa
5941 agtaca (SEQ ID NO:3)
```

FIG. 4A

```
   1 tttttttttt tttttttgctt aaaaaaaagc catgacggct ctcccacaat tcatcttccc
  61 tgcgccatct ttgtattatt tctaatttat tttggatgtc aaaaggcact gatgaagata
 121 ttttctctgg agtctccttc tttctaaccc ggctctcccg atgtgaaccg agccgtcgtc
 181 cgcccgccgc cgccgccgcc gccgccgccg cccgccccgc agcccaccat gtctcgccgc
 241 aagcaaggca accccagca cttaagcaaa cgggaattct cgcccgagcc tcttgaagcc
 301 attcttacag atgatgaacc agaccacggc ccgttgggag ctccagaagg ggatcatgac
 361 ctcctcacct gtgggcagtg ccagatgaac ttcccattgg gggacattct tattttatc
 421 gagcacaaac ggaaacaatg caatggcagc ctctgcttag aaaaagctgt ggataagcca
 481 ccttcccctt caccaatcga gatgaaaaaa gcatccaatc ccgtggaggt tggcatccag
 541 gtcacgccag aggatgacga ttgtttatca acgtcatcta gaggaatttg ccccaaacag
 601 gaacacatag cagataaact tctgcactgg aggggcctct cctcccctcg ttctgcacat
 661 ggagctctaa tccccacgcc tgggatgagt gcagaatatg ccccgcaggg tatttgtaaa
 721 gatgagccca gcagctacac atgtacaact tgcaaacagc cattcaccag tgcatggttt
 781 ctcttgcaac acgcacagaa cactcatgga ttaagaatct acttagaaag cgaacacgga
 841 agtcccctga ccccgcgggt tggtatccct tcaggactag gtgcagaatg tccttcccag
 901 ccacctctcc atgggattca tattgcagac aataacccct ttaacctgct aagaatacca
 961 ggatcagtat cgagagaggc ttccggcctg gcagaagggc gctttccacc cactcccccc
1021 ctgtttagtc caccaccgag acatcacttg gacccccacc gcatagagcg cctggggcg
1081 gaagagatgg ccctggccac ccatcacccg agtgcctttg acagggtgct gcggttgaat
1141 ccaatggcta tggagcctcc cgccatggat ttctctagga gacttagaga gctggcaggg
1201 aacacgtcta gcccaccgct gtccccaggc cggcccagcc ctatgcaaag gttactgcaa
1261 ccattccagc caggtagcaa gccgccttc ctggcgacgc cccccctccc tcctctgcaa
1321 tccgccctc ctccctccca gccccggtc aagtccaagt catgcgagtt ctgcggcaag
1381 acgttcaaat ttcagagcaa cctggtggtg caccggcgca gccacacggg cgagaagccc
1441 tacaagtgca acctgtgcga ccacgcgtgc acccaggcca gcaagctgaa gcgccacatg
1501 aagacgcaca tgcacaaatc gtcccccatg acggtcaagt ccgacgacgg tctctccacc
1561 gccagctccc cggaacccgg caccagcgac ttggtgggca gcgccagcag cgcgctcaag
1621 tccgtggtgg ccaagttcaa gagcgagaac gaccccaacc tgatcccgga gaacggggac
1681 gaggaggaag aggaggacga cgaggaagag gaagaagagg aggaagagga ggaggaggag
1741 ctgacggaga gcgagagggt ggactacggc ttcgggctga gcctggaggc ggcgcgccac
1801 cacgagaaca gctcgcgggg cgcggtcgtg ggcgtgggcg acgagagccg cgccctgccc
1861 gacgtcatgc agggcatggt gctcagctcc atgcagcact tcagcgaggc cttccaccag
1921 gtcctgggcg agaagcataa gcgcggccac ctggccgagg ccgagggcca cagggacact
1981 tgcgacgaag actcggtggc cggcgagtcg accgcatag acgatggcac tgttaatggc
2041 cgcggctgct ccccgggcga gtcggcctcg gggggcctgt ccaaaaagct gctgctgggc
```

FIG. 4B

```
2101 agccccagct cgctgagccc cttctctaag cgcatcaagc tcgagaagga gttcgacctg
2161 cccccggccg cgatgcccaa cacggagaac gtgtactcgc agtggctcgc cggctacgcg
2221 gcctccaggc agctcaaaga tcccttcctt agcttcggag actccagaca atcgcctttt
2281 gcctcctcgt cggagcactc ctcggagaac gggagtttgc gcttctccac accgcccggg
2341 gagctggacg gagggatctc ggggcgcagc ggcacgggaa gtggagggag cacgccccat
2401 attagtggtc cgggcccggg caggcccagc tcaaaagagg gcagacgcag cgacacttgt
2461 tcttcacaca cccccattcg gcgtagtacc cagagagctc aagatgtgtg gcagttttcg
2521 gatggaagct cgagagccct taagttctga gaaaatttga agcccccagg ggtggggtgg
2581 acgcgtgccg cccagtcgac gtcagcgtgg tctgtcatcc tgctagtttg tgatgttttc
2641 tgacagtagc ctccaagaag ccgttgtgcg aagacagagt cctgcagagt ccttccagcc
2701 taggcctgca gcgccatttt atttatattt tttaataaaa agtaaaaaca aaaaaacaga
2761 cccacattgg aacagtgaat cagtcccata gagagggccc gtggaccatc gctgtcatga
2821 gtgatgccct ggcccttctg aaaccagcca acctaattac ctgtattgtg gaaatgcgca
2881 tgagtcccca accccttgtt tctatacatt ctatgttgtc ttttaaaaag tgtgcttaac
2941 attgacacaa taaatgttgg agctttaggt ggtgtttgct tgttctttaa tttttaatgc
3001 ttataagaca atgaggctgc ttatgatttt gtacttctgt acctgtttcc tacagacacc
3061 catcgggtgg gtaggaggaa cagatttgag aaatgggcag gagatgtagg aggggaacta
3121 ggttaccgct tatcagatgg cataaatttt caaggagaat caaaatgcaa aacttgggaa
3181 taaatcatag caatatcata attaatgtag tagtaatatt gctgtttatt aatgctgaag
3241 tgtggttttc ctaactgtct gacttataat ttgcatacca ttaaataatg cataatatgg
3301 cacgccgaat cctgttttc aaatatatgc ttttggtggc taccatgcag gatttgaatt
3361 tgtcttttaa tttagcttag gaaagaacat cactgggcga gcggtaaatc ctaaagaagg
3421 tgataaatgt cagtagtttc ttattaaata ttctaatttt aggttcccaa accttcagga
3481 aatatatctt aatgcagaca aacaaacata aaacttcttt agtacttaca tcaggaaatt
3541 tggggcagat tttagagggg ggaaattata ggaggaaaga agttcacatc agaacagaca
3601 atcacagcaa tgctctattc cttagaaatt agtgccacaa ataagttaca tctacaaaca
3661 ggtggtaaaa attctttctg gcccagttaa tttgcacaga acttttctca gtttggtatt
3721 ttttactgct tggagatcca agagagaatt agaaacaaca tagcaaatta aaataggttt
3781 gtcaataata gagctcagac acctgtgtgc tgtagattca catacaggcc gtgaacctaa
3841 gtggggaaaa tcctacctat ccaccttctg gctagattac ctagcttagt gaaaagatag
3901 ccaaataatt ggcatgtgaa ttatttcctg cttattcata ataaataatg actgtcta
        (SEQ ID NO:4)
```

FIG. 5A

```
   1 tttttttttt tttttttgctt aaaaaaaagc catgacggct ctcccacaat tcatcttccc
  61 tgcgccatct ttgtattatt tctaatttat tttggatgtc aaaaggcact gatgaagata
 121 ttttctctgg agtctccttc tttctaaccc ggctctcccg atgtgaaccg agccgtcgtc
 181 cgcccgccgc cgccgccgcc gccgccgccg cccgccccgc agcccaccat gtctcgccgc
 241 aagcaaggca accccagca cttaagcaaa cgggaattct cgcccgagcc tcttgaagcc
 301 attcttacag atgatgaacc agaccacggc ccgttgggag ctccagaagg ggatcatgac
 361 ctcctcacct gtgggcagtg ccagatgaac ttcccattgg gggacattct tattttatc
 421 gagcacaaac ggaaacaatg caatggcagc ctctgcttag aaaaagctgt ggataagcca
 481 ccttcccctt caccaatcga gatgaaaaaa gcatccaatc ccgtggaggt tggcatccag
 541 gtcacgccag aggatgacga ttgtttatca acgtcatcta gaggaatttg ccccaaacag
 601 gaacacatag cagataaact tctgcactgg aggggcctct cctcccctcg ttctgcacat
 661 ggagctctaa tccccacgcc tgggatgagt gcagaatatg ccccgcaggg tatttgtaaa
 721 gatgagccca gcagctacac atgtacaact tgcaaacagc cattcaccag tgcatggttt
 781 ctcttgcaac acgcacagaa cactcatgga ttaagaatct acttagaaag cgaacacgga
 841 agtcccctga ccccgcgggt tcttcacaca ccccattcg gcgtagtacc cagagagctc
 901 aagatgtgtg gcagttttcg gatggaagct cgagagccct taagttctga gaaaatttga
 961 agcccccagg ggtggggtgg acgcgtgccg cccagtcgac gtcagcgtgg tctgtcatcc
1021 tgctagtttg tgatgttttc tgacagtagc ctccaagaag ccgttgtgcg aagacagagt
1081 cctgcagagt ccttccagcc taggcctgca gcgccatttt atttatattt tttaataaaa
1141 agtaaaaaca aaaaaacaga cccacattgg aacagtgaat cagtcccata gagagggccc
1201 gtggaccatc gctgtcatga gtgatgccct ggcccttctg aaaccagcca acctaattac
1261 ctgtattgtg gaaatgcgca tgagtcccca accccttgtt tctatacatt ctatgttgtc
1321 ttttaaaaag tgtgcttaac attgacacaa taaatgttgg agctttaggt ggtgtttgct
1381 tgttctttaa tttttaatgc ttataagaca atgaggctgc ttatgatttt gtacttctgt
1441 acctgtttcc tacagacacc catcgggtgg gtaggaggaa cagatttgag aaatgggcag
1501 gagatgtagg aggggaacta ggttaccgct tatcagatgg cataaatttt caaggagaat
1561 caaaatgcaa aacttgggaa taaatcatag caatatcata attaatgtag tagtaatatt
1621 gctgtttatt aatgctgaag tgtggttttc ctaactgtct gacttataat ttgcatacca
1681 ttaaataatg cataatatgg cacgccgaat cctgttttc aaatatatgc ttttggtggc
1741 taccatgcag gatttgaatt tgtcttttaa tttagcttag gaaagaacat cactgggcga
1801 gcggtaaatc ctaaagaagg tgataaatgt cagtagtttc ttattaaata ttctaatttt
1861 aggttcccaa accttcagga aatatatctt aatgcagaca acaaacata aaacttcttt
1921 agtacttaca tcaggaaatt tggggcagat tttagagggg ggaaattata ggaggaaaga
1981 agttcacatc agaacagaca atcacagcaa tgctctattc cttagaaatt agtgccacaa
2041 ataagttaca tctacaaaca ggtggtaaaa attctttctg gcccagttaa tttgcacaga
```

FIG. 5B

```
2101 acttttctca gtttggtatt ttttactgct tggagatcca gaagagaatt agaaacaaca
2161 tagcaaatta aaataggttt gtcaataata gagctcagac acctgtgtgc tgtagattca
2221 catacaggcc gtgaacctaa gtggggaaaa tcctacctat ccaccttctg gctagattac
2281 ctagcttagt gaaaagatag ccaaataatt ggcatgtgaa ttatttcctg cttattcata
2341 ataaataatg actgtcta (SEQ ID NO:5)
```

FIG. 6A

```
   1 gacgttcaag ttcgcaggga cgtcacgtcc gcacttgaac ttgcagctca gggggggcttt
  61 tgccattttt ttcatctctc tctctccctc tatccctctt ctctcttcct ctctctcttt
 121 tttttcctta aaaaaaaaaa agccatgacg gctctcccac aattcatctt ccctgcgcca
 181 tctttgtatt atttctaatt tatttggat gtcaaaaggc actgatgaag atattttctc
 241 tggagtctcc ttctttctaa cccggctctc ccgatgtgaa ccgagccgtc gtccgcacgc
 301 cgccgccgcc gccgccgccc gccccgcagc ccaccatgtc tcgccgcaag caaggcaaac
 361 cccagcactt aagcaaacgg gaattctcgc ccgaacctct tgaagccatt cttacagatg
 421 atgaaccaga ccatggcccg ttgggagctc cagaagggga ccacgacctt ctcacctgtg
 481 ggcagtgcca gatgaatttc ccactggggg acattcttat ttttatcgag cacaaacgga
 541 aacaatgcaa tggcagcctc tgcttagaaa aaggtgtgga taagccgcct tccccttctc
 601 ccatcgagat gaaaaaggca tccaatcctg tggaggttgg catccaggtc acgccagagg
 661 atgacgattg tttatcaacg tcatctagag gaatttgccc caaacaggaa cacatagcag
 721 ataaacttct gcactggagg ggcctgtcct ctcctcggtc tgcacacgga gctctaatcc
 781 ccacgcccgg gatgagtgca gaatatgccc cgcagggtat ttgtaaagat gagcccagca
 841 gctacacatg tacaacttgc aaacagccat tcaccagtgc atggtttctc ttgcaacacg
 901 cacagaacac tcatggatta agaatctact tagaaagtga acacggaagt cccctgaccc
 961 cgcgggttgg tatcccttca ggactaggtg cagaatgtcc ttcccagcca cctctccatg
1021 ggattcatat tgcagacaat aaccccttta acctgctaag aataccagga tcagtatcga
1081 gagaggcttc cggcctggca gaagggcgct ttccacccac tccccccctg tttagtccac
1141 caccgagaca tcacttggac ccccaccgca tagagcgcct gggggcggaa gagatggccc
1201 tggccaccca tcacccgagt gcctttgaca gggtgctgcg gttgaatcca atggctatgg
1261 agcctcccgc catggatttc tctaggagac ttagagagct ggcagggaac acgtctagtc
1321 caccgctgtc cccaggccgg cccagtccta tgcaaaggtt actgcaacca ttccagccag
1381 gtagcaagcc acccttcctg gcgacgcccc ccctccctcc tctgcaatcc gcccctcctc
1441 cctcccaacc cccggtcaag tccaagtcat gcgagttctg cggcaagacg ttcaaatttc
1501 agagcaactt ggtggttcac cgacgcagcc atactggtga aagccctat aagtgcaacc
1561 tgtgcgacca cgcgtgcaca caggccagca agctgaagcg tcacatgaag acacacatgc
1621 acaaatcgtc ccccatgaca gtcaagtccg acgatggcct ctccacagcc agctccccgg
1681 aacctggtac cagcgacctg gtgggcagcg ccagcagtgc gctcaagtca gtggtggcca
1741 agttcaagag tgagaacgac cccaacttga tcccagagaa cggggatgag gaggaagagg
1801 aggacgacga ggaagaagaa gaagaggagg aagaggagga ggaggagctg acggagagcg
1861 agagggtgga ctacggcttc gggctgagcc tggaggctgc acgccaccat gagaacagct
1921 ctcggggcgc agtggtgggc gtggcgacg agggccgcgc cctgccgat gtcatgcagg
1981 gcatggtgct cagctccatg cagcacttca gcgaggcctt ccaccaggtc ctgggcgaaa
2041 agcataagcg tagccacctg gccgaggccg agggccatag ggacacttgt gatgaagact
```

FIG. 6B

```
2101 cggtggccgg tgagtcagac cgcatagacg atggcactgt taatggtcgt ggctgctccc
2161 ccggcgaatc ggcttcgggg ggtctgtcca aaaagctgct gctgggtagc cccagctcgc
2221 tgagcccctt ctccaagcgc atcaagctgg agaaggagtt tgacctgccc ccggccgcga
2281 tgcctaacac ggagaacgtg tattcgcagt ggctcgctgg ctatgcggcc tccaggcagc
2341 tcaaagatcc cttccttact ttcggagact ccagacaatc gccttttgcc tcctcatcag
2401 agcactcctc ggagaacggg agcttgcgct tctccacacc gcccggggag ctggacggag
2461 ggatctcagg gcgcagcggc acaggaagtg gagggagcac gccccatatt agtggtccgg
2521 gcccggcag gcccagctca aaagagggca gacgcagcga cacttgtcct tcacacaccc
2581 ccgttcggcg tagtaccccg cgagctcaag atgtgtggca gttttcggat ggaagctcaa
2641 gaacccttaa gttctgagaa actttgaagc ccccaagggc ggggcggaca tgcgccgccc
2701 agccgacgtc aacgtgctcc gttatcctgc tagattgtga tgttttctga cagtagcctc
2761 caagaagaca agagtcctgc cgagtcctcc cagcctgggc ctgcagtgcc attttattta
2821 tattttttaa taaacgtaa aaacaaaaaa aaccagaccc acattggaac agtgaacccg
2881 tcccatccag agggccctag gactgccgca gttggagcga cgtccaaccc ttttgaaacc
2941 agccaaccta attcccgta ctgtggaaat gagcatgacc cctgacccct tgtttctata
3001 cattctatgt tgtcttttaa aaagtgtgct taacattgac ataataaatg ttggagcttt
3061 aggcggtgtg tgcttgtttt ttaattttta atgctcgtaa gacaatgtgg ctgcttcagg
3121 ctttatgtct gtgtactttt tttccttcag aagctcatag ggtgagcaga aggaccagac
3181 tcaagtgcca ggcaggagac ctagaaaagg aagtaggctt ttcagatggc atacattttc
3241 aaagaaaatc aaaatgcaaa gctagggat aaatcatagt aatatcataa ttaatgtagt
3301 agtattgctg tttattaatg ctgacgtgtg tttttcctct ctgacttata atttgcatac
3361 cattaaataa tgcataaata tggcacactg aatccttttt caaatacacg cttttggtga
3421 ctacc (SEQ ID NO: 6)
```

FIG. 7

```
   1 gacgttcaag ttcgcaggga cgtcacgtcc gcacttgaac ttgcagctca gggggctttt
  61 tgccattttt ttcatctctc tctctccctc tatccctctt ctctcttcct ctctctcttt
 121 tttttcctta aaaaaaaaaa agccatgacg gctctcccac aattcatctt ccctgcgcca
 181 tctttgtatt atttctaatt tattttggat gtcaaaaggc actgatgaag atattttctc
 241 tggagtctcc ttctttctaa cccggctctc ccgatgtgaa ccgagccgtc gtccgcacgc
 301 cgccgccgcc gccgccgccc gccccgcagc ccaccatgtc tcgccgcaag caaggcaaac
 361 cccagcactt aagcaaacgg gaattctcgc ccgaacctct tgaagccatt cttacagatg
 421 atgaaccaga ccatgggcccg ttgggagctc cagaagggga ccacgacctt ctcacctgtg
 481 ggcagtgcca gatgaatttc ccactggggg acattcttat ttttatcgag cacaaacgga
 541 aacaatgcaa tggcagcctc tgcttagaaa aaggtgtgga taagccgcct tcccttctc
 601 ccatcgagat gaaaaaggca tccaatcctg tggaggttgg catccaggtc acgccagagg
 661 atgacgattg tttatcaacg tcatctagag gaatttgccc caaacaggaa cacatagcag
 721 ataaacttct gcactggagg ggcctgtcct ctcctcggtc tgcacacgga gctctaatcc
 781 ccacgcccgg gatgagtgca gaatatgccc cgcagggtat ttgtaaagat gagcccagca
 841 gctacacatg tacaacttgc aaacagccat tcaccagtgc atggtttctc ttgcaacacg
 901 cacagaacac tcatggatta agaatctact tagaaagtga acacggaagt cccctgaccc
 961 cgcgggtcct tcacacaccc ccgttcggcg tagtaccccg cgagctcaag atgtgtggca
1021 gttttcggat ggaagctcaa gaacccttaa ggttctgagaa actttgaagc ccccaagggc
1081 ggggcggaca tgcgccgccc agccgacgtc aacgtgctcc gttatcctgc tagattgtga
1141 tgttttctga cagtagcctc caagaagaca agagtcctgc cgagtcctcc cagcctgggc
1201 ctgcagtgcc attttattta tattttttaa taaaacgtaa aaacaaaaaa aaccagaccc
1261 acattggaac agtgaacccg tcccatccag agggccctag gactgccgca gttggagcga
1321 cgtccaaccc ttttgaaacc agccaaccta attcccgta ctgtggaaat gagcatgacc
1381 cctgacccct gtttctata cattctatgt gtcttttaa aaagtgtgct taacattgac
1441 ataataaatg ttggagcttt aggcggtgtg tgcttgtttt ttaattttta atgctcgtaa
1501 gacaatgtgg ctgcttcagg ctttatgtct gtgtactttt tttccttcag aagctcatag
1561 ggtgagcaga aggaccagac tcaagtgcca ggcaggagac ctagaaaagg aagtaggctt
1621 ttcagatggc atacattttc aaagaaaatc aaaatgcaaa gctagggat aaatcatagt
1681 aatatcataa ttaatgtagt agtattgctg tttattaatg ctgacgtgtg ttttcctct
1741 ctgacttata atttgcatac cattaaataa tgcataaata tggcacactg aatccttttt
1801 caaatacacg cttttggtga ctacc (SEQ ID NO: 7)
```

FIG. 8

```
   1 agagcagacg cggcgcgcga cggtgtgaag ttacagcccg gccagccgaa cctcttgaag
  61 ccattcttac agatgatgaa ccagaccatg gcccgttggg agctccagaa ggggaccacg
 121 accttctcac ctgtgggcag tgccagatga atttcccact gggggacatt cttattttta
 181 tcgagcacaa acggaaacaa tgcaatggca gcctctgctt agaaaaaggt gtggataagc
 241 cgccttcccc ttctcccatc gagatgaaaa aggcatccaa tcctgtggag gttggcatcc
 301 aggtcacgcc agaggatgac gattgtttat caacgtcatc tagaggaatt tgccccaaac
 361 aggaacacat agcagataaa cttctgcact ggaggggcct gtcctctcct cggtctgcac
 421 acggagctct aatccccacg cccgggatga gtgcagaata tgccccgcag ggtatttgta
 481 aagatgagcc cagcagctac acatgtacaa cttgcaaaca gccattcacc agtgcatggt
 541 ttctcttgca acacgcacag aacactcatg gattaagaat ctacttagaa agtgaacacg
 601 gaagtcccct gacccgcgg gtccttcaca cacccccgtt cggcgtagta ccccgcgagc
 661 tcaagatgtg tggcagtttt cggatggaag ctcaagaacc cttaagttct gagaaacttt
 721 gaagccccca agggcggggc ggacatgcgc cgcccagccg acgtcaacgt gctccgttat
 781 cctgctagat tgtgatgttt tctgacagta gcctccaaga agacaagagt cctgccgagt
 841 cctcccagcc tgggcctgca gtgccatttt atttatattt tttaataaaa cgtaaaaaca
 901 aaaaaaacca gacccacatt ggaacagtga acccgtccca tccagagggc cctaggactg
 961 ccgcagttgg agcgacgtcc aacccttttg aaaccagcca acctaattac ccgtactgtg
1021 gaaatgagca tgacccctga ccccttgttt ctatacattc tatgttgtct tttaaaaagt
1081 gtgcttaaca ttgacataat aaatgttgga gctttaggcg gtgtgtgctt gttttttaat
1141 ttttaatgct cgtaagacaa tgtggctgct tcaggcttta tgtctgtgta cttttttttcc
1201 ttcagaagct catagggtga gcagaaggac cagactcaag tgccaggcag gagacctaga
1261 aaaggaagta ggcttttcag atggcataca ttttcaaaga aaatcaaaat gcaaagctag
1321 gggataaatc atagtaatat cataattaat gtagtagtat tgctgtttat taatgctgac
1381 gtgtgttttt cctctctgac ttataatttg cataccatta aataatgcat aaatatggca
1441 cactgaatcc tttttcaaat acacgctttt ggtgactacc (SEQ ID NO:8)
```

COMPOSITIONS AND METHODS FOR INHIBITING EXPRESSION OF KLF-1 AND BCL11A GENES

CROSS REFERENCE TO RELATED APPLICATIONS

This application is the U.S. National Phase Application under 35 U.S.C. §371 of International Application No. PCT/US 2011/064275, filed Dec. 9, 2011, which claims the benefit of priority to U.S. Provisional Application Ser. No. 61/422,049, filed on Dec. 10, 2010, the contents of which are hereby incorporated by reference in their entirety.

FIELD OF THE INVENTION

The invention relates to the specific inhibition of the expression of the KLF1 and BCL11A genes.

BACKGROUND OF THE INVENTION

Normal adult hemoglobin comprises four globin proteins, two of which are alpha (α) proteins and two of which are beta (β) proteins. During mammalian fetal development, particularly in humans, the fetus produces fetal hemoglobin, which comprises two γ-globin proteins, instead of the two β-globin proteins. During fetal development or infancy, depending on the particular species and individual, a globin switch occurs, referred to as the "fetal switch", at which point, erythrocytes in the fetus switch from making predominantly γ-globin to making predominantly β-globin. The developmental switch from production of predominantly fetal hemoglobin or HbF ($\alpha_2\gamma_2$) to production of adult hemoglobin or HbA ($\alpha_2\beta_2$) begins at about 28 to 34 weeks of gestation and continues shortly after birth until HbA becomes predominant. This switch results primarily from decreased transcription of the γ-globin genes and increased transcription of β-globin genes.

Abnormalities in hemoglobulin protein and function are associated with hemoglobinopathies. Hemoglobinopathies encompass a number of anemias of genetic origin in which there is a decreased production and/or increased destruction (hemolysis) of red blood cells (RBCs). These also include genetic defects that result in the production of abnormal hemoglobins with a concomitant impaired ability to maintain oxygen concentration. Some such disorders involve the failure to produce normal β-globin in sufficient amounts, while others involve the failure to produce normal β-globin entirely. The disorders associated with abnormalities in the β-globin protein are referred to generally as β-hemoglobinopathies. For example, β-thalassemias result from a partial or complete defect in the expression of the β-globin gene, leading to deficient or absent HbA. Sickle cell anemia results from a point mutation in the β-globin structural gene, leading to the production of an abnormal (sickled) hemoglobin (HbS). HbS RBCs are more fragile than normal RBCs and undergo hemolysis more readily, leading eventually to anemia (Atweh, (2001) *Semin. Hematol.* 38(4):367-73).

Kruppel-like factor 1 (erythroid) (KLF1) is a transcription factor involved in regulating adult globin expression. KLF1 is expressed in erythroid cells and positively regulates the adult β-globin gene. KLF1 is also an important activator of BCL11A, which encodes a suppressor of fetal hemoglobin. Loss-of-function mutations in the KLF1 gene have been associated with hereditary persistence of fetal hemoglobin (HPFH), which is characterized by persistent high levels of HbF in adults. The developmental switch from human fetal (γ) to adult (β) hemoglobin represents a clinically important example of developmental gene regulation. The transcription factor BCL11A is a central mediator of the γ-globin silencing and hemoglobin switching that occurs in erythroid progenitor cells. KLF1 has been suggested to control globin gene switching by directly activating β-globin and indirectly repressing γ-globin gene expression. Knockdown of KLF1 in human and mouse adult erythroid progenitors markedly reduced BCL11A levels and increased human γ-globin/β-globin expression ratios (Zhou et al. (2010) *Nat. Genet.* 42:742-744).

The need exists for identifying novel therapeutics that modulate one or more of: fetal switch, activation of fetal hemoglobin (HbF), thus altering globin chain levels, e.g., the ratio of γ-globin to β-globin. Such therapeutics can be used to treat subjects with a variety of abnormalities in hemoglobulin protein and function, such as hemoglobinopathies.

SUMMARY OF THE INVENTION

The present invention describes methods and iRNA compositions for modulating the expression of a KLF1 gene and/or a BCL11A gene. In certain embodiments, expression of KLF1 is reduced or inhibited using a KLF-specific iRNA, thereby leading to a decreased expression of adult β-globin genes. Reduced expression of KLF1 gene can also negatively regulate expression of BCL11A, thus leading to higher levels of γ (fetal) globin relative to β-globin levels. Alternatively, or in combination with inhibition of KLF1 gene expression, expression of BCL11A can be reduced or inhibited using a BCL11A-specific iRNA, thereby causing higher levels of γ (fetal) globin relative to β-globin levels. Thus, inhibition of KLF1 and/or a BCL11A gene expression using an iRNA composition featured in the invention can be a useful approach to therapies aimed at reducing the expression of adult β-globin genes, and/or increasing fetal hemoglobin (HbF) production. Such inhibition can be useful in treating hemoglobinopathies, such as β-hemoglobinopathies, sickle cell disease and the β-thalassemias.

Accordingly, described herein are compositions and methods that effect the RNA-induced silencing complex (RISC)-mediated cleavage of RNA transcripts of the KLF1 and BCL11A genes, such as in a cell or mammal. Also described are compositions and methods for treating pathological conditions and diseases caused by the expression of KLF1 and BCL11A genes, such as hemoglobinopathies, e.g., β-hemoglobinopathies, sickle cell anemia and the β-thalassemias.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of KLF1 expression in a cell or mammal. In another embodiment, an iRNA as described herein effects inhibition of one or more transcript variants of BCL11A expression in a cell or mammal (e.g., transcript variant 1, 2, and/or 3).

The iRNAs included in the compositions featured herein encompass a dsRNA having an RNA strand (the antisense strand) having a region that is 30 nucleotides or less, generally 19-24 nucleotides in length, that is substantially complementary to at least part of an mRNA transcript of a KLF1 gene (e.g., a mouse or human KLF1 gene) (also referred to herein as a "KLF1-specific iRNA"). Alternatively, or in combination, iRNAs encompass a dsRNA having an RNA strand (the antisense strand) having a region that is 30 nucleotides or less, generally 19-24 nucleotides in length, that is substantially complementary to at least part of an mRNA transcript of a BCL11A gene (e.g., a mouse or human variant 1, 2 or 3 of a BCL11A gene) (also referred to herein as a "BCL11A-specific iRNA"). In certain embodiments, an iRNA encompass a dsRNA having an RNA strand (the antisense strand) having a region that is substantially complementary to exon 4 of BCL11A, e.g., exon 4 of human BCL11A variants 1-3. In one embodiment, the iRNA encompass a dsRNA having an antisense strand comprising a region substantially complementary to at least a region of exon 4 of BCL11a variant 2, e.g., a region of exon 4 that includes nucleotides 716-2458, or a fragment thereof, of SEQ ID NO: 4 depicted in FIG. 4A-4B (e.g., a region that includes nucleotides 860-2410, or a fragment thereof, of SEQ ID NO: 4, e.g., a region of SEQ ID NO:4 as shown in Table 4). In another embodiment, the iRNA encompass a dsRNA having an antisense strand comprising a region substantially complementary to at least a region of exon 4 of BCL11a variant 1 (e.g., a region of exon 4 that includes nucleotides 716-5946, or a fragment thereof, of SEQ ID NO: 3 depicted in FIG. 3A-3C). In yet another embodiment, the iRNA encompass a dsRNA having an antisense strand comprising a region substantially complementary to at least a region of exon 4 of BCL11a variant 3 (e.g., a region of exon 4 that includes nucleotides 716-858, or a fragment thereof, of SEQ ID NO: 5; depicted in FIG. 5A-5C).

In other embodiments, an iRNA encompasses a dsRNA having an RNA strand (the antisense strand) having a region that is substantially complementary to a portion of a BCL11A or KLF1 mRNA according to Tables 2A-1, 2A-2, 2A-3, 2B and 2C, and Tables 3, 4, 5, 6 and 7. In one embodiment, the iRNA encompasses a dsRNA having an RNA strand (the antisense strand) having a region that is substantially complementary to a portion a KLF1 mRNA, e.g., a human KLF1 mRNA (e.g., a human KLF1 mRNA from nucleotides 1251-1568 of SEQ ID NO:1, or a portion thereof). In another embodiment, the iRNA encompasses a dsRNA having an RNA strand (the antisense strand) having a region that is substantially complementary to a portion a BCL11A mRNA, e.g., a human BCL11 mRNA (e.g., a human BCL11 mRNA from nucleotides 415-720 of SEQ ID NO:1, or a portion thereof).

Thus, depending on the context, the term iRNA may refer to KLF1-specific iRNA, BCL11A-specific iRNA, or collectively to both).

In one embodiment, an iRNA for inhibiting expression of a KLF1 or BCL11A gene includes at least two sequences that are complementary to each other. The iRNA includes a sense strand having a first sequence and an antisense strand having a second sequence. The antisense strand includes a nucleotide sequence that is substantially complementary to at least part of an mRNA encoding KLF1 or a BCL11A transcript, and the region of complementarity is 30 nucleotides or less, and at least 15 nucleotides in length. Generally, the iRNA is 19 to 24, e.g., 19 to 21 nucleotides in length. In some embodiments the iRNA is from about 15 to about 25 nucleotides in length, and in other embodiments the iRNA is from about 25 to about 30 nucleotides in length. An iRNA targeting KLF1, upon contacting with a cell expressing KLF1, inhibits the expression of a KLF1 gene by at least 10%, at least 20%, at least 25%, at least 30%, at least 35% or at least 40% or more, such as when assayed by a method as described herein. In one embodiment, the iRNA targeting KLF1 is formulated in a stable nucleic acid lipid particle (SNALP). An iRNA targeting one or more transcript variants of BCL11A, upon contacting with a cell expressing the one or more transcript variants of BCL11A, inhibits the expression of a BCL11A transcript variant by at least 10%, at least 20%, at least 25%, at least 30%, at least 35% or at least 40% or more, such as when assayed by a method as described herein. In one embodiment, the iRNA targeting a BCL11A transcript variant is formulated in a stable nucleic acid lipid particle (SNALP).

In one embodiment, an iRNA featured herein includes a first sequence of a dsRNA that is selected from the group consisting of the sense sequences of Tables 2A-1, 2A-2, 2A-3, 2B and 2C, and Tables 3, 4, 5, 6 and 7, and a second sequence that is selected from the group consisting of the corresponding antisense sequences of Tables 2A-1, 2A-2, 2A-3, 2B and 2C, and Tables 3, 4, 5, 6 and 7. The iRNA molecules featured herein can include naturally occurring nucleotides or can include at least one modified nucleotide, including, but not limited to a 2'-O-methyl modified nucleotide, a nucleotide having a 5'-phosphorothioate group, and a terminal nucleotide linked to a cholesteryl derivative. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Generally, such a modified sequence will be based on a first sequence of said iRNA selected from the group consisting of the sense sequences of Tables 2A-1, 2A-2, 2A-3, 2B and 2C, and Tables 3, 4, 5, 6 and 7, and a second sequence selected from the group consisting of the corresponding antisense sequences of Tables 2A-1, 2A-2, 2A-3, 2B and 2C, and Tables 3, 4, 5, 6 and 7.

In one embodiment, an iRNA featured herein includes a sense sequence of a KLF1 dsRNA selected from the group consisting of SEQ ID NO:89, SEQ ID NO:55, SEQ ID NO:33, SEQ ID NO:79 and of SEQ ID NO:63; and an antisense sequence of a KLF1 dsRNA selected from the group consisting of SEQ ID NO:90, SEQ ID NO:56, SEQ ID NO:34, SEQ ID NO:80 and SEQ ID NO:64. In another embodiment, an iRNA featured herein includes a sense sequence of a KLF1 dsRNA selected from the group consisting of SEQ ID NO:558, SEQ ID NO:614, SEQ ID NO:612, SEQ ID NO:586 and of SEQ ID NO:604; and an antisense sequence of a KLF1 dsRNA selected from the group consisting of SEQ ID NO:559, SEQ ID NO:615, SEQ ID NO:613, SEQ ID NO:587 and of SEQ ID NO:605.

In one embodiment, an iRNA featured herein includes a sense sequence of a BCL11A dsRNA selected from the group consisting of SEQ ID NO:201, SEQ ID NO:257, SEQ ID NO:241, SEQ ID NO:239, SEQ ID NO:672 and SEQ ID NO:679; and an antisense sequence of a BCL11A dsRNA selected from the group consisting of SEQ ID NO:202, SEQ ID NO:258, SEQ ID NO:242, SEQ ID NO:240, SEQ ID NO:673 and SEQ ID NO:680. In certain embodiments, the BCL11A dsRNA has a modified sequence that includes a sense sequence of a BCL11A dsRNA selected from the group consisting of SEQ ID NO:293, SEQ ID NO:331, SEQ ID NO:329, SEQ ID NO:632 and SEQ ID NO:638; and an antisense sequence of a BCL11A dsRNA selected from the group consisting of SEQ ID NO:294, SEQ ID NO:332, SEQ ID NO:330, SEQ ID NO:633 and SEQ ID NO:639.

In one embodiment, an iRNA as described herein targets a wildtype KLF1 RNA or a wildtype BCL11A transcript variant, and in another embodiment, the iRNA targets a mutant transcript (e.g., a KLF1 RNA carrying an allelic variant). For example, an iRNA featured in the invention can target a polymorphic variant, such as a single nucleotide polymorphism (SNP), of KLF1 or BCL11A. In another embodiment, the iRNA targets both a wildtype and a mutant KLF1 or BCL11A transcript. In yet another embodiment, the iRNA targets a particular transcript variant of KLF1 or BCL11A (e.g., BCL11A variant 1, variant 2 or variant 3). In yet another embodiment, the iRNA agent targets multiple transcript variants (e.g., at least two or all three variants of BCL11A). For example, the iRNA agent targets each of variants 1, 2 and 3 of BCL11A. In another embodiment, the iRNA agent targets multiple transcript variants in multiple species. For example, the iRNA agent targets each of variants 1, 2 and 3 of BCL11A from human and from mouse.

In one embodiment, an iRNA featured in the invention targets a non-coding region of a KLF1 RNA transcript or BCL11A RNA variant transcript, such as the 5' or 3' untranslated region of a transcript.

In one aspect, the invention provides a cell containing at least one of the iRNAs featured in the invention. The cell is generally a mammalian cell, such as a human cell. In some embodiments, the cell is a hematopoietic cell, such as an erythroid cell (e.g., a red blood cell), or a progenitor cell thereof (e.g., an erythroid progenitor cell).

In another aspect, the invention provides a pharmaceutical composition for inhibiting the expression of a KLF1 gene or a BCL11A variant transcript in an organism, generally a human subject. The composition typically includes one or more of the iRNAs described herein and a pharmaceutically acceptable carrier or delivery vehicle. In one embodiment, the composition is used for treating a hemoglobinopathy, e.g., a sickle cell disease, such as a sickle cell disease.

In another embodiment, the pharmaceutical composition is formulated for administration of a dosage regimen described herein, e.g., not more than once every four weeks, not more than once every three weeks, not more than once every two weeks, or not more than once every week. In another embodiment, the administration of the pharmaceutical composition can be maintained for a month or longer, e.g., one, two, three, or six months, or one year or longer.

In another embodiment, a composition containing an iRNA featured in the invention, e.g., a dsRNA targeting KLF-1 or BCL11A, is administered with a non-iRNA therapeutic agent, such as an agent known to treat a hemoglobinopathy, or a symptom of a hemoglobinopathy. In another embodiment, a composition containing an iRNA featured in the invention, e.g., a dsRNA targeting KLF-1 or BCL11A, is administered along with a non-iRNA therapeutic regimen, such as a blood transfusion, or administration of hydroxyurea or erythropoietin. For example, an iRNA featured in the invention can be administered following a blood transfusion, and optionally also in combination with an iron chelator. In another example, an iRNA featured in the invention can be administered following a bone marrow transplant. The KLF-1 iRNA and BCL11A iRNA can be administered alone, or in combination, simultaneously or sequentially.

In one embodiment, a KLF1 or BCL11A iRNA is administered to a patient, and then the non-iRNA agent or therapeutic regimen is administered to the patient (or vice versa). In another embodiment, a KLF1 or BCL11A iRNA and the non-iRNA therapeutic agent or therapeutic regimen are administered at the same time.

In another aspect, the invention provides a method for reducing or inhibiting the expression of a KLF-1 or BCL11A gene, or a combination thereof, in a cell (e.g., a hematopoietic (e.g., an erythroid) cell, or a progenitor cell thereof). The method includes:

(a) introducing into the cell a double-stranded ribonucleic acid (dsRNA), wherein the dsRNA includes at least two sequences that are complementary to each other. The dsRNA has a sense strand having a first sequence and an antisense strand having a second sequence; the antisense strand has a region of complementarity that is substantially complementary to at least a part of an mRNA encoding KLF1 or BCL11A, or a combination thereof, and where the region of complementarity is 30 nucleotides or less, i.e., 15-30 nucleotides in length, and generally 19-24 nucleotides in length, and where the dsRNA individually or in combination, upon contact with a cell expressing KLF1 or BCL11A, inhibits expression of a KLF1 or BCL11A gene by at least 10%, e.g., at least 20%, at least 30%, at least 40% or more; and (b) maintaining the cell produced in step (a) for a time sufficient to obtain degradation of the mRNA transcript of the KLF1 or BCL11A gene, thereby reducing or inhibiting expression of a KLF1 or BCL11A gene in the cell.

In certain embodiments, the cell (e.g., the hematopoietic (e.g., an erythroid) progenitor cell) is a mammalian cell (e.g., of human, non-human primate, or rodent cell).

In one embodiment, the cell is treated ex vivo, in vitro, or in vivo (e.g., the cell is present in a subject (e.g., a patient in need of treatment, prevention and/or management of a hemoglobinopathy). In one embodiment, the subject is a mammal (e.g., a human) at risk, or diagnosed with a hemoglobinopathy, e.g., a β-hemoglobinopathy. In another embodiment, the hemoglobinopathy is a sickle cell disease. In another embodiment, the hemoglobinopathy is a sickle cell disease, including but not limited to, sickle cell anemia (SS), sickle-hemoglobin C disease (HbSC), sickle $β^+$-thalassemia (HbS/β+), SE disease, and sickle $β^0$-thalassemia (HbS/β$^0$). In another embodiment, the hemoglobinopathy is β-thalassemia.

In one embodiment, the dsRNA introduced reduces or inhibits expression of a KLF1 or BCL11A gene, or a combination thereof, in the cell.

In one embodiment, the dsRNA introduced reduces or inhibits expression of a KLF1 gene by at least 10%, 20%, 30%, 40%, 50% or more compared to a reference value, e.g., an untreated cell. Without being bound by theory, KLF1 is a transcription factor that regulates the expression of BCL11A, a downstream target. Thus, reducing expression of the KLF1 gene is likely to reduce KLF1 protein, which in turn will leads to a decrease in the expression of BCL11A.

In other embodiments, the dsRNA introduced reduces or inhibits expression of a BCL11A gene by at least 10%, 20%, 30%, 40%, 50% or more compared to a reference value, e.g., an untreated cell.

In other embodiments, a combination of the dsRNA is introduced, wherein at least two of the dsRNA are substantially complementary to at least a part of an mRNA encoding KLF1 and BCL11A, thereby reducing or inhibiting the expression of each of a KLF1 gene and a BCL11A gene by at least 10%, 20%, 30%, 40%, 50% or more compared to a reference value, e.g., an untreated cell.

In other aspects, the invention provides methods for treating, preventing or managing pathological processes mediated by KLF1 or BCL11A expression. In one embodiment, the method includes administering to a subject, e.g., a patient in need of such treatment, prevention or management, an effective (e.g., a therapeutically or prophylactically effective) amount of one or more of the iRNAs featured in the invention. In one embodiment, the patient has a hemoglobinopathy. In another embodiment, administration of the iRNA targeting KLF1 or BCL11A alleviates or relieves the severity of at least one symptom of a KLF1- or BCL11A-mediated disorder in the patient.

In one embodiment, the patient is a mammal (e.g., a human) at risk, or that has been diagnosed with, a hemoglobinopathy. In a further embodiment, the hemoglobinopathy is a β-hemoglobinopathy. In another embodiment, the hemoglobinopathy is a sickle cell disease, including but not limited to, sickle cell anemia (SS), sickle-hemoglobin C disease (HbSC), sickle β+-thalassemia (HbS/β+), SE disease, and sickle β0-thalassemia (HbS/β0). In another embodiment, the hemoglobinopathy is β-thalassemia.

In another aspect, the invention provides methods for increasing fetal hemoglobin levels in a cell (e.g., a hematopoietic (e.g., an erythroid) cell). The method includes contacting the cell with an effective amount of one or more of the iRNAs targeting KLF1 and/or BCL11A, e.g., one or more of the iRNAs disclosed herein, thereby increasing the expression of fetal hemoglobin in the cell, or its progeny, relative to the cell prior to contacting. In one embodiment, the increase in fetal hemoglobin levels is effected by one or more of delaying a fetal switch from fetal hemoglobin to adult hemoglobin, or by reactivating fetal hemoglobin (HbF) in the adult stage. Such methods can be used to treat (e.g., ameliorate the clinical severity) of β-hemoglobin disorders, such as sickle cell anemia and β-thalassemias.

In another aspect, the invention provides methods for decreasing β-globin levels in a cell (e.g., a hematopoietic (e.g., an erythroid) cell). The method includes contacting the cell with one or more of the iRNAs targeting KLF1, e.g., one or more of the iRNAs disclosed herein, in an amount effective to reduce expression of KLF1, thereby decreasing the expression of β-globin in the cell, or its progeny, relative to the cell prior to contacting. In one embodiment, the β-globin has an abnormality in structure or function, e.g., a point mutation in a β-globin structural gene that leads to the production of an abnormal (sickled) hemoglobin (HbS) in Sickle cell anemia.

In one embodiment, the contacting step is effected ex vivo, in vitro, or in vivo. For example, the cell can be present in a subject, e.g., a mammal (e.g., a human) at risk, or that has been diagnosed with, a hemoglobinopathy. In a further embodiment, the hemoglobinopathy is a β-hemoglobinopathy. In another embodiment, the hemoglobinopathy is a sickle cell disease, including but not limited to, sickle cell anemia (SS), sickle-hemoglobin C disease (HbSC), sickle β+-thalassemia (HbS/β+), SE disease, and sickle β0-thalassemia (HbS/β0). In another embodiment, the hemoglobinopathy is β-thalassemia.

In a further embodiment, the cell is a hematopoietic (e.g., an erythroid) cell. For example, the cell can be a progenitor cell of the erythroid lineage.

In one aspect, the invention provides a vector for inhibiting the expression of a KLF1 gene or a BCL11A gene in a cell. In one embodiment, the vector includes at least one regulatory sequence operably linked to a nucleotide sequence that encodes at least one strand of an iRNA as described herein. In one embodiment the vector comprises at least one strand of a KLF1 iRNA, and in another embodiment, the vector comprises at least one strand of a BCL11A iRNA. In another embodiment, the vector comprises at least one strand of a KLF1 iRNA and at least one strand of a BCL11A iRNA. In one embodiment, the vector comprising at least one strand of a KLF1 iRNA and at least one strand of a BCL11A iRNA further comprises a regulatory sequence that regulates expression of the at least one strand of a KLF1 iRNA and at least one strand of a BCL11A iRNA. In another embodiment, the vector comprising at least one strand of a KLF1 iRNA and at least one strand of a BCL11A iRNA comprises a first regulatory sequence that regulates expression of the at least one strand of a KLF1 iRNA and a second regulatory sequence that regulates expression of the at least one strand of a BCL11A iRNA.

In another aspect, the invention provides a cell containing a vector for inhibiting the expression of a KLF1 or a BCL11A gene in a cell. The vector includes a regulatory sequence operably linked to a nucleotide sequence that encodes at least one strand of one of the iRNAs as described herein. In one embodiment, the cell is a hematopoietic (e.g., an erythroid) cell. For example, the cell can be a progenitor cell of the erythroid lineage.

In yet another aspect, the invention provides a composition containing a KLF1 iRNA, in combination with a BCL11A iRNA, and further in combination with a third iRNA targeting a third gene involved in a pathological disease, and useful for treating the disease, e.g., a hemoglobinopathy.

All publications, patent applications, patents, and other references mentioned herein are incorporated by reference in their entirety.

The details of various embodiments of the invention are set forth in the description below. Other features, objects, and advantages of the invention will be apparent from the description and the drawings, and from the claims.

DESCRIPTION OF THE DRAWINGS

FIG. 1 depicts the sequence of human KLF1 mRNA (Ref. Seq. NM_006563.3, SEQ ID NO: 1).

FIG. 2 depicts the sequence of mouse KLF1 mRNA (Ref. Seq. NM_010635.2 (GI:225543579), SEQ ID NO: 2).

FIGS. 3A-3C depict the sequence of human BCL11A variant 1 mRNA (Ref. Seq. NM_022893.3 (GI:148539885), SEQ ID NO: 3).

FIGS. 4A-4B depict the sequence of human BCL11A variant 2 mRNA (Ref. Seq. NM_018014.3 (GI:148539884), SEQ ID NO: 4).

FIGS. 5A-5B depict the sequence of human BCL11A variant 3 mRNA (Ref. Seq. NM_138559.1 (GI:20336312), SEQ ID NO: 5).

FIGS. 6A-6B depict the sequence of mouse BCL11A variant 1 mRNA (Ref. Seq. NM_016707.3 (GI:226530130), SEQ ID NO: 6).

FIG. 7 depicts the sequence of mouse BCL11A variant 2 mRNA (Ref. Seq. NM_001159289.1 (GI:22653015.1), SEQ ID NO: 7).

FIG. 8 depicts the sequence of mouse BCL11A variant 3 mRNA (Ref. Seq. NM_001159290.1 (GI:226530196), SEQ ID NO: 8).

FIGS. 9A-9B depict the $IC_{50}$ plots of select BLC11a siRNA duplexes, with silencing of BCL11a activity expressed as the fraction mRNA message remaining relative to the negative control siRNA AD-1955. FIGS. 9C-9D depict the $IC_{50}$ plots of select BLC11a siRNA duplexes, with silencing of BCL11a activity expressed as the fraction mRNA message remaining relative to that of the lowest tested siRNA dose.

FIG. 10A depicts the dose dependent knockdown of BCL11a expression 24 hours post transfection with BCL11a siRNA (using LNP-009, also referred to herein as "AF-009"). FIG. 10B depicts the increased expression of mouse embryonic hemoglobin genes εγ and bh1 measured 72 hours post transfection with BCL11a siRNA (using LNP-012, also referred to herein as "AF-012").

FIG. 11A depicts the knockdown of BCL11a expression 72 and 96 hours post transfection with BCL11a siRNA. FIG. 11B depicts the increased expression of the mouse embryonic hemoglobin gene εγ measured at both 72 and 96 hours post siRNA transfection.

FIG. 12A depicts the detection of mouse adult hemoglobin βmaj at the E16 developmental stage, and subsequent developmental time points, including E18, as well as in the bone marrow; but no significant expression in the E12 developmental stage. FIG. 12B depicts the detection of mouse embryonic hemoglobin εγ only in the E12 developmental stage, and in no subsequent developmental stages or in the bone marrow. FIG. 12C depicts the detection of mouse embryonic hemoglobin bh1 also only in the E12 developmental stage, and not in the bone marrow or spleen.

FIG. 13A depicts the dose dependent knockdown of KLF1 expression 24 hours post transfection with KLF1 siRNA (encapsulated in AF-009). FIG. 13B depicts the increased expression of mouse embryonic hemoglobin genes εγ and bh1 measured 72 hours post transfection with KLF1 siRNA (encapsulated in AF-009).

FIG. 14E depicts a diagram of the mouse hemoglobin genes.

DETAILED DESCRIPTION OF THE INVENTION

Figure 9A:
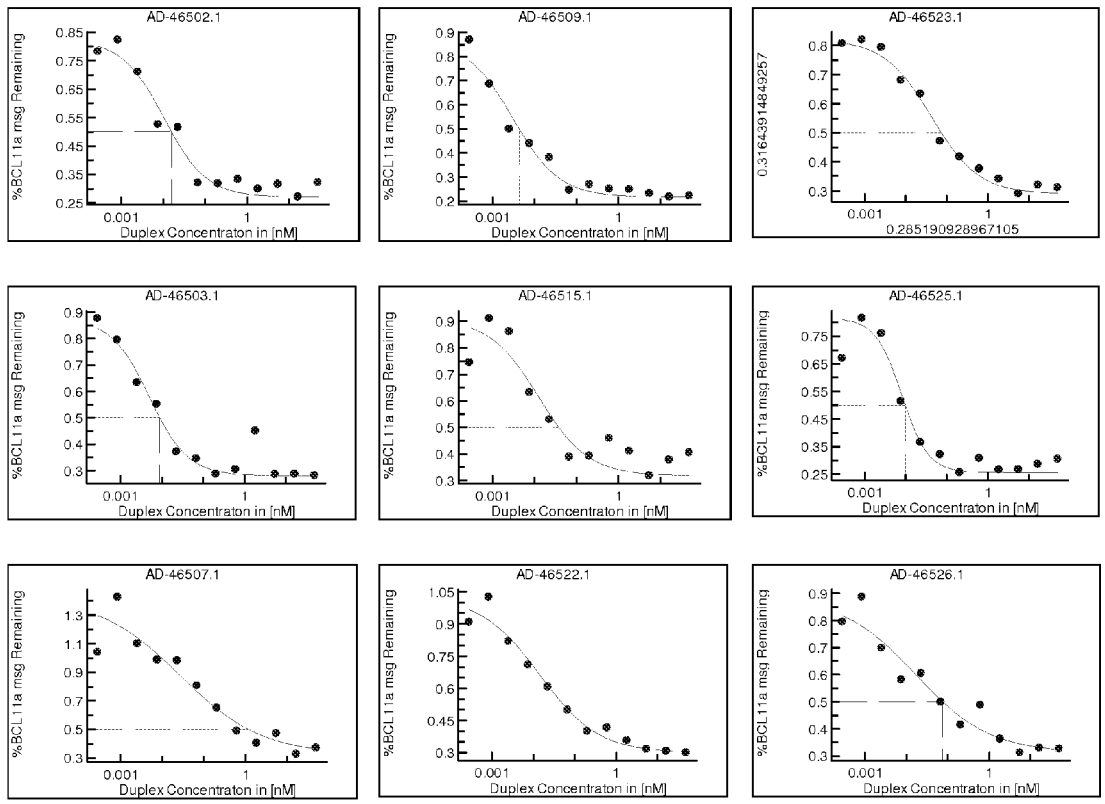
FIGS. 9A-9D depict the $IC_{50}$ plots of select BCL11a siRNA duplexes in in vitro screens.
Figure 9B:
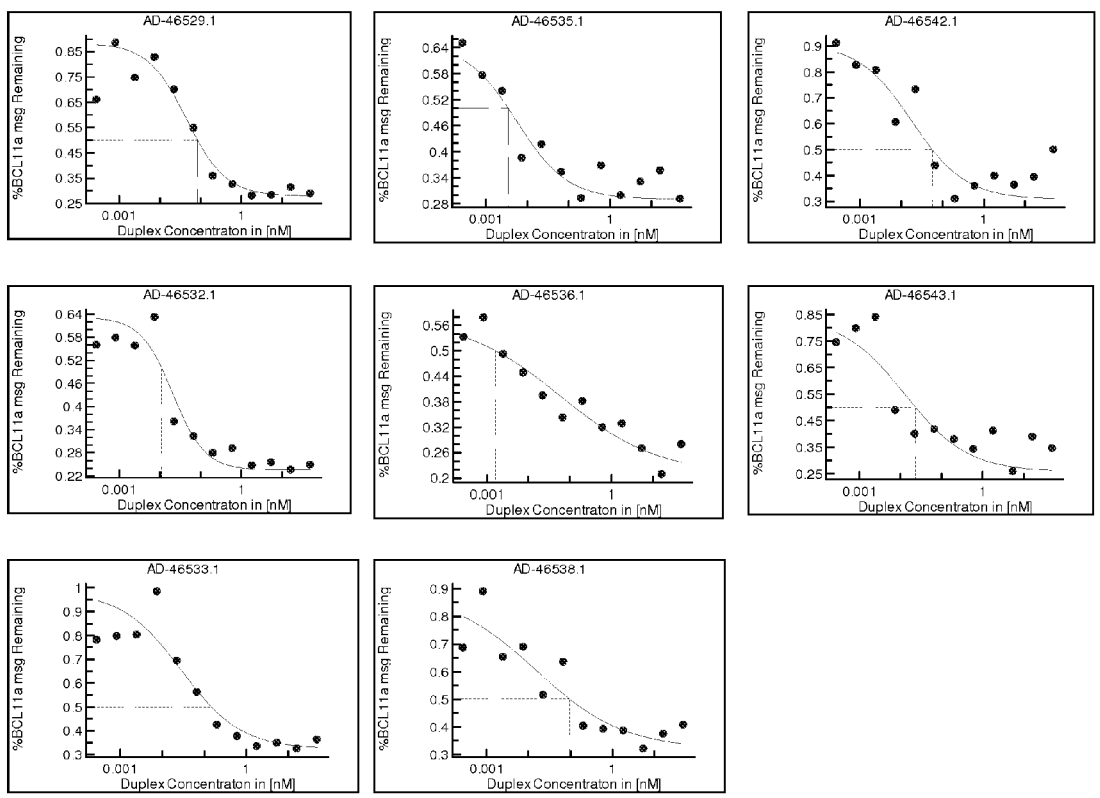
Figure 9C:
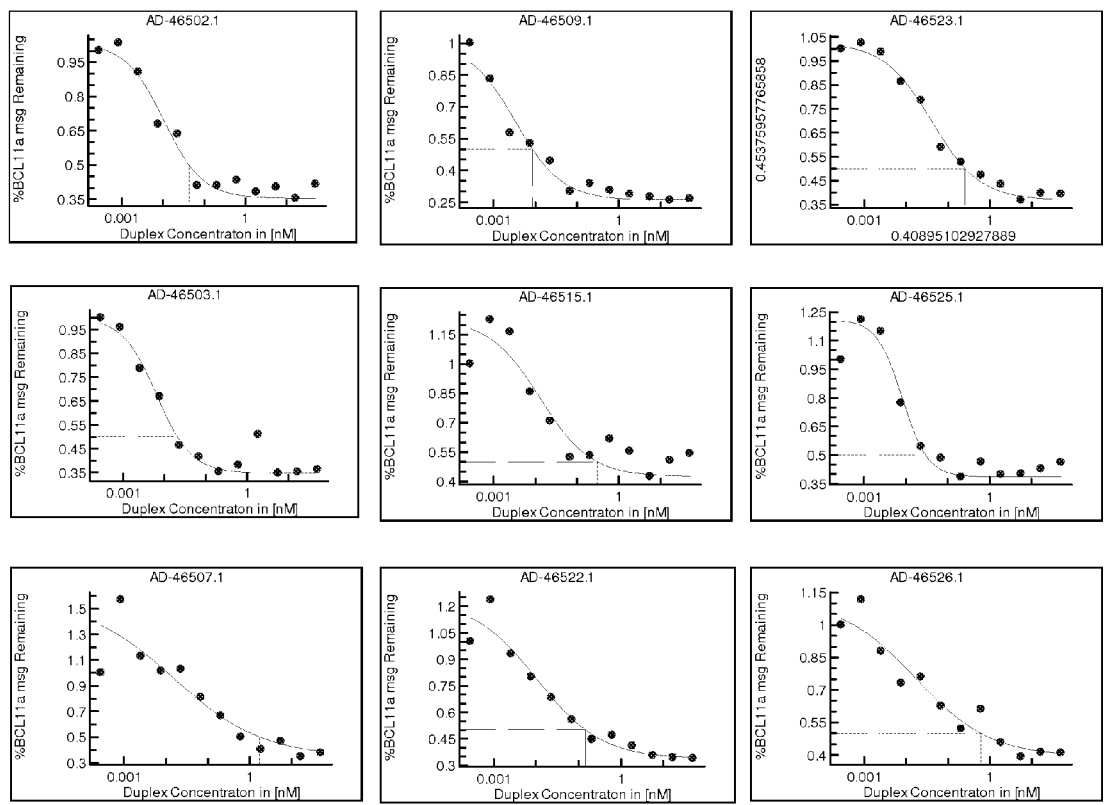
Figure 9D:
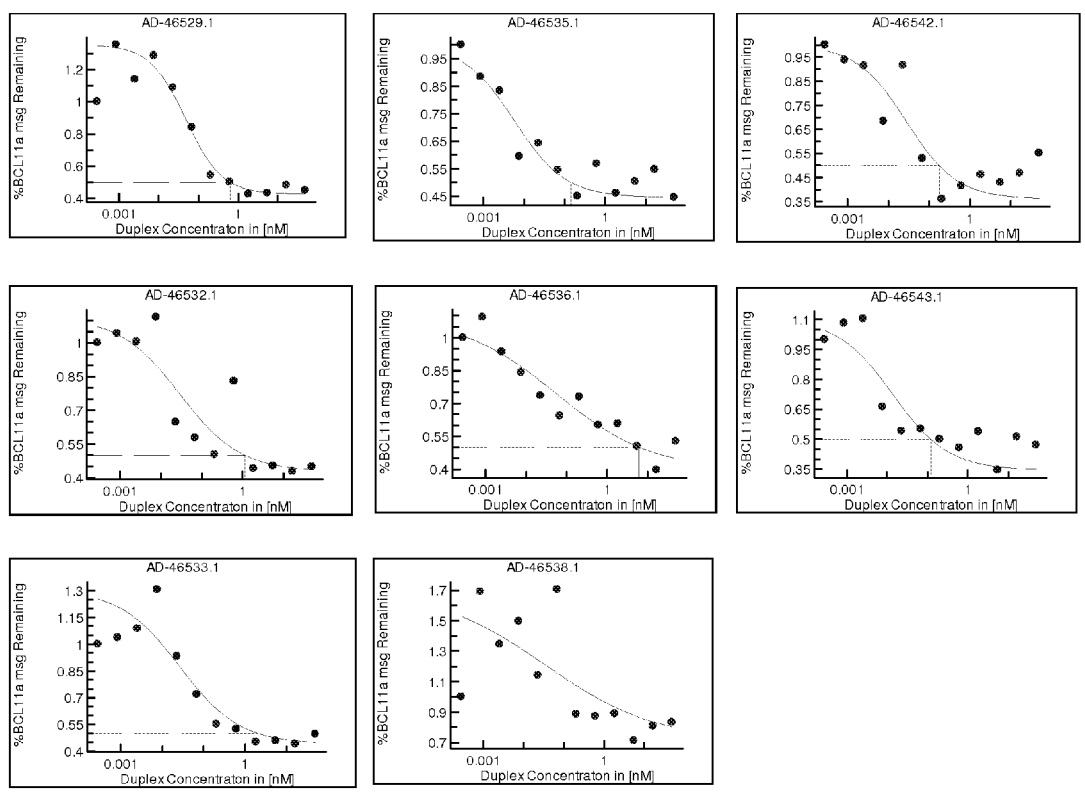

Described herein are iRNAs and methods of using them for inhibiting the expression of a KLF1 gene and/or BCL11A gene in a cell or a mammal where the iRNA targets a KLF1 gene and/or BCL11A gene. Also provided are compositions and methods for treating pathological conditions and diseases, such as hemoglobinopathies (e.g., β-hemoglobinopathies, sickle cell disease (SCD) and the β-thalassemias), in a mammal caused by or modulated by the expression of a KLF1 gene and/or BCL11A gene. iRNA directs the sequence-specific degradation of mRNA through a process known as RNA interference (RNAi).

The human β-globin locus contains the linked embryonic (ε), fetal (Gγ and Aγ), and adult (δ and β) globin genes. These genes are expressed sequentially during development. Fetal hemoglobin (HbF) is a tetramer of two adult α-globin polypeptides and two fetal β-like γ-globin polypeptides. During gestation, the duplicated γ-globin genes constitute the predominant genes transcribed from the β-globin locus. Following birth, γ-globin becomes progressively replaced by adult β-globin, a process referred to as the "fetal switch." The developmental switch from production of predominantly fetal hemoglobin or HbF ($\alpha_2\gamma_2$) to production of adult hemoglobin or HbA ($\alpha_2\beta_2$) begins at about 28 to 34 weeks of gestation and continues shortly after birth at which point HbA becomes predominant. This switch results primarily from decreased transcription of the γ-globin genes and increased transcription of β-globin genes. This switch is of particular clinical relevance.

Hemoglobinopathies encompass a number of anemias of genetic origin in which there is a decreased production and/or increased destruction (hemolysis) of red blood cells (RBCs). These disorders also include genetic defects that result in the production of abnormal hemoglobins with a concomitant impaired ability to maintain oxygen concentration. Some such disorders involve the failure to produce normal β-globin in sufficient amounts, while others involve the failure to produce normal β-globin entirely. These disorders specifically associated with the β-globin protein are referred to generally as β-hemoglobinopathies. For example, β-thalassemias result from a partial or complete defect in the expression of the β-globin gene, leading to an imbalance of the α and β chains of Hb. β-thalassemias result from mutations with either non-expressing ($\beta^\circ$) or low expressing ($\beta^+$) alleles in chromosome 11. The clinical severity correlates with the allele deficiencies. For example, normal individuals have a β/β genotype; individuals with minor or trait β-thalassemia have a $\beta/\beta^\circ$ or $\beta/\beta^+$ genotype; β-thalassemia intermedia individuals have a $\beta^\circ/\beta^+$; and β-thalassemia major phenotypes have a $\beta^\circ/\beta^\circ$ or $\beta^+/\beta^+$ genotype (reviewed in Muncie and Campbell (2009) *AM J Phys.* 80(4):339-344). The clinical features of β-thalassemia major can be detected between 6-24 months of age with failure to thrive. Additional symptoms include hemolysis (e.g., anemia and splenomegaly); ineffective erythropoiesis (e.g., bone marrow drive (skeletal changes), hepato-splenomegaly, consumption of haematinics, and high uric acid in blood); infections; and leg ulcers. Complications of treatment include iron overload (endocrinopathy, liver fibrosis and cardiac fibrosis). Therapeutic modalities for the management of β-thalassemia major include red cell transfusions, iron chelation, antibiotics, antivirals, and stem cell or bone marrow transplants. Other modalities under investigation include treatment with hydroxyurea, butyric acid, HbF inducing agents and gene therapy.

Sickle cell anemia results from a point mutation in the β-globin structural gene, leading to the production of an abnormal (sickled) hemoglobin (HbS). HbS RBCs are more fragile than normal RBCs and undergo hemolysis more readily, leading eventually to anemia (Atweh (2001), *Semin. Hematol.* 38(4):367-73). The clinical features of sickle cell disease (SCD) include hemolysis (e.g., anemia, jaundice, cholelithiasis, aplastic crisis and hemolytic crisis) and vaso-occlusive disease (e.g., dactylitis, autosplenectomy, acute chest syndrome, stroke, priapism, renal papillary necrosis, infarctive or sequestration crisis, and leg ulcers, among others). Therapeutic modalities for the management of SCD include treatment with hydroxyurea (hydroxycarbamide), red cell transfusions, iron chelation, antibiotics and stem cell or bone marrow transplants.

Therapeutic approaches aimed at reducing globin chain imbalance in patients with β-hemoglobinopathies have focused on the pharmacologic manipulation of fetal hemoglobin (α2γ2; HbF). The upstream γ globin genes are frequently intact and fully functional in the majority of patients with β-hemoglobinopathies. Thus, delaying the switch or reactivating fetal hemoglobin (HbF) in the adult stage has been shown to ameliorate the clinical severity of β-hemoglobin disorders, such as sickle cell anemia and β-thalassemias (Atweh, (2001) *Semin. Hematol.* 38(4):367-73). The therapeutic potential of such approaches is suggested by the fact that SCD symptoms are not evident until infancy or childhood, which correlated with a reduction in the levels of HbF (e.g., HbF is typically less than 5% total Hb at 6 months, whereas it is less than 1% at 2 years). In addition, natural HbF levels correlate with the level of morbidity in response to cerebrovascular accidents. For example, there is approximately a 5-fold decrease in frequency of cerebrovascular accidents in patients with greater than 10% levels of HbF, as opposed to patients who have lower levels of HbF (Powars et al. (1984) *Blood* 63:921-926). Furthermore, observations of the mild phenotype of individuals with co-inheritance of both homozygous β-thalassemia and hereditary persistence of fetal hemoglobin (HPFH), as well as by those patients with homozygous β°-thalassemia who synthesize no adult hemoglobin, but in whom a reduced requirement for transfusions is observed in the presence of increased concentrations of fetal hemoglobin. Multiple publications establish a link between HbF levels and β-thalassemia severity (reviewed in, for example, Thein et al. (2009) *Hum Mol Gen Br J Haematol* 145: 455-467). Therapeutic augmentation of HbF in hydroxyurea-treated SCD patients compared to untreated patients leads to a lower rate of crisis (e.g., 2.5 vs 4.5 crises per year) (Charache et al. (1995) *NEJM* 332(20):1317-22). In addition, certain populations of adult patients with β chain abnormalities have higher than normal levels of fetal hemoglobin (HbF); these patients have been observed to have a milder clinical course of disease than patients with normal adult levels of HbF. Moreover, therapeutic trials have shown conversion to transfusion independence with HbF-inducing agents in β-thalassemia major or intermedia (Perrine, S. P. (2005) *Hematology* 1: 37-44). In patients with adult hemoglobin disorders increased levels of HbF can reduce disease severity, morbidity and mortality (reviewed in *Br. J. Haematol.* 102: 415-422 (1998) and Bunn, N. *Engl. J. Med.* 328: 129-131 (1993)). Thus, β-hemoglobinopathies, such as sickle cell anemia and the β-thalassemias, can be ameliorated by increased HbF levels.

Recent human genetic studies focused on natural variation in the level of HbF expression in human populations has shed some light on the developmental control of hemoglobin switching and silencing of γ-globin expression (Thein and Menzel (2009) *Br J Haematol.* 145:455-467; Thein et al. (2009) *Hum Mol Genet* 18:R216-R233). The gene BCL11A encodes a zinc finger transcription factor; knockdown of BCL11A enhances HbF expression in human erythroid progenitors (Sankaran et al. (2008) *Science* 322: 1839-1842). BCL11A modulation is able to modify the phenotype of homozygous β-thalassemia by augmenting HbF levels in Sardinian population (Uda et al. (2008) PNAS 105(5):1620-5). BCL11A accounts for approximately 15% of HbF variability in Northern Europeans (Menzel et al. (2007) *Nat. Gen.* 39, 1197-1199). Alternative names for BCL11A include B-cell CLL/lymphoma 11A; B-cell lymphoma/leukemia 11A; BCL-11A; BCL11A-L, -XL, and -S; COUP-TF-interacting protein 1; CTIP1; HBFQTL5; KIAA1809; Ecotropic viral integration site 9 protein homolog; EVI9; EVI-9; FLJ34997; C2H2-type zinc finger protein; Zinc finger protein 856; and ZNF856. BCL11a is expressed in fetal brain, germinal center cells, erythroid cells, bone marrow and fetal liver leukocyte precursors. BCL11a functions as a myeloid and B-cell protooncogene. Mice deficient in BCL11a produce myeloid and erythroid cells, but show undetectable B cells and thymocyte maturation. The mRNA sequences of three variants of human BCL11A are provided in FIGS. 3, 4, 5, 6 and 7, respectively, and the mRNA sequences of three variants of mouse BCL11A are provided in FIGS. 6, 7, and 8, respectively.

Abundant expression of full length forms of BCL11A is developmentally restricted to adult erythroid cells (Sankaran et al. (2008) supra; Sankaran et al. (2009) *Nature* 460:1093-1097). Downregulation of BCL11A expression in adult human erythroid precursors leads to robust induction of HbF (Sankaran et al. (2008) supra). Knock-out of BCL11A in transgenic mice harboring the human β-globin locus prevents proper silencing of endogenous mouse β-like embryonic genes and human γ-globin genes in adult erythroid cells of the fetal liver (Sankaran et al. (2009) supra). Moreover, the presence of a BCL11A genetic variant ameliorates the clinical severity in β-thalassemia. This variant has been shown to be associated with HbF levels. Thus, the BCL11A transcription factor is a negative regulator of γ-globin expression. Inhibition of BCL11A gene expression or activity can be a useful approach to therapies aimed at increasing HbF production, such as treatment of β-hemoglobinopathies, such as sickle cell anemia and the β-thalassemias.

Expression of BCL11A is regulated by KLF1 (also known as Erythroid krueppel-like transcription factor (EKLF), INLU, Krueppel-like factor 1, or Kruppel-like factor 1). KLF1 is a zinc-finger transcription factor that is expressed in erythroid cells and positively regulates the adult β-globin gene (Miller, I. J. et al. (1993) *Mol Cell Biol* 13:2776-2786; Donze, D. et al. (1995) *J Biol. Chem.* 270:1955-1959). KLF1 is an erthroid-specific transcription factor that induces high level expression of adult β-globin, induces BCL11a (which silences γ-globin) and other erythroid genes. KLF1+/−individuals typically have lower levels of BCL11a, higher HbF, and are generally healthy (Borg et al. (2010) *Nat. Genetics* 43: 295-301). The mRNA sequence of human KLF1 mRNA is provided in FIG. 1. The mRNA sequence of mouse KLF1 mRNA is provided in FIG. 2.

KLF1 plays an important role in hemoglobin metabolism and membrane stability in primitive erythroid cells. KLF1 is also an important activator of BCL11A, which encodes a suppressor of fetal hemoglobin. Knockdown of KLF1 in human and mouse adult erythroid progenitors markedly reduced BCL11A levels and increased human β-globin/β-globin expression ratios (Zhou et al. (2010) *Nat. Genet.* 42:742-744). Loss-of-function mutations in the KLF1 gene have been associated with hereditary persistence of fetal hemoglobin (HPFH), which is characterized by persistent high levels of HbF in adults (Borg et al. (2010) supra).

Thus, KLF1 upregulates expression of BCL11A in erythroid cells. BCL11A expression, in turn, represses γ-globin expression, thus leading to low γ (fetal) globin levels relative to β (adult) globin levels. In certain embodiments, inhibition of KLF1 is expected to decrease expression of the adult β-globin gene. Alternatively, or in combination, inhibition of KLF1 is expected to decrease expression of BCL11A, thus leading to higher levels of γ (fetal) globin relative to β globin levels. In certain embodiments, other targets can be considered in addition to induction of HbF, for example, suppression of hemoglobin α. Accordingly, inhibition of KLF1 gene expression or activity, e.g., in erythroid precursors (e.g., adult eythroid precursors) can be a useful approach to therapies aimed at decreasing KLF1, and/or increasing HbF production. Additional targets that can be inhibited (e.g., by partial silencing), along or in combination with a KLF1 gene and/or a BCL11A gene include Myb, Sox6 and/or COUP-TFII genes. Such inhibition can be useful in treating β-hemoglobinopathies, such as sickle cell anemia and the β-thalassemias.

The present invention describes methods and iRNA compositions for modulating the expression of a KLF1 gene and/or a BCL11A gene. In certain embodiments, expression of KLF1 is reduced or inhibited using a KLF-specific iRNA, thereby leading to a decreased expression of adult β-globin genes. Reduced expression of KLF1 gene can also negatively regulate expression of BCL11A, thus leading to higher levels of γ (fetal) globin relative to β globin levels. Alternatively, or in combination with inhibition of KLF1 gene expression, expression of BCL11A can be reduced or inhibited using a BCL11A-specific iRNA, thereby causing higher levels of γ (fetal) globin relative to β globin levels. Thus, inhibition of KLF1 and/or a BCL11A gene expression or activity using the iRNA compositions featured in the invention can be a useful approach to therapies aimed at reducing the expression of adult β-globin genes, and/or increasing fetal hemoglobin (HbF) production. Such inhibition can be useful in treating hemoglobinopathies, such as β-hemoglobinopathies, sickle cell disease and the β-thalassemias.

The iRNAs of the compositions featured herein include an RNA strand (the antisense strand) having a region which is 30 nucleotides or less in length, i.e., 15-30 nucleotides in length, generally 19-24 nucleotides in length, which region is substantially complementary to at least part of an mRNA transcript of a KLF1 gene or a BCL11A gene (also referred to herein as a "KLF1-specific iRNA" and a "BCL11A-specific iRNA," respectively). The use of these iRNAs enables the targeted degradation of mRNAs of genes that are implicated in pathologies associated with KLF1 and BCL11A expression in mammals, e.g., hemoglobinopathies. Very low dosages of KLF1-specific iRNAs and/or BCL11A-specific iRNAs can specifically and efficiently mediate RNAi, resulting in significant inhibition of expression of a KLF1 and/or BCL11A gene. iRNAs targeting KLF1 or BCL11A can specifically and efficiently mediate RNAi, resulting in significant inhibition of expression of a KLF1 or BCL11A gene, e.g., in cell based assays. Thus, methods and compositions including these iRNAs are useful for treating pathological processes that can be mediated by down regulating KLF1 and/or BCL11A, such as hemoglobinopathies, including but not limited to, sickle cell anemia (SS), sickle-hemoglobin C disease (HbSC), β-thalassemia, SE disease, and sickle β⁰-thalassemia (HbS/β⁰).

The following description discloses how to make and use compositions containing iRNAs to inhibit the expression of a KLF1 and/or BCL11A gene, as well as compositions and methods for treating diseases and disorders caused by or modulated by the expression of this gene. Embodiments of the pharmaceutical compositions featured in the invention include an iRNA having an antisense strand comprising a region which is 30 nucleotides or less in length, generally 19-24 nucleotides in length, which region is substantially complementary to at least part of an RNA transcript of a KLF1 gene or BCL11A gene, together with a pharmaceutically acceptable carrier. Embodiments of compositions featured in the invention also include an iRNA having an antisense strand having a region of complementarity which is 30 nucleotides or less in length, generally 19-24 nucleotides in length, and is substantially complementary to at least part of an RNA transcript of a KLF1 gene or BCL11A gene.

Accordingly, in some aspects, pharmaceutical compositions containing a KLF1 gene and/or BCL11A iRNA and a pharmaceutically acceptable carrier, methods of using the compositions to inhibit expression of a KLF1 gene and/or BCL11A gene, and methods of using the pharmaceutical compositions to treat diseases caused by expression of a KLF1 gene and/or BCL11A gene are featured in the invention.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

As used herein, "BCL11A" (also known as Evi9, Ctip1, B-cell CLL/lymphoma 11A (zinc finger protein); BCL11A-L, -XL, and -S; COUP-TF-interacting protein 1; CTIP1; HBFQTL5; KIAA1809; Ecotropic viral integration site 9 protein homolog; EVI9; EVI-9; C2H2-type zinc finger protein) refers to a transcription factor that is predominantly expressed in erythroid cells. As used herein "BCL11A protein" means any protein variant of BCL11A (including, e.g., variants 1, 2, 3), from any species (e.g., mouse, human non-human primate), as well as any mutants, and fragments thereof that retain a BCL11A activity. Similarly, a "BCL11A transcript" refers to any transcript variant of BCL11A, e.g., variant 1, 2, or 3, from any species, e.g., mouse, human, or non-human primate. The sequence of human BCL11A variant 1 mRNA transcript can be found at NM_022893.3 (FIG. 3; SEQ ID NO: 3). The sequence of human BCL11A variant 2 mRNA transcript can be found at NM_018014.3 (FIG. 4; SEQ ID NO: 4). The sequence of human BCL11A variant 3 mRNA transcript can be found at NM_138559.1 (FIG. 5; SEQ ID NO: 5). The sequence of mouse BCL11A variant 1 mRNA transcript can be found at NM_016707.3 (GI: 226530130) (FIG. 6; SEQ ID NO: 6). The sequence of mouse BCL11A variant 2 mRNA transcript can be found at NM_001159289.1 (GI:226530151) (FIG. 7; SEQ ID NO: 7). The sequence of mouse BCL11A variant 3 mRNA transcript can be found at NM_001159290.1 (GI:226530196) (FIG. 8; SEQ ID NO: 8).

The amino acid sequence of BCL11a variant 2 (SEQ ID NO: 4) differs from the canonical sequence (SEQ ID NO: 3) as follows: amino acids 745-773 of the canonical sequence (SEQ ID NO.: 3): EYCGKVFKNCSNLTVHRRSHT-GERPYKCE (SEQ ID NO.: 622); are replaced with amino acids SSHTPIRRSTQRAQDVWQFSDGSSRALKF (SEQ ID NO: 623); and amino acids 774-835 of the canonical sequence (SEQ ID NO: 3) are missing. The amino acid sequence of BCL11a variant 3 (SEQ ID NO: 5) differs from the canonical sequence (SEQ ID NO: 3) as follows: amino acids 212-243 of the canonical sequence (SEQ ID NO: 3): GIPSGLGAECPSQPPLHGIHIADNNPFNLLRI (SEQ ID NO: 624) are replaced with amino acids LHTPPFGV-VPRELKMCGSFRMEAREPLSSEKI (SEQ ID NO: 625); and amino acids 244-835 are not present.

In one embodiment, the iRNA comprises a stand that is complementary to exon 4 of BCL11a, e.g., human BCL11a. BCL11a variant 2 (NM_018014.3; SEQ ID NO: 4) is characterized by a long form of exon 4. Exemplary exon 4 sequences of BCL11a variants 1, 2 and 3, include Exon 4 of BLC11a variant 2 (SEQ ID NO.: 4) corresponds to nucleotides 716-2458 of SEQ ID NO:4 depicted in FIG. 4A-4B; Exon 4 of BLC11a variant 1 (NM_022893.3; SEQ ID NO: 3)

corresponds to nucleotides 716-5946 of SEQ ID NO: 3 depicted in FIG. 3A-3C; and Exon 4 of BLC11a variant 3 (NM_138559; SEQ ID NO.: 5) corresponds to nucleotides 716-858 of SEQ ID NO: 5; depicted in FIG. 5A-5B.

As used herein, "Krueppel-like factor 1" or "KLF1" (also known as Erythroid krueppel-like transcription factor (EKLF), Kruppel-like factor 1, INLU, and HBFQTL6) refers to a transcription factor that is predominantly expressed in erythroid cells. As used herein "KLF1 protein" means any protein variant of KLF1 from any species (e.g., mouse, human non-human primate), as well as any mutants and fragments thereof that retain a KLF1 activity. Similarly, a "KLF1 transcript" refers to any transcript of KLF1, e.g., from any species, e.g., mouse, human, or non-human primate. The sequence of human KLF1 mRNA transcript can be found at NM_006563.3 (FIG. 1; SEQ ID NO: 1). The sequence of mouse KLF1 mRNA transcript can be found at NM_010635.2 (FIG. 2; SEQ ID NO: 2).

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of KLF1 expression. In another embodiment, an iRNA as described herein effects inhibition of BCL11A expression.

As used herein, "target sequence" refers to a contiguous portion of the nucleotide sequence of an mRNA molecule formed during the transcription of a BCL11A gene or a KLF1 gene, including mRNA that is a product of RNA processing of a primary transcription product. The target portion of the sequence will be at least long enough to serve as a substrate for iRNA-directed cleavage at or near that portion. For example, the target sequence will generally be from 9-36 nucleotides in length, e.g., 15-30 nucleotides in length, including all sub-ranges therebetween. As non-limiting examples, the target sequence can be from 15-30 nucleotides, 15-26 nucleotides, 15-23 nucleotides, 15-22 nucleotides, 15-21 nucleotides, 15-20 nucleotides, 15-19 nucleotides, 15-18 nucleotides, 15-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 20-30 nucleotides, 20-26 nucleotides, 20-25 nucleotides, 20-24 nucleotides, 20-23 nucleotides, 20-22 nucleotides, 20-21 nucleotides, 21-30 nucleotides, 21-26 nucleotides, 21-25 nucleotides, 21-24 nucleotides, 21-23 nucleotides, or 21-22 nucleotides.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they may form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but are not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding KLF1 or BCL11A). For example, a polynucleotide is complementary to at least a part of a KLF1 mRNA if the sequence is substantially complementary to a non-interrupted portion of an mRNA encoding KLF1. As another example, a polynucleotide is complementary to at least a part of a BCL11A mRNA if the sequence is substantially complementary to a non-interrupted portion of an mRNA encoding BCL11A.

The term "double-stranded RNA" or "dsRNA," as used herein, refers to an iRNA that includes an RNA molecule or complex of molecules having a hybridized duplex region that comprises two anti-parallel and substantially complementary nucleic acid strands, which will be referred to as having "sense" and "antisense" orientations with respect to a target RNA. The duplex region can be of any length that permits specific degradation of a desired target RNA through a RISC pathway, but will typically range from 9 to 36 base pairs in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 and any sub-range therein between, including, but not limited to 15-30 base pairs, 15-26 base pairs, 15-23 base pairs, 15-22 base pairs, 15-21 base pairs, 15-20 base pairs, 15-19 base pairs, 15-18 base pairs, 15-17 base pairs, 18-30 base pairs, 18-26 base pairs, 18-23 base pairs, 18-22 base pairs, 18-21 base pairs, 18-20 base pairs, 19-30 base pairs, 19-26 base pairs, 19-23 base pairs, 19-22 base pairs, 19-21 base pairs, 19-20 base pairs, 20-30 base pairs, 20-26 base pairs, 20-25 base pairs, 20-24 base pairs, 20-23 base pairs, 20-22 base pairs, 20-21 base pairs, 21-30 base pairs, 21-26 base pairs, 21-25 base pairs, 21-24 base pairs, 21-23 base pairs, or 21-22 base pairs. dsRNAs generated in the cell by processing with Dicer and similar enzymes are generally in the range of 19-22 base pairs in length. One strand of the duplex region of a dsDNA comprises a sequence that is substantially complementary to a region of a target RNA. The two strands forming the duplex structure can be from a single RNA molecule having at least one self-complementary region, or can be formed from two or more separate RNA molecules. Where the duplex region is formed from two strands of a single molecule, the molecule can have a duplex region separated by a single stranded chain of nucleotides (herein referred to as a "hairpin loop") between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by means other than a hairpin loop, the connecting structure is referred to as a "linker." The term "siRNA" is also used herein to refer to a dsRNA as described above.

The skilled artisan will recognize that the term "RNA molecule" or "ribonucleic acid molecule" encompasses not only RNA molecules as expressed or found in nature, but also analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure or in the ribose-phosphate backbone structure, e.g., as described herein below. However, the molecules comprising ribonucleoside analogs or derivatives must retain the ability to form a duplex. As non-limiting examples, an RNA molecule can also include at least one modified ribonucleoside including but not limited to a 2'-O-methyl modified nucleotides, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the dsRNA molecule. The modifications need not be the same for each of such a plurality of modified ribonucleosides in an RNA molecule. In one embodiment, modified RNAs contemplated for use in methods and compositions described herein are peptide nucleic acids (PNAs) that have the ability to form the required duplex structure and that permit or mediate the specific degradation of a target RNA via a RISC pathway.

In one aspect, a modified ribonucleoside includes a deoxyribonucleoside. In such an instance, an iRNA agent can comprise one or more deoxynucleosides, including, for example, a deoxynucleoside overhang(s), or one or more deoxynucleosides within the double stranded portion of a dsRNA. However, it is self evident that under no circumstances is a double stranded DNA molecule encompassed by the term "iRNA."

In one aspect, an RNA interference agent includes a single stranded RNA that interacts with a target RNA sequence to direct the cleavage of the target RNA. Without wishing to be bound by theory, long double stranded RNA introduced into plants and invertebrate cells is broken down into siRNA by a Type III endonuclease known as Dicer (Sharp et al., *Genes Dev.* 2001, 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleaves the target to induce silencing (Elbashir, et al., (2001) *Genes Dev.* 15:188). Thus, in one aspect the invention relates to a single stranded RNA that promotes the formation of a RISC complex to effect silencing of the target gene.

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) may be on the sense strand, the antisense strand or any combination thereof. Furthermore, the nucleotide(s) of an overhang can be present on the 5' end, 3' end or both ends of either an antisense or sense strand of a dsRNA.

In one embodiment, the antisense strand of a dsRNA has a 1-10 nucleotide overhang at the 3' end and/or the 5' end. In one embodiment, the sense strand of a dsRNA has a 1-10 nucleotide overhang at the 3' end and/or the 5' end. In another embodiment, one or more of the nucleotides in the overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double-stranded over its entire length.

The term "antisense strand" or "guide strand" refers to the strand of an iRNA, e.g., a dsRNA, which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 5, 4, 3, or 2 nucleotides of the 5' and/or 3' terminus.

The term "sense strand," or "passenger strand" as used herein, refers to the strand of an iRNA that includes a region that is substantially complementary to a region of the antisense strand as that term is defined herein.

As used herein, the term "SNALP" refers to a stable nucleic acid-lipid particle. A SNALP represents a vesicle of lipids coating a reduced aqueous interior comprising a nucleic acid such as an iRNA or a plasmid from which an iRNA is transcribed. SNALPs are described, e.g., in U.S. Patent Application Publication Nos. 20060240093, 20070135372, and in International Application No. WO 2009082817. These applications are incorporated herein by reference in their entirety.

"Introducing into a cell," when referring to an iRNA, means facilitating or effecting uptake or absorption into the cell, as is understood by those skilled in the art. Absorption or uptake of an iRNA can occur through unaided diffusive or active cellular processes, or by auxiliary agents or devices. The meaning of this term is not limited to cells in vitro; an iRNA may also be "introduced into a cell," wherein the cell is part of a living organism. In such an instance, introduction into the cell will include the delivery to the organism. For example, for in vivo delivery, iRNA can be injected into a tissue site or administered systemically. In vivo delivery can also be by a β-glucan delivery system, such as those described in U.S. Pat. Nos. 5,032,401 and 5,607,677, and U.S. Publication No. 2005/0281781, which are hereby incorporated by reference in their entirety. In vitro introduction into a cell includes methods known in the art such as electroporation and lipofection. Further approaches are described herein below or known in the art.

As used herein, the term "modulate the expression of," refers to at an least partial "inhibition" or partial "activation" of a BCL11A or a KLF1 gene expression in a cell treated with an iRNA composition as described herein compared to the expression of BCL11A or KLF1 in an untreated cell.

The terms "activate," "enhance," "up-regulate the expression of," "increase the expression of," and the like, in so far as they refer to a BCL11A or a KLF1 gene, herein refer to the at least partial activation of the expression of a BCL11A or a KLF1 gene, as manifested by an increase in the amount of BCL11A or KLF1 mRNA, which may be isolated from or detected in a first cell or group of cells in which a BCL11A or a KLF1 gene is transcribed and which has or have been treated such that the expression of a BCL11A or a KLF1 gene is increased, as compared to a second cell or group of cells substantially identical to the first cell or group of cells but which has or have not been so treated (control cells).

In one embodiment, expression of a BCL11A or a KLF1 gene is activated by at least about 10%, 15%, 20%, 25%, 30%, 35%, 40%, 45%, or 50% by administration of an iRNA as described herein. In some embodiments, a BCL11A or a KLF1 gene is activated by at least about 60%, 70%, or 80% by administration of an iRNA featured in the invention. In some embodiments, expression of a BCL11A or a KLF1 gene is activated by at least about 85%, 90%, or 95% or more by administration of an iRNA as described herein. In some embodiments, the BCL11A or KLF1 gene expression is increased by at least 1-fold, at least 2-fold, at least 5-fold, at least 10-fold, at least 50-fold, at least 100-fold, at least 500-fold, at least 1000 fold or more in cells treated with an iRNA as described herein compared to the expression in an untreated cell. Activation of expression by small dsRNAs is described, for example, in Li et al., 2006 *Proc. Natl. Acad. Sci. U.S.A.* 103:17337-42, and in US20070111963 and US2005226848, each of which is incorporated herein by reference.

The terms "silence," "inhibit the expression of," "down-regulate the expression of," "suppress the expression of," and the like, in so far as they refer to a BCL11A or a KLF1 gene, herein refer to the at least partial suppression of the expression of a BCL11A or a KLF1 gene, as manifested by a reduction of the amount of BCL11A or KLF1 mRNA which may be isolated from or detected in a first cell or group of cells in which a BCL11A or a KLF1 gene is transcribed and which has or have been treated such that the expression of a BCL11A or a KLF1 gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to BCL11A or KLF1 gene expression, e.g., the amount of protein encoded by a BCL11A or a KLF1 gene, or the number of cells displaying a certain phenotype, e.g., lack of or decreased cytokine production. In principle, BCL11A or KLF1 gene silencing may be determined in any cell expressing BCL11A or KLF1, either constitutively or by genomic engineering, and by any appropriate assay. However, when a reference is needed in order to determine whether a given iRNA inhibits the expression of the BCL11A or KLF1 gene by a certain degree and therefore is encompassed by the instant invention, the assays provided in the Examples below shall serve as such reference.

For example, in certain instances, expression of a BCL11A or a KLF1 gene is suppressed by at least about 10%, 15%, 20%, 25%, 30%, 35%, 40%, 45%, or 50% by administration of an iRNA featured in the invention. In some embodiments, a BCL11A or a KLF1 gene is suppressed by at least about 60%, 70%, or 80% by administration of an iRNA featured in the invention. In some embodiments, a BCL11A or a KLF1 gene is suppressed by at least about 85%, 90%, 95%, 98%, 99%, or more by administration of an iRNA as described herein.

As used herein in the context of BCL11A or KLF1 expression, the terms "treat," "treatment," and the like, refer to relief from or alleviation of pathological processes mediated by BCL11A or KLF1 expression. In the context of the present invention insofar as it relates to any of the other conditions recited herein below (other than pathological processes mediated by BCL11A or KLF1 expression), the terms "treat," "treatment," and the like mean to relieve or alleviate at least one symptom associated with such condition, or to slow or reverse the progression or anticipated progression of such condition, such as slowing the progression of a malignancy or cancer, or increasing the clearance of an infectious organism to alleviate/reduce the symptoms caused by the infection, e.g., hepatitis caused by infection with a hepatitis virus.

By "lower" in the context of a disease marker or symptom is meant a statistically significant decrease in such level. The decrease can be, for example, at least 10%, at least 20%, at least 30%, at least 40% or more, and is typically down to a level accepted as within the range of normal for an individual without such disorder.

As used herein, the phrases "therapeutically effective amount" and "prophylactically effective amount" refer to an amount that provides a therapeutic benefit in the treatment, prevention, or management of pathological processes mediated by BCL11A or KLF1 expression or an overt symptom of pathological processes mediated by BCL11A or KLF1 expression. The specific amount that is therapeutically effective can be readily determined by an ordinary medical practitioner, and may vary depending on factors known in the art, such as, for example, the type of pathological processes mediated by BCL11A or KLF1 expression, the patient's history and age, the stage of pathological processes mediated by BCL11A or KLF1 expression, and the administration of other agents that inhibit pathological processes mediated by BCL11A or KLF1 expression.

As used herein, a "pharmaceutical composition" comprises a pharmacologically effective amount of an iRNA and a pharmaceutically acceptable carrier. As used herein, "pharmacologically effective amount," "therapeutically effective amount" or simply "effective amount" refers to that amount of an iRNA effective to produce the intended pharmacological, therapeutic or preventive result. For example, if a given clinical treatment is considered effective when there is at least a 10% reduction in a measurable parameter associated with a disease or disorder, a therapeutically effective amount of a drug for the treatment of that disease or disorder is the amount necessary to effect at least a 10% reduction in that parameter. For example, a therapeutically effective amount of an iRNA targeting BCL11A or KLF1 can reduce BCL11A or KLF1 protein levels by at least 10%.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Agents included in drug formulations are described further herein below.

II. Double-Stranded Ribonucleic Acid (dsRNA)

Described herein are iRNA agents that inhibit the expression of the BCL11A or KLF1 gene. In one embodiment, the iRNA agent includes double-stranded ribonucleic acid (dsRNA) molecules for inhibiting the expression of a BCL11A or a KLF1 gene in a cell or mammal, e.g., in a human having a cancer or infectious disease, where the dsRNA includes an antisense strand having a region of complementarity which is complementary to at least a part of an mRNA formed in the expression of a BCL11A or a KLF1 gene, and where the region of complementarity is 30 nucleotides or less in length, generally 19-24 nucleotides in length, and where the dsRNA, upon contact with a cell expressing the BCL11A or a KLF1 gene, inhibits the expression of the BCL11A or KLF1 gene by at least 10% as assayed by, for example, a PCR or branched DNA (bDNA)-based method, or by a protein-based method, such as by Western blot. In one embodiment, the iRNA agent activates the expression of a BCL11A or a KLF1 gene in a cell or mammal. Expression of a BCL11A or a KLF1 gene in cell culture, such as in COS cells, HeLa cells, primary hepatocytes, HepG2 cells, primary cultured cells or in a biological sample from a subject can be assayed by measuring BCL11A or KLF1 mRNA levels, such as by bDNA or TaqMan assay, or by measuring protein levels, such as by immunofluorescence analysis, using, for example, Western Blotting or flow cytometric techniques.

A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence, derived from the sequence of an mRNA formed during the expression of a BCL11A or a KLF1 gene. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, e.g., 15-30 nucleotides in length.

One of skill in the art will also recognize that the duplex region is a primary functional portion of a dsRNA, e.g., a duplex region of 9 to 36, e.g., 15-30 base pairs. Thus, in one embodiment, to the extent that it becomes processed to a functional duplex of e.g., 15-30 base pairs that targets a desired RNA for cleavage, an RNA molecule or complex of RNA molecules having a duplex region greater than 30 base pairs is a dsRNA. Thus, an ordinarily skilled artisan will recognize that in one embodiment, then, an miRNA is a dsRNA. In another embodiment, a dsRNA is not a naturally occurring miRNA. In another embodiment, an iRNA agent useful to target BCL11A or KLF1 expression is not generated in the target cell by cleavage of a larger dsRNA.

A dsRNA as described herein may further include one or more single-stranded nucleotide overhangs. The dsRNA can be synthesized by standard methods known in the art as further discussed below, e.g., by use of an automated DNA synthesizer, such as are commercially available from, for example, Biosearch, Applied Biosystems, Inc. In one embodiment, a BCL11A or a KLF1 gene is a human BCL11A or a KLF1 gene. In another embodiment the BCL11A or a KLF1 gene is a mouse or a rat BCL11A or KLF1 gene. In specific embodiments, the first sequence is a sense strand of a dsRNA that includes a sense sequence from Table 2A-1, 2A-2, 2A-3, Table 2B, or Table 2C, or Tables 3-7, and the second sequence is an antisense strand of a dsRNA that includes an antisense sequence from Table 2A-1, 2A-2, 2A-3, Table 2B, or Table 2C, or Tables 3-7. Alternative dsRNA agents that target sequences other than those of the dsRNAs of Table 2A-1, 2A-2, 2A-3, Table 2B, and Table 2C, and Tables 3-7 can readily be determined using the target sequence and the flanking BCL11A or KLF1 sequence.

In one aspect, a dsRNA will include at least nucleotide sequences, whereby the sense strand is selected from the groups of sequences provided in Table 2A-1, 2A-2, 2A-3, Table 2B, and Table 2C, and in Table 3-7, and the corresponding antisense strand of the sense strand selected from Table 2A-1, 2A-2, 2A-3, Table 2B, and Table 2C, and Tables 3-7. In this aspect, one of the two sequences is complementary to the other of the two sequences, with one of the sequences being substantially complementary to a sequence of an mRNA generated by the expression of a BCL11A or KLF1 gene. As such, in this aspect, a dsRNA will include two oligonucleotides, where one oligonucleotide is described as the sense strand in Table 2A-1, 2A-2, 2A-3, Table 2B, or Table 2C, or Tables 3-7, and the second oligonucleotide is described as the corresponding antisense strand of the sense strand from Table 2A-1, 2A-2, 2A-3, Table 2B, or Table 2C, or Tables 3-7. As described elsewhere herein and as known in the art, the complementary sequences of a dsRNA can also be contained as self-complementary regions of a single nucleic acid molecule, as opposed to being on separate oligonucleotides.

The skilled person is well aware that dsRNAs having a duplex structure of between 20 and 23, but specifically 21, base pairs have been hailed as particularly effective in inducing RNA interference (Elbashir et al., EMBO 2001, 20:6877-6888). However, others have found that shorter or longer RNA duplex structures can be effective as well. In the embodiments described above, by virtue of the nature of the oligonucleotide sequences provided in Table 2A-1, 2A-2, 2A-3, Table 2B, and Table 2C, and Tables 3, 4, 5, 6 and 7, dsRNAs described herein can include at least one strand of a length of minimally 21 nt. It can be reasonably expected that shorter duplexes having one of the sequences of Table 2A-1, 2A-2, 2A-3, Table 2B, and Table 2C, and Tables 3, 4, 5, 6 and 7 minus only a few nucleotides on one or both ends may be similarly effective as compared to the dsRNAs described above. Hence, dsRNAs having a partial sequence of at least 15, 16, 17, 18, 19, 20, or more contiguous nucleotides from one of the sequences of Table 2A-1, 2A-2, 2A-3, Table 2B, or Table 2C, or Tables 3-7, and differing in their ability to inhibit the expression of a BCL11A or a KLF1 gene by not more than 5, 10, 15, 20, 25, or 30% inhibition from a dsRNA comprising the full sequence, are contemplated according to the invention.

In addition, the RNAs provided in Table 2A-1, 2A-2, 2A-3, Table 2B, and Table 2C, and Tables 3, 4, 5, 6 and 7, identify a site in a BCL11A or a KLF1 transcript that is susceptible to RISC-mediated cleavage. As such, the present invention further features iRNAs that target within one of such sequences. As used herein, an iRNA is said to target within a particular site of an RNA transcript if the iRNA promotes cleavage of the transcript anywhere within that particular site. Such an iRNA will generally include at least 15 contiguous nucleotides from one of the sequences provided in Table 2A-1, 2A-2, 2A-3, Table 2B, and Table 2C, and Tables 3, 4, 5, 6 and 7 coupled to additional nucleotide sequences taken from the region contiguous to the selected sequence in a BCL11A or a KLF1 gene.

While a target sequence is generally 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that may serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, while the sequences identified, for example, in Table 2A-1, 2A-2, 2A-3, Table 2B, and Table 2C, and Tables 3, 4, 5, 6 and 7 represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified, e.g., in Table 2A-1, 2A-2, 2A-3, Table 2B, and Table 2C, and Tables 3, 4, 5, 6 and 7, further optimization could be achieved by systematically either adding or removing nucleotides to generate longer or shorter sequences and testing those and sequences generated by walking a window of the longer or shorter size up or down the target RNA from that point. Again, coupling this approach to generating new candidate targets with testing for effectiveness of iRNAs based on those target sequences in an inhibition assay as known in the art or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes, etc.) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch not be located in the center of the region of complementarity. If the antisense strand of the iRNA contains mismatches to the target sequence, it is preferable that the mismatch be restricted to be within the last 5 nucleotides from either the 5' or 3' end of the region of complementarity. For example, for a 23 nucleotide iRNA agent RNA strand which is complementary to a region of a BCL11A or a KLF1 gene, the RNA strand generally does not contain any mismatch within the central 13 nucleotides. The methods described herein or methods known in the art can be used to determine whether an iRNA containing a mismatch to a target sequence is effective in inhibiting the expression of a BCL11A or a KLF1 gene. Consideration of the efficacy of iRNAs with mismatches in inhibiting expression of a BCL11A or a KLF1 gene is important, especially if the particular region of complementarity in a BCL11A or a KLF1 gene is known to have polymorphic sequence variation within the population.

In one embodiment, at least one end of a dsRNA has a single-stranded nucleotide overhang of 1 to 4, generally 1 or 2 nucleotides. dsRNAs having at least one nucleotide overhang have unexpectedly superior inhibitory properties relative to their blunt-ended counterparts. In yet another embodiment, the RNA of an iRNA, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in this invention include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476, 301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs may also contain one or more substituted sugar moieties. The iRNAs, e.g., dsRNAs, featured herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_n$OCH$_3$, O($CH_2$)$_n$NH$_2$, O($CH_2$)$_n$CH$_3$, O($CH_2$)$_n$ONH$_2$, and O($CH_2$)$_n$ON[($CH_2$)$_n$CH$_3$)]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy(2'-O—CH$_2$CH$_2$OCH$_3$, also known as 2'-O-(2-methoxyethyl) or 2'-MOE) (Martin et al., *Helv. Chim. Acta*, 1995, 78:486-504) i.e., an alkoxy-alkoxy group. Another exemplary modification is 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$, also described in examples herein below.

Other modifications include 2'-methoxy(2'-OCH$_3$), 2'-aminopropoxy(2'-OCH$_2$CH$_2$CH$_2$NH$_2$) and 2'-fluoro (2'-F). Similar modifications may also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193).

Representative U.S. patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA featured in the invention involves chemically linking to the RNA one or more ligands, moieties or conjugates that enhance the activity, cellular distribution or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-5-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

In one embodiment, a ligand alters the distribution, targeting or lifetime of an iRNA agent into which it is incorporated. In some embodiments, a ligand provides an enhanced affinity for a selected target, e.g, molecule, cell or cell type, compartment, e.g., a cellular or organ compartment, tissue, organ or region of the body, as, e.g., compared to a species absent such a ligand. Typical ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an α helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B 12, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one ligand, the ligand is a lipid or lipid-based molecule. Such a lipid or lipid-based molecule can typically bind a serum protein, such as human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In one embodiment, the lipid based ligand binds HSA. For example, the ligand can bind HSA with a sufficient affinity such that distribution of the conjugate to a non-kidney tissue is enhanced. However, the affinity is typically not so strong that the HSA-ligand binding cannot be reversed.

In another embodiment, the lipid based ligand binds HSA weakly or not at all, such that distribution of the conjugate to the kidney is enhanced. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, such as a helical cell-permeation agent. In one embodiment, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is typically an α-helical agent, and can have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO:1). An RFGF analogue (e.g., amino acid sequence AALLPVLLAAP (SEQ ID NO:2)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO:3)) and the *Drosophila Antennapedia* protein (RQIKIWFQNRRMKWKK (SEQ ID NO: 4)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Typically, the peptide or peptidomimetic tethered to a dsRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an dsRNA agent to tumors of a variety of other tissues, including the lung, kidney, spleen, or liver (Aoki et al., Cancer Gene Therapy 8:783-787, 2001). Typically, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver a iRNA agent to a tumor cell expressing $\alpha_v\beta_3$ (Haubner et al., Jour. Nucl. Med., 42:326-336, 2001).

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; each of which is herein incorporated by reference.

It is not necessary for all positions in a given compound to be uniformly modified, and in fact more than one of the aforementioned modifications may be incorporated in a single compound or even at a single nucleoside within an iRNA. The present invention also includes iRNA compounds that are chimeric compounds. "Chimeric" iRNA compounds, or "chimeras," in the context of the present invention, are iRNA compounds, e.g., dsRNAs, that contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., Biochem. Biophys. Res. Comm., 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction may be performed either with the RNA still bound to the solid support or following cleavage of the RNA, in solution phase. Purification of the RNA conjugate by HPLC typically affords the pure conjugate.

Delivery of iRNA

The delivery of an iRNA to a subject in need thereof can be achieved in a number of different ways. In vivo delivery can be performed directly by administering a composition comprising an iRNA, e.g. a dsRNA, to a subject. Alternatively, delivery can be performed indirectly by administering one or more vectors that encode and direct the expression of the iRNA. These alternatives are discussed further below.

Direct Delivery

In general, any method of delivering a nucleic acid molecule can be adapted for use with an iRNA (see e.g., Akhtar S. and Julian R L. (1992) Trends Cell. Biol. 2(5):139-144 and WO94/02595, which are incorporated herein by reference in their entireties). However, there are three factors that are important to consider in order to successfully deliver an iRNA molecule in vivo: (a) biological stability of the delivered molecule, (2) preventing non-specific effects, and (3) accumulation of the delivered molecule in the target tissue. The non-specific effects of an iRNA can be minimized by local administration, for example by direct injection or implantation into a tissue (as a non-limiting example, a tumor) or topically administering the preparation. Local administration to a treatment site maximizes local concentration of the agent, limits the exposure of the agent to systemic tissues that may otherwise be harmed by the agent or that may degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) Retina 24:132-138) and subretinal injections in mice (Reich, S J., et al (2003) Mol. Vis. 9:210-216) were both shown to prevent neovascularization in an experimental model of age-related macular degeneration. In addition, direct intratumoral injection of a dsRNA in mice reduces tumor volume (Pille, J., et al (2005) Mol. Ther. 11:267-274) and can prolong survival of tumor-bearing mice (Kim, W J., et al (2006) Mol. Ther. 14:343-350; Li, S., et al (2007) Mol. Ther. 15:515-523). RNA interference has also shown success with local delivery to the CNS by direct injection (Dorn, G., et al. (2004) Nucleic Acids 32:e49; Tan, P H., et al (2005) Gene Ther. 12:59-66; Makimura, H., et al (2002) BMC Neurosci. 3:18; Shishkina, G T., et al (2004) Neuroscience 129:521-528; Thakker, E R., et al (2004) Proc. Natl. Acad. Sci. U.S.A. 101:17270-17275; Akaneya, Y., et al (2005) J. Neurophysiol. 93:594-602) and to the lungs by intranasal administration (Howard, K A., et al (2006) Mol. Ther. 14:476-484; Zhang, X., et al (2004) J. Biol. Chem. 279:10677-10684; Bitko, V., et al (2005) Nat. Med. 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) Nature 432:173-178). Conjugation of an iRNA to an aptamer has been shown to inhibit tumor growth and mediate tumor regression in a mouse model of prostate cancer (McNamara, J O., et al (2006) Nat. Biotechnol. 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) Journal of Controlled Release 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) J. Mol. Biol 327:761-766; Verma, U N., et al (2003) Clin. Cancer Res. 9:1291-1300; Arnold, A S et al (2007) J. Hypertens. 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) Nature 441:111-114), cardiolipin (Chien, P Y., et al (2005) Cancer Gene Ther. 12:321-328; Pal, A., et al (2005) Int J. Oncol. 26:1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

Vector Encoded dsRNAs

In another aspect, iRNA targeting the BCL11A or KLF1 gene can be expressed from transcription units inserted into DNA or RNA vectors (see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054, 299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as an inverted repeat joined by a linker polynucleotide sequence such that the dsRNA has a stem and loop structure.

An iRNA expression vector is typically a DNA plasmid or viral vector. An expression vector compatible with eukaryotic cells, e.g., with vertebrate cells, can be used to produce recombinant constructs for the expression of an iRNA as described herein. Eukaryotic cell expression vectors are well known in the art and are available from a number of commercial sources. Typically, such vectors contain convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

An iRNA expression plasmid can be transfected into a target cell as a complex with a cationic lipid carrier (e.g., Oligofectamine) or a non-cationic lipid-based carrier (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct may be incorporated into vectors capable of episomal replication, e.g EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, FASEB J. 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-β-D1-thiogalactopyranoside (IPTG). A person skilled in the art would be able to choose the appropriate regulatory/promoter sequence based on the intended use of the iRNA transgene.

In a specific embodiment, viral vectors that contain nucleic acid sequences encoding an iRNA can be used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding an iRNA are cloned into one or more vectors, which facilitates delivery of the nucleic acid into a patient. More detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). A suitable AV vector for expressing an iRNA featured in the invention, a method for constructing the recombinant AV vector, and a method for delivering the vector into target cells, are described in Xia H et al. (2002), Nat. Biotech. 20: 1006-1010.

Use of Adeno-associated virus (AAV) vectors is also contemplated (Walsh et al., Proc. Soc. Exp. Biol. Med. 204:289-300 (1993); U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Another typical viral vector is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), J Virol 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

III. Pharmaceutical Compositions Containing iRNA

In one embodiment, the invention provides pharmaceutical compositions containing an iRNA, as described herein, and a pharmaceutically acceptable carrier. The pharmaceutical composition containing the iRNA is useful for treating a disease or disorder associated with the expression or activity of a BCL11A or a KLF1 gene, such as pathological processes mediated by BCL11A or KLF1 expression. Such pharmaceutical compositions are formulated based on the mode of delivery. For example, compositions can be formulated for systemic administration via parenteral delivery, e.g., by intravenous (IV) delivery, or compositions can be formulated for direct delivery into the brain parenchyma, e.g., by infusion into the brain, such as by continuous pump infusion.

The pharmaceutical compositions featured herein are administered in dosages sufficient to inhibit expression of BCL11A or KLF1 genes. In general, a suitable dose of iRNA will be in the range of 0.01 to 200.0 milligrams per kilogram body weight of the recipient per day, generally in the range of 1 to 50 mg per kilogram body weight per day. For example, the dsRNA can be administered at 0.05 mg/kg, 0.5 mg/kg, 1 mg/kg, 1.5 mg/kg, 2 mg/kg, 3 mg/kg, 10 mg/kg, 20 mg/kg, 30 mg/kg, 40 mg/kg, or 50 mg/kg per single dose. The pharmaceutical composition may be administered once daily, or the iRNA may be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

The effect of a single dose on BCL11A or KLF1 levels can be long lasting, such that subsequent doses are administered at not more than 3, 4, or 5 day intervals, or at not more than 1, 2, 3, or 4 week intervals.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by BCL11A or KLF1 expression. Such models can be used for in vivo testing of iRNA, as well as for determining a therapeutically effective dose. A suitable mouse model is, for example, a mouse containing a transgene expressing human BCL11A or KLF1.

The present invention also includes pharmaceutical compositions and formulations that include the iRNA compounds featured in the invention. The pharmaceutical compositions of the present invention may be administered in a number of ways depending upon whether local or systemic treatment is desired and upon the area to be treated. Administration may be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as a tissue that produces erythrocytes. For example, the iRNA can be delivered to bone marrow, liver (e.g., hepatocyes of liver), lymph glands, spleen, lungs (e.g., pleura of lungs) or spine. In one embodiment, the iRNA is delivered to bone marrow.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention may be encapsulated within liposomes or may form complexes thereto, in particular to cationic liposomes. Alternatively, iRNAs may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

Liposomal Formulations

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to traverse intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S. T. P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{1215G}$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Nucleic Acid Lipid Particles

In one embodiment, a BCL11A or a KLF1 dsRNA featured in the invention is fully encapsulated in the lipid formulation, e.g., to form a SPLP, pSPLP, SNALP, or other nucleic acid-lipid particle. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1.

The cationic lipid may be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid may comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2,2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid may be from about 5 mol % to about 90 mol %, about 10 mol %, or about 58 mol % if cholesterol is included, of the total lipid present in the particle.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles may be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

LNP01

In one embodiment, the lipidoid ND98.4HCl (MW 1487) (see U.S. patent application Ser. No. 12/056,230, filed Mar. 26, 2008, which is herein incorporated by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

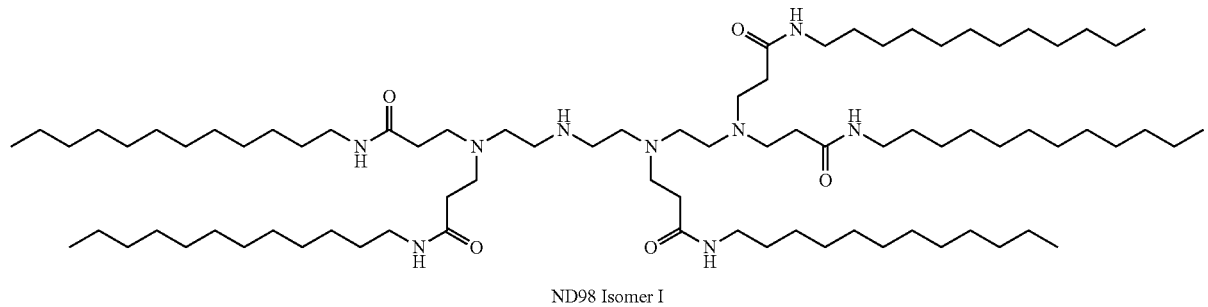

Formula 1

ND98 Isomer I

LNP01 formulations are described, e.g., in International Application Publication No. WO 2008/042973, which is hereby incorporated by reference.

Additional exemplary lipid-dsRNA formulations are as follows:

| | Cationic Lipid | cationic lipid/non-cationic lipid/cholesterol/PEG-lipid conjugate Lipid:siRNA ratio |
|---|---|---|
| SNALP | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA~7:1 |
| S-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200) | C12-200/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |

| Cationic Lipid | | cationic lipid/non-cationic lipid/cholesterol/PEG-lipid conjugate Lipid:siRNA ratio |
|---|---|---|
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)
SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.
XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Ser. No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.
MC3 comprising formulations are described, e.g., in U.S. Provisional Ser. No. 61/244,834, filed Sep. 22, 2009, U.S. Provisional Ser. No. 61/185,800, filed Jun. 10, 2009, and International Application No. PCT/US10/28224, filed Jun. 10, 2010, which are hereby incorporated by reference.
ALNY-100 comprising formulations are described, e.g., International patent application number PCT/US09/63933, filed on Nov. 10, 2009, which is hereby incorporated by reference.
C12-200 comprising formulations are described in U.S. Provisional Ser. No. 61/175,770, filed May 5, 2009 and International Application No. PCT/US10/33777, filed May 5, 2010, which are hereby incorporated by reference.

Synthesis of Cationic Lipids.

Any of the compounds, e.g., cationic lipids and the like, used in the nucleic acid-lipid particles featured in the invention may be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(=O)alkyl, —C(=O)alkenyl, and —C(=O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (=O) two hydrogen atoms are replaced. In this regard, substituents include oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$, wherein n is 0, 1 or 2, R$^x$ and R$^y$ are the same or different and independently hydrogen, alkyl or heterocycle, and each of said alkyl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$.

"Halogen" means fluoro, chloro, bromo and iodo.

In some embodiments, the methods featured in the invention may require the use of protecting groups. Protecting group methodology is well known to those skilled in the art (see, for example, PROTECTIVE GROUPS IN ORGANIC SYNTHESIS, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In one embodiments, nucleic acid-lipid particles featured in the invention are formulated using a cationic lipid of formula A:

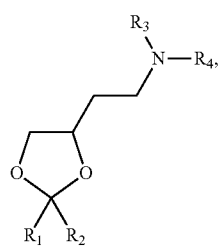

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above may be made by the following Reaction Schemes 1 or 2, wherein all substituents are as defined above unless indicated otherwise.

Scheme 1

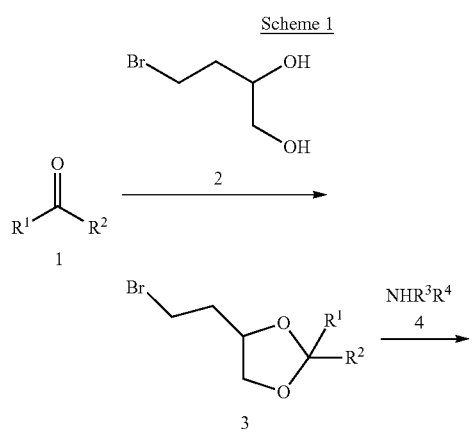

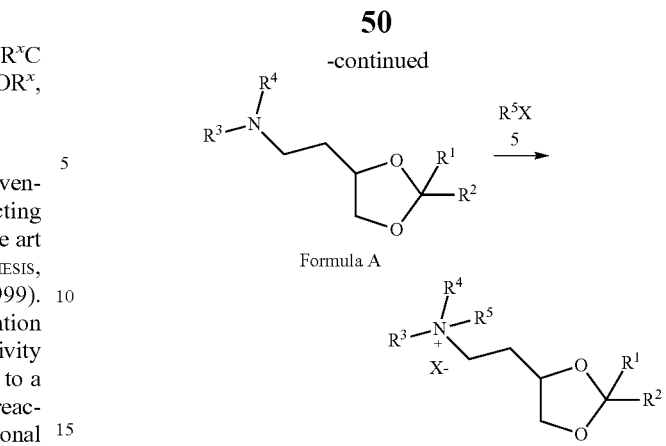

Lipid A, where R$_1$ and R$_2$ are independently alkyl, alkenyl or alkynyl, each can be optionally substituted, and R$_3$ and R$_4$ are independently lower alkyl or R$_3$ and R$_4$ can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

Scheme 2

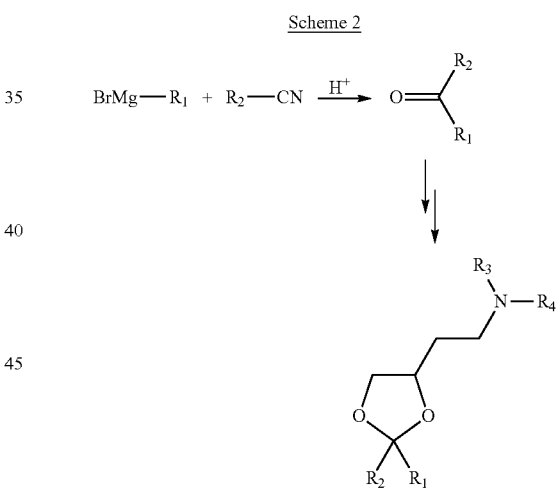

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl 4-(dimethylamino)butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g).

Synthesis of ALNY-100

Synthesis of ketal 519 [ALNY-100] was performed using the following scheme 3:

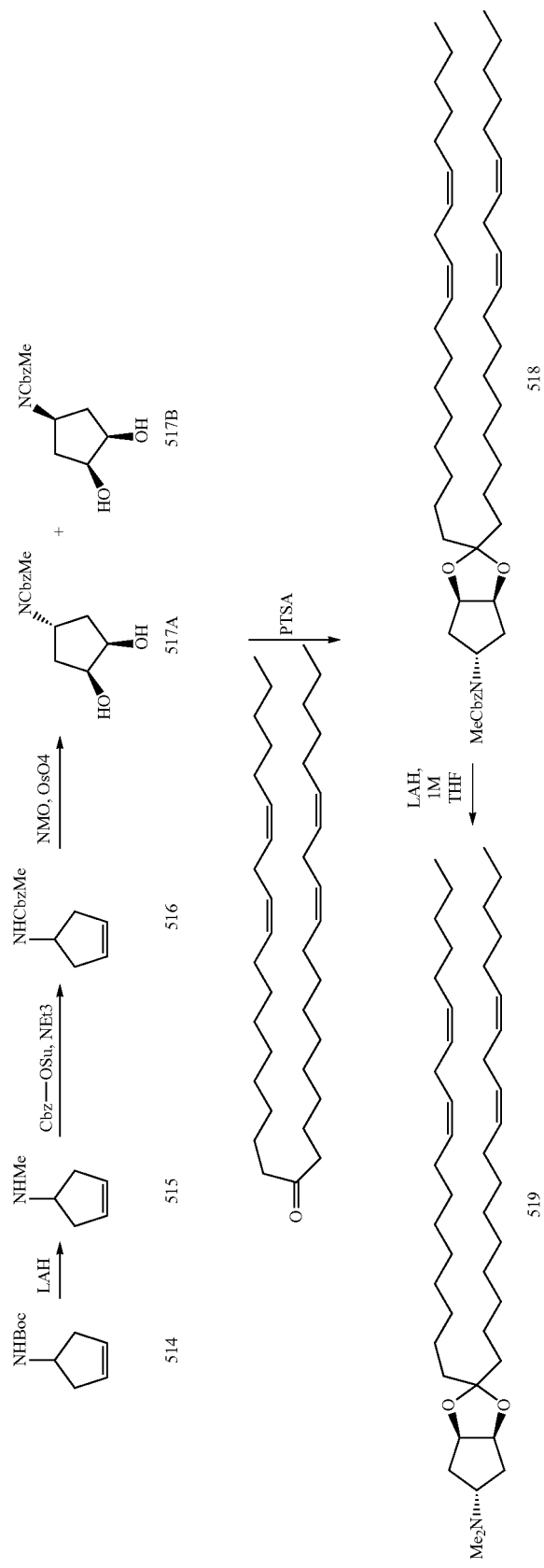

Synthesis of 515:

To a stirred suspension of LiAlH4 (3.74 g, 0.09852 mol) in 200 ml anhydrous THF in a two neck RBF (1 L), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g 1H-NMR (DMSO, 400 MHz): δ=9.34 (broad, 2H), 5.68 (s, 2H), 3.74 (m, 1H), 2.66-2.60 (m, 2H), 2.50-2.45 (m, 5H).

Synthesis of 516:

To a stirred solution of compound 515 in 100 mL dry DCM in a 250 mL two neck RBF, was added NEt3 (37.2 mL, 0.2669 mol) and cooled to 0 0 C under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated NaHCO3 solution (1×50 mL). The organic layer was then dried over anhyd. Na2SO4 and the solvent was evaporated to give crude material which was purified by silica gel column chromatography to get 516 as sticky mass. Yield: 11 g (89%). 1H-NMR (CDCl3, 400 MHz): δ=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H]—232.3 (96.94%).

Synthesis of 517A and 517B:

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO4 (0.275 g, 0.00108 mol) in tert-butanol at room temperature. After completion of the reaction (~3 h), the mixture was quenched with addition of solid Na2SO3 and resulting mixture was stirred for 1.5 h at room temperature. Reaction mixture was diluted with DCM (300 mL) and washed with water (2×100 mL) followed by saturated NaHCO3 (1×50 mL) solution, water (1×30 mL) and finally with brine (1×50 mL). Organic phase was dried over an.Na2SO4 and solvent was removed in vacuum. Silica gel column chromatographic purification of the crude material was afforded a mixture of diastereomers, which were separated by prep HPLC. Yield: ~6 g crude 517A—Peak-1 (white solid), 5.13 g (96%). 1H-NMR (DMSO, 400 MHz): δ=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS-[M+H]—266.3, [M+NH4+]—283.5 present, HPLC—97.86%. Stereochemistry confirmed by X-ray.

Synthesis of 518:

Using a procedure analogous to that described for the synthesis of compound 505, compound 518 (1.2 g, 41%) was obtained as a colorless oil. 1H-NMR (CDCl3, 400 MHz): δ=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC-98.65%.

General Procedure for the Synthesis of Compound 519:

A solution of compound 518 (1 eq) in hexane (15 mL) was added in a drop-wise fashion to an ice-cold solution of LAH in THF (1 M, 2 eq). After complete addition, the mixture was heated at 40° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. 13C NMR=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for C44H80NO2 (M+H)+ Calc. 654.6, Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total dsRNA concentration in the formulation, as well as the entrapped fraction, is estimated using a dye exclusion assay. A sample of the formulated dsRNA can be incubated with an RNA-binding dye, such as Ribogreen (Molecular Probes) in the presence or absence of a formulation disrupting surfactant, e.g., 0.5% Triton-X100. The total dsRNA in the formulation can be determined by the signal from the sample containing the surfactant, relative to a standard curve. The entrapped fraction is determined by subtracting the "free" dsRNA content (as measured by the signal in the absence of surfactant) from the total dsRNA content. Percent entrapped dsRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. In some embodiments, oral formulations are those in which dsRNAs featured in the invention are administered in conjunction with one or more penetration enhancers surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention may be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations featured in the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions featured in the present invention may be formulated into any of many possible dosage forms such as, but not limited to, tablets, capsules, gel capsules, liquid syrups, soft gels, suppositories, and enemas. The compositions may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Additional Formulations

Emulsions

The compositions of the present invention may be prepared and formulated as emulsions. Emulsions are typically heterogeneous systems of one liquid dispersed in another in the form of droplets usually exceeding 0.1 µm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: non-ionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of iRNAs and nucleic acids are formulated as microemulsions. A microemulsion may be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention may also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Penetration Enhancers

In one embodiment, the present invention employs various penetration enhancers to effect the efficient delivery of nucleic acids, particularly iRNAs, to the skin of animals. Most drugs are present in solution in both ionized and non-ionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty Acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile Salts: The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents: Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of β-diketones (enamines) (see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-Chelating Non-Surfactants: As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of iRNAs at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPass$^a$ D1 Transfection Reagent (New England Biolabs; Ipswich, Mass., USA), LyoVec™/LipoGen™ (Invivogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances that increase the viscosity of the suspension including, for example, sodium carboxymethylcellulose, sorbitol and/or dextran. The suspension may also contain stabilizers.

In some embodiments, pharmaceutical compositions featured in the invention include (a) one or more iRNA compounds and (b) one or more biologic agents which function by a non-RNAi mechanism. Examples of such biologic agents include agents that interfere with an interaction of BCL11A and at least one of the BCL11A-binding partners, e.g., at least one of GATA, FOG-1 and a component of a NuRD complex. Other examples of such biologic agents include agents that interfere with an interaction of KLF1 and at least one of the KLF1-binding partners.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are typical.

The data obtained from cell culture assays and animal studies can be used in formulating a range of dosage for use in humans. The dosage of compositions featured in the invention lies generally within a range of circulating concentrations that include the ED50 with little or no toxicity. The dosage may vary within this range depending upon the dosage form employed and the route of administration utilized. For any compound used in the methods featured in the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration, as discussed above, the iRNAs featured in the invention can be administered in combination with other known agents effective in treatment of pathological processes mediated by BCL11A or KLF1 expression. In any event, the administering physician can adjust the amount and timing of iRNA administration on the basis of results observed using standard measures of efficacy known in the art or described herein.

Methods for Treating Diseases Caused by Expression of a BCL11a or a KLF1 Gene

The invention relates in particular to the use of an iRNA targeting BCL11A or KLF1-mediated disorder or disease. For example, an iRNA targeting a BCL11A or KLF1 gene, or a combination thereof, is used for treatment of hemoglobinopathies. In one embodiment, the subject, e.g., the mammal, is at risk of having, or has been diagnosed, with a hemoglobinopathy. As used herein, the term "hemoglobinopathy" means any defect in the structure or function of a hemoglobin of an individual. It includes defects in the primary, secondary, tertiary or quaternary structure of hemoglobin. The defects can be caused by any mutation, such as deletion mutations or substitution mutations in the coding regions of the β-globin gene, or mutations in, or deletions of, the promoters or enhancers of such genes that cause a reduction in the amount of hemoglobin produced as compared to a normal or standard condition. The term further includes any decrease in the amount or effectiveness of hemoglobin, whether normal or abnormal, caused by external factors such as disease, chemotherapy, toxins, poisons, or the like. In one embodiment, the hemoglobinopathy is a β-hemoglobinopathy, and in another embodiment, the hemoglobinopathy is an α-hemoglobinopathy. In another embodiment, the hemoglobinopathy is a β-thalassemia, a hemoglobin CC or hemoglobin EE disease. In another embodiment, the hemoglobinopathy is a sickle cell disease.

In thalassemias, the bone marrow synthesizes insufficient amounts of a hemoglobin chain; this in turn reduces the production of red blood cells and causes anemia. Either the α or the β chain may be affected, but β thalassemias are more common; newborn babies are healthy because their bodies still produce HbF, which does not have β chains; during the first few months of life, the bone marrow switches to producing HbA, and symptoms start to appear.

β-thalassemias result from mutation with either non-expressing ($\beta^0$) or low expressing ($\beta^+$) alleles. β-thalassemias vary in severity depending on the genotype, and include minor/trait β-thalassemia ($\beta/\beta^0$ or $\beta/\beta+$), intermedia β-thalassemia ($\beta^0/\beta+$), and major β-thalassemia ($\beta^0/\beta^0$ or $\beta^+/\beta^+$).

Hemoglobin C results from a mutation in the beta globin gene and is the predominant hemoglobin found in people with hemoglobin C disease ($\alpha_2\beta^c_2$). Hemoglobin C disease (also called hemoglobin CC disease) is relatively benign, producing a mild hemolytic anemia and splenomegaly. Hemoglobin E results from a mutation in the hemoglobin β chain. People with hemoglobin E (also called hemoglobin EE) disease have a mild hemolytic anemia and mild splenomegaly.

Symptoms of β-thalassemias include, e.g., hemolysis, which causes anemia and splenomegaly; ineffective erythropoiesis, which causes bone marrow drive (skeletal changes), hepato-splenomegaly, consumption of haematinics (megablastic anemia), and high uric acid in blood; leg ulcers, infections, and complication due to therapy, e.g., iron overload, which causes endocrinopathy, liver fibrosis and cardiac fibrosis. Administration of an iRNA agent that targets BCL11A or KLF1, or a combination thereof, can be effective to treat one or more of these symptoms.

As used herein, "sickle cell disease" includes, but is not limited to, sickle cell anemia (SS), sickle-hemoglobin, C disease (HbSC), sickle $β^+$-thalassemia (HbS/β+), sickle $β^0$-thalassemia (HbS/$β^0$) and SE disease.

Sickle cell disease is a genetic disorder characterized by the presence of hemoglobin S (Hb S), which causes red blood cells to change from their usual biconcave disc shape to a crescent or sickle shape during deoxygenation. The red blood cell resumes a normal configuration, but after repeated cycles of "sickling and unsickling" the red blood cell becomes damaged permanently, and hemolysis occurs. The hemolysis is responsible for the anemia that is the hallmark of sickle cell disease. Symptoms of sickle-cell disease include, e.g., hemolysis, jaundice, cholelithiasis, aplastic crisis, hemolytic crisis, vaso-occlusive disease, which causes dactylitis, autosplenectomy, acute chest shyndrome, stroke priapism, renal papillary necrosis, infarctive crisis, sequestration crisis and leg ulcers. Administration of an iRNA agent that targets BCL11A or KLF1, or a combination thereof, can be effective to treat one or more of these symptoms.

The treatment according to the present invention ameliorates one or more symptoms associated with the disorder by increasing the amount of fetal hemoglobin in the individual. Symptoms typically associated with a hemoglobinopathy, include for example, anemia, tissue hypoxia, organ dysfunction, vaso-occlusive crises, abnormal hematocrit values, ineffective erythropoiesis, abnormal reticulocyte (erythrocyte) count, abnormal iron load, the presence of ring sideroblasts, splenomegaly, hepatomegaly, impaired peripheral blood flow, dyspnea, increased hemolysis, jaundice, anemic pain crises, acute chest syndrome, splenic sequestration, priapism, stroke, hand-foot syndrome, and pain such as angina pectoris.

In another aspect, the invention provides a method for increasing fetal hemoglobin levels and/or decreasing γ-globulin levels in a hematopoietic progenitor cell (e.g., an erythroid cell). The method includes contacting a hematopoietic progenitor cell (e.g., an erythroid cell) with an iRNA targeting a BCL11A or KLF1 gene, or a combination thereof, in an amount effective to increase fetal hemoglobin expression, relative to expression prior to such contacting. In one embodiment, the hematopoietic progenitor cell is present in a subject (e.g., a mammal) in need thereof. In other embodiments, the hematopoietic progenitor cell is contacted ex vivo or in vitro, and the cell or its progeny is administered to said subject.

The term "increasing" or "decreasing" fetal hemoglobin levels or "γ-globulin levels" is intended to refer to at least 5%, 10%, 20%, 30%, 40%, 50% or more difference (e.g., increase or decrease relative to a reference value, e.g., a reference where no iRNA is added).

"Hematopoietic progenitor cell" as the term is used herein, refers to cells of a stem cell lineage that give rise to all the blood cell types including the myeloid (monocytes and macrophages, neutrophils, basophils, eosinophils, erythrocytes, megakaryocytes/platelets, dendritic cells), and the lymphoid lineages (T-cells, B-cells, NK-cells). An "erythroid cell" indicates a cell that undergoes erythropoeisis such that upon final differentiation it forms an erythrocyte or red blood cell (RBC). Such cells belong to one of three lineages, erythroid, lymphoid, and myeloid, originating from bone marrow haematopoietic progenitor cells. Upon exposure to specific growth factors and other components of the haematopoietic microenvironment, haematopoietic progenitor cells can mature through a series of intermediate differentiation cellular types, all intermediates of the erythroid lineage, into RBCs. Thus, "erythroid cells" comprise hematopoietic progenitor cells, rubriblasts, prorubricytes, erythroblasts, metarubricytes, reticulocytes, and erythrocytes.

In some embodiment, the hematopoietic progenitor cell has at least one of the cell surface marker characteristic of haematopoietic progenitor cells: CD34+, CD59+, Thy1/CD90+, $CD38^{lo}/-$, and c-kit/CD117+. Typically, the hematopoietic progenitor cells express several of these marker. In some embodiment, the hematopoietic progenitor cells of the erythroid lineage have the cell surface marker characteristic of the erythroid lineage: CD71 and Ter119.

In certain embodiments, the iRNA is administered in an amount such that it improves a hemoglobin deficiency. Assays for evaluating of the effects of the iRNA, and optimizing delivery of iRNA, to modulating bone marrow erythropoiesis and extramedullary erythropoiesis are describes in the Examples below. In certain embodiments, the iRNA is administered such that it targets erythrocyte or erythroid progenitors. Assays for evaluating such effects can include evaluating fetal (embryonic)/adult Hb ratio in bone marrow using an iRNA against KLF1 and/or BCL11a. Additional assays can include the evaluation of iRNA delivery to extramedullary sites. In such assays, the fetal (embryonic)/adult Hb ratio in the liver and spleen can be measured in anemia and/or SCD models.

The invention further relates to the use of an iRNA or a pharmaceutical composition thereof, e.g., for treating a hemoglobinopathy, in combination with other pharmaceuticals and/or other therapeutic methods, e.g., with known pharmaceuticals and/or known therapeutic methods, such as, for example, those which are currently employed for treating these disorders. In one embodiment, the iRNA or pharmaceutical composition thereof can be administered in conjunction with one or more inducers of fetal hemoglobin (e.g., 5-azacytidine, hydroxyurea, sodium phenylbuturate, etc) (see e.g., Perrine et al., *Hematology Am Soc. Hematol. Educ. Program* 2005:38-44), which is hereby incorporated by reference in its entirety).

Exemplary agents and treatment modalities that can be used in combination with an iRNA agent that targets BCL11A or KLF1, or a combination thereof, include one or more of: hydroxyuria (hydroxycarbamide), erythropoietin, 5-azacytidine, butyric acid and analogs thereof (e.g., γ-aminobutyric acid, phenylbutyrate, valproic acid), phenylacetic and phenylalkyl acids analogs, iron chelators (e.g., to bind excess iron), antibiotics and antivirals, blood transfusions (e.g., red blood cell transfusion) and bone marrow transplants (e.g., stem cell/bone marrow transplants), or a combination thereof.

For example, the iRNAs (or pharmaceutical composition thereof) featured in the invention can be used in combination with hydroxyuria and/or erythropoietin to treat sickle-cell disease. Hydroxyuria and erythropoietin can stimulate the bone marrow to produce more fetal hemoglobin, HbF. HbF can transport oxygen but does not polymerize, so the red blood cells cannot sickle. Thus, these drugs can prevent vaso-occlusive crises.

γ-aminobutyric acid can act as a fetal hemoglobin inducer (Perrine et al., Biochem Biophys Res Commun. 148(2):694-700 (1987)). Subsequent studies showed that butyrate stimulated globin production in adult baboons (Constantoulakis et al., Blood. December; 72(6): 1961-7 (1988)), and it induced γ-globin in erythroid progenitors in adult animals or patients with sickle cell anemia (Perrine et al., Blood. 74(1):454-9 (1989)). Derivatives of short chain fatty acids such as phenylbutyrate (Dover et al., Br J Haematol. 88(3):555-61 (1994)) and valproic acid (Liakopoulou et al., 1: Blood. 186(8):3227-35 (1995)) also have been shown to induce HbF in vivo. Given the large number of short chain fatty acid analogs or derivatives of this family, there are a number of potential compounds of this family more potent than butyrate. Phenylacetic and phenylalkyl acids (Torkelson et al., Blood Cells MoI Dis. 22(2): 150-8. (1996)), which were discovered during subsequent studies, were considered potential HbF inducers as they belonged to this family of compounds.

Identifying natural regulators of HbF induction and production could provide a means to devise therapeutic interventions that overcome the various drawbacks of therapies currently available. Recent genome-wide association studies have yielded insights into the genetic basis of numerous complex diseases and traits (McCarthy et al., Nat Rev Genet 9, 356 (2008) and Manolio et. al. J Clin Invest 118, 1590 (2008)). Two genome-wide association studies have identified three major loci containing a set of five common single nucleotide polymorphisms (SNPs) that account for –20% of the variation in HbF levels (Lettre et al., Proc Natl Acad Sci USA (2008); Uda et al., Proc Natl Acad Sci USA 105, 1620 (2008); Menzel et al., Nat Genet 39, 1197 (2007)). Moreover, several of these variants appear to predict the clinical severity of sickle cell disease (Lettre et al., Proc Natl Acad Sci USA (2008)) and at least one of these SNPs may also affect clinical outcome in β-thalassemia (Uda et al., Proc Natl Acad Sci USA 105, 1620 (2008)). The SNP with the largest effect size, explaining over 10% of the variation in HbF, is located in the second intron of a gene on chromosome 2, BCL11A. Whereas BCL11A has been investigated for its role in lymphocyte development (Liu et al., Nat Immunol 4, 525 (2003) and Liu et al., MoI Cancer 5, 18 (2006)), its role in red blood cell production or globin gene regulation has not been previously assessed. The results of recent genetic association studies provide candidate genes to interrogate for their involvement in control of the γ-globin genes, such as BCL11A and KLF1.

Efficacy of treatment or amelioration of disease can be assessed, for example by detection of amelioration of the symptoms of the hemoglobinopathy, slow the course of hemoglobinopathy disease progression, slow or inhibit a symptom of a hemoglobinopathy, slow or inhibit the establishment of secondary symptoms of a hemoglobinopathy or inhibit the development of a secondary symptom of a hemoglobinopathy. The effective amount for the treatment of the hemoglobinopathy depends on the type of hemoglobinopathy to be treated, the severity of the symptoms, the subject being treated, the age and general condition of the subject, the mode of administration and so forth. For any given case, an appropriate "effective amount" can be determined by one of ordinary skill in the art using routine experimentation. It is well within the ability of one skilled in the art to monitor efficacy of treatment or prevention by measuring any one of such parameters, or any combination of parameters. In connection with the administration of an iRNA targeting KLF1 or BCL11A or pharmaceutical composition thereof, "effective against" a hemoglobinopathy indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of cancer.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, e.g., at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

The iRNA and an additional therapeutic agent can be administered in combination in the same composition, e.g., parenterally, or the additional therapeutic agent can be administered as part of a separate composition or by another method described herein.

Patients can be administered a therapeutic amount of iRNA, such as 0.5 mg/kg, 1.0 mg/kg, 1.5 mg/kg, 2.0 mg/kg, or 2.5 mg/kg dsRNA. The iRNA can be administered by intravenous infusion over a period of time, such as over a 5 minute, 10 minute, 15 minute, 20 minute, or 25 minute period. The administration is repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the iRNA can reduce BCL11A or KLF1 levels, e.g., in a cell, tissue, blood, urine or other compartment of the patient by at least 10%, at least 15%, at least 20%, at least 25%, at least 30%, at least 40%, at least 50%, at least 60%, at least 70%, at least 80% or at least 90% or more.

Before administration of a full dose of the iRNA, patients can be administered a smaller dose, such as a 5% infusion reaction, and monitored for adverse effects, such as an allergic reaction, or for elevated lipid levels or blood pressure. In another example, the patient can be monitored for unwanted effects.

Methods for Modulating Expression of a KLF1 or BCL11a Gene

In yet another aspect, the invention provides a method for modulating (e.g., inhibiting or activating) the expression of a KLF1 or BCL11A gene in a mammal.

In one embodiment, the method includes administering a composition described herein, e.g., a composition comprising an iRNA that targets KLF1 or BCL11A, to the mammal such that expression of the target KLF1 or BCL11A gene is decreased, such as for an extended duration, e.g., at least two, three, four days or more, e.g., one week, two weeks, three weeks, or four weeks or longer.

In another embodiment, the method includes administering a composition as described herein to a mammal such that expression of the target KLF1 or BCL11A gene is increased by e.g., at least 10% compared to an untreated animal. In some embodiments, the activation of KLF1 or BCL11A occurs over an extended duration, e.g., at least two, three, four days or more, e.g., one week, two weeks, three weeks, four weeks, or more. Without wishing to be bound by theory, an iRNA can activate KLF1 or BCL11A expression by stabilizing the KLF1 or BCL11A mRNA transcript, interacting with a promoter in the genome, and/or inhibiting an inhibitor of KLF1 or BCL11A expression.

The iRNAs useful for the methods and compositions featured in the invention specifically target RNAs (primary or processed) of the KLF1 or BCL11A gene. Compositions and methods for inhibiting the expression of these KLF1 or BCL11A genes using iRNAs can be prepared and performed as described elsewhere herein.

In one embodiment, the method includes administering a composition containing an iRNA, where the iRNA includes a nucleotide sequence that is complementary to at least a part of an RNA transcript of the KLF1 or BCL11A gene of the mammal to be treated. When the organism to be treated is a mammal such as a human, the composition may be administered by any means known in the art including, but not limited to oral, intraperitoneal, or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration. In certain embodiments, the compositions are administered by intravenous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1 iRNA Synthesis

Source of Reagents

Where the source of a reagent is not specifically given herein, such reagent may be obtained from any supplier of reagents for molecular biology at a quality/purity standard for application in molecular biology.

Oligonucleotide Synthesis.

All oligonucleotides are synthesized on an AKTAoligopilot synthesizer. Commercially available controlled pore glass solid support (dT-CPG, 500 Å, Prime Synthesis) and RNA phosphoramidites with standard protecting groups, 5'-O-dimethoxytrityl N6-benzoyl-2'-t-butyldimethylsilyl-adenosine-3'-O—N,N'-diisopropyl-2-cyanoethylphosphoramidite, 5'-O-dimethoxytrityl-N4-acetyl-2'-t-butyldimethylsilyl-cytidine-3'-O—N,N'-diisopropyl-2-cyanoethylphosphoramidite, 5'-O-dimethoxytrityl-N2-isobutryl-2'-t-butyldimethylsilyl-guanosine-3'-O—N,N'-diisopropyl-2-cyanoethylphosphoramidite, and 5'-O-dimethoxytrityl-2'-t-butyldimethylsilyl-uridine-3'-O—N,N'-diisopropyl-2-cyanoethylphosphoramidite (Pierce Nucleic Acids Technologies) were used for the oligonucleotide synthesis. The 2'-F phosphoramidites, 5'-O-dimethoxytrityl-N4-acetyl-2'-fluoro-cytidine-3'-O—N,N'-diisopropyl-2-cyanoethyl-phosphoramidite and 5'-O-dimethoxytrityl-2'-fluoro-uridine-3'-O—N,N'-diisopropyl-2-cyanoethyl-phosphoramidite are purchased from (Promega). All phosphoramidites are used at a concentration of 0.2M in acetonitrile ($CH_3CN$) except for guanosine which is used at 0.2M concentration in 10% THF/ANC (v/v). Coupling/recycling time of 16 minutes is used. The activator is 5-ethyl thiotetrazole (0.75M, American International Chemicals); for the PO-oxidation iodine/water/pyridine is used and for the PS-oxidation PADS (2%) in 2,6-lutidine/ACN (1:1 v/v) is used.

3'-ligand conjugated strands are synthesized using solid support containing the corresponding ligand. For example, the introduction of cholesterol unit in the sequence is performed from a hydroxyprolinol-cholesterol phosphoramidite. Cholesterol is tethered to trans-4-hydroxyprolinol via a 6-aminohexanoate linkage to obtain a hydroxyprolinol-cholesterol moiety. 5'-end Cy-3 and Cy-5.5 (fluorophore) labeled iRNAs are synthesized from the corresponding Quasar-570 (Cy-3) phosphoramidite are purchased from Biosearch Technologies. Conjugation of ligands to 5'-end and or internal position is achieved by using appropriately protected ligand-phosphoramidite building block. An extended 15 min coupling of 0.1 M solution of phosphoramidite in anhydrous $CH_3CN$ in the presence of 5-(ethylthio)-1H-tetrazole activator to a solid-support-bound oligonucleotide. Oxidation of the internucleotide phosphite to the phosphate is carried out using standard iodine-water as reported (1) or by treatment with tert-butyl hydroperoxide/acetonitrile/water (10:87:3) with 10 min oxidation wait time conjugated oligonucleotide. Phosphorothioate is introduced by the oxidation of phosphite to phosphorothioate by using a sulfur transfer reagent such as DDTT (purchased from AM Chemicals), PADS and or Beaucage reagent. The cholesterol phosphoramidite is synthesized in house and used at a concentration of 0.1 M in dichloromethane. Coupling time for the cholesterol phosphoramidite is 16 minutes.

Deprotection I (Nucleobase Deprotection)

After completion of synthesis, the support is transferred to a 100 mL glass bottle (VWR). The oligonucleotide is cleaved from the support with simultaneous deprotection of base and phosphate groups with 80 mL of a mixture of ethanolic ammonia [ammonia:ethanol (3:1)] for 6.5 h at 55° C. The bottle is cooled briefly on ice and then the ethanolic ammonia mixture is filtered into a new 250-mL bottle. The CPG is washed with 2×40 mL portions of ethanol/water (1:1 v/v). The volume of the mixture is then reduced to ~30 mL by roto-vap. The mixture is then frozen on dry ice and dried under vacuum on a speed vac.

Deprotection II (Removal of 2'-TBDMS Group)

The dried residue is resuspended in 26 mL of triethylamine, triethylamine trihydrofluoride (TEA.3HF) or pyridine-HF and DMSO (3:4:6) and heated at 60° C. for 90 minutes to remove the tert-butyldimethylsilyl (TBDMS) groups at the 2' position. The reaction is then quenched with 50 mL of 20 mM sodium acetate and the pH is adjusted to 6.5. Oligonucleotide is stored in a freezer until purification.

Analysis

The oligonucleotides are analyzed by high-performance liquid chromatography (HPLC) prior to purification and selection of buffer and column depends on nature of the sequence and or conjugated ligand.

HPLC Purification

The ligand-conjugated oligonucleotides are purified by reverse-phase preparative HPLC. The unconjugated oligonucleotides are purified by anion-exchange HPLC on a TSK gel column packed in house. The buffers are 20 mM sodium phosphate (pH 8.5) in 10% $CH_3CN$ (buffer A) and 20 mM sodium phosphate (pH 8.5) in 10% $CH_3CN$, 1M NaBr (buffer B). Fractions containing full-length oligonucleotides are pooled, desalted, and lyophilized. Approximately 0.15 OD of desalted oligonucleotidess are diluted in water to 150 µL and then pipetted into special vials for CGE and LC/MS analysis. Compounds are then analyzed by LC-ESMS and CGE.

iRNA Preparation

For the general preparation of iRNA, equimolar amounts of sense and antisense strand are heated in 1×PBS at 95° C. for 5 min and slowly cooled to room temperature. Integrity of the duplex is confirmed by HPLC analysis.

Nucleic acid sequences are represented below using standard nomenclature, and specifically the abbreviations of Table 1.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | adenosine |
| C | cytidine |
| G | guanosine |
| T | thymidine |
| U | uridine |
| N | any nucleotide (G, A, C, T or U) |
| a | 2'-O-methyladenosine |
| c | 2'-O-methylcytidine |
| g | 2'-O-methylguanosine |
| u | 2'-O-methyluridine |
| dT | 2'-deoxythymidine |
| s | phosphorothioate linkage |

Example 2

KLF1 or BCL11A siRNA Design and Synthesis

Transcripts

Oligonucleotide design for KLF1 siRNAs was carried out to identify siRNAs targeting the gene encoding the human "KLF1 molecule" and the orthologous sequences from mice (*Mus musculus*). The design process used the KLF1 transcripts NM_006563.3, SEQ ID NO: 1 (human) or NM_010635.2 (GI:225543579), SEQ ID NO: 2 (mouse). All sequences were obtained from the NCBI Refseq collection.

Oligonucleotide design for BCL11A siRNAs was carried out to identify siRNAs targeting the gene encoding the human "BCL11A molecule" (including variants 1, 2 and 3) and the orthologous sequences from mice (*Mus musculus*). The design process used the human BCL11A variant 1 mRNA (Ref. Seq. NM_022893.3 (GI:148539885), SEQ ID NO: 3); human BCL11A variant 2 mRNA (Ref. Seq. NM_018014.3 (GI:148539884), SEQ ID NO: 4); human BCL11A variant 3 mRNA (Ref. Seq. NM_018014.3 (GI:20336312), SEQ ID NO: 5); mouse BCL11A variant 1 mRNA (Ref. Seq. NM_016707.3 (GI:226530130), SEQ ID NO: 6); mouse BCL11A variant 2 mRNA (Ref. Seq. NM_016707.3 (GI:226530130), SEQ ID NO: 7); and mouse BCL11A variant 3 mRNA (Ref. Seq. NM_001159290.1 (GI:226530196), SEQ ID NO: 8).

Sense and antisense human and mouse KLF1 or human BCL11A (variants 1, 2 and 3) derived siRNA oligos were synthesized. The oligos are presented in Table 2A-1, 2A-2, 2A-3, Table 2B and 2C.

siRNA Design and Specificity Prediction

The specificity of the 19mer oligo sets was predicted from each sequence. The KLF1 or BCL11A siRNAs were used in a comprehensive search against their respective human, or mouse and rat transcriptomes (defined as the set of NM_ and XM_ records within the NCBI Refseq set) using the FASTA algorithm. The Python script 'offtargetFasta.py' was then used to parse the alignments and generate a score based on the position and number of mismatches between the siRNA and any potential 'off-target' transcript. The off-target score is weighted to emphasize differences in the 'seed' region of siRNAs, in positions 2-9 from the 5' end of the molecule. The off-target score is calculated as follows: mismatches between the oligo and the transcript are given penalties. A mismatch in the seed region in positions 2-9 of the oligo is given a penalty of 2.8; mismatches in the putative cleavage sites 10 and 11 are given a penalty of 1.2, and all other mismatches a penalty of 1. The off-target score for each oligo-transcript pair is then calculated by summing the mismatch penalties. The lowest off-target score from all the oligo-transcript pairs is then determined and used in subsequent sorting of oligos. Both siRNAs strands were assigned to a category of specificity according to the calculated scores: a score above 3 qualifies as highly specific, equal to 3 as specific and between 2.2 and 2.8 as moderate specific. In picking which oligos to synthesize, we sorted from high to low by the off-target score of the antisense strand and took the best (lowest off-target score) oligo pairs.

Synthesis of KLF1 or BCL11A Sequences

KLF1 or BCL11A sequences can be synthesized on a MerMade 192 synthesizer at 1 µmol scale.

For all the sequences in the list, 'endolight' chemistry was applied as detailed below.

- All pyrimidines (cytosine and uridine) in the sense strand contained 2'-O-Methyl bases (2' O-Methyl C and 2'-O-Methyl U)
- In the antisense strand, pyrimidines adjacent to (towards 5' position) ribo A nucleoside were replaced with their corresponding 2-O-Methyl nucleosides
- A two base dTsdT extension at 3' end of both sense and anti sense sequences was introduced
- The sequence file was converted to a text file to make it compatible for loading in the MerMade 192 synthesis software Synthesis, Cleavage and Deprotection:

The synthesis of KLF1 or BCL11A sequences can use solid supported oligonucleotide synthesis using phosphoramidite chemistry.

The synthesis of the above sequences can be performed at 1 um scale in 96 well plates. The amidite solutions are prepared at 0.1M concentration and ethyl thio tetrazole (0.6M in Acetonitrile) is used as activator.

The synthesized sequences can be cleaved and deprotected in 96 well plates, using methylamine in the first step and fluoride reagent in the second step. The crude sequences can be precipitated using acetone:ethanol (80:20) mix and the pellet can be re-suspended in 0.02M sodium acetate buffer. Samples from each sequence can be analyzed by LC-MS to confirm the identity, UV for quantification and a selected set of samples by IEX chromatography to determine purity.

Purification and Desalting:

KLF1 or BCL11A sequences can be purified on AKTA explorer purification system using Source 15Q column. A column temperature of 65C is maintained during purification. Sample injection and collection is performed in 96 well (1.8 mL-deep well) plates. A single peak corresponding to the full length sequence is collected in the eluent. The purified sequences are desalted on a Sephadex G25 column using AKTA purifier. The desalted KLF1 or BCL11A sequences are analyzed for concentration (by UV measurement at A260) and purity (by ion exchange HPLC). The single strands are then submitted for annealing.

In vitro Screening:

Cell Culture and Transfections:

RKO or Hep3B (ATCC, Manassas, Va.) cells are grown to near confluence at 37° C. in an atmosphere of 5% $CO_2$ in McCoy's or EMEM (respectively) (ATCC) supplemented with 10% FBS, streptomycin, and glutamine (ATCC) before being released from the plate by trypsinization. Reverse transfection is carried out by adding 5 µl of Opti-MEM to 5 µl of siRNA duplexes per well into a 96-well plate along with 10 µl of Opti-MEM plus 0.2 µl of Lipofectamine RNAiMax per well (Invitrogen, Carlsbad Calif. cat #13778-150) and incubated at room temperature for 15 minutes. 80 µl of complete growth media without antibiotic containing $2.0 \times 10^4$ Hela cells are then added. Cells are incubated for 24 hours prior to RNA purification. Experiments were performed at 0.1 or 10 nM final duplex concentration for single dose screens with each of the BCL11A or KLF1 duplexes.

Total RNA Isolation Using MagMAX-96 Total RNA Isolation Kit (Applied Biosystem, Forer City Calif., Part #: AM1830):

Cells are harvested and lysed in 140 µl of Lysis/Binding Solution then mixed for 1 minute at 850 rpm using and Eppendorf Thermomixer (the mixing speed was the same throughout the process). Twenty micro liters of magnetic beads and Lysis/Binding Enhancer mixture were added into cell-lysate and mixed for 5 minutes. Magnetic beads are captured using magnetic stand and the supernatant was removed without disturbing the beads. After removing supernatant, magnetic beads are washed with Wash Solution 1 (isopropanol added) and mixed for 1 minute. Beads are capture again and supernatant removed. Beads are then washed with 150 µl Wash Solution 2 (Ethanol added), captured and supernatant was removed. 50 ul of DNase mixture (MagMax turbo DNase Buffer and Turbo DNase) is then added to the beads and they are mixed for 10 to 15 minutes. After mixing, 100 µl of RNA Rebinding Solution is added and mixed for 3 minutes. Supernatant was removed and magnetic beads are washed again with 150 µl Wash Solution 2 and mixed for 1 minute and supernatant is removed completely. The magnetic beads were mixed for 2 minutes to dry before RNA was eluted with 50 µl of water.

cDNA Synthesis Using ABI High Capacity cDNA Reverse Transcription Kit (Applied Biosystems, Foster City, Calif., Cat #4368813):

A master mix of 2 µl 10× Buffer, 0.8 µl 25× dNTPs, 2 µl Random primers, 1 µl Reverse Transcriptase, 1 µl RNase inhibitor and 3.2 µl of H2O per reaction were added into 10 µl total RNA. cDNA is generated using a Bio-Rad C-1000 or S-1000 thermal cycler (Hercules, Calif.) through the following steps: 25° C. 10 min, 37° C. 120 min, 85° C. 5 sec, 4° C. hold.

Real Time PCR:

2 µl of cDNA were added to a master mix containing 0.5 µl GAPDH TaqMan Probe (Applied Biosystems Cat #4326317E), 0.5 µl BCL11A or a KLF1 TaqMan probe (Applied Biosystems cat #Hs01125301_m1) and 5 µl Roche Probes Master Mix (Roche Cat #04887301001) in a total of 10 µl per well in a LightCycler 480 384 well plate (Roche cat #0472974001). Real time PCR was done in a LightCycler 480 Real Time PCR machine (Roche). Each duplex was tested in at least two independent transfections. For those siRNAs that were tested in RKO and Hep3B cells, at least three transfections are performed. Each transfection is assayed by qPCR in duplicate.

Real time data were analyzed using the ΔΔCt method. Each sample was normalized to GAPDH expression and knockdown was assessed relative to cells transfected with the non-targeting duplex AD-1955. IC50s were defined using a 4 parameter fit model in XLfit.

TABLE 2A-1

Human KLF1 Single Strands and Duplex Sequences

| SEQ ID NO: (sense) | Position of 5' base on transcript NM_006563.3 | sense (5'-3') | antisense (5'-3') | SEQ ID NO: (antisense) |
|---|---|---|---|---|
| 9 | 149 | AGUGGUGGCGCUCCGAAGA | UCUUCGGAGCGCCACCACU | 10 |
| 11 | 210 | GCCCCUCCACGUGAAGUCU | AGACUUCACGUGGAGGGGC | 12 |
| 13 | 393 | CGAGACUCUGGGCGCAUAU | AUAUGCGCCCAGAGUCUCG | 14 |
| 15 | 440 | UUUUGGGUUCGGAGGAUCA | UGAUCCUCCGAACCCAAAA | 16 |
| 17 | 448 | UCGGAGGAUCACUCGGGUU | AACCCGAGUGAUCCUCCGA | 18 |
| 19 | 554 | UGGCGCUGCAACCGGUGUA | UACACCGGUUGCAGCGCCA | 20 |
| 21 | 761 | CCUCCUUCCUGAGUUGUUU | AAACAACUCAGGAAGGAGG | 22 |
| 23 | 856 | AAGCGAGGCCGACGUUCGU | ACGAACGUCGGCCUCGCUU | 24 |
| 25 | 1088 | AGCUCUGCCCACGUGCUUU | AAAGCACGUGGGCAGAGCU | 26 |
| 27 | 1158 | GCCCUGGCACUUGGACUCU | AGAGUCCAAGUGCCAGGGC | 28 |
| 29 | 1162 | UGGCACUUGGACUCUCCUA | UAGGAGAGUCCAAGUGCCA | 30 |
| 31 | 1174 | UCUCCUAGUGACUGGGGAU | AUCCCCAGUCACUAGGAGA | 32 |
| 33 | 1251 | UGGUUUUCCCACGAAUGGA | UCCAUUCGUGGGAAAACCA | 34 |

TABLE 2A-1 -continued

Human KLF1 Single Strands and Duplex Sequences

| SEQ ID NO: (sense) | Position of 5' base on transcript NM_006563.3 | sense (5'-3') | antisense (5'-3') | SEQ ID NO: (antisense) |
|---|---|---|---|---|
| 35 | 1255 | UUUCCCACGAAUGGACCCU | AGGGUCCAUUCGUGGGAAA | 36 |
| 37 | 1277 | CUGGACUCGCGUUCCCAAA | UUUGGGAACGCGAGUCCAG | 38 |
| 39 | 1292 | CAAAGAUCCACCCAAAUAU | AUAUUUGGGUGGAUCUUUG | 40 |
| 41 | 1308 | UAUCAAACACGGACCCAUA | UAUGGGUCCGUGUUUGAUA | 41 |
| 43 | 1345 | UCUUACGGAAAAUCCGACA | UGUCGGAUUUUCCGUAAGA | 44 |
| 45 | 1346 | CUUACGGAAAAUCCGACAA | UUGUCGGAUUUUCCGUAAG | 46 |
| 47 | 1350 | CGGAAAAUCCGACAAGCCU | AGGCUUGUCGGAUUUUCCG | 48 |
| 49 | 1351 | GGAAAAUCCGACAAGCCUU | AAGGCUUGUCGGAUUUUCC | 50 |
| 51 | 1390 | GAGAUGUCCAAACUGUCGU | ACGACAGUUUGGACAUCUC | 52 |
| 53 | 1393 | AUGUCCAAACUGUCGUGCA | UGCACGACAGUUUGGACAU | 54 |
| 55 | 1394 | UGUCCAAACUGUCGUGCAA | UUGCACGACAGUUUGGACA | 56 |
| 57 | 1395 | GUCCAAACUGUCGUGCAAA | UUUGCACGACAGUUUGGAC | 58 |
| 59 | 1399 | AAACUGUCGUGCAAACCCA | UGGGUUUGCACGACAGUUU | 60 |
| 61 | 1407 | GUGCAAACCCAGUGAGACA | UGUCUCACUGGGUUUGCAC | 62 |
| 63 | 1419 | UGAGACAGACCGCCAAAUA | UAUUUGGCGGUCUGUCUCA | 64 |
| 65 | 1420 | GAGACAGACCGCCAAAUAA | UUAUUUGGCGGUCUGUCUC | 66 |
| 67 | 1421 | AGACAGACCGCCAAAUAAA | UUUAUUUGGCGGUCUGUCU | 68 |
| 69 | 1425 | AGACCGCCAAAUAAACGGA | UCCGUUUAUUUGGCGGUCU | 70 |
| 71 | 1429 | CGCCAAAUAAACGGACUCA | UGAGUCCGUUUAUUUGGCG | 72 |
| 73 | 1434 | AAUAAACGGACUCAGUGGA | UCCACUGAGUCCGUUUAUU | 74 |
| 75 | 1442 | GACUCAGUGGACACUCAGA | UCUGAGUGUCCACUGAGUC | 76 |
| 77 | 1521 | CUGGGUCUAGAAAGCGGCU | AGCCGCUUUCUAGACCCAG | 78 |
| 79 | 1537 | GCUCCUGAAGGUCCCUUAU | AUAAGGGACCUUCAGGAGC | 80 |
| 81 | 1538 | CUCCUGAAGGUCCCUUAUU | AAUAAGGGACCUUCAGGAG | 82 |
| 83 | 1540 | CCUGAAGGUCCCUUAUUGU | ACAAUAAGGGACCUUCAGG | 84 |
| 85 | 1548 | UCCCUUAUUGUGGCUGAUA | UAUCAGCCACAAUAAGGGA | 86 |
| 87 | 1549 | CCCUUAUUGUGGCUGAUAU | AUAUCAGCCACAAUAAGGG | 88 |
| 89 | 1550 | CCUUAUUGUGGCUGAUAUU | AAUAUCAGCCACAAUAAGG | 90 |
| 91 | 1556 | UGUGGCUGAUAUUAACUGU | ACAGUUAAUAUCAGCCACA | 92 |
| 93 | 1575 | CAAUGGUUAUGGGUCCUAU | AUAGGACCCAUAACCAUUG | 94 |
| 95 | 1576 | AAUGGUUAUGGGUCCUAUA | UAUAGGACCCAUAACCAUU | 96 |
| 97 | 1577 | AUGGUUAUGGGUCCUAUAA | UUAUAGGACCCAUAACCAU | 98 |
| 99 | 1578 | UGGUUAUGGGUCCUAUAAA | UUUAUAGGACCCAUAACCA | 100 |
| 101 | 1579 | GGUUAUGGGUCCUAUAAAA | UUUUAUAGGACCCAUAACC | 102 |

TABLE 2A-2

Human KLF1 Unmodified siRNA Duplex Sequences

| Duplex ID | SEQ ID NO.: (sense) | Sense sequence | Position in NM_006563.3 | Antisense Sequence | SEQ ID NO.: (antisense) |
|---|---|---|---|---|---|
| AD-46099.1 | 59 | AAACUGUCGUGCAAACCCA | 1399-1417 | UGGGUUUGCACGACAGUUU | 60 |
| AD-46132.1 | 23 | AAGCGAGGCCGACGUUCGU | 856-874 | ACGAACGUCGGCCUCGCUU | 24 |
| AD-46094.1 | 73 | AAUAAACGGACUCAGUGGA | 1434-1452 | UCCACUGAGUCCGUUUAUU | 74 |
| AD-46113.1 | 95 | AAUGGUUAUGGGUCCUAUA | 1576-1594 | UAUAGGACCCAUAACCAUU | 96 |
| AD-46123.1 | 67 | AGACAGACCGCCAAAUAAA | 1421-1439 | UUUAUUUGGCGGUCUGUCU | 68 |
| AD-46129.1 | 69 | AGACCGCCAAAUAAACGGA | 1425-1443 | UCCGUUUAUUUGGCGGUCU | 70 |
| AD-46091.1 | 25 | AGCUCUGCCCACGUGCUUU | 1088-1106 | AAAGCACGUGGGCAGAGCU | 26 |
| AD-46090.1 | 9 | AGUGGUGGCGCUCCGAAGA | 149-167 | UCUUCGGAGCGCCACCACU | 10 |
| AD-46119.1 | 97 | AUGGUUAUGGGUCCUAUAA | 1577-1595 | UUAUAGGACCCAUAACCAU | 98 |
| AD-46128.1 | 53 | AUGUCCAAACUGUCGUGCA | 1393-1411 | UGCACGACAGUUUGGACAU | 54 |
| AD-46133.1 | 39 | CAAAGAUCCACCCAAAUAU | 1292-1310 | AUAUUUGGGUGGAUCUUUG | 40 |
| AD-46107.1 | 93 | CAAUGGUUAUGGGUCCUAU | 1575-1593 | AUAGGACCCAUAACCAUUG | 94 |
| AD-46136.1 | 87 | CCCUUAUUGUGGCUGAUAU | 1549-1567 | AUAUCAGCCACAAUAAGGG | 88 |
| AD-46126.1 | 21 | CCUCCUUCCUGAGUUGUUU | 761-779 | AAACAACUCAGGAAGGAGG | 22 |
| AD-46124.1 | 83 | CCUGAAGGUCCCUUAUUGU | 1540-1558 | ACAAUAAGGGACCUUCAGG | 84 |
| AD-46095.1 | 89 | CCUUAUUGUGGCUGAUAUU | 1550-1568 | AAUAUCAGCCACAAUAAGG | 90 |
| AD-46095.3 | 89 | CCUUAUUGUGGCUGAUAUU | 1550-1568 | AAUAUCAGCCACAAUAAGG | 90 |
| AD-46102.1 | 13 | CGAGACUCUGGGCGCAUAU | 393-411 | AUAUGCGCCCAGAGUCUCG | 14 |
| AD-46135.1 | 71 | CGCCAAAUAAACGGACUCA | 1429-1447 | UGAGUCCGUUUAUUUGGCG | 72 |
| AD-46110.1 | 47 | CGGAAAAUCCGACAAGCCU | 1350-1368 | AGGCUUGUCGGAUUUUCCG | 48 |
| AD-46118.1 | 81 | CUCCUGAAGGUCCCUUAUU | 1538-1556 | AAUAAGGGACCUUCAGGAG | 82 |
| AD-46127.1 | 37 | CUGGACUCGCGUUCCCAAA | 1277-1295 | UUUGGGAACGCGAGUCCAG | 38 |
| AD-46106.1 | 77 | CUGGGUCUAGAAAGCGGCU | 1521-1539 | AGCCGCUUUCUAGACCCAG | 78 |
| AD-46104.1 | 45 | CUUACGGAAAAUCCGACAA | 1346-1364 | UUGUCGGAUUUUCCGUAAG | 46 |
| AD-46100.1 | 75 | GACUCAGUGGACACUCAGA | 1442-1460 | UCUGAGUGUCCACUGAGUC | 76 |
| AD-46117.1 | 65 | GAGACAGACCGCCAAAUAA | 1420-1438 | UUAUUUGGCGGUCUGUCUC | 66 |
| AD-46122.1 | 51 | GAGAUGUCCAAACUGUCGU | 1390-1408 | ACGACAGUUUGGACAUCUC | 52 |
| AD-46096.1 | 11 | GCCCUCCACGUGAAGUCU | 210-228 | AGACUUCACGUGGAGGGGC | 12 |
| AD-46097.1 | 27 | GCCCUGGCACUUGGACUCU | 1158-1176 | AGAGUCCAAGUGCCAGGGC | 28 |
| AD-46112.1 | 79 | GCUCCUGAAGGUCCCUUAU | 1537-1555 | AUAAGGGACCUUCAGGAGC | 80 |
| AD-46116.1 | 49 | GGAAAAUCCGACAAGCCUU | 1351-1369 | AAGGCUUGUCGGAUUUUCC | 50 |
| AD-46093.1 | 57 | GUCCAAACUGUCGUGCAAA | 1395-1413 | UUUGCACGACAGUUUGGAC | 58 |
| AD-46105.1 | 61 | GUGCAAACCCAGUGAGACA | 1407-1425 | UGUCUCACUGGGUUUGCAC | 62 |
| AD-46092.1 | 41 | UAUCAAACACGGACCCAUA | 1308-1326 | UAUGGGUCCGUGUUUGAUA | 41 |
| AD-46130.1 | 85 | UCCCUUAUUGUGGCUGAUA | 1548-1566 | UAUCAGCCACAAUAAGGGA | 86 |
| AD-53284.1 | 85 | UCCCUUAUUGUGGCUGAUAUU | 1546-1568 | AAUAUCAGCCACAAUAAGGGACC | 86 |
| AD-53290.1 | 85 | UCCCUUAUUGUGGCUGAUAUU | 1546-1568 | AAUAUCAGCCACAAUAAGGGACC | 86 |

TABLE 2A-2 -continued

Human KLF1 Unmodified siRNA Duplex Sequences

| Duplex ID | SEQ ID NO.: (sense) | Sense sequence | Position in NM_006563.3 | Antisense Sequence | SEQ ID NO.: (antisense) |
|---|---|---|---|---|---|
| AD-53295.1 | 85 | UCCCUUAUUGUGGCUGAUAUU | 1546-1568 | AAUAUCAGCCACAAUAAGGGACC | 86 |
| AD-53301.1 | 85 | UCCCUUAUUGUGGCUGAUAUU | 1546-1568 | AAUAUCAGCCACAAUAAGGGACC | 86 |
| AD-53307.1 | 85 | UCCCUUAUUGUGGCUGAUAUU | 1546-1568 | AAUAUCAGCCACAAUAAGGGACC | 86 |
| AD-53308.1 | 85 | UCCCUUAUUGUGGCUGAUAUU | 1546-1568 | AAUAUCAGCCACAAUAAGGGACC | 86 |
| AD-53309.1 | 85 | UCCCUUAUUGUGGCUGAUAUU | 1546-1568 | AAUAUCAGCCACAAUAAGGGACC | 86 |
| AD-53310.1 | 85 | UCCCUUAUUGUGGCUGAUAUU | 1546-1568 | AAUAUCAGCCACAAUAAGGGACC | 86 |
| AD-53311.1 | 85 | UCCCUUAUUGUGGCUGAUAUU | 1546-1568 | AAUAUCAGCCACAAUAAGGGACC | 86 |
| AD-53312.1 | 85 | UCCCUUAUUGUGGCUGAUAUU | 1546-1568 | AAUAUCAGCCACAAUAAGGGACC | 86 |
| AD-53313.1 | 85 | UCCCUUAUUGUGGCUGAUAUU | 1546-1568 | AAUAUCAGCCACAAUAAGGGACC | 86 |
| AD-53314.1 | 85 | UCCCUUAUUGUGGCUGAUAUU | 1546-1568 | AAUAUCAGCCACAAUAAGGGACC | 86 |
| AD-53315.1 | 85 | UCCCUUAUUGUGGCUGAUAUU | 1546-1568 | AAUAUCAGCCACAAUAAGGGACC | 86 |
| AD-53316.1 | 85 | UCCCUUAUUGUGGCUGAUAUU | 1546-1568 | AAUAUCAGCCACAAUAAGGGACC | 86 |
| AD-53317.1 | 85 | UCCCUUAUUGUGGCUGAUAUU | 1546-1568 | AAUAUCAGCCACAAUAAGGGACC | 86 |
| AD-53318.1 | 85 | UCCCUUAUUGUGGCUGAUAUU | 1546-1568 | AAUAUCAGCCACAAUAAGGGACC | 86 |
| AD-53319.1 | 85 | UCCCUUAUUGUGGCUGAUAUU | 1546-1568 | AAUAUCAGCCACAAUAAGGGACC | 86 |
| AD-53320.1 | 85 | UCCCUUAUUGUGGCUGAUAUU | 1546-1568 | AAUAUCAGCCACAAUAAGGGACC | 86 |
| AD-53321.1 | 85 | UCCCUUAUUGUGGCUGAUAUU | 1546-1568 | AAUAUCAGCCACAAUAAGGGACC | 86 |
| AD-53322.1 | 85 | UCCCUUAUUGUGGCUGAUAUU | 1546-1568 | AAUAUCAGCCACAAUAAGGGACC | 86 |
| AD-46114.1 | 17 | UCGGAGGAUCACUCGGGUU | 448-466 | AACCCGAGUGAUCCUCCGA | 18 |
| AD-46109.1 | 31 | UCUCCUAGUGACUGGGGAU | 1174-1192 | AUCCCCAGUCACUAGGAGA | 32 |
| AD-46098.1 | 43 | UCUUACGGAAAAUCCGACA | 1345-1363 | UGUCGGAUUUUCCGUAAGA | 44 |
| AD-46111.1 | 63 | UGAGACAGACCGCCAAAUA | 1419-1437 | UAUUUGGCGGUCUGUCUCA | 64 |
| AD-46103.1 | 29 | UGGCACUUGGACUCUCCUA | 1162-1180 | UAGGAGAGUCCAAGUGCCA | 30 |
| AD-46120.1 | 19 | UGGCGCUGCAACCGGUGUA | 554-572 | UACACCGGUUGCAGCGCCA | 20 |
| AD-46125.1 | 99 | UGGUUAUGGGUCCUAUAAA | 1578-1596 | UUUAUAGGACCCAUAACCA | 100 |
| AD-46115.1 | 33 | UGGUUUUCCCACGAAUGGA | 1251-1269 | UCCAUUCGUGGGAAAACCA | 34 |
| AD-46134.1 | 55 | UGUCCAAACUGUCGUGCAA | 1394-1412 | UUGCACGACAGUUUGGACA | 56 |
| AD-46101.1 | 91 | UGUGGCUGAUAUUAACUGU | 1556-1574 | ACAGUUAAUAUCAGCCACA | 92 |
| AD-46121.1 | 35 | UUUCCCACGAAUGGACCCU | 1255-1273 | AGGGUCCAUUCGUGGGAAA | 36 |
| AD-46108.1 | 15 | UUUUGGGUUCGGAGGAUCA | 440-458 | UGAUCCUCCGAACCCAAAA | 16 |

TABLE 2A-3

Human KLF1 Modified siRNA Duplex Sequences

| Duplex ID | SEQ ID NO.: (sense) | Sense sequence | Position in NM_006563.3 | Antisense Sequence | SEQ ID NO.: (antisense) |
|---|---|---|---|---|---|
| AD-46099.1 | 528 | AAAcuGucGuGcAAAcccAdTsdT | 1399-1417 | UGGGUUUGcACGAcAGUUUdTsdT | 529 |
| AD-46132.1 | 530 | AAGcGAGGccGAcGuucGudTsdT | 856-874 | ACGAACGUCGGCCUCGCUUdTsdT | 531 |
| AD-46094.1 | 532 | AAuAAAcGGAcucAGuGGAdTsdT | 1434-1452 | UCcACUGAGUCCGUUuAUUdTsdT | 533 |

TABLE 2A-3 -continued

Human KLF1 Modified siRNA Duplex Sequences

| Duplex ID | SEQ ID NO.: (sense) | Sense sequence | Position in NM_006563.3 | Antisense Sequence | SEQ ID NO.: (antisense) |
|---|---|---|---|---|---|
| AD-46113.1 | 534 | AAuGGuuAuGGGuccuAuAdTsdT | 1576-1594 | uAuAGGACCcAuAACcAUUdTsdT | 535 |
| AD-46123.1 | 536 | AGAcAGAccGccAAAuAAAdTsdT | 1421-1439 | UUuAUUUGGCGGUCUGUCUdTsdT | 537 |
| AD-46129.1 | 538 | AGAccGccAAAuAAAcGGAdTsdT | 1425-1443 | UCCGUuuAUUUGGCGGUCUdTsdT | 539 |
| AD-46091.1 | 540 | AGcucuGcccAcGuGcuuudTsdT | 1088-1106 | AAAGcACGUGGGcAGAGCUdTsdT | 541 |
| AD-46090.1 | 542 | AGuGGuGGcGcuccGAAGAdTsdT | 149-167 | UCUUCGGAGCGCcACcACUdTsdT | 543 |
| AD-46119.1 | 544 | AuGGuuAuGGGuccuAuAAdTsdT | 1577-1595 | UuAuAGGACCcAuAACcAUUdTsdT | 545 |
| AD-46128.1 | 546 | AuGuccAAAcuGucGuGcAdTsdT | 1393-1411 | UGcACGAcAGUUUGGAcAUdTsdT | 547 |
| AD-46133.1 | 548 | cAAAGAuccAcccAAAuAudTsdT | 1292-1310 | AuAUUUGGGuGGAUCUUUGdTsdT | 549 |
| AD-46107.1 | 550 | cAAuGGuuAuGGGuccuAudTsdT | 1575-1593 | AuAGGACCcAuAACcAUUGdTsdT | 551 |
| AD-46136.1 | 552 | cccuuAuuGuGGcuGAuAudTsdT | 1549-1567 | AuAucAGCcAcAAuAAGGGdTsdT | 553 |
| AD-46126.1 | 554 | ccuccuuccuGAGuuGuuudTsdT | 761-779 | AAAcAACUcAGGAAGGAGGdTsdT | 555 |
| AD-46124.1 | 556 | ccuGAAGGucccuuAuuGudTsdT | 1540-1558 | AcAAuAAGGGACCUUcAGGdTsdT | 557 |
| AD-46095.1 | 558 | ccuuAuuGuGGcuGAuAuudTsdT | 1550-1568 | AAuAUcAGCcAcAAuAAGGdTsdT | 559 |
| AD-46095.3 | 560 | ccuuAuuGuGGcuGAuAuudTsdT | 1550-1568 | AAuAUcAGCcAcAAuAAGGdTsdT | 561 |
| AD-46102.1 | 562 | cGAGAcucuGGGcGcAuAudTsdT | 393-411 | AuAUGCGCCcAGAGUCUCGdTsdT | 563 |
| AD-46135.1 | 564 | cGccAAAuAAAcGGAcucAdTsdT | 1429-1447 | UGAGUCCGUUuAUUUGGCGdTsdT | 565 |
| AD-46110.1 | 566 | cGGAAAAuccGAcAAGccudTsdT | 1350-1368 | AGGCUUGUCGGAUUUUCCGdTsdT | 567 |
| AD-46118.1 | 568 | cuccuGAAGGucccuuAuudTsdT | 1538-1556 | AAuAAGGGACCUUcAGGAGdTsdT | 569 |
| AD-46127.1 | 570 | cuGGAcucGcGuucccAAAdTsdT | 1277-1295 | UUUGGGAACGCGAGUCCAGdTsdT | 571 |
| AD-46106.1 | 572 | cuGGGucuAGAAAGcGGcudTsdT | 1521-1539 | AGCCGCUUUCuAGACCCAGdTsdT | 573 |
| AD-46104.1 | 574 | cuuAcGGAAAAuccGAcAAdTsdT | 1346-1364 | UUGUCGGAUUUUCCGuAAGdTsdT | 575 |
| AD-46100.1 | 576 | GAcucAGuGGAcAcucAGAdTsdT | 1442-1460 | UCUGAGUGUCcACUGAGUCdTsdT | 577 |
| AD-46117.1 | 578 | GAGAcAGAccGccAAAuAAdTsdT | 1420-1438 | UuAUUUGGCGGUCUGUCUCdTsdT | 579 |
| AD-46122.1 | 580 | GAGAuGuccAAAcuGucGudTsdT | 1390-1408 | ACGAcAGUUUGGAcAUCUCdTsdT | 581 |
| AD-46096.1 | 582 | GccccuccAcGuGAAGucudTsdT | 210-228 | AGACUUcACGUGGAGGGGCdTsdT | 583 |
| AD-46097.1 | 584 | GcccuGGcAcuuGGAcucudTsdT | 1158-1176 | AGAGUCcAAGUGCcAGGGCdTsdT | 585 |
| AD-46112.1 | 586 | GcuccuGAAGGucccuuAudTsdT | 1537-1555 | AuAAGGGACCUUcAGGAGCdTsdT | 587 |
| AD-46116.1 | 588 | GGAAAAuccGAcAAGccuudTsdT | 1351-1369 | AAGGCUUGUCGGAUUUUCCdTsdT | 589 |
| AD-46093.1 | 590 | GuccAAAcuGucGuGcAAAdTsdT | 1395-1413 | UUUGcACGAcAGUUUGGACdTsdT | 591 |
| AD-46105.1 | 592 | GuGcAAAcccAGuGAGAcAdTsdT | 1407-1425 | UGUCUcACUGGGUUUGcACdTsdT | 593 |
| AD-46092.1 | 594 | uAucAAAcAcGGAcccAuAdTsdT | 1308-1326 | uAUGGGUCCGUGUUUGAuAdTsdT | 595 |
| AD-46130.1 | 596 | ucccuuAuuGuGGcuGAuAdTsdT | 1548-1566 | uAUcAGCcAcAAuAAGGGAdTsdT | 597 |
| AD-53284.1 | 598 | UCCCUUAUUGUGGCUGAUAUU | 1546-1568 | AAUAUCAGCCACAAUAAGGGACC | 599 |
| AD-53290.1 | 560 | UfcCfcUfuAfuUfgUfgGfcUfgAfuAfuUf | 1546-1568 | aAfuAfuCfaGfcCfaCfaAfuAfaGfgGfaCfc | 561 |
| AD-53295.1 | 562 | UfcCfcUfuAfuUfgUfgGfcUfgAfuAfusUf | 1546-1568 | aAfuAfuCfaGfcCfaCfaAfuAfaGfgGfasCfsc | 563 |
| AD-53301.1 | 564 | UfcCfcUfuAfuUfgUfgGfcUfgAfuAfusUf | 1546-1568 | aAfuAfuCfaGfcCfacaAfuAfaGfgGfasCfs | 565 |

TABLE 2A-3 -continued

Human KLF1 Modified siRNA Duplex Sequences

| Duplex ID | SEQ ID NO.: (sense) | Sense sequence | Position in NM_006563.3 | Antisense Sequence | SEQ ID NO.: (antisense) |
|---|---|---|---|---|---|
| AD-53307.1 | 566 | UfcCfcUfuauUfGfUfgGfcUfgAfuAfusUf | 1546-1568 | aAfuAfuCfaGfcCfacaAfUfAfaGfgGfasCfsc | 567 |
| AD-53308.1 | 568 | UfcCfcUfUfAfuUfGfUfgGfcUfgAfuAfusUf | 1546-1568 | aAfuAfuCfaGfcCfacaAfuaaGfgGfasCfsc | 569 |
| AD-53309.1 | 570 | UfcCfcuuAfuUfGfUfgGfcUfgAfuAfusUf | 1546-1568 | aAfuAfuCfaGfcCfacaAfuAfAfGfgGfasCfsc | 571 |
| AD-53310.1 | 572 | UfcCfCfUfuAfuUfGfUfgGfcUfgAfuAfusUf | 1546-1568 | aAfuAfuCfaGfcCfacaAfuAfaggGfasCfsc | 573 |
| AD-53311.1 | 574 | UfcccUfuAfuUfGfUfgGfcUfgAfuAfusUf | 1546-1568 | aAfuAfuCfaGfcCfacaAfuAfaGfGfgGfasCfsc | 575 |
| AD-53312.1 | 576 | UfCfCfcUfuAfuUfGfUfgGfcUfgAfuAfusUf | 1546-1568 | aAfuAfuCfaGfcCfacaAfuAfaGfggasCfsc | 577 |
| AD-53313.1 | 578 | ucCfcUfuAfuUfGfUfgGfcUfgAfuAfusUf | 1546-1568 | aAfuAfuCfaGfcCfacaAfuAfaGfgGfAfsCfsc | 579 |
| AD-53314.1 | 580 | UfcCfcUfuAfuUfGfUfgGfcUfgAfuAfusUf | 1546-1568 | aAfuAfuCfaGfcCfacaAfuAfaGfgGfascsc | 581 |
| AD-53315.1 | 582 | UfcCfcUfuAfuUfGfUfgGfcUfggcUfgAfuAfusUf | 1546-1568 | aAfuAfuCfaGfcCfCfacaAfuAfaGfgGfasCfsc | 583 |
| AD-53316.1 | 584 | UfcCfcUfuAfuUfGfUfgGfcUfgCfUfgAfuAfusUf | 1546-1568 | aAfuAfuCfagcCfacaAfuAfaGfgGfasCfsc | 585 |
| AD-53317.1 | 586 | UfcCfcUfuAfuUfGfUfgGfcUfgGfcugAfuAfusUf | 1546-1568 | aAfuAfuCfAfGfcCfacaAfuAfaGfgGfasCfsc | 587 |
| AD-53318.1 | 588 | UfcCfcUfuAfuUfGfUfgGfcUfGfAfuAfusUf | 1546-1568 | aAfuAfucaGfcCfacaAfuAfaGfgGfasCfsc | 589 |
| AD-53319.1 | 590 | UfcCfcUfuAfuUfGfUfgGfcUfgauAfusUf | 1546-1568 | aAfuAfUfCfaGfcCfacaAfuAfaGfgGfasCfsc | 591 |
| AD-53320.1 | 592 | UfcCfcUfuAfuUfGfUfgGfcUfgAfUfAfusUf | 1546-1568 | aAfuauCfaGfcCfacaAfuAfaGfgGfasCfsc | 593 |
| AD-53321.1 | 594 | UfcCfcUfuAfuUfGfUfgGfcUfgAfuausUf | 1546-1568 | aAfUfAfuCfaGfcCfacaAfuAfaGfgGfasCfsc | 595 |
| AD-53322.1 | 596 | UfcCfcUfuAfuUfGfUfgGfcUfgAfuAfUfsUf | 1546-1568 | aauAfuCfaGfcCfacaAfuAfaGfgGfasCfsc | 597 |
| AD-46114.1 | 598 | ucGGAGGAucAcucGGGuudTsdT | 448-466 | AACCCGAGUGAUCCUCCGAdTsdT | 599 |
| AD-46109.1 | 600 | ucuccuAGuGAcuGGGGAudTsdT | 1174-1192 | AUCCCcAGUcACuAGGAGAdTsdT | 601 |
| AD-46098.1 | 602 | ucuuAcGGAAAAuccGAcAdTsdT | 1345-1363 | UGUCGGAUUUUCCGuAAGAdTsdT | 603 |
| AD-46111.1 | 604 | uGAGAcAGAccGccAAAuAdTsdT | 1419-1437 | uAUUUGGCGGUCUGUCUcAdTsdT | 605 |
| AD-46103.1 | 606 | uGGcAcuuGGAcucuccuAdTsdT | 1162-1180 | uAGGAGAGUCcAAGUGCcAdTsdT | 607 |
| AD-46120.1 | 608 | uGGcGcuGcAAccGGuGuAdTsdT | 554-572 | uAcACCGGUUGcAGCGCcAdTsdT | 609 |
| AD-46125.1 | 610 | uGGuuAuGGGuccuAuAAAdTsdT | 1578-1596 | UUuAuAGGACCcAuAACcAdTsdT | 611 |
| AD-46115.1 | 612 | uGGuuucccAcGAAuGGAdTsdT | 1251-1269 | UCcAUUCGUGGGAAAACcAdTsdT | 613 |
| AD-46134.1 | 614 | uGuccAAAcuGucGuGcAAdTsdT | 1394-1412 | UUGcACGAcAGUUUGGAcAdTsdT | 615 |
| AD-46101.1 | 616 | uGuGGcuGAuAuuAAcuGudTsdT | 1556-1574 | AcAGUuAAuAUcAGCcAcAdTsdT | 617 |
| AD-46121.1 | 618 | uuucccAcGAAuGGAcccudTsdT | 1255-1273 | AGGGUCcAUUCGUGGGAAAdTsdT | 619 |
| AD-46108.1 | 620 | uuuuGGGuucGGAGGAucAdTsdT | 440-458 | UGAUCCUCCGAACCcAAAAdTsdT | 621 |

TABLE 2B

Mouse KLF1 Single Strands and Duplex Sequences

| SEQ ID NO: (sense) | Position of 5' base on transcript NM_010635.2 | sense (5'-3') | antisense (5'-3') | SEQ ID NO: (antisense) |
|---|---|---|---|---|
| 103 | 13 | GAGCCCUCCAAGAAACUUU | AAAGUUUCUUGGAGGGCUC | 104 |
| 105 | 24 | GAAACUUUCCUAGCCUCAU | AUGAGGCUAGGAAAGUUUC | 106 |
| 107 | 37 | CCUCAUAGCCCAUGAGGCA | UGCCUCAUGGGCUAUGAGG | 108 |
| 109 | 111 | GCUGAGACUGUCUUACCCU | AGGGUAAGACAGUCUCAGC | 110 |
| 111 | 114 | GAGACUGUCUUACCCUCCA | UGGAGGGUAAGACAGUCUC | 112 |
| 113 | 174 | GAGGACUUCCUCAAGUGGU | ACCACUUGAGGAAGUCCUC | 114 |
| 115 | 197 | GUCUGAGGAGACGCAGGAU | AUCCUGCGUCUCCUCAGAC | 116 |
| 117 | 247 | CGUCCCAUCACGUGAGUCU | AGACUCACGUGAUGGGACG | 118 |
| 119 | 250 | CCCAUCACGUGAGUCUGAA | UUCAGACUCACGUGAUGGG | 120 |
| 121 | 251 | CCAUCACGUGAGUCUGAAA | UUUCAGACUCACGUGAUGG | 122 |
| 123 | 264 | CUGAAAUCGGAGGACCCUU | AAGGGUCCUCCGAUUUCAG | 124 |
| 125 | 294 | GAUGAGAGGGACGUGACCU | AGGUCACGUCCCUCUCAUC | 126 |
| 127 | 315 | GCGUGGGACCCGGAUCUUU | AAAGAUCCGGGUCCCACGC | 128 |
| 129 | 316 | CGUGGGACCCGGAUCUUUU | AAAAGAUCCGGGUCCCACG | 130 |
| 131 | 323 | CCCGGAUCUUUUCCUUACA | UGUAAGGAAAAGAUCCGGG | 132 |
| 133 | 324 | CCGGAUCUUUUCCUUACAA | UUGUAAGGAAAAGAUCCGG | 134 |
| 135 | 325 | CGGAUCUUUUCCUUACAAA | UUUGUAAGGAAAAGAUCCG | 136 |
| 137 | 340 | CAAACUUUCCAGGUUCCGA | UCGGAACCUGGAAAGUUUG | 138 |
| 139 | 344 | CUUUCCAGGUUCCGAGUCU | AGACUCGGAACCUGGAAAG | 140 |
| 141 | 403 | GGCCAGUGGCACAGUUCGA | UCGAACUGUGCCACUGGCC | 142 |
| 143 | 781 | CUUCCUUCUUGAAUUGUCU | AGACAAUUCAAGAAGGAAG | 144 |
| 145 | 887 | CAGCCGGCGAACUUUGGCA | UGCCAAAGUUCGCCGGCUG | 146 |
| 147 | 892 | GGCGAACUUUGGCACCUAA | UUAGGUGCCAAAGUUCGCC | 148 |
| 149 | 894 | CGAACUUUGGCACCUAAGA | UCUUAGGUGCCAAAGUUCG | 150 |
| 151 | 1050 | GCUCGCUCAGACGAACUGA | UCAGUUCGUCUGAGCGAGC | 152 |
| 153 | 1082 | GAAGCACACUGGACAUCGU | ACGAUGUCCAGUGUGCUUC | 154 |
| 155 | 1114 | GCCUCUGCCCACGUGCUUU | AAAGCACGUGGGCAGAGGC | 156 |
| 157 | 1141 | CUGACCACUUAGCUCUGCA | UGCAGAGCUAAGUGGUCAG | 158 |
| 159 | 1146 | CACUUAGCUCUGCACAUGA | UCAUGUGCAGAGCUAAGUG | 160 |
| 161 | 1190 | CAAGGACUGGGGAUGAAAU | AUUUCAUCCCCAGUCCUUG | 162 |
| 163 | 1196 | CUGGGGAUGAAAUAAGAGU | ACUCUUAUUUCAUCCCCAG | 164 |
| 165 | 1200 | GGAUGAAAUAAGAGUGGAU | AUCCACUCUUAUUUCAUCC | 166 |
| 167 | 1213 | GUGGAUCCAAGGACCGUAU | AUACGGUCCUUGGAUCCAC | 168 |
| 169 | 1219 | CCAAGGACCGUAUCCCAAA | UUUGGGAUACGGUCCUUGG | 170 |
| 171 | 1233 | CCAAAAGAUGGGCCAUUAU | AUAAUGGCCCAUCUUUUGG | 172 |
| 173 | 1242 | GGGCCAUUAUAUAGUCCUA | UAGGACUAUAUAAUGGCCC | 174 |

TABLE 2B -continued

Mouse KLF1 Single Strands and Duplex Sequences

| SEQ ID NO: (sense) | Position of 5' base on transcript NM_010635.2 | sense (5'-3') | antisense (5'-3') | SEQ ID NO: (antisense) |
|---|---|---|---|---|
| 175 | 1246 | CAUUAUAUAGUCCUACCCA | UGGGUAGGACUAUAUAAUG | 176 |
| 177 | 1279 | CAGAAGACCAUACAAAGGA | UCCUUUGUAUGGUCUUCUG | 178 |
| 179 | 1296 | GAGCCUUCAGGACAAACCU | AGGUUUGUCCUGAAGGCUC | 180 |
| 181 | 1303 | CAGGACAAACCUCACAUGU | ACAUGUGAGGUUUGUCCUG | 182 |
| 183 | 1351 | GACCCAGCAAUAUAGACCA | UGGUCUAUAUUGCUGGGUC | 184 |
| 185 | 1368 | CACCAGAUAAAUCAACUCA | UGAGUUGAUUUAUCUGGUG | 186 |
| 187 | 1431 | GAUGGACUGGGGUGAGAUU | AAUCUCACCCCAGUCCAUC | 188 |
| 189 | 1482 | CCCAUCUGCUAGGAUUGUU | AACAAUCCUAGCAGAUGGG | 190 |
| 191 | 1487 | CUGCUAGGAUUGUUGUCGU | ACGACAACAAUCCUAGCAG | 192 |
| 193 | 1493 | GGAUUGUUGUCGUUACUAU | AUAGUAACGACAACAAUCC | 194 |
| 195 | 1494 | GAUUGUUGUCGUUACUAUA | UAUAGUAACGACAACAAUC | 196 |

TABLE 2C

BCL11A Single Strands and Duplex Sequences to match transcript variants 1, 2 and 3 of human and mouse BCL11A (human sequence references NM_022893.3 (variant 1), NM_018014.3 (variant 2), and NM_138559.1 (variant 3)) Table 2C includes unmodified siRNAs targeting all BCL11a isoforms.

| Duplex Name | SEQ ID NO.: | Sense Sequence | Position relative to NM_022893.3 SEQ ID NO: 3 | Start | SEQ ID NO.: | Antisense Sequence |
|---|---|---|---|---|---|---|
|  | 197 | UUCUUAUUUUAUCGAGCA | 407-425 | 407 | 198 | UGCUCGAUAAAAUAAGAA |
|  | 229 | UUGUUUAUCAACGUCAUCU | 561-579 | 561 | 230 | AGAUGACGUUGAUAAACAA |
|  | 291 | AUUAAGAAUCUACUUAGAA | 810-828 | 810 | 292 | UUCUAAGUAGAUUCUUAAU |
| AD-46498.1 | 213 | CCAGAGGAUGACGAUUGUU | 547-565 | 547 | 214 | AACAAUCGUCAUCCUCUGG |
| AD-46500.1 | 245 | AGGAACACAUAGCAGAUAA | 599-617 | 599 | 246 | UUAUCUGCUAUGUGUUCCU |
| AD-46501.1 | 261 | GCCCAGCAGCUACACAUGU | 726-744 | 726 | 262 | ACAUGUGUAGCUGCUGGGC |
| AD-46502.1 | 277 | CACAGAACACUCAUGGAUU | 794-812 | 794 | 278 | AAUCCAUGAGUGUUCUGUG |
| AD-46503.1 | 199 | UAUUUUUAUCGAGCACAAA | 411-429 | 411 | 200 | UUUGUGCUCGAUAAAAAUA |
| AD-46504.1 | 215 | CAGAGGAUGACGAUUGUUU | 548-566 | 548 | 216 | AAACAAUCGUCAUCCUCUG |
| AD-46505.1 | 231 | UGUUUAUCAACGUCAUCUA | 562-580 | 562 | 232 | UAGAUGACGUUGAUAAACA |
| AD-46506.1 | 247 | GGAACACAUAGCAGAUAAA | 600-618 | 600 | 248 | UUUAUCUGCUAUGUGUUCC |
| AD-46507.1 | 263 | CCCAGCAGCUACACAUGUA | 727-745 | 727 | 264 | UACAUGUGUAGCUGCUGGG |
| AD-46508.1 | 279 | CAGAACACUCAUGGAUUAA | 796-814 | 796 | 280 | UUAAUCCAUGAGUGUUCUG |
| AD-46509.1 | 201 | UUUAUCGAGCACAAACGGA | 415-433 | 415 | 202 | UCCGUUUGUGCUCGAUAAA |
| AD-46510.1 | 217 | AGAGGAUGACGAUUGUUUA | 549-567 | 549 | 218 | UAAACAAUCGUCAUCCUCU |
| AD-46511.1 | 233 | UUUAUCAACGUCAUCUAGA | 564-582 | 564 | 234 | UCUAGAUGACGUUGAUAAA |
| AD-46512.1 | 249 | ACAUAGCAGAUAAACUUCU | 605-623 | 605 | 250 | AGAAGUUUAUCUGCUAUGU |
| AD-46513.1 | 265 | AGCUACACAUGUACAACUU | 733-751 | 733 | 266 | AAGUUGUACAUGUGUAGCU |

TABLE 2C -continued

BCL11A Single Strands and Duplex Sequences to match transcript variants 1, 2 and 3 of human and mouse BCL11A (human sequence references NM_022893.3 (variant 1), NM_018014.3 (variant 2), and NM_138559.1 (variant 3)) Table 2C includes unmodified siRNAs targeting all BCL11a isoforms.

| Duplex Name | SEQ ID NO.: | Sense Sequence | Position relative to NM_022893.3 SEQ ID NO: 3 | Start | SEQ ID NO.: | Antisense Sequence |
|---|---|---|---|---|---|---|
| AD-46514.1 | 281 | GAACACUCAUGGAUUAAGA | 798-816 | 798 | 282 | UCUUAAUCCAUGAGUGUUC |
| AD-46515.1 | 203 | AUGGCAGCCUCUGCUUAGA | 443-461 | 443 | 204 | UCUAAGCAGAGGCUGCCAU |
| AD-46516.1 | 219 | GAGGAUGACGAUUGUUUAU | 550-568 | 550 | 220 | AUAAACAAUCGUCAUCCUC |
| AD-46517.1 | 235 | AUCAACGUCAUCUAGAGGA | 567-585 | 567 | 236 | UCCUCUAGAUGACGUUGAU |
| AD-46518.1 | 251 | UGCCCCGCAGGGUAUUUGU | 699-717 | 699 | 252 | ACAAAUACCCUGCGGGGCA |
| AD-46519.1 | 267 | UACACAUGUACAACUUGCA | 736-754 | 736 | 268 | UGCAAGUUGUACAUGUGUA |
| AD-46520.1 | 283 | AACACUCAUGGAUUAAGAA | 799-817 | 799 | 284 | UUCUUAAUCCAUGAGUGUU |
| AD-46521.1 | 205 | GCAGCCUCUGCUUAGAAAA | 446-464 | 446 | 206 | UUUUCUAAGCAGAGGCUGC |
| AD-46522.1 | 221 | GGAUGACGAUUGUUUAUCA | 552-570 | 552 | 222 | UGAUAAACAAUCGUCAUCC |
| AD-46523.1 | 237 | UCAACGUCAUCUAGAGGAA | 568-586 | 568 | 238 | UUCCUCUAGAUGACGUUGA |
| AD-46524.1 | 253 | GCCCCGCAGGGUAUUUGUA | 700-718 | 700 | 254 | UACAAAUACCCUGCGGGGC |
| AD-46525.1 | 269 | ACACAUGUACAACUUGCAA | 737-755 | 737 | 270 | UUGCAAGUUGUACAUGUGU |
| AD-46526.1 | 285 | ACACUCAUGGAUUAAGAAU | 800-818 | 800 | 286 | AUUCUUAAUCCAUGAGUGU |
| AD-46527.1 | 207 | CAGCCUCUGCUUAGAAAAA | 447-465 | 447 | 208 | UUUUUCUAAGCAGAGGCUG |
| AD-46528.1 | 223 | GACGAUUGUUUAUCAACGU | 556-574 | 556 | 224 | ACGUUGAUAAACAAUCGUC |
| AD-46529.1 | 239 | ACGUCAUCUAGAGGAAUUU | 571-589 | 571 | 240 | AAAUUCCUCUAGAUGACGU |
| AD-46530.1 | 255 | CCCCGCAGGGUAUUUGUAA | 701-719 | 701 | 256 | UUACAAAUACCCUGCGGGG |
| AD-46531.1 | 271 | UACAACUUGCAAACAGCCA | 744-762 | 744 | 272 | UGGCUGUUUGCAAGUUGUA |
| AD-46532.1 | 287 | ACUCAUGGAUUAAGAAUCU | 802-820 | 802 | 288 | AGAUUCUUAAUCCAUGAGU |
| AD-46533.1 | 209 | ACGCCAGAGGAUGACGAUU | 544-562 | 544 | 210 | AAUCGUCAUCCUCUGGCGU |
| AD-46534.1 | 225 | CGAUUGUUUAUCAACGUCA | 558-576 | 558 | 226 | UGACGUUGAUAAACAAUCG |
| AD-46535.1 | 241 | CAAACAGGAACACAUAGCA | 594-612 | 594 | 242 | UGCUAUGUGUUCCUGUUUG |
| AD-46536.1 | 257 | CCCGCAGGGUAUUUGUAAA | 702-720 | 702 | 258 | UUUACAAAUACCCUGCGGG |
| AD-46537.1 | 273 | AACACGCACAGAACACUCA | 788-806 | 788 | 274 | UGAGUGUUCUGUGCGUGUU |
| AD-46538.1 | 289 | GAUUAAGAAUCUACUUAGA | 809-827 | 809 | 290 | UCUAAGUAGAUUCUUAAUC |
| AD-46539.1 | 211 | GCCAGAGGAUGACGAUUGU | 546-564 | 546 | 212 | ACAAUCGUCAUCCUCUGGC |
| AD-46540.1 | 227 | GAUUGUUUAUCAACGUCAU | 559-577 | 559 | 228 | AUGACGUUGAUAAACAAUC |
| AD-46541.1 | 243 | CAGGAACACAUAGCAGAUA | 598-616 | 598 | 244 | UAUCUGCUAUGUGUUCCUG |
| AD-46542.1 | 259 | CGCAGGGUAUUUGUAAAGA | 704-722 | 704 | 260 | UCUUUACAAAUACCCUGCG |
| AD-46543.1 | 275 | GCACAGAACACUCAUGGAU | 793-811 | 793 | 276 | AUCCAUGAGUGUUCUGUGC |

TABLE 3

Modified siRNAs targeting all BCL11a isoforms.

| Duplex Name | SEQ ID NO.: | Sense OligoSeq | Position relative to NM_022893.3 SEQ ID NO: 3 | Start | SEQ ID NO.: | Antisense OligoSeq |
|---|---|---|---|---|---|---|
| AD-46498.1 | 305 | ccAGAGGAuGAcGAuuGuudTsdT | 547-565 | 547 | 306 | AAcAAUCGUcAUCCUCUGGdTsdT |
| AD-46500.1 | 335 | AGGAAcAcAuAGcAGAuAAdTsdT | 599-617 | 599 | 336 | UuAUCUGCuAUGUGUUCCUdTsdT |
| AD-46501.1 | 351 | GcccAGcAGcuAcAcAuGudTsdT | 726-744 | 726 | 352 | AcAUGUGuAGCUGCUGGGCdTsdT |
| AD-46502.1 | 367 | cAcGAAcAcucAuGGAuudTsdT | 794-812 | 794 | 368 | AAUCcAUGAGUGUUCUGUGdTsdT |
| AD-46503.1 | 291 | uAuuuuuAucGAGcAcAAAdTsdT | 411-429 | 411 | 292 | UUUGUGCUCGAuAAAAAuAdTsdT |
| AD-46504.1 | 307 | cAGAGGAuGAcGAuuGuuudTsdT | 548-566 | 548 | 308 | AAAcAAUCGUcAUCCUCUGdTsdT |
| AD-46505.1 | 321 | uGuuuAucAAcGucAucuAdTsdT | 562-580 | 562 | 322 | uAGAUGACGUUGAuAAAcAdTsdT |
| AD-46506.1 | 337 | GGAAcAcAuAGcAGAuAAAdTsdT | 600-618 | 600 | 338 | UUuAUCUGCuAUGUGUUCCdTsdT |
| AD-46507.1 | 353 | cccAGcAGcuAcAcAuGuAdTsdT | 727-745 | 727 | 354 | uAcAUGUGuAGCUGCUGGGdTsdT |
| AD-46508.1 | 369 | cAGAAcAcucAuGGAuuAAdTsdT | 796-814 | 796 | 370 | UuAAUCcAUGAGUGUUCUGdTsdT |
| AD-46509.1 | 293 | uuuAucGAGcAcAAAcGGAdTsdT | 415-433 | 415 | 294 | UCCGUUUGUGCUCGAuAAAdTsdT |
| AD-46510.1 | 309 | AGAGGAuGAcGAuuGuuuAdTsdT | 549-567 | 549 | 310 | uAAAcAAUCGUcAUCCUCUdTsdT |
| AD-46511.1 | 323 | uuuAucAAcGucAucuAGAdTsdT | 564-582 | 564 | 324 | UCuAGAUGACGUUGAuAAAdTsdT |
| AD-46512.1 | 339 | AcAuAGcAGAuAAAcuucudTsdT | 605-623 | 605 | 340 | AGAAGUUuAUCUGCuAUGUdTsdT |
| AD-46513.1 | 355 | AGcuAcAcAuGuAcAAcuudTsdT | 733-751 | 733 | 356 | AAGUUGuAcAUGUGuAGCUdTsdT |
| AD-46514.1 | 371 | GAAcAcucAuGGAuuAAGAdTsdT | 798-816 | 798 | 372 | UCUuAAUCcAUGAGUGUUCdTsdT |
| AD-46515.1 | 295 | AuGGcAGccucuGcuuAGAdTsdT | 443-461 | 443 | 296 | UCuAAGcAGAGGCUGCcAUdTsdT |
| AD-46516.1 | 311 | GAGGAuGAcGAuuGuuuAudTsdT | 550-568 | 550 | 312 | AuAAAcAAUCGUcAUCCUCdTsdT |
| AD-46517.1 | 325 | AucAAcGucAucuAGAGGAdTsdT | 567-585 | 567 | 326 | UCCUCuAGAUGACGUUGAUdTsdT |
| AD-46518.1 | 341 | uGccccGcAGGGuAuuuGudTsdT | 699-717 | 699 | 342 | AcAAAuACCCUGCGGGGcAdTsdT |
| AD-46519.1 | 357 | uAcAcAuGuAcAAcuuGcAdTsdT | 736-754 | 736 | 358 | UGcAAGUUGuAcAUGUGuAdTsdT |
| AD-46520.1 | 373 | AAcAcucAuGGAuuAAGAAdTsdT | 799-817 | 799 | 374 | UUCUuAAUCcAUGAGUGUUdTsdT |
| AD-46521.1 | 297 | GcAGccucuGcuuAGAAAAdTsdT | 446-464 | 446 | 298 | UUUUCuAAGcAGAGGCUGCdTsdT |
| AD-46522.1 | 313 | GGAuGAcGAuuGuuuAucAdTsdT | 552-570 | 552 | 314 | UGAuAAAcAAUCGUcAUCCdTsdT |
| AD-46523.1 | 327 | ucAAcGucAucuAGAGGAAdTsdT | 568-586 | 568 | 328 | UUCCUCuAGAUGACGUUGAdTsdT |
| AD-46524.1 | 343 | GccccGcAGGGuAuuuGuAdTsdT | 700-718 | 700 | 344 | uAcAAAuACCCUGCGGGGCdTsdT |
| AD-46525.1 | 359 | AcAcAuGuAcAAcuuGcAAdTsdT | 737-755 | 737 | 360 | UUGcAAGUUGuAcAUGUGUdTsdT |
| AD-46526.1 | 375 | AcAcucAuGGAuuAAGAAudTsdT | 800-818 | 800 | 376 | AUUCUuAAUCcAUGAGUGUdTsdT |
| AD-46527.1 | 299 | cAGccucuGcuuAGAAAAAdTsdT | 447-465 | 447 | 300 | UUUUUCuAAGcAGAGGCUGCdTsdT |
| AD-46528.1 | 315 | GAcGAuuGuuuAucAAcGudTsdT | 556-574 | 556 | 316 | ACGUUGAuAAAcAAUCGUCdTsdT |
| AD-46529.1 | 329 | AcGucAucuAGAGGAuuuAdTsdT | 571-589 | 571 | 330 | AAAUCCUCuAGAUGACGUUdTsdT |
| AD-46530.1 | 345 | ccccGcAGGGuAuuuGuAAdTsdT | 701-719 | 701 | 346 | UuAcAAAuACCCUGCGGGGdTsdT |
| AD-46531.1 | 361 | uAcAAcuuGcAAAcAGccAdTsdT | 744-762 | 744 | 362 | UGGCUGUUUGcAAGUUGuAdTsdT |
| AD-46532.1 | 377 | AcucAuGGAuuAAGAAucudTsdT | 802-820 | 802 | 378 | AGAUUCUuAAUCcAUGAGUdTsdT |
| AD-46533.1 | 301 | AcGccAGAGGAuGAcGAuudTsdT | 544-562 | 544 | 302 | AAUCGUcAUCCUCUGGCGUdTsdT |
| AD-46534.1 | 317 | cGAuuGuuuAucAAcGucAdTsdT | 558-576 | 558 | 318 | UGACGUUGAuAAAcAAUCGdTsdT |

TABLE 3 -continued

Modified siRNAs targeting all BCL11a isoforms.

| Duplex Name | SEQ ID NO.: | Sense OligoSeq | Position relative to NM_022893.3 SEQ ID NO: 3 | Start | SEQ ID NO.: | Antisense OligoSeq |
|---|---|---|---|---|---|---|
| AD-46535.1 | 331 | cAAAcAGGAAcAcAuAGcAdTsdT | 594-612 | 594 | 332 | UGCuAUGUGUUCCUGUUUGdTsdT |
| AD-46536.1 | 347 | cccGcAGGGuAuuuGuAAAdTsdT | 702-720 | 702 | 348 | UUuAcAAAuACCCUGCGGGdTsdT |
| AD-46537.1 | 363 | AAcAcGcAcAGAAcAcucAdTsdT | 788-806 | 788 | 364 | UGAGUGUUCUGUGCGUGUUdTsdT |
| AD-46538.1 | 379 | GAuuAAGAAucuAcuuAGAdTsdT | 809-827 | 809 | 380 | UCuAAGuAGAUUCUuAAUCdTsdT |
| AD-46539.1 | 303 | GccAGAGGAuGAcGAuuGudTsdT | 546-564 | 546 | 304 | AcAAUCGUcAUCCUCUGGCdTsdT |
| AD-46540.1 | 319 | GAuuGuuuAucAAcGucAudTsdT | 559-577 | 559 | 320 | AUGACGUUGAuAAAcAAUCdTsdT |
| AD-46541.1 | 333 | cAGGAAcAcAuAGcAGAuAdTsdT | 598-616 | 598 | 334 | uAUCUGCuAUGUGUUCCUGdTsdT |
| AD-46542.1 | 349 | cGcAGGGuAuuuGuAAAGAdTsdT | 704-722 | 704 | 350 | UCUUuAcAAAuACCCUGCGdTsdT |
| AD-46543.1 | 365 | GcAcAGAAcAcucAuGGAudTsdT | 793-811 | 793 | 366 | AUCcAUGAGUGUUCUGUGCdTsdT |

TABLE 4

Unmodified siRNAs specifically targeting BCL11a with the long form of exon 4.

| Duplex Name | SEQ ID NO.: | Sense Sequence | Position relative to NM_018014.3 SEQ ID NO: 4 | sStart | SEQ ID NO.: | Antisense Sequence |
|---|---|---|---|---|---|---|
| AD-52060.1 | 81 | UGGUAUCCCUUCAGGACUA | 861-879 | 861 | 382 | UAGUCCUGAAGGGAUACCA |
| AD-52061.1 | 97 | AUACCAGGAUCAGUAUCGA | 955-973 | 955 | 398 | UCGAUACUGAUCCUGGUAU |
| AD-52062.1 | 13 | CCAGCCCUAUGCAAAGGUU | 1235-1253 | 1235 | 414 | AACCUUUGCAUAGGGCUGG |
| AD-52063.1 | 29 | GUCGGACCGCAUAGACGAU | 2007-2025 | 2007 | 430 | AUCGUCUAUGCGGUCCGAC |
| AD-52064.1 | 45 | AGGGAGCACGCCCCAUAUU | 2385-2403 | 2385 | 446 | AAUAUGGGGCGUGCUCCCU |
| AD-52065.1 | 83 | CUAGGUGCAGAAUGUCCUU | 877-895 | 877 | 384 | AAGGACAUUCUGCACCUAG |
| AD-52066.1 | 99 | ACCAGGAUCAGUAUCGAGA | 957-975 | 957 | 400 | UCUCGAUACUGAUCCUGGU |
| AD-52067.1 | 15 | AAAGGUUACUGCAACCAUU | 1247-1265 | 1247 | 416 | AAUGGUUGCAGUAACCUUU |
| AD-52068.1 | 31 | CGCUGAGCCCCUUCUCUAA | 2111-2129 | 2111 | 432 | UUAGAGAAGGGGCUCAGCG |
| AD-52069.1 | 47 | GGGAGCACGCCCCAUAUUA | 2386-2404 | 2386 | 448 | UAAUAUGGGGCGUGCUCCC |
| AD-52070.1 | 85 | GCCACCUCUCCAUGGGAUU | 900-918 | 900 | 386 | AAUCCCAUGGAGAGGUGGC |
| AD-52071.1 | 01 | CACCACCGAGACAUCACUU | 1031-1049 | 1031 | 402 | AAGUGAUGUCUCGGUGGUG |
| AD-52072.1 | 17 | AGUCCAAGUCAUGCGAGUU | 1352-1370 | 1352 | 418 | AACUCGCAUGACUUGGACU |
| AD-52073.1 | 33 | GCCCUUCUCUAAGCGCAU | 2117-2135 | 2117 | 434 | AUGCGCUUAGAGAAGGGGC |
| AD-52074.1 | 49 | GAGCACGCCCCAUAUUAGU | 2388-2406 | 2388 | 450 | ACUAAUAUGGGGCGUGCUC |
| AD-52075.1 | 87 | UGCAGACAAUAACCCCUUU | 924-942 | 924 | 388 | AAAGGGGUUAUUGUCUGCA |
| AD-52076.1 | 03 | CAGGGUGCUGCGGUUGAAU | 1122-1140 | 1122 | 404 | AUUCAACCGCAGCACCCUG |
| AD-52077.1 | 19 | CGCCACCACGAGAACAGCU | 1795-1813 | 1795 | 420 | AGCUGUUCUCGUGGUGGCG |
| AD-52078.1 | 35 | CUCCAGGCAGCUCAAAGAU | 2223-2241 | 2223 | 436 | AUCUUUGAGCUGCCUGGAG |
| AD-52079.1 | 51 | CACGCCCCAUAUUAGUGGU | 2391-2409 | 2391 | 452 | ACCACUAAUAUGGGGCGUG |
| AD-52080.1 | 89 | ACAAUAACCCCUUUAACCU | 929-947 | 929 | 390 | AGGUUAAAGGGGUUAUUGU |

TABLE 4 -continued

Unmodified siRNAs specifically targeting BCL11a with the long form of exon 4.

| Duplex Name | SEQ ID NO.: | Sense Sequence | Position relative to NM_018014.3 SEQ ID NO: 4 | sStart | SEQ ID NO.: | Antisense Sequence |
|---|---|---|---|---|---|---|
| AD-52081.1 | 05 | CGGUUGAAUCCAAUGGCUA | 1132-1150 | 1132 | 406 | UAGCCAUUGGAUUCAACCG |
| AD-52082.1 | 21 | GUCCUGGGCGAGAAGCAUA | 1921-1939 | 1921 | 422 | UAUGCUUCUCGCCCAGGAC |
| AD-52083.1 | 37 | AGGCAGCUCAAAGAUCCCU | 2227-2245 | 2227 | 438 | AGGGAUCUUUGAGCUGCCU |
| AD-52084.1 | 91 | CCCCUUUAACCUGCUAAGA | 936-954 | 936 | 392 | UCUUAGCAGGUUAAAGGGG |
| AD-52085.1 | 07 | GAGCCUCCCGCCAUGGAUU | 1153-1171 | 1153 | 408 | AAUCCAUGGCGGGAGGCUC |
| AD-52086.1 | 23 | UCCUGGGCGAGAAGCAUAA | 1922-1940 | 1922 | 424 | UUAUGCUUCUCGCCCAGGA |
| AD-52087.1 | 39 | GGCAGCUCAAAGAUCCCUU | 2228-2246 | 2228 | 440 | AAGGGAUCUUUGAGCUGCC |
| AD-52088.1 | 93 | CCUUUAACCUGCUAAGAAU | 938-956 | 938 | 394 | AUUCUUAGCAGGUUAAAGG |
| AD-52089.1 | 09 | AGCCUCCCGCCAUGGAUUU | 1154-1172 | 1154 | 410 | AAAUCCAUGGCGGGAGGCU |
| AD-52090.1 | 25 | GACACUUGCGACGAAGACU | 1975-1993 | 1975 | 426 | AGUCUUCGUCGCAAGUGUC |
| AD-52091.1 | 41 | CUCAAAGAUCCCUUCCUUA | 2233-2251 | 2233 | 442 | UAAGGAAGGGAUCUUUGAG |
| AD-52092.1 | 95 | AGAAUACCAGGAUCAGUAU | 952-970 | 952 | 396 | AUACUGAUCCUGGUAUUCU |
| AD-52093.1 | 11 | GGAUUUCUCUAGGAGACUU | 1167-1185 | 1167 | 412 | AAGUCUCCUAGAGAAAUCC |
| AD-52094.1 | 27 | AGUCGGACCGCAUAGACGA | 2006-2024 | 2006 | 428 | UCGUCUAUGCGGUCCGACU |
| AD-52095.1 | 43 | ACUCCAGACAAUCGCCUUU | 2261-2279 | 2261 | 444 | AAAGGCGAUUGUCUGGAGU |

TABLE 5

Modified siRNAs specifically targeting BCL11a with the long form of exon 4.

| Duplex Name | SEQ ID NO.: | Sense OligoSeq | Position relative to NM_018014.3 SEQ ID NO:4 | Start | SEQ ID NO.: | Antisense OligoSeq |
|---|---|---|---|---|---|---|
| AD-52060.1 | 453 | uGGuAucccuucAGGAcuAdTsdT | 861-879 | 861 | 454 | uAGUCCUGAAGGGAuACcAdTsdT |
| AD-52061.1 | 469 | AuAccAGGAucAGuAucGAdTsdT | 955-973 | 955 | 470 | UCGAuACUGAUCCUGGuAUdTsdT |
| AD-52062.1 | 485 | ccAGcccuAuGcAAAGGuudTsdT | 1235-1253 | 1235 | 486 | AACCUUUGcAuAGGGCUGGdTsdT |
| AD-52063.1 | 501 | GucGGAccGcAuAGAcGAudTsdT | 2007-2025 | 2007 | 502 | AUCGUCuAUGCGGUCCGACdTsdT |
| AD-52064.1 | 517 | AGGGAGcAcGccccAuAuudTsdT | 2385-2403 | 2385 | 518 | AAuAUGGGGCGUGCUCCCUdTsdT |
| AD-52065.1 | 455 | cuAGGuGcAGAAuGuccuudTsdT | 877-895 | 877 | 456 | AAGGAcAUUCUGcACCuAGdTsdT |
| AD-52066.1 | 471 | AccAGGAucAGuAucGAGAdTsdT | 957-975 | 957 | 472 | UCUCGAuACUGAUCCUGGUdTsdT |
| AD-52067.1 | 487 | AAAGGuuAcuGcAAccAuudTsdT | 1247-1265 | 1247 | 488 | AAUGGUUGcAGuAACCUUUdTsdT |
| AD-52068.1 | 503 | cGcuGAGcccuucucuAAdTsdT | 2111-2129 | 2111 | 504 | UuAGAGAAGGGGCUcAGCGdTsdT |
| AD-52069.1 | 519 | GGGAGcAcGccccAuAuuAdTsdT | 2386-2404 | 2386 | 520 | uAAuAUGGGGCGUGCUCCCdTsdT |
| AD-52070.1 | 457 | GccAccucuccAuGGGAuudTsdT | 900-918 | 900 | 458 | AAUCCcAUGGAGAGGUGGCdTsdT |
| AD-52071.1 | 473 | cAccAccGAGAcAucAcuudTsdT | 1031-1049 | 1031 | 474 | AAGUGAUGUCUCGGUGGUGdTsdT |
| AD-52072.1 | 489 | AGuccAAGucAuGcGAGuudTsdT | 1352-1370 | 1352 | 490 | AACUCGcAUGACUUGGACUdTsdT |
| AD-52073.1 | 505 | GccccuucucuAAGcGcAudTsdT | 2117-2135 | 2117 | 506 | AUGCGCUuAGAGAAGGGGCdTsdT |
| AD-52074.1 | 521 | GAGcAcGccccAuAuuAGudTsdT | 2388-2406 | 2388 | 522 | ACuAAuAUGGGGCGUGCUCdTsdT |
| AD-52075.1 | 459 | uGcAGAcAAuAAccccuuudTsdT | 924-942 | 924 | 460 | AAAGGGGUuAUUGUCUGcAdTsdT |

TABLE 5 -continued

Modified siRNAs specifically targeting BCL11a with the long form of exon 4.

| Duplex Name | SEQ ID NO.: | Sense OligoSeq | Position relative to NM_018014.3 SEQ ID NO:4 | Start | SEQ ID NO.: | Antisense OligoSeq |
|---|---|---|---|---|---|---|
| AD-52076.1 | 475 | cAGGGuGcuGcGGuuGAAudTsdT | 1122-1140 | 1122 | 476 | AUUcAACCGcAGcACCCUGdTsdT |
| AD-52077.1 | 491 | cGccAccAcGAGAAcAGcudTsdT | 1795-1813 | 1795 | 492 | AGCUGUUCUCGUGGUGGCGdTsdT |
| AD-52078.1 | 507 | cuccAGGcAGcucAAAGAudTsdT | 2223-2241 | 2223 | 508 | AUCUUUGAGCUGCCUGGAGdTsdT |
| AD-52079.1 | 523 | cAcGccccAuAuuAGuGGudTsdT | 2391-2409 | 2391 | 524 | ACcACuAuAUGGGGCGUGdTsdT |
| AD-52080.1 | 461 | AcAAuAAccccuuuAAccudTsdT | 929-947 | 929 | 462 | AGGUuAAAGGGGUuAUUGUdTsdT |
| AD-52081.1 | 477 | cGGuuGAAuccAAuGGcuAdTsdT | 1132-1150 | 1132 | 478 | uAGCcAUUGGAUUcAACCGdTsdT |
| AD-52082.1 | 493 | GuccuGGGcGAGAAGcAuAdTsdT | 1921-1939 | 1921 | 494 | uAUGCUUCUCGCCcAGGACdTsdT |
| AD-52083.1 | 509 | AGGcAGcucAAAGAucccudTsdT | 2227-2245 | 2227 | 510 | AGGGAUCUUUGAGCUGCCUdTsdT |
| AD-52084.1 | 463 | ccccuuuAAccuGcuAAGAdTsdT | 936-954 | 936 | 464 | UCUuAGcAGGUuAAAGGGGdTsdT |
| AD-52085.1 | 479 | GAGccuccCGccAuGGAuudTsdT | 1153-1171 | 1153 | 480 | AAUCcAUGGCGGGAGGCUCdTsdT |
| AD-52086.1 | 495 | uccuGGGcGAGAAGcAuAAdTsdT | 1922-1940 | 1922 | 496 | UuAUGCUUCUCGCCcAGGAdTsdT |
| AD-52087.1 | 511 | GGcAGcucAAAGAucccuudTsdT | 2228-2246 | 2228 | 512 | AAGGGAUCUUUGAGCUGCCdTsdT |
| AD-52088.1 | 465 | ccuuuAAccuGcuAAGAAudTsdT | 938-956 | 938 | 466 | AUUCUuAGcAGGUuAAAGGdTsdT |
| AD-52089.1 | 481 | AGccuccCGccAuGGAuuudTsdT | 1154-1172 | 1154 | 482 | AAAUCcAUGGCGGGAGGCUdTsdT |
| AD-52090.1 | 497 | GAcAcuuGcGAcGAAGAcudTsdT | 1975-1993 | 1975 | 498 | AGUCUUCGUCGcAAGUGUCdTsdT |
| AD-52091.1 | 513 | cucAAAGAucccuuccuuAdTsdT | 2233-2251 | 2233 | 514 | uAAGGAAGGGAUCUUUGAGdTsdT |
| AD-52092.1 | 467 | AGAAuAccAGGAucAGuAudTsdT | 952-970 | 952 | 468 | AuACUGAUCCUGGuAUUCUdTsdT |
| AD-52093.1 | 483 | GGAuuucucuAGGAGAcuudTsdT | 1167-1185 | 1167 | 484 | AAGUCUCCuAGAGAAAUCCdTsdT |
| AD-52094.1 | 499 | AGucGGAccGcAuAGAcGAdTsdT | 2006-2024 | 2006 | 500 | UCGUCuAUGCGGUCCGACUdTsdT |
| AD-52095.1 | 515 | AcuccAGAcAAucGccuuudTsdT | 2261-2279 | 2261 | 516 | AAAGGCGAUUGUCUGGAGUdTsdT |

TABLE 6

Unmodified siRNAs targeting BCL11a.

| Duplex Name | SEQ ID NO.: (unmodified sense oligo sequence) | Unmodified Sense Sequence | SEQ ID NO.: (unmodified anti-sense oligo sequence) | Unmodified Anti-sense oligo Sequence |
|---|---|---|---|---|
| AD-46509.6 | 666 | UUUAUCGAGCACAAACGGA | 667 | UCCGUUUGUGCUCGAUAAA |
| AD-53263.1 | 668 | UUUUUAUCGAGCACAAACGGA | 669 | UCCGUUUGUGCUCGAUAAAAUA |
| AD-53264.1 | 670 | UUUUUAUCGAGCACAAACGGA | 671 | UCCGUUUGUGCUCGAUAAAAUA |
| AD-53268.1 | 672 | UUUUUAUCGAGCACAAACGGA | 673 | UCCGUUUGUGCUCGAUAAAAUA |
| AD-53269.1 | 674 | UUUUUAUCGAGCACAAACGGA | 675 | UCCGUUUGUGCUCGAUAAAAUA |
| AD-53270.1 | 676 | UUUUUAUCGAGCACAAACGGA | 678 | UCCGUUUGUGCUCGAUAAAAUA |
| AD-53275.1 | 679 | UUUUUAUCGAGCACAAACGGA | 680 | UCCGUUUGUGCUCGAUAAAAUA |
| AD-53276.1 | 681 | UUUUUAUCGAGCACAAACGGA | 682 | UCCGUUUGUGCUCGAUAAAAUA |
| AD-53279.1 | 683 | UUUUUAUCGAGCACAAACGGA | 684 | UCCGUUUGUGCUCGAUAAAAUA |
| AD-53280.1 | 685 | UUUUUAUCGAGCACAAACGGA | 686 | UCCGUUUGUGCUCGAUAAAAUA |

TABLE 6 -continued

Unmodified siRNAs targeting BCL11a.

| Duplex Name | SEQ ID NO.: (unmodified sense oligo sequence) | Unmodified Sense Sequence | SEQ ID NO.: (unmodified anti-sense oligo sequence) | Unmodified Anti-sense oligo Sequence |
| --- | --- | --- | --- | --- |
| AD-53281.1 | 687 | UUUUUAUCGAGCACAAACGGA | 688 | UCCGUUUGUGCUCGAUAAAAAUA |
| AD-53285.1 | 689 | UUUUUAUCGAGCACAAACGGA | 690 | UCCGUUUGUGCUCGAUAAAAAUA |
| AD-53286.1 | 691 | UUUUUAUCGAGCACAAACGGA | 692 | UCCGUUUGUGCUCGAUAAAAAUA |
| AD-53287.1 | 693 | UUUUUAUCGAGCACAAACGGA | 694 | UCCGUUUGUGCUCGAUAAAAAUA |
| AD-53291.1 | 695 | UUUUUAUCGAGCACAAACGGA | 696 | UCCGUUUGUGCUCGAUAAAAAUA |
| AD-53292.1 | 697 | UUUUUAUCGAGCACAAACGGA | 698 | UCCGUUUGUGCUCGAUAAAAAUA |
| AD-53296.1 | 699 | UUUUUAUCGAGCACAAACGGA | 700 | UCCGUUUGUGCUCGAUAAAAAUA |
| AD-53297.1 | 701 | UUUUUAUCGAGCACAAACGGA | 702 | UCCGUUUGUGCUCGAUAAAAAUA |
| AD-53302.1 | 703 | UUUUUAUCGAGCACAAACGGA | 704 | UCCGUUUGUGCUCGAUAAAAAUA |
| AD-53303.1 | 705 | UUUUUAUCGAGCACAAACGGA | 706 | UCCGUUUGUGCUCGAUAAAAAUA |

TABLE 7

Modified siRNAs targeting BCL11a.

| Duplex Name | SEQ ID NO.: (Modified Sense Oligo) | Modified Sense Oligo Sequence | SEQ ID NO.: (Modified Anti-sense Oligo) | Modified Antisense Oligo Sequence |
| --- | --- | --- | --- | --- |
| AD-46509.6 | 626 | uuuAucGAGcAcAAAcGGAdTsdT | 627 | UCCGUUUGUGCUCGAuAAAdTsdT |
| AD-53263.1 | 628 | uuUfuUfaUfcGfAfGfcAfcAfaAfcGfgsAf | 629 | uCfcGfuUfuGfuGfcucGfaUfaAfaAfAfsUfsa |
| AD-53264.1 | 630 | UfuUfuUfaUfcGfAfGfcAfcAfaAfcGfgsAf | 631 | uCfcGfuUfuGfuGfcucGfaUfaAfaAfasusa |
| AD-53268.1 | 632 | UUUUUAUCGAGCACAAACGGA | 633 | UCCGUUUGUGCUCGAUAAAAAUA |
| AD-53269.1 | 634 | UfuUfuUfaUfcGfAfGfcacAfaAfcGfgsAf | 635 | uCfcGfuUfuGfUfGfcucGfaUfaAfaAfasUfsa |
| AD-53270.1 | 636 | UfuUfuUfaUfcGfAfGfcAfCfAfaAfcGfgsAf | 637 | uCfcGfuUfuguGfcucGfaUfaAfaAfasUfsa |
| AD-53275.1 | 638 | UfuUfuUfaUfcGfAfGfcAfcaaAfcGfgsAf | 639 | uCfcGfuUfUfGfuGfcucGfaUfaAfaAfasUfsa |
| AD-53276.1 | 640 | UfuUfuUfaUfcGfAfGfcAfcAfAfAfcGfgsAf | 641 | uCfcGfuuuGfuGfcucGfaUfaAfaAfasUfsa |
| AD-53279.1 | 642 | UfuUfuUfaUfcGfaGfcAfcAfaAfcGfgsAf | 643 | uCfcGfuUfuGfuGfcUfcGfaUfaAfaAfasUfsa |
| AD-53280.1 | 644 | UfuUfuUfaUfcGfAfGfcAfcAfaacGfgsAf | 645 | uCfcGfUfUfuGfuGfcucGfaUfaAfaAfasUfsa |
| AD-53281.1 | 646 | UfuUfuUfaUfcGfAfGfcAfcAfaAfCfGfgsAf | 647 | uCfcguUfuGfuGfcucGfaUfaAfaAfasUfsa |
| AD-53285.1 | 648 | UfuUfuUfaUfcGfAfGfcAfcAfaAfcGfgsAf | 649 | uCfcGfuUfuGfuGfcucGfaUfaAfaAfasUfsa |
| AD-53286.1 | 650 | UfuUfuUfaUfcGfAfGfcAfcAfaAfcggsAf | 651 | uCfCfGfuUfuGfuGfcucGfaUfaAfaAfasUfsa |
| AD-53287.1 | 652 | UfuUfuUfaUfcGfAfGfcAfcAfaAfcGfGfsAf | 653 | uccGfuUfuGfuGfcucGfaUfaAfaAfasUfsa |
| AD-53291.1 | 654 | UfuUfuUfaucGfAfGfcAfcAfaAfcGfgsAf | 655 | uCfcGfuUfuGfuGfcucGfAfUfaAfaAfasUfsa |
| AD-53292.1 | 656 | UfuUfuUfAfUfcGfAfGfcAfcAfaAfcGfgsAf | 657 | uCfcGfuUfuGfuGfcucGfauaAfaAfasUfsa |
| AD-53296.1 | 658 | UfuUfuuaUfcGfAfGfcAfcAfaAfcGfgsAf | 659 | uCfcGfuUfuGfuGfcucGfaUfAfAfaAfasUfsa |
| AD-53297.1 | 660 | UfuUfUfUfaUfcGfAfGfcAfcAfaAfcGfgsAf | 661 | uCfcGfuUfuGfuGfcucGfaUfaaaAfasUfsa |
| AD-53302.1 | 662 | UfuuuUfaUfcGfAfGfcAfcAfaAfcGfgsAf | 663 | uCfcGfuUfuGfuGfcucGfaUfaAfAfAfasUfsa |
| AD-53303.1 | 664 | UfUfUfuUfaUfcGfAfGfcAfcAfaAfcGfgsAf | 665 | uCfcGfuUfuGfuGfcucGfaUfaAfaaasUfsa |

Example 3

In vitro Screening of BCL11a siRNA Duplexes for BCL11a Knockdown Activity

BCL11a siRNA duplexes were screened for the ability to knockdown BCL11a expression in vitro. Knockdown of both endogenous and exogenously expressed BLC11a were evaluated.

In vitro Screening:
Cell Culture and Transfections:

H441, WI-38, or Hep3B cells (ATCC, Manassas, Va.) were grown to near confluence at 37° C. in an atmosphere of 5% $CO_2$ in RPMI (for H441), EMEM (for WI-38 and Hep3B) (ATCC) supplemented with 10% FBS, streptomycin, and glutamine (ATCC) before being released from the plate by trypsinization. Transfection was carried out by adding 14.8 ul of Opti-MEM plus 0.2 ul of Lipofectamine RNAiMax per well (Invitrogen, Carlsbad Calif. cat #13778-150) to 5 ul of siRNA duplexes per well into a 96-well plate and incubated at room temperature for 15 minutes. 80 ul of complete growth media without antibiotic containing ~$2\times10^4$ HeLa or Hep3B cells were then added to the siRNA mixture. Cells were incubated for either 24 or 120 hours prior to RNA purification. For knockdown of endogenously expressed BCL11a, single dose experiments were performed at 10 nM and 0.1 nM final duplex concentration and dose response experiments were done at 10, 1, 0.5, 0.1, 0.05, 0.01, 0.005, 0.001, 0.0005, 0.0001, 0.00005, 0.00001 nM final duplex concentration. For screens in which BCL11a was expressed from a plasmid the final siRNA concentration was 50 nM.

Total RNA Isolation Using DYNABEADS mRNA Isolation Kit (Invitrogen, Part #: 610-12):

Cells were harvested and lysed in 150 ul of Lysis/Binding Buffer then mixed for 5 minute at 850 rpm using an Eppendorf Thermomixer (the mixing speed was the same throughout the process). Ten microliters of magnetic beads and 80 ul Lysis/Binding Buffer mixture were added to a round bottom plate and mixed for 1 minute. Magnetic beads were captured using magnetic stand and the supernatant was removed without disturbing the beads. After removing the supernatant, the lysed cells were added to the remaining beads and mixed for 5 minutes. After removing supernatant, magnetic beads were washed twice with 150 ul Wash Buffer A and mixed for 1 minute. Beads were captured again and the supernatant removed. Beads were then washed with 150 ul Wash Buffer B, captured and the supernatant removed. Beads were next washed with 150 ul Elution Buffer, captured and the supernatant removed. Beads were allowed to dry for 2 minutes. After drying, 50 ul of Elution Buffer was added and mixed for 5 minutes at 70° C. Beads were captured on a magnet for 5 minutes. 40 ul of the supernatant was removed and added to another 96 well plate.

cDNA Synthesis Using ABI High Capacity cDNA Reverse Transcription Kit (Applied Biosystems, Foster City, Calif., Cat #4368813):

A master mix of 2 ul of 10× Buffer, 0.8 ul of 25× dNTPs, 2 ul of Random primers, 1 ul of Reverse Transcriptase, 1 ul of RNase inhibitor and 3.2 ul of H2O per reaction were added to 10 ul total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Real Time PCR:

2 µl of cDNA was added to a master mix containing 0.5 µl of GAPDH TaqMan Probe (Applied Biosystems Cat #4326317E), 0.5 µl of BCL11a TaqMan probe (Applied Biosystems cat #Hs01093198_m1 or Hs01093199_m1 or Hs00256254_m1 or Hs00250581_s1) and 5 µl of Lightcycler 480 probe master mix (Roche Cat #04887301001) per well in a 384 well 50 plate (Roche cat #04887301001). Real time PCR was done in an ABI 7900HT Real Time PCR system (Applied Biosystems) using the ΔΔCt(RQ) assay. Each duplex was tested in two independent transfections and each transfection was assayed in duplicate.

To calculate relative fold change in BCL11a expression, real time PCR data were analyzed using the ΔΔCt method and normalized to assays performed with cells transfected with 10 nM of the control siRNA AD-1955, or mock transfected cells. IC50s were calculated using a 4 parameter fit model using XLFit and normalized to cells transfected with AD-1955 over the same dose range, or to its own lowest dose.

TaqMan probes that recognize BCL11a and the RefSeq gene models they are predicted to detect are included in Table 8. Yes, indicates that the probe is expected to detect the isoform; No, indicates that the probe is not expected to detect the isoform; and Long, indicates that the RefSeq model contains the form of BCL11a with a long version of exon 4.

TABLE 8

BCL11a TaqMan probe specificity.

| | Hs01093199_m1 | Hs01093198_m1 | Hs00250581_s1* | Hs00256254_m1 |
|---|---|---|---|---|
| NM_018014.3 (long) (SEQ ID NO: 4) | Yes | No | No | Yes |
| NM_138559.1 (SEQ ID NO: 5) | No | Yes | No | Yes |
| NM_022893.3 (long) (SEQ ID NO: 3) | No | No | Yes | Yes |

Exogenous Screening:

siRNA mediated knockdown of BCL11a was also screened in an exogenous assay using an expression clone purchased from Origene (CAT# RC205816) containing the BCL11a sequence corresponding to NM_018014.2 and neomycin (Neo), which was used for normalization. Cos7 cells were sequentially transfected with 1 ng, 15 ng or 30 ng of the BCL11a plasmid and each of the siRNAs so that the final siRNA concentration was 50 nM. For transfection, 0.5 ul of Lipofectamine 2000 (Invitrogen) was mixed with 14.5 ul of Opti-MEM and 5 ul of plasmid to make a final plasmid concentration of 1, 15, or 30 ng/well. 20 ul of the mixture was distributed to each well of a 96 well plate and 80 ul of media containing ~$2\times10^4$ Cos7 cells was then added. After 4 hours, the media was removed and cells were retransfected with siRNA to give a final concentration of 50 nM. siRNA transfection was performed as described above. After 24 hrs, the cells were harvested and prepared as described and analyzed as above for qPCR except that Neo, rather than GAPDH was used as the endogenous control gene to control for plasmid copy number. Expression of each transcript was quantified using qPCR with gene specific BCL11a and Neomycin TaqMan probes (Hs00256254_m1 and Table 9). Table 10 includes the sequence of the primers and probes that made up the TaqMan assay used to detect Neo used as an endogenous control in the experiment.

TABLE 9

Neomycin TaqMan assay sequence.

| | |
|---|---|
| Forward Primer: | Neo F1 |
| Forward Primer Sequence: | TATTGCTGAAGAGCTTGG |
| Forward Primer SEQ ID NO.: | 525 |
| Reverse Primer: | Neo R1 |
| Reverse Primer Sequence: | GTCAAGAAGGCGATAGAA |
| ReversePrimer SEQ ID NO.: | 256 |
| TaqMan Probe: | Neo TP1 |
| TaqMan Probe Sequence: | TAAAGCACGAGGAAGCGG |
| TaqMan Probe SEQ ID NO.: | 527 |

In vitro Knockdown of Endogenous BCL11a Expression by BCL11a siRNA Duplexes.

Table 10 illustrates the knockdown of BCL11a in the two cell lines, H441 and WI-38, by BCL11a modified siRNA duplexes (Table 3 and Table 5). Silencing is expressed as the fraction RNA message remaining relative to the negative (luciferase) control siRNA AD-1955. Data were generated as described above following transfection of 10 nM of each siRNA. qPCR was run using the BCL11a TaqMan probe Hs00256254_m1.

TABLE 10

BCL11a expression in single dose screen in H441 and WI-38 cell lines.

| Duplex Name | H441 | WI-38 |
|---|---|---|
| AD-46498.1 | 0.89 | 1.74 |
| AD-46500.1 | 0.87 | 1.08 |
| AD-46501.1 | 1.01 | 1.28 |
| AD-46502.1 | 0.51 | 0.62 |
| AD-46503.1 | 0.43 | 0.62 |
| AD-46504.1 | 0.74 | 0.85 |
| AD-46505.1 | 0.82 | 1.07 |
| AD-46506.1 | 0.71 | 0.62 |
| AD-46507.1 | 0.59 | 0.67 |
| AD-46508.1 | 0.71 | 0.81 |
| AD-46509.1 | 0.3 | 0.34 |
| AD-46510.1 | 0.88 | 1.06 |
| AD-46511.1 | 0.93 | 0.92 |
| AD-46512.1 | 0.88 | 1.01 |
| AD-46513.1 | 0.79 | 1.14 |
| AD-46514.1 | 0.75 | 0.68 |
| AD-46515.1 | 0.55 | 0.56 |
| AD-46516.1 | 0.79 | 0.95 |
| AD-46517.1 | 0.83 | 0.81 |
| AD-46518.1 | 0.78 | 0.89 |
| AD-46519.1 | 0.94 | 0.79 |
| AD-46520.1 | 0.7 | 0.71 |
| AD-46521.1 | 0.66 | 0.67 |
| AD-46522.1 | 0.43 | 0.71 |
| AD-46523.1 | 0.51 | 0.62 |

TABLE 10-continued

BCL11a expression in single dose screen in H441 and WI-38 cell lines.

| Duplex Name | H441 | WI-38 |
|---|---|---|
| AD-46524.1 | 0.89 | 1.02 |
| AD-46525.1 | 0.5 | 0.54 |
| AD-46526.1 | 0.71 | 0.58 |
| AD-46527.1 | 0.83 | 0.68 |
| AD-46528.1 | 0.93 | 0.95 |
| AD-46529.1 | 0.82 | 0.85 |
| AD-46530.1 | 0.89 | 0.92 |
| AD-46531.1 | 0.74 | 0.57 |
| AD-46532.1 | 0.49 | 0.56 |
| AD-46533.1 | 0.55 | 0.5 |
| AD-46534.1 | 0.83 | 0.74 |
| AD-46535.1 | 0.44 | 0.63 |
| AD-46536.1 | 0.53 | 0.88 |
| AD-46537.1 | 0.81 | 0.8 |
| AD-46538.1 | 0.61 | 0.65 |
| AD-46539.1 | 0.69 | 0.57 |
| AD-46540.1 | 0.61 | 0.63 |
| AD-46541.1 | 0.8 | 0.68 |
| AD-46542.1 | 0.76 | 0.77 |
| AD-46543.1 | 0.54 | 0.61 |
| AD-1955 | 0.92 | 0.87 |
| AD-1955 | 0.95 | 0.9 |
| AD-1955 | 0.96 | 0.95 |
| AD-1955 | 0.97 | 0.96 |
| AD-1955 | 0.98 | 1 |
| AD-1955 | 0.99 | 1 |
| AD-1955 | 1.1 | 1.1 |
| AD-1955 | 1.16 | 1.27 |

In vitro Knockdown of the Long Form of BCL11a by BCL11a siRNA Duplexes.

In order to identify siRNAs that can specifically silence the long form of BCL11a; Hep3B cells were transfected with BCL11a modified siRNA duplexes (Table 3 and Table 5), processed as described above for qPCR, and probed with each of the 4 TaqMan probes in Table 8. Silencing of BCL11a by the siRNA duplex is expressed as the fraction RNA message remaining relative to the negative control siRNA AD-1955 (Table 11). As illustrated in Table 11, the siRNAs that show silencing when probed with TaqMan probe Hs01093199_m1 are specific for exon 4 long form.

TABLE 11

BCL11a expression in single dose screen to identify siRNAs that target transcripts with the long form of exon 4.

| Duplex ID | 10 nM Avg | 10 nM STDEV | 0.1 nM Avg | 0.1 nM STDEV |
|---|---|---|---|---|
| | Probe Hs01093198_m1 | | | |
| AD-52060.1 | 1.06 | 0.12 | 1.11 | 0.06 |
| AD-52061.1 | 0.79 | 0.05 | 0.88 | 0.00 |
| AD-52062.1 | 1.10 | 0.08 | 1.01 | 0.12 |
| AD-52063.1 | 0.98 | 0.11 | 1.00 | 0.06 |
| AD-52064.1 | 0.95 | 0.00 | 1.03 | 0.07 |
| AD-52065.1 | 1.18 | 0.04 | 1.05 | 0.07 |
| AD-52066.1 | 0.68 | 0.02 | 1.00 | 0.04 |
| AD-52067.1 | 1.14 | 0.09 | 1.06 | 0.02 |
| AD-52068.1 | 0.90 | 0.19 | 1.03 | 0.10 |
| AD-52069.1 | 0.92 | 0.04 | 0.96 | 0.01 |
| AD-52070.1 | 1.06 | 0.05 | 1.31 | 0.15 |
| AD-52071.1 | 1.08 | 0.26 | 1.17 | 0.11 |
| AD-52072.1 | 1.14 | 0.10 | 1.10 | 0.03 |
| AD-52073.1 | 1.04 | 0.01 | 1.12 | 0.02 |
| AD-52074.1 | 1.07 | 0.01 | 1.08 | 0.09 |
| AD-52075.1 | 1.24 | 0.04 | 1.17 | 0.05 |
| AD-52076.1 | 1.02 | 0.12 | 1.03 | 0.05 |
| AD-52077.1 | 0.77 | 0.34 | 1.29 | 0.07 |
| AD-52078.1 | 1.03 | 0.10 | 1.13 | 0.03 |
| AD-52079.1 | 1.15 | 0.13 | 0.96 | 0.16 |

TABLE 11-continued

BCL11a expression in single dose screen to identify siRNAs that target transcripts with the long form of exon 4.

| Duplex ID | 10 nM Avg | 10 nM STDEV | 0.1 nM Avg | 0.1 nM STDEV |
|---|---|---|---|---|
| AD-52080.1 | 1.13 | 0.08 | 1.12 | 0.09 |
| AD-52081.1 | 1.26 | 0.01 | 1.12 | 0.06 |
| AD-52082.1 | 1.04 | 0.11 | 1.15 | 0.14 |
| AD-52083.1 | 1.27 | 0.04 | 1.29 | 0.00 |
| AD-52084.1 | 1.31 | 0.24 | 1.04 | 0.12 |
| AD-52085.1 | 1.07 | 0.10 | 0.98 | 0.13 |
| AD-52086.1 | 1.00 | 0.00 | 1.22 | 0.07 |
| AD-52087.1 | 1.34 | 0.01 | 1.21 | 0.10 |
| AD-52088.1 | 1.02 | 0.20 | 1.08 | 0.20 |
| AD-52089.1 | 1.37 | 0.11 | 1.08 | 0.01 |
| AD-52090.1 | 0.81 | 0.01 | 1.11 | 0.32 |
| AD-52091.1 | 1.00 | 0.11 | 1.11 | 0.21 |
| AD-52092.1 | 1.16 | 0.02 | 1.17 | 0.06 |
| AD-52093.1 | 1.23 | 0.05 | 1.08 | 0.00 |
| AD-52094.1 | 1.00 | 0.14 | 1.07 | 0.01 |
| AD-52095.1 | 1.12 | 0.10 | 1.11 | 0.13 |
| Probe Hs01093199_m1 | | | | |
| AD-52060.1 | 0.92 | 0.14 | 1.00 | 0.16 |
| AD-52061.1 | 0.46 | 0.01 | 0.27 | 0.01 |
| AD-52062.1 | 0.77 | 0.04 | 0.84 | 0.02 |
| AD-52063.1 | 0.97 | 0.19 | 1.00 | 0.00 |
| AD-52064.1 | 0.76 | 0.09 | 0.96 | 0.08 |
| AD-52065.1 | 0.31 | 0.07 | 0.35 | 0.01 |
| AD-52066.1 | 0.43 | 0.04 | 0.45 | 0.03 |
| AD-52067.1 | 0.36 | 0.05 | 0.44 | 0.11 |
| AD-52068.1 | 0.90 | 0.28 | 1.03 | 0.08 |
| AD-52069.1 | 0.92 | 0.13 | 0.93 | 0.04 |
| AD-52070.1 | 0.75 | 0.01 | 1.19 | 0.05 |
| AD-52071.1 | 1.02 | 0.12 | 1.10 | 0.06 |
| AD-52072.1 | 0.49 | 0.09 | 0.44 | 0.05 |
| AD-52073.1 | 1.05 | 0.08 | 1.06 | 0.12 |
| AD-52074.1 | 0.71 | 0.11 | 0.89 | 0.05 |
| AD-52075.1 | 0.86 | 0.07 | 0.79 | 0.05 |
| AD-52076.1 | 1.23 | 0.05 | 1.04 | 0.08 |
| AD-52077.1 | 0.83 | 0.63 | 1.33 | 0.36 |
| AD-52078.1 | 0.69 | 0.10 | 0.95 | 0.05 |
| AD-52079.1 | 0.65 | 0.07 | 0.77 | 0.09 |
| AD-52080.1 | 0.90 | 0.06 | 0.94 | 0.17 |
| AD-52081.1 | 1.12 | 0.13 | 1.06 | 0.08 |
| AD-52082.1 | 0.74 | 0.13 | 1.07 | 0.07 |
| AD-52083.1 | 1.16 | 0.08 | 1.27 | 0.01 |
| AD-52084.1 | 1.02 | 0.29 | 0.91 | 0.01 |
| AD-52085.1 | 1.25 | 0.24 | 1.06 | 0.10 |
| AD-52086.1 | 1.02 | 0.03 | 1.22 | 0.15 |
| AD-52087.1 | 1.28 | 0.11 | 1.23 | 0.14 |
| AD-52088.1 | 0.39 | 0.02 | 0.43 | 0.08 |
| AD-52089.1 | 1.58 | 0.13 | 1.15 | 0.05 |
| AD-52090.1 | 1.03 | 0.08 | 1.29 | 0.26 |
| AD-52091.1 | 0.43 | 0.04 | 0.49 | 0.16 |
| AD-52092.1 | 1.04 | 0.05 | 1.09 | 0.11 |
| AD-52093.1 | 0.73 | 0.15 | 0.83 | 0.09 |
| AD-52094.1 | 0.45 | 0.18 | 0.72 | 0.01 |
| AD-52095.1 | 0.22 | 0.04 | 0.30 | 0.02 |
| Probe Hs00256254_m1 | | | | |
| AD-52060.1 | 0.99 | 0.01 | 1.10 | 0.09 |
| AD-52061.1 | 0.73 | 0.07 | 0.78 | 0.04 |
| AD-52062.1 | 1.02 | 0.11 | 1.17 | 0.22 |
| AD-52063.1 | 0.96 | 0.11 | 0.97 | 0.04 |
| AD-52064.1 | 0.96 | 0.08 | 1.01 | 0.01 |
| AD-52065.1 | 1.02 | 0.01 | 0.93 | 0.04 |
| AD-52066.1 | 0.72 | 0.03 | 0.87 | 0.09 |
| AD-52067.1 | 0.94 | 0.02 | 0.95 | 0.10 |
| AD-52068.1 | 1.00 | 0.18 | 1.19 | 0.06 |
| AD-52069.1 | 1.03 | 0.05 | 1.04 | 0.04 |
| AD-52070.1 | 1.10 | 0.04 | 1.14 | 0.03 |
| AD-52071.1 | 1.15 | 0.13 | 1.24 | 0.02 |
| AD-52072.1 | 0.88 | 0.02 | 1.07 | 0.02 |
| AD-52073.1 | 1.17 | 0.11 | 1.25 | 0.03 |
| AD-52074.1 | 1.04 | 0.03 | 1.03 | 0.11 |
| AD-52075.1 | 1.34 | 0.01 | 1.12 | 0.11 |
| AD-52076.1 | 1.17 | 0.01 | 1.12 | 0.06 |
| AD-52077.1 | 1.19 | 0.07 | 1.22 | 0.14 |
| AD-52078.1 | 1.11 | 0.03 | 1.19 | 0.04 |
| AD-52079.1 | 1.13 | 0.04 | 1.17 | 0.16 |
| AD-52080.1 | 1.20 | 0.04 | 1.11 | 0.05 |
| AD-52081.1 | 1.08 | 0.08 | 1.15 | 0.03 |
| AD-52082.1 | 1.13 | 0.07 | 1.13 | 0.06 |
| AD-52083.1 | 1.33 | 0.01 | 1.22 | 0.01 |
| AD-52084.1 | 1.13 | 0.03 | 1.12 | 0.03 |
| AD-52085.1 | 1.10 | 0.04 | 1.08 | 0.04 |
| AD-52086.1 | 1.11 | 0.06 | 1.15 | 0.02 |
| AD-52087.1 | 1.41 | 0.15 | 1.14 | 0.02 |
| AD-52088.1 | 0.87 | 0.11 | 0.90 | 0.12 |
| AD-52089.1 | 1.21 | 0.05 | 1.26 | 0.03 |
| AD-52090.1 | 1.39 | 0.07 | 1.41 | 0.12 |
| AD-52091.1 | 0.90 | 0.07 | 1.00 | 0.02 |
| AD-52092.1 | 1.32 | 0.30 | 1.21 | 0.08 |
| AD-52093.1 | 1.04 | 0.08 | 1.10 | 0.00 |
| AD-52094.1 | 0.88 | 0.09 | 1.10 | 0.16 |
| AD-52095.1 | 0.93 | 0.04 | 0.97 | 0.09 |
| Probe Hs00250581_s1 | | | | |
| AD-52060.1 | 0.93 | 0.13 | 1.13 | 0.22 |
| AD-52061.1 | 1.06 | 0.05 | 0.85 | 0.04 |
| AD-52062.1 | 0.91 | 0.10 | 1.05 | 0.37 |
| AD-52063.1 | 0.82 | 0.36 | 0.94 | 0.12 |
| AD-52064.1 | 0.99 | 0.08 | 1.00 | 0.12 |
| AD-52065.1 | 0.78 | 0.02 | 0.86 | 0.01 |
| AD-52066.1 | 0.84 | 0.02 | 0.90 | 0.01 |
| AD-52067.1 | 0.89 | 0.03 | 0.94 | 0.12 |
| AD-52068.1 | 1.16 | 0.12 | 1.38 | 0.25 |
| AD-52069.1 | 1.27 | 0.15 | 1.08 | 0.01 |
| AD-52070.1 | 1.06 | 0.05 | 1.24 | 0.00 |
| AD-52071.1 | 1.39 | 0.03 | 1.37 | 0.09 |
| AD-52072.1 | 0.94 | 0.00 | 0.98 | 0.02 |
| AD-52073.1 | 1.22 | 0.14 | 1.39 | 0.10 |
| AD-52074.1 | 1.01 | 0.08 | 0.98 | 0.02 |
| AD-52075.1 | 1.38 | 0.03 | 1.23 | 0.15 |
| AD-52076.1 | 1.36 | 0.10 | 1.37 | 0.11 |
| AD-52077.1 | 1.60 | 0.19 | 1.33 | 0.15 |
| AD-52078.1 | 1.19 | 0.14 | 1.21 | 0.04 |
| AD-52079.1 | 1.10 | 0.09 | 1.43 | 0.46 |
| AD-52080.1 | 1.20 | 0.04 | 1.28 | 0.05 |
| AD-52081.1 | 1.01 | 0.11 | 1.30 | 0.18 |
| AD-52082.1 | 1.26 | 0.01 | 1.29 | 0.01 |
| AD-52083.1 | 1.57 | 0.04 | 1.42 | 0.06 |
| AD-52084.1 | 1.06 | 0.03 | 1.15 | 0.03 |
| AD-52085.1 | 1.32 | 0.26 | 1.20 | 0.03 |
| AD-52086.1 | 1.32 | 0.00 | 1.42 | 0.14 |
| AD-52087.1 | 1.61 | 0.17 | 1.28 | 0.02 |
| AD-52088.1 | 0.88 | 0.07 | 0.94 | 0.18 |
| AD-52089.1 | 1.43 | 0.01 | 1.41 | 0.02 |
| AD-52090.1 | 2.65 | 0.04 | 1.93 | 0.12 |
| AD-52091.1 | 1.04 | 0.15 | 1.02 | 0.02 |
| AD-52092.1 | 1.31 | 0.20 | 1.29 | 0.09 |
| AD-52093.1 | 1.29 | 0.04 | 1.27 | 0.10 |
| AD-52094.1 | 1.12 | 0.16 | 1.34 | 0.09 |
| AD-52095.1 | 0.82 | 0.08 | 0.74 | 0.18 |

In vitro Knockdown of Exogenously Expressed BCL11a by BCL11a siRNA Duplexes.

Table 12 illustrates the knockdown of exogenously expressed BCL11a in the COST cell line, by BCL11a modified siRNA duplexes (Table 3 and Table 5). Silencing is expressed as the fraction mRNA message remaining relative to the negative control siRNA AD-1955. Data were generated as described above following transfection of 50 nM of each siRNA.

TABLE 12

Single siRNA dose knockdown of exogenously expressed BCL11a in Cos7 cells.

| Duplex Name | Ave 50 nM siRNA/30 ng BCL11a plasmid | SD 30 ng | Ave 50 nM siRNA/15 ng BCL11a plasmid | SD 15 ng | Ave 50 nM siRNA/15 ng BCL11a plasmid | SD 1 ng |
|---|---|---|---|---|---|---|
| AD-46498.1 | 0.58 | 0.02 | 0.64 | 0.09 | 0.88 | 0.62 |
| AD-46500.1 | 0.77 | 0.07 | 0.78 | 0.14 | 0.94 | 0.31 |
| AD-46501.1 | 0.81 | 0.03 | 0.74 | 0.04 | 1.11 | 0.23 |
| AD-46502.1 | 0.26 | 0.03 | 0.30 | 0.05 | 0.36 | 0.13 |
| AD-46503.1 | 0.25 | 0.01 | 0.29 | 0.04 | 0.28 | 0.06 |
| AD-46504.1 | 0.56 | 0.09 | 0.45 | 0.01 | 0.46 | 0.08 |
| AD-46505.1 | 0.73 | 0.03 | 0.64 | 0.03 | 0.95 | 0.27 |
| AD-46506.1 | 0.59 | 0.03 | 0.68 | 0.03 | 0.67 | 0.08 |
| AD-46507.1 | 0.24 | 0.03 | 0.30 | 0.01 | 0.51 | 0.09 |
| AD-46508.1 | 0.56 | 0.01 | 0.68 | 0.08 | 0.98 | 0.17 |
| AD-46509.1 | 0.20 | 0.02 | 0.26 | 0.01 | 0.29 | 0.00 |
| AD-46510.1 | 0.70 | 0.04 | 0.71 | 0.25 | 0.49 | 0.20 |
| AD-46511.1 | 0.71 | 0.01 | 0.74 | 0.03 | 0.94 | 0.40 |
| AD-46512.1 | 0.82 | 0.08 | 0.87 | 0.15 | 0.71 | 0.06 |
| AD-46513.1 | 0.36 | 0.04 | 0.47 | 0.07 | 0.57 | 0.17 |
| AD-46514.1 | 0.28 | 0.02 | 0.46 | 0.09 | 0.57 | 0.43 |
| AD-46515.1 | 0.38 | 0.03 | 0.36 | 0.03 | 0.59 | 0.36 |
| AD-46516.1 | 0.60 | 0.09 | 0.67 | 0.16 | 0.44 | 0.20 |
| AD-46517.1 | 0.86 | 0.04 | 0.92 | 0.10 | 0.48 | 0.11 |
| AD-46518.1 | 0.74 | 0.01 | 0.82 | 0.04 | 0.71 | 0.25 |
| AD-46519.1 | 0.51 | 0.06 | 0.48 | 0.03 | 0.45 | 0.27 |
| AD-46520.1 | 0.30 | 0.00 | 0.45 | 0.00 | 0.45 | 0.02 |
| AD-46521.1 | 0.44 | 0.01 | 0.46 | 0.06 | 0.37 | 0.03 |
| AD-46522.1 | 0.23 | 0.03 | 0.28 | 0.00 | 1.36 | 1.54 |
| AD-46523.1 | 0.39 | 0.07 | 0.36 | 0.02 | 0.39 | 0.05 |
| AD-46524.1 | 0.69 | 0.09 | 0.74 | 0.15 | 0.77 | 0.00 |
| AD-46525.1 | 0.27 | 0.03 | 0.34 | 0.04 | 0.68 | 0.15 |
| AD-46526.1 | 0.27 | 0.02 | 0.30 | 0.01 | 0.41 | 0.02 |
| AD-46527.1 | 0.83 | 0.25 | 0.67 | 0.13 | 0.68 | 0.26 |
| AD-46528.1 | 0.99 | 0.22 | 0.78 | 0.06 | 0.62 | 0.28 |
| AD-46529.1 | 0.52 | 0.42 | 0.33 | 0.07 | 0.38 | 0.11 |
| AD-46530.1 | 0.88 | 0.05 | 0.82 | 0.01 | 0.46 | 0.02 |
| AD-46531.1 | 0.59 | 0.10 | 0.63 | 0.05 | 0.60 | 0.11 |
| AD-46532.1 | 0.61 | 0.54 | 0.29 | 0.06 | 0.34 | 0.08 |
| AD-46533.1 | 0.39 | 0.05 | 0.39 | 0.06 | 0.35 | 0.07 |
| AD-46534.1 | 0.67 | 0.04 | 0.78 | 0.11 | 0.67 | 0.15 |
| AD-46535.1 | 0.30 | 0.04 | 0.28 | 0.03 | 0.21 | 0.06 |
| AD-46536.1 | 0.24 | 0.05 | 0.25 | 0.01 | 0.67 | 0.56 |
| AD-46537.1 | 0.40 | 0.05 | 0.51 | 0.06 | 0.61 | 0.08 |
| AD-46538.1 | 0.35 | 0.09 | 0.42 | 0.03 | 0.31 | 0.08 |
| AD-46539.1 | 0.49 | 0.03 | 0.44 | 0.01 | 0.63 | 0.45 |
| AD-46540.1 | 0.42 | 0.04 | 0.39 | 0.07 | 0.55 | 0.22 |
| AD-46541.1 | 0.75 | 0.03 | 0.71 | 0.03 | 0.87 | 0.23 |
| AD-46542.1 | 0.37 | 0.01 | 0.36 | 0.02 | 0.39 | 0.09 |
| AD-46543.1 | 0.26 | 0.01 | 0.30 | 0.02 | 0.34 | 0.11 |

$IC_{50}$ of Select BCL11a siRNA Duplexes in in vitro Screen.

Tables 13-14 and FIGS. 9A-9D illustrate the $IC_{50}$ of select BCL11a duplexes determined from the knockdown of exogenously expressed BCL11a in the COST cell line, by BCL11a modified siRNA duplexes (Table 3 and Table 5). Data were generated as described above following transfection of each siRNA duplex. Silencing of BCL11a is expressed as the fraction mRNA message remaining relative to the negative control siRNA AD-1955 (Table 13 and FIGS. 9A-9B) or to that of the lowest tested siRNA dose (Table 14 and FIGS. 9C-9D). $IC_{50}$ plots are an average of 2 biological replicates. As illustrated in Tables 13-14 and FIGS. 9A-9D, the majority of BLC11a siRNA duplexes knocked down BCL11a gene expression even at the lowest tested siRNA dose.

TABLE 13

$IC_{50}$ of select BCL11a siRNA duplexes normalized to AD-1955.

| Duplex Tested | IC50: in [nM] Normalized to AD-1955 |
|---|---|
| AD-46536.1 | 0.002 |
| AD-46535.1 | 0.003 |
| AD-46509.1 | 0.004 |
| AD-46529.1 | 0.004 |
| AD-46503.1 | 0.009 |
| AD-46525.1 | 0.009 |
| AD-46502.1 | 0.016 |
| AD-46523.1 | 0.016 |
| AD-46543.1 | 0.024 |
| AD-46515.1 | 0.038 |
| AD-46532.1 | 0.038 |
| AD-46542.1 | 0.057 |
| AD-46522.1 | 0.069 |
| AD-46533.1 | 0.069 |
| AD-46538.1 | 0.096 |
| AD-46507.1 | 1.166 |
| AD-46526.1 | 1.166 |

TABLE 14

IC$_{50}$ of select BCL11a siRNA duplexes normalized to the lowest tested BCL11a siRNA dose.

| Duplex Tested | IC50: in [nM] normalized to Lowest Dose |
|---|---|
| AD-46509.1 | 0.009 |
| AD-46503.1 | 0.020 |
| AD-46525.1 | 0.030 |
| AD-46502.1 | 0.043 |
| AD-46543.1 | 0.120 |
| AD-46535.1 | 0.144 |
| AD-46522.1 | 0.144 |
| AD-46542.1 | 0.173 |
| AD-46523.1 | 0.260 |
| AD-46515.1 | 0.304 |
| AD-46526.1 | 0.602 |
| AD-46529.1 | 0.627 |
| AD-46532.1 | 1.118 |
| AD-46507.1 | 1.730 |
| AD-46533.1 | 1.037 |
| AD-46536.1 | 6.153 |
| AD-46538.1 | #Intersect |

Efficacy of Select BCL11a siRNA Duplexes in in vitro Screen.

Table 15 illustrates the efficacy of select BCL11a siRNA duplexes determined as described above. Silencing of BCL11a is expressed as the fraction mRNA message remaining relative to the negative control siRNA AD-1955 (Table 15).

TABLE 15

Efficacy of select BCL11a siRNA duplexes in in vitro screen.

| Duplex ID | 10 nM Avg | 10 nM SD | 0.1 nM Avg | 0.1 nM SD | Dose response IC50 (nM) |
|---|---|---|---|---|---|
| AD-46509.6 | 0.18 | 0.02 | 0.25 | 0.02 | 0.025 |
| AD-53263.1 | 0.53 | 0.09 | 0.82 | 0.13 | |
| AD-53264.1 | 0.50 | 0.07 | 0.66 | 0.13 | |
| AD-53268.1 | 0.25 | 0.01 | 0.36 | 0.07 | 0.120 |
| AD-53269.1 | 0.63 | 0.09 | 0.79 | 0.06 | |
| AD-53270.1 | 0.51 | 0.11 | 0.73 | 0.11 | |
| AD-53275.1 | 0.26 | 0.06 | 0.51 | 0.10 | 0.505 |
| AD-53276.1 | 0.68 | 0.03 | 0.84 | 0.05 | |
| AD-53279.1 | 0.77 | 0.08 | 1.02 | 0.03 | |
| AD-53280.1 | 0.32 | 0.08 | 0.64 | 0.20 | 0.664 |
| AD-53281.1 | 0.53 | 0.05 | 0.73 | 0.14 | |
| AD-53285.1 | 0.48 | 0.06 | 0.83 | 0.05 | |
| AD-53286.1 | 0.58 | 0.05 | 0.82 | 0.21 | |
| AD-53287.1 | 0.81 | 0.07 | 0.92 | 0.07 | |
| AD-53291.1 | 0.64 | 0.05 | 0.81 | 0.05 | |
| AD-53292.1 | 0.50 | 0.01 | 0.75 | 0.18 | |
| AD-53296.1 | 0.58 | 0.05 | 0.76 | 0.15 | |
| AD-53297.1 | 0.67 | 0.08 | 0.76 | 0.12 | |
| AD-53302.1 | 0.51 | 0.08 | 0.74 | 0.05 | |
| AD-53303.1 | 0.83 | 0.05 | 1.11 | 0.20 | |
| AD-1955 | 1.00 | 0.00 | | | |
| naive | 0.91 | 0.09 | | | |

Selected exemplary siRNA duplexes showing inhibitory activities included:

For inhibition of human KLF1, AD-46095 showed an IC50 of 36 pM.

TABLE 15A

The sequences of selected sense and antisense umodified duplexes are as follows:

| Duplex ID | SEQ ID NO: | Sense | Position at 5' end of SEQ ID NO: 1 | Antisense | SEQ ID NO: |
|---|---|---|---|---|---|
| AD-46095.1 | 89 | CCUUAUUGUGGCUGAUAUU | 1550-1568 | AAUAUCAGCCACAAUAAGG | 90 |
| AD-46134.1 | 55 | UGUCCAAACUGUCGUGCAA | 1394-1412 | UUGCACGACAGUUUGGACA | 56 |
| AD-46115.1 | 33 | UGGUUUUCCCACGAAUGGA | 1251-1269 | UCCAUUCGUGGGAAAACCA | 34 |
| AD-46112.1 | 79 | GCUCCUGAAGGUCCCUUAU | 1537-1555 | AUAAGGGACCUUCAGGAGC | 80 |
| AD-46111.1 | 63 | UGAGACAGACCGCCAAAUA | 1419-1437 | UAUUUGGCGGUCUGUCUCA | 64 |

TABLE 15B

Corresponding modified duplex sequences

| Duplex ID | SEQ ID NO: | Sense | Position at 5' end of SEQ ID NO: 1 | Antisense | SEQ ID NO: |
|---|---|---|---|---|---|
| AD-46095.1 | 558 | ccuuAuuGuGGcuGAuAuudTsdT | 1550-1568 | AAuAUcAGCcAcAAuAAGGdTsdT | 559 |
| AD-46134.1 | 614 | uGuccAAAcuGucGuGcAAdTsdT | 1394-1412 | UUGcACGAcAGUUUGGAcAdTsdT | 615 |
| AD-46115.1 | 612 | uGGuuuucccAcGAAuGGAdTsdT | 1251-1269 | UCcAUUCGUGGGAAAACcAdTsdT | 613 |
| AD-46112.1 | 586 | GcuccuGAAGGucccuuAudTsdT | 1537-1555 | AuAAGGGACCUUcAGGAGCdTsdT | 587 |
| AD-46111.1 | 604 | uGAGAcAGAccGccAAAuAdTsdT | 1419-1437 | uAUUUGGCGGUCUGUCUcAdTsdT | 605 |

For inhibition of human and mouse BCL11a, AD-46509 showed an IC50 of 4 pM.

The sequences of selected sense and antisense unmodified duplexes are as follows:

Positions are relative to NM_022893.3 (SEQ ID NO:3).

TABLE 15C

| Duplex ID | SEQ ID NO: | Sense | Position at 5' end of SEQ ID NO: 3 | Antisense | SEQ ID NO: | Duplex ID |
|---|---|---|---|---|---|---|
| AD-46509.1 | 201 | UUUAUCGAGCACAAACGGA | 415-433 | 415 | 202 | UCCGUUUGUGCUCGAUAAA |
| AD-46536.1 | 257 | CCCGCAGGGUAUUUGUAAA | 702-720 | 702 | 258 | UUUACAAAUACCCUGCGGG |
| AD-46535.1 | 241 | CAAACAGGAACACAUAGCA | 594-612 | 594 | 242 | UGCUAUGUGUUCCUGUUUG |
| AD-46529.1 | 239 | ACGUCAUCUAGAGGAAUUU | 571-589 | 571 | 240 | AAAUUCCUCUAGAUGACGU |

Corresponding modified duplex sequences

TABLE 15D

| Duplex ID | SEQ ID NO: | Sense | Position at 5' end of SEQ ID NO: 3 | Antisense | SEQ ID NO: | Duplex ID |
|---|---|---|---|---|---|---|
| AD-46509.1 | 293 | uuuAucGAGcAcAAAcGGAdTsdT | 415-433 | 415 | 294 | UCCGUUUGUGCUCGAuAAAdTsdT |
| AD-46535.1 | 331 | cAAAcAGGAAcAcAuAGcAdTsdT | 594-612 | 594 | 332 | UGCuAUGUGUUCCUGUUUGdTsdT |
| AD-46529.1 | 329 | AcGucAucuAGAGGAAuuudTsdT | 571-589 | 571 | 330 | AAAUUCCUCuAGAUGACGUdTsdT |

Additional selected duplexes include:

AD53268:

Modified Sense: SEQ ID NO:632

Unmodified Sense: SEQ ID NO:672

Modified Anti-sense: SEQ ID NO:633

Unmodified anti-sense: SEQ ID NO:673

AD-53275:

Modified Sense: SEQ ID NO:638

Unmodified sense: SEQ ID NO:679

Modified Anti-sense: SEQ ID NO:639

Unmodified anti-sense: SEQ ID NO:680

For inhibition of mouse KLF1, AD-46151 (sense sequence: cuuuccAGGuuccGAGucudTsdT, SEQ ID NO: 681, and antisense sequence AGACUCGGAACCUG-GAAAGdTsdT, SEQ ID NO: 682) showed an IC50 of 3 pM.

Example 4

Figure 10A:
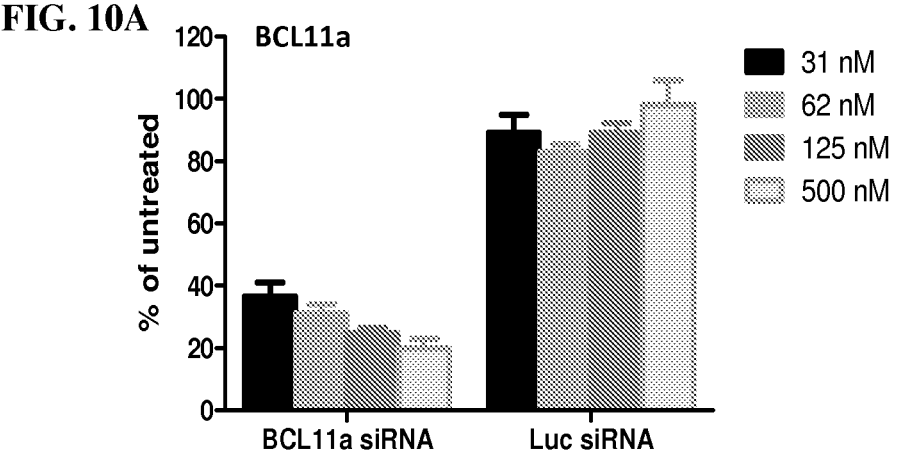
FIGS. 10A and 10B depict the increased expression of mouse embryonic hemoglobin post BCL11a siRNA mediated knockdown of BCL11a in a murine erythroleukemic cell line.
Figure 10B:
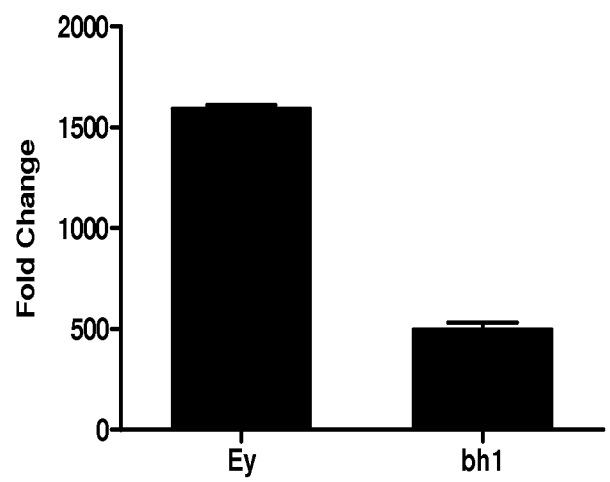

In vitro Mouse Embryonic Hemoglobin Switching Post BCL11a Knockdown by BCL11a siRNA Duplex In order to evaluate the effect of BCL11a siRNA-mediated silencing of BCL11a on embryonic hemoglobin switching, MEL cells were transfected with a BCL11a siRNA or control Luc siRNA. BCL11a siRNA duplexes were transfected at concentrations of 31 nM, 62 nM, 125 nM, or 500 nM, (using the AF-009 (also called LNP09) delivery vehicle). Twenty four hours post transfection the level of BCL11a expression was evaluated as described above. As illustrated in FIG. 10A, there was a dose dependent knockdown of BCL11a expression 24 hours post transfection with BCL11a siRNA. This knockdown of BCL11a expression correlated with increased expression of the mouse embryonic hemoglobin genes εγ and bh1, measured 72 hours post siRNA transfection (FIG. 10B).

Figure 11A:
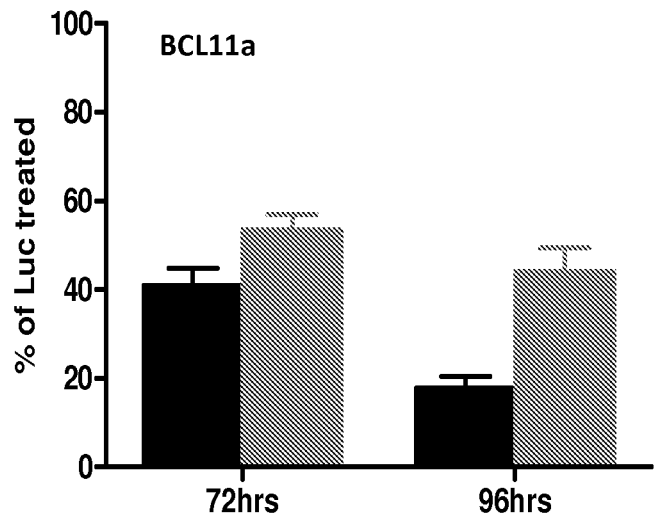
FIGS. 11A and 11B depict the increased expression of mouse embryonic hemoglobin post BCL11a siRNA mediated knockdown of BCL11a in murine bone marrow progenitor cells.
Figure 11B:
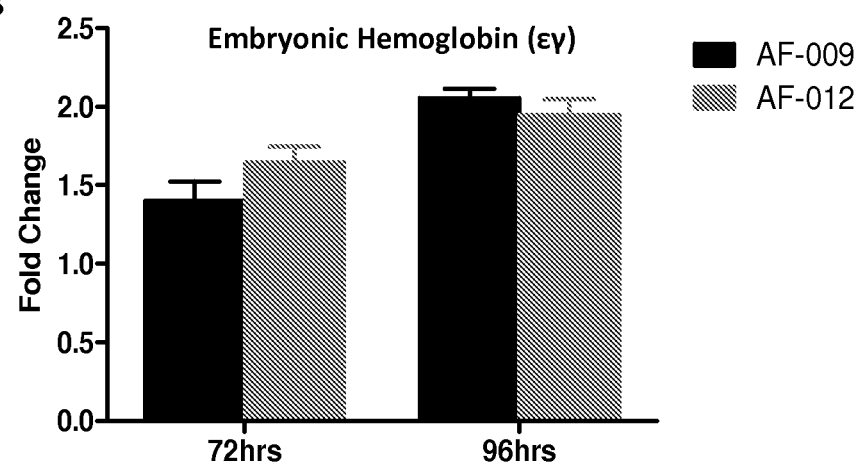

In addition, mouse bone marrow progenitor cells were isolated by negative selection and cultured in erythroid differentiation media. The cells were subsequently transfected with 1 µM BCL11a siRNA or control Luc siRNA using two separate siRNA delivery vehicles (AF-009 or AF-012 (also called LNP12). Seventy-two and ninety-six hours post transfection, the level of BCL11a expression was evaluated as described above. As illustrated in FIG. 11A, knockdown of BCL11a expression at both 72 and 96 hours post transfection with BCL11a siRNA was observed. This knockdown of BCL11a expression correlated with increased expression of the mouse embryonic hemoglobin gene εγ, measured at both 72 and 96 hours post siRNA transfection (FIG. 11B).

Example 5

In vivo Detection of Mouse Embryonic Hemoglobin Switching

Figure 12A:
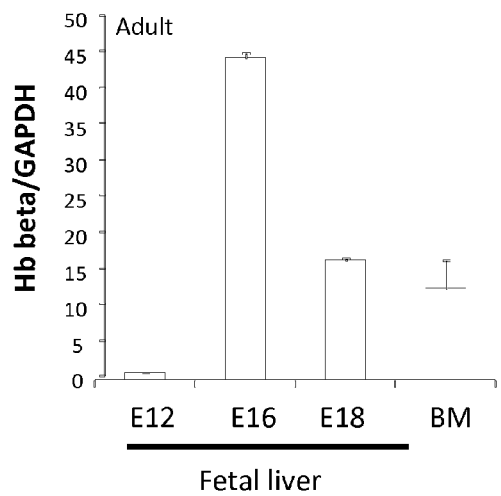
FIGS. 12A-12C depict the detection of mouse hemoglobin switching in vivo.
Figure 12B:
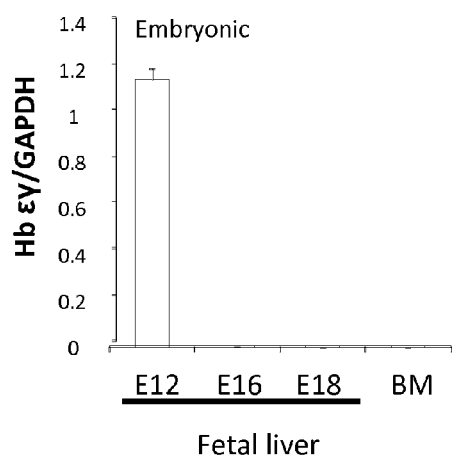
Figure 12C:
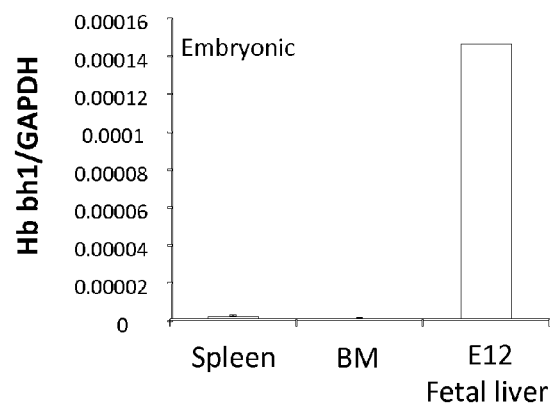

In addition, mouse embryonic hemoglobin switching can be detected in vivo. As shown in FIGS. 12A-12C, mouse adult globin (bmaj) was detected at the E16 developmental stage, and later developmental time points, including E18, as well as in the bone marrow. Bmaj is depicted in FIG. 12 as Hb beta. No significant expression was detected in the E12 developmental stage (FIG. 12A). However, embryonic globin εγ (eps) was only detected in E12 fetal liver samples. Embryonic globin εγ was no longer expressed in later developmental time points, including E16 and E18, nor in the mouse bone marrow (FIG. 12B). Embryonic globin bh1 was also detected at the E12 developmental stage and not in the mouse bone marrow or spleen (FIG. 12C). A schematic representation of the hemoglobin genes is depicted in FIG. 12E. These data demonstrate the ability to detect mouse embryonic hemoglobin switching in vivo.

Example 6

In vitro Screening of KLF siRNA Duplexes for KLF Knockdown Activity

KLF siRNA duplexes were screened for the ability to knockdown KLF expression in vitro. Knockdown of both endogenous and exogenously expressed KLF were evaluated.
In vitro Screening:
Cell Culture and Transfections:
Cos7 cells (ATCC, Manassas, Va.) were grown to near confluence at 37° C. in an atmosphere of 5% $CO_2$ in DMEM (ATCC) supplemented with 10% FBS, streptomycin, and glutamine (ATCC) before being released from the plate by trypsinization.
KLF1 was screened in an exogenous assay using an expression clone purchased from Origene (CAT# SC323869) containing the KLF1 sequence corresponding to NM_006563.2 and neomycin, which was used for normalization. Cos7 cells were sequentially transfected with 15 ng or 30 ng of the KLF1 plasmid and each of the siRNAs so that the final siRNA concentration was 50 nM, 5 nM or 0.5 nM for efficacy screens and in 12, 3 fold dilutions between 50 nM and 300 pM for dose response screens. For transfection, 0.5 ul of Lipofectamine 2000 (Invitrogen) was mixed with 14.5 ul of Opti-MEM and 5 ul of plasmid to reach the final plasmid concentration. 20 ul of the mixture was distributed to each well of a 96 well plate and 80 ul of media containing ~$2 \times 10^4$ Cos7 cells was then added. After 4 hours, media was removed and cells were retransfected with siRNA. After 24 hrs, cells were harvested and prepared for qPCR.

Total RNA Isolation Using DYNABEADS® mRNA Isolation Kit (Invitrogen, Part #: 610-12):
Cells were harvested and lysed in 150 µl of Lysis/Binding Buffer then mixed for 5 minute at 850 rpm using an Eppendorf® Thermomixer (the mixing speed was the same throughout the process). Ten microliters of magnetic beads and 80 µl of Lysis/Binding Buffer mixture were added to a round bottom plate and mixed for 1 minute. Magnetic beads were captured using a magnetic stand and the supernatant was removed without disturbing the beads. After removing supernatant, the lysed cells were added to the remaining beads and mixed for 5 minutes. After removing supernatant, the magnetic beads were washed 2 times with 150 µl Wash Buffer A and mixed for 1 minute. Beads were capture again and the supernatant removed. The beads were then washed with 150 µl Wash Buffer B, captured and supernatant was removed. The beads were next washed with 150 µl Elution Buffer, captured and supernatant removed. The beads were allowed to dry for 2 minutes. After drying, 50 µl of Elution Buffer was added and mixed for 5 minutes at 70° C. Beads were captured on magnet for 5 minutes. 40 µl of supernatant was removed and added to another 96 well plate.
cDNA Synthesis Using ABI High Capacity cDNA Reverse Transcription Kit (Applied Biosystems, Foster City, Calif., Cat #4368813):
A master mix of 2 µl 10× Buffer, 0.8 µl 25× dNTPs, 2 µl Random primers, 1 µl Reverse Transcriptase, 1 µl RNase inhibitor and 3.2 µl of H2O per reaction were added into 10 µl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.
Real Time PCR:
2 µl of cDNA were added to a master mix containing 0.5 µl Neo TaqMan Probe (Table 9), 0.5 µl KLF1 TaqMan probe (Applied Biosystems cat #Hs00610592_m1) and 5 µl Lightcycler 480 probe master mix (Roche Cat #04887301001) per well in a 384 well 50 plates (Roche cat #04887301001). Real time PCR was done in an ABI 7900HT Real Time PCR system (Applied Biosystems) using the ΔΔCt(RQ) assay. Each duplex was tested in at least two independent transfections and each transfection was assayed in duplicate, unless otherwise noted in the summary tables.
To calculate relative fold change, real time data were analyzed using the ΔΔCt method and normalized to assays performed with cells transfected with AD-1955, or mock transfected cells. IC50s were calculated using a 4 parameter fit model using XLFit and normalized to cells transfected with AD-1955 over the same dose range, or to its own lowest dose.
In vitro Efficacy of 19Mer KLF siRNA Duplexes for KLF Silencing Activity.
Table 16 illustrates the knockdown of KLF in COST cells transfected with 19mer modified siRNA duplexes targeting KLF (Table 2A-3). The data is expressed as a fraction of KLF message remaining in cells transfected with siRNAs targeting KLF, relative to cells transfected with a negative control siRNA, AD-1955. All siRNAs were transfected at least two times and qPCR reactions were performed in duplicate. Cos7 cells were sequentially transfected with 15 ng or 30 ng of the KLF1 plasmid and each of the siRNAs.

TABLE 16

| 19mer KLF siRNA duplex efficacy screen. | | |
| --- | --- | --- |
| Duplex ID | Avg fold change | STDEV |
| AD-46090.1 | 1 | 0.05 |
| AD-46091.1 | 1.14 | 0.24 |
| AD-46092.1 | 0.31 | 0.16 |

TABLE 16-continued

19mer KLF siRNA duplex efficacy screen.

| Duplex ID | Avg fold change | STDEV |
|---|---|---|
| AD-46093.1 | 0.79 | 0.22 |
| AD-46094.1 | 1.08 | 0.23 |
| AD-46095.1 | 0.18 | 0.09 |
| AD-46096.1 | 0.99 | 0.53 |
| AD-46097.1 | 1.32 | 0.32 |
| AD-46098.1 | 0.36 | 0.15 |
| AD-46099.1 | 1.01 | 0.3 |
| AD-46100.1 | 0.49 | 0.16 |
| AD-46101.1 | 0.64 | 0.1 |
| AD-46102.1 | 1.14 | 0.7 |
| AD-46103.1 | 1.23 | 0.29 |
| AD-46104.1 | 0.51 | 0.13 |
| AD-46105.1 | 0.33 | 0.12 |
| AD-46106.1 | 0.66 | 0.22 |
| AD-46107.1 | 0.75 | 0.05 |
| AD-46108.1 | 0.33 | 0.1 |
| AD-46109.1 | 0.59 | 0.22 |
| AD-46110.1 | 0.19 | 0.1 |
| AD-46111.1 | 0.19 | 0.05 |
| AD-46112.1 | 0.21 | 0.11 |
| AD-46113.1 | 0.58 | 0.23 |
| AD-46114.1 | 0.93 | 0.14 |
| AD-46115.1 | 0.18 | 0.06 |
| AD-46116.1 | 0.41 | 0.14 |
| AD-46117.1 | 0.25 | 0.09 |
| AD-46118.1 | 0.53 | 0.21 |
| AD-46119.1 | 0.92 | 0.13 |
| AD-46120.1 | 1.18 | 0.86 |
| AD-46121.1 | 0.75 | 0.11 |
| AD-46122.1 | 0.83 | 0.42 |
| AD-46123.1 | 0.34 | 0.07 |
| AD-46124.1 | 0.91 | 0.37 |
| AD-46125.1 | 0.65 | 0.15 |
| AD-46126.1 | 0.41 | 0.12 |
| AD-46127.1 | 0.57 | 0.12 |
| AD-46128.1 | 0.36 | 0.12 |
| AD-46129.1 | 0.77 | 0.18 |
| AD-46130.1 | 0.66 | 0.37 |
| AD-46132.1 | 0.57 | 0.1 |
| AD-46133.1 | 0.47 | 0.07 |
| AD-46134.1 | 0.19 | 0.05 |
| AD-46135.1 | 0.54 | 0.03 |
| AD-46136.1 | 0.45 | 0.2 |
| AD-1955 | 1.03 | 0.02 |

$IC_{50}$ of Select 19Mer KLF siRNA Duplexes in in vitro Dose Response Screen.

Table 17 illustrates the $IC_{50}$ value of select 19mer KLF siRNA duplexes in in vitro dose response screen. 19mer KLF siRNA duplexes that were efficacious in the initial single dose screen (Table 16), were tested for KLF knockdown activity in a dose response. For normalization, knockdown of KLF was measured relative to the non-targeting control, AD-1955. Each siRNA duplex was screened in duplicate and an $IC_{50}$ calculated for each experiment ($IC_{50}A$ and $IC_{50}B$), as well as an average $IC_{50}$ (Avg $IC_{50}$).

TABLE 17

$IC_{50}$ of select 19mer KLF siRNA duplexes in in vitro dose response screen.

| Duplex ID | IC-50 A (nM) | IC-50 B (nM) | Avg IC50 (nM) |
|---|---|---|---|
| AD-46115.1 | 0.0767 | 0.3087 | 0.1648 |
| AD-46111.1 | 0.1524 | 0.3724 | 0.2993 |
| AD-46110.1 | 0.3455 | 1.935 | 0.9737 |
| AD-46095.1 | 0.02 | 0.0588 | 0.0364 |
| AD-46134.1 | 0.0234 | 0.1253 | 0.0684 |
| AD-46112.1 | 0.4053 | 0.0638 | 0.2237 |
| AD-46117.1 | 5.3373 | 0.2518 | 1.2338 |

In vitro Efficacy of 21/23Mer KLF siRNA Duplexes for KLF Silencing Activity.

Table 18 illustrates the knockdown of KLF in COST cells transfected with 21/23mer modified siRNA duplexes targeting KLF (Table 5). The data is expressed as a fraction of KLF message remaining in cells transfected with siRNAs targeting KLF, relative to cells transfected with a negative control siRNA, AD-1955. All siRNAs were transfected at least two times and qPCR reactions were performed in duplicate. Cos7 cells were sequentially transfected with 15 ng or 30 ng of the KLF1 plasmid and each of the siRNAs so that the final siRNA concentration was 50 nM, 5 nM or 0.5 nM

TABLE 18

21/23mer KLF siRNA duplex efficacy screen.

| | 50 nM | | 5 nM | | 0.5 nM | |
|---|---|---|---|---|---|---|
| Duplex ID | Avg | STDEV | Avg | STDEV | Avg | STDEV |
| AD-46095.3 | 0.303 | 0.191 | 0.21 | 0.037 | 0.283 | 0.062 |
| AD-53284.1 | 0.46 | 0.047 | 0.329 | 0.065 | 0.645 | 0.059 |
| AD-53290.1 | 0.287 | 0.065 | 0.364 | 0.221 | 0.685 | 0.182 |
| AD-53295.1 | 1.088 | 0.097 | 0.79 | 0.239 | 0.53 | 0.1 |
| AD-53301.1 | 0.918 | 0.08 | 0.871 | 0.192 | 0.903 | 0.064 |
| AD-53321.1 | 0.444 | 0.303 | 0.711 | 0.189 | 0.511 | 0.101 |
| AD-53307.1 | 0.308 | 0.047 | 0.328 | 0.074 | 0.465 | 0.072 |
| AD-53309.1 | 0.267 | 0.055 | 0.257 | 0.033 | 0.522 | 0.126 |
| AD-53311.1 | 0.266 | 0.021 | 0.292 | 0.033 | 0.432 | 0.037 |
| AD-53313.1 | 0.249 | 0.034 | 0.303 | 0.063 | 0.521 | 0.106 |
| AD-53315.1 | 0.307 | 0.106 | 0.421 | 0.247 | 0.762 | 0.126 |
| AD-53317.1 | 0.257 | 0.051 | 0.407 | 0.109 | 0.673 | 0.116 |
| AD-53319.1 | 0.236 | 0.066 | 0.236 | 0.081 | 0.573 | 0.212 |
| AD-53322.1 | 0.461 | 0.155 | 0.286 | 0.163 | 0.296 | 0.043 |
| AD-53308.1 | 0.24 | 0.017 | 0.338 | 0.045 | 0.433 | 0.045 |
| AD-53310.1 | 0.249 | 0.013 | 0.314 | 0.061 | 0.497 | 0.093 |
| AD-53312.1 | 0.23 | 0.021 | 0.251 | 0.019 | 0.499 | 0.056 |
| AD-53314.1 | 0.237 | 0.047 | 0.274 | 0.058 | 0.476 | 0.075 |
| AD-53316.1 | 0.296 | 0.129 | 0.571 | 0.168 | 0.657 | 0.19 |
| AD-53318.1 | 0.381 | 0.051 | 0.414 | 0.09 | 0.786 | 0.107 |
| AD-53320.1 | 0.274 | 0.05 | 0.42 | 0.136 | 0.477 | 0.124 |
| AD-1955 | 1.01 | 0.14 | | | | |
| Mock | 0.98 | 0.19 | | | | |

Example 7

Figure 13A:
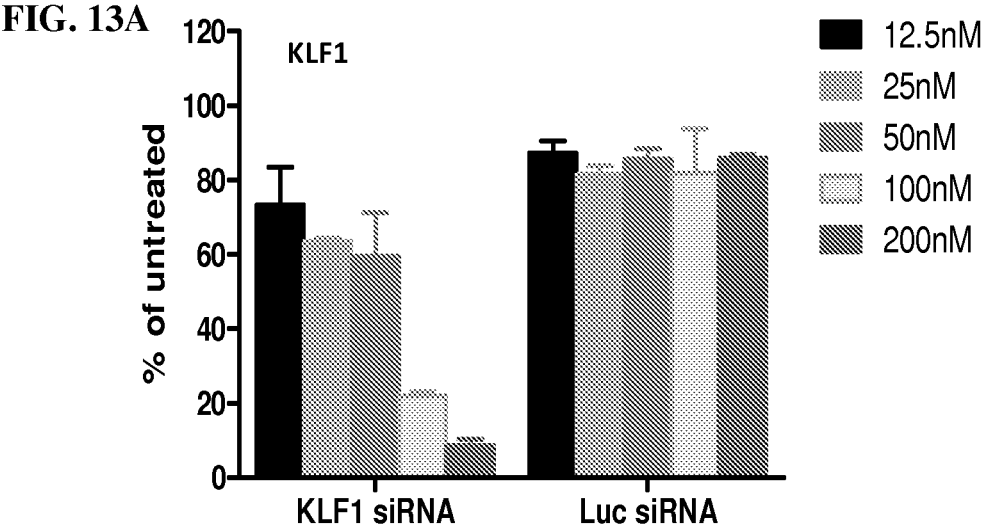
FIGS. 13A and 13B depict increased expression of mouse embryonic hemoglobin post KLF1 siRNA mediated knockdown of KLF1 in a murine erythroleukemic cell line.
Figure 13B:
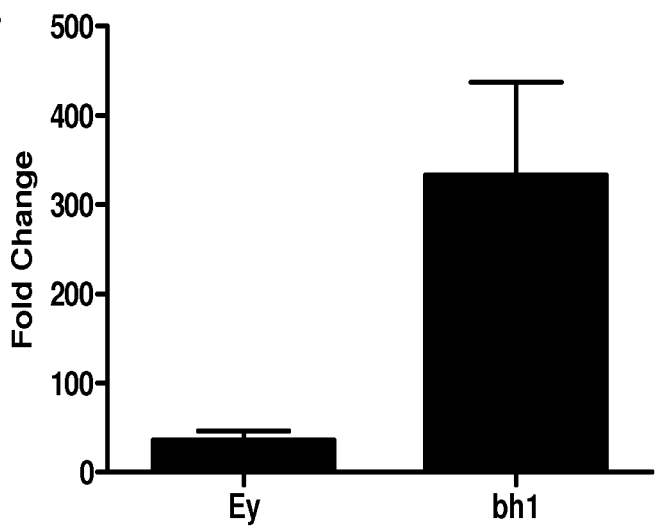

In vitro Mouse Embryonic Hemoglobin Switching Post KLF1 Knockdown by KLF1 siRNA Duplex In order to evaluate the effect of KLF1 siRNA mediated silencing of KLF1 on embryonic hemoglobin switching, MEL cells were transfected with a KLF1 siRNA or control Luc siRNA. KLF1 siRNA duplexes were transfected at concentrations of 12.5 nM, 25 nM, 50 nM, 100 nM, or 200 nM (using the AF-009 delivery vehicle). Twenty four hours post transfection the level of KLF1 expression was evaluated as described above. As illustrated in FIG. 13A, there was a dose dependent knockdown of KLF1 expression 24 hours post transfection with KLF1 siRNA. This knockdown of KLF1 expression correlated with increased expression of the mouse embryonic hemoglobin genes εγ and bh1 measured 72 hours post siRNA transfection (FIG. 13B).

Example 8

In vivo Detection of Selective Inhibition of mKLF mRNA in vivo

Figure 14A:
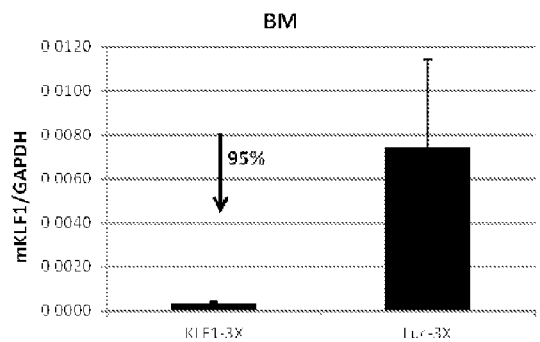
FIGS. 14A-14E depict the selective inhibition of mKLF1 mRNA in the bone marrow and spleen, and increased expression of mouse embryonic hemoglobin genes εγ, using mKLF1 iRNA at a concentration of 3×1 mg/kg encapsulated in AF-012. A 95% reduction of mKLF1, normalized to GAPDH loading control, was detected in the treated bone marrow; a 75% reduction of mKLF1, normalized to GAPDH loading control, was detected in the treated spleen. Increased expression of mouse embryonic hemoglobin genes εγ in bone marrow (FIG. 14B) and spleen (FIG. 14D) is detected after treatment with mKLF1 iRNA.
Figure 14C:
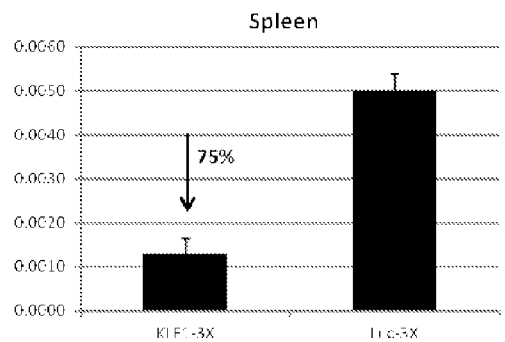
Figure 14B:
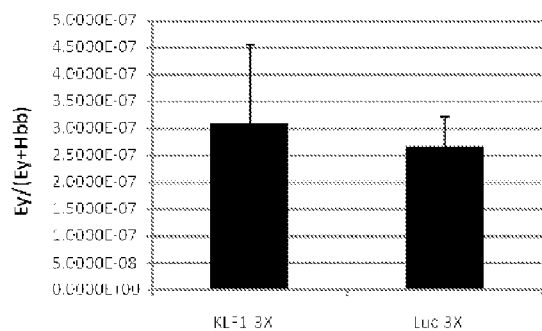
Figure 14D:
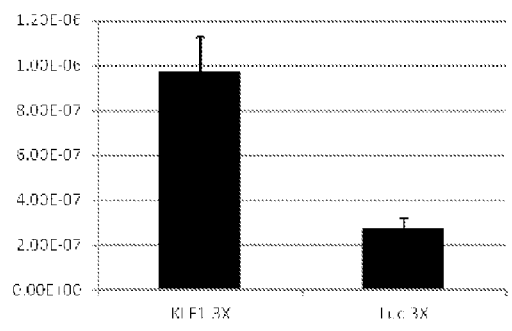
Figure 14E:

FIGS. 14A-14E further depict the selective inhibition of mKLF1 mRNA in the bone marrow and spleen in vivo, and increased expression of mouse embryonic hemoglobin genes εγ, using mKLF1 iRNA at a concentration of 3×1 mg/kg encapsulated in AF-012. A 95% reduction of mKLF1, normalized to GAPDH loading control, relative to luciferase, was detected in the treated bone marrow; a 75% reduction of mKLF1, normalized to GAPDH loading control, was detected in the treated spleen. Increased expression of mouse embryonic hemoglobin genes εγ in bone marrow (FIG. 14B) and spleen (FIG. 14D) is detected after treatment with mKLF1 iRNA. FIG. 14E depicts a schematic representation of the hemoglobin genes.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A double-stranded ribonucleic acid (dsRNA) for inhibiting expression of BCL11A, wherein said dsRNA comprises a sense strand and an antisense strand, wherein said antisense strand comprises a region of complementarity to a BCL11A variant RNA transcript consisting of SEQ ID NO:667 or SEQ ID NO:633, and wherein said dsRNA comprises at least one modified nucleotide.

2. The dsRNA of claim 1, wherein the sense strand consists of the sequence of SEQ ID NO:666 or SEQ ID NO:632.

3. The dsRNA of claim 1, wherein at least one of said modified nucleotide is chosen from: a 2'-O-methyl modified nucleotide, a nucleotide comprising a 5'-phosphorothioate group, or a terminal nucleotide linked to a cholesteryl derivative or dodecanoic acid bisdecylamide group.

4. The dsRNA of claim 1, wherein said modified nucleotide is chosen from: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, or a non-natural base comprising nucleotide.

5. The dsRNA of claim 1, wherein the antisense strand has a region of complementarity to a BCL11A variant transcript of at least 17 nucleotides in length.

6. The dsRNA of claim 5, wherein the region of complementarity is between 19 and 21 nucleotides in length.

7. The dsRNA of claim 1, wherein the sense strand is no more than 30 nucleotides in length.

8. The dsRNA of claim 1, wherein at least one strand comprises a 3' overhang of at least 1 or 2 nucleotides.

9. The dsRNA of claim 1, further comprising a ligand.

10. The dsRNA of claim 9, wherein the ligand is conjugated to the 3' end of the sense strand of the dsRNA.

11. The dsRNA of claim 7, wherein the sense strand is between 19 and 24 nucleotides in length.

12. A cell containing the dsRNA of claim 1.

13. A pharmaceutical composition for inhibiting expression of a BCL11A gene comprising the dsRNA of claim 1.

14. The pharmaceutical composition of claim 13, further comprising a lipid formulation.

15. The pharmaceutical composition of claim 14, wherein the lipid formulation is a MC3 formulation.

16. A method of inhibiting BCL11A expression in a cell, the method comprising:
   (a) introducing into the cell the dsRNA of claim 1; and
   (b) maintaining the cell produced in step (a) for a time sufficient to obtain degradation of the mRNA transcript of a BCL11A gene, thereby inhibiting expression of the BCL11A gene, or a combination thereof, in the cell.

17. The method of claim 16, wherein the cell is present in a subject in need of treatment, prevention and/or management of a hemoglobinopathy.

18. The method of claim 16, wherein the BCL11A expression is inhibited by at least 30%.

19. The method of claim 16, wherein the dsRNA of claim 1 has an $IC_{50}$ in the range of 0.001-7 nM.

20. A method of treating a disorder mediated by BCL11A expression comprising administering to a human in need of such treatment a therapeutically effective amount of the dsRNA of claim 1.

21. The method of claim 20, wherein the human is at risk, or is diagnosed with a hemoglobinopathy chosen from a β-hemoglobinopathy, sickle cell disease, or a β-thalassemia.

22. A methods for increasing fetal hemoglobin levels in an erythroid cell, comprising contacting the cell with one or more of the dsRNA of claim 1, in an amount effective to increase fetal hemoglobin levels in the cell, or its progeny.

23. The method of claim 22, wherein the cell is present in a subject at risk of having or having a β-hemoglobin disorders, sickle cell anemia or β-thalassemia.

24. A method for decreasing β-globin levels in an erythroid cell, comprising contacting the cell with one or more of the dsRNA of claim 1, in an amount effective to reduce expression of BCL11A, thereby decreasing the expression of β-globin in the cell, or its progeny.

25. The method of claim 24, wherein the dsRNA is administered at a concentration of 0.01 mg/kg-5 mg/kg bodyweight of the subject.

26. A vector encoding the dsRNA of claim 1.

27. A cell comprising the vector of claim 26.

28. The dsRNA of claim 1, wherein at least one end of the dsRNA is blunt.

29. The dsRNA of claim 1, wherein the dsRNA comprises a duplex region between 15-30 base pairs.

30. The dsRNA of claim 9, wherein the ligand is a cell or tissue targeting group chosen from a lectin, a glycoprotein, a lipid, or an antibody that binds to a specified cell type.

31. The dsRNA of claim 9, wherein the ligand is a multivalent galactose, N-acetyl-galactosamine, an N-acetyl-galacosamine multivalent mannose, or a cholesterol.

32. A double-stranded ribonucleic acid (dsRNA) for inhibiting expression of BCL11A, wherein said dsRNA comprises a sense strand sequence consisting of SEQ ID NO:626 and an antisense strand sequence consisting of SEQ ID NO:627.

33. The dsRNA of claim 32, further comprising a ligand.

34. The dsRNA of claim 33, wherein the ligand is conjugated to the 3' end of the sense strand of the dsRNA.

35. The dsRNA of claim 33, wherein the ligand is a cell or tissue targeting group chosen from a lectin, a glycoprotein, a lipid, or an antibody that binds to a specified cell type.

36. The dsRNA of claim 33, wherein the ligand is a multivalent galactose, N-acetyl-galactosamine, an N-acetyl-galacosamine multivalent mannose, or a cholesterol.

37. A cell containing the dsRNA of claim 32.

38. A pharmaceutical composition for inhibiting expression of a BCL11A gene comprising the dsRNA of claim 32.

39. The pharmaceutical composition of claim 38, further comprising a lipid formulation.

40. The pharmaceutical composition of claim 39, wherein the lipid formulation is a MC3 formulation.

41. A vector encoding the dsRNA of claim 32.

42. A cell comprising the vector of claim 41.

43. The dsRNA of claim 1, wherein the antisense strand consists of SEQ ID NO:627.

44. The dsRNA of claim 1, wherein the antisense strand consists of SEQ ID NO:639.

* * * * *

SEQUENCE LISTING

```
<160> NUMBER OF SEQ ID NOS: 754

<210> SEQ ID NO 1
<211> LENGTH: 1615
<212> TYPE: DNA
<213> ORGANISM: Homo sapiens

<400> SEQUENCE: 1
tcagagttca cgaggcagcc gaggaagagg aggcttgagg cccagggtgg gcaccagcca      60
gccatggcca cagccgagac cgccttgccc tccatcagca cactgaccgc cctgggcccc     120
ttcccggaca cacaggatga cttcctcaag tggtggcgct ccgaagaggc gcaggacatg     180
ggcccgggtc ctcctgaccc cacggagccg cccctccacg tgaagtctga ggaccagccc     240
ggggaggaag aggacgatga gaggggcgcg gacgccacct gggacctgga tctcctcctc     300
accaacttct cgggcccgga gcccggtggc gcgcccagaa cctgcgctct ggcgcccagc     360
gaggcctccg gggcgcaata tccgccgccg cccgagactc tgggcgcata tgctggcggc     420
ccggggctgg tggctgggct tttgggttcg gaggatcact cgggttgggt gcgccctgcc     480
ctgcgagccc gggctcccga cgccttcgtg ggcccagccc tggctccagc cccggccccc     540
gagcccaagg cgctggcgct gcaaccggtg taccggggc ccggcgccgg ctcctcgggt     600
ggctacttcc cgcggaccgg gctttcagtg cctgcggcgt cgggcgcccc ctacgggcta     660
ctgtccgggt accccgcgat gtacccggcg cctcagtacc aagggcactt ccagctcttc     720
cgcgggctcc agggacccgc gcccggtccc gccacgtccc cctccttcct gagttgtttg     780
ggacccggga cggtgggcac tggactcggg gggactgcag aggatccagg tgtgatagcc     840
gagaccgcgc catccaagcg aggccgacgt tcgtgggcgc gcaagaggca ggcagcgcac     900
acgtgcgcgc acccgggttg cggcaagagc tacaccaaga gctcccacct gaaggcgcat     960
ctgcgcacgc acacagggga gaagccatac gcctgcacgt gggaaggctg cggctggaga    1020
ttcgcgcgct cggacgagct gacccgccac taccggaaac acacgggca gcgccccttc    1080 cgctgccagc tctgcccacg tgctttttcg cgctctgacc acctggcctt gcacatgaag    1140
cgccaccttt gagccctgcc ctggcacttg gactctccta gtgactgggg atgggacaag    1200
aagcctgttt ggtggtctct tcacacggac gcgcgtgaca caatgctggg tggttttccc    1260
acgaatggac cctctcctgg actcgcgttc ccaaagatcc acccaaatat caaacacgga    1320
cccatagaca gccctggggg agcctcttac ggaaaatccg acaagccttc agccacaggg    1380
agccacacag agatgtccaa actgtcgtgc aaacccagtg agacagaccg ccaaataaac    1440
ggactcagtg gacactcaga ccagctccca gatggccctg gacagcagga gagggtgtgg    1500
gatgaggctt cccagagacc ctgggtctag aaagcggctc ctgaaggtcc cttattgtgg    1560
ctgatattaa ctgtcaatgg ttatgggtcc tataaaaatg cccctcccag ataaa         1615
```

```
<210> SEQ ID NO 2
<211> LENGTH: 1534
<212> TYPE: DNA
<213> ORGANISM: Mus musculus

<400> SEQUENCE: 2
gtgggcagac aggagccctc caagaaactt tcctagcctc atagcccatg aggcagaaga      60
gagagaggag gcctgaggtc cagggtggac accagccagc catggcctca gctgagactg     120
tcttaccctc catcagtaca ctcaccaccc tgggacagtt cctggacacc caggaggact     180
tcctcaagtg gtggcggtct gaggagacgc aggatttggg gccggggccc ccgaatccca     240
cggggccgtc ccatcacgtg agtctgaaat cggaggaccc ttccggagag gacgatgaga     300
gggacgtgac ctgtgcgtgg gacccggatc ttttccttac aaactttcca ggttccgagt     360
ctcccggcac ttcccggacc tgtgccctgg cgcccagcgt ggggccagtg cacagttcg      420 agccgcctga gtctctgggc gcctatgcgg gtggcccagg gttggtgact gggcctttgg     480
gctccgagga gcacacaagc tgggcgcacc cgactccgag accccagcc cctgaaccct      540 tcgtggcccc tgcctggcc ccgggactcg ctcccaaggc tcagccctcg tactccgact      600
cgcgagcggg ctccgtaggg ggcttcttcc cgcgggcggg gcttgcggtg cccgcagctc     660
caggcgcccc ctatgggctg ctgtcgggat accccgcgct gtaccccgcg ccacagtacc     720
aaggccactt ccagctcttt cgcgggctcg cggcgcttc tgctggtccc acggcgcccc      780
cttccttctt gaattgtctg ggacctggga ctgtggccac agaactcggg gccactgcga     840
tcgccggaga cgcaggcttg tccccgggaa ctgcgccgcc caaacgcagc cggcgaactt     900
tggcacctaa gaggcaggcg gcacatacgt gcgggcacga aggctgcggg aagagctaca     960
ccaagagctc gcacctcaag gcgcacctgc gcacgcacac gggagagaag ccttatgcct    1020
gctcctggga cggctgtgac tggaggttcg ctcgctcaga cgaactgacg cgccactacc    1080
ggaagcacac tggacatcgt cccttctgct gtggcctctg cccacgtgct ttttcacgct    1140
ctgaccactt agctctgcac atgaagcgtc acctctgagt gatcctgcac aaggactggg    1200
gatgaaataa gagtggatcc aaggaccgta tcccaaaaga tgggccatta tatagtccta    1260
cccagatcaa aaactgacca gaagaccata caaaggagcc ttcaggacaa acctcacatg    1320
tcctcaggga gccccacaca tggccccaca gacccagcaa tatagaccac cagataaatc    1380
aactcaaatg gaccctaga ccagaggagt gaccctgtgt cctggacgca gatggactgg     1440
ggtgagattt cctaagatct agaagggagc ttcacactgt gcccatctgc taggattgtt    1500
gtcgttacta taaaaatttc ccatataaaa ccag                                1534

<210> SEQ ID NO 3
<211> LENGTH: 5946
<212> TYPE: DNA
<213> ORGANISM: Homo sapiens

<400> SEQUENCE: 3
tttttttttt tttttttgctt aaaaaaaagc catgacggct ctcccacaat tcatcttccc      60
tgcgccatct ttgtattatt tctaatttat tttggatgtc aaaaggcact gatgaagata     120
ttttctctgg agtctccttc tttctaaccc ggctctcccg atgtgaaccg agccgtcgtc     180 cgccgccgc cgccgccgcc gccgccgccg cccgcccgc agccaccat gtctcgccgc      240 aagcaaggca acccccagca cttaagcaaa cgggaattct cgcccgagcc tcttgaagcc    300
attcttacag atgatgaacc agaccacggc ccgttgggag ctccagaagg ggatcatgac    360
```

```
ctcctcacct gtgggcagtg ccagatgaac ttcccattgg gggacattct tatttttatc    420
gagcacaaac ggaaacaatg caatggcagc ctctgcttag aaaaagctgt ggataagcca    480
ccttcccctt caccaatcga gatgaaaaaa gcatccaatc ccgtggaggt tggcatccag    540
gtcacgccag aggatgacga ttgtttatca acgtcatcta gaggaatttg ccccaaacag    600
gaacacatag cagataaact tctgcactgg aggggcctct cctcccctcg ttctgcacat    660
ggagctctaa tccccacgcc tgggatgagt gcagaatatg ccccgcaggg tatttgtaaa    720
gatgagccca gcagctacac atgtacaact tgcaaacagc cattcaccag tgcatggttt    780
ctcttgcaac acgcacagaa cactcatgga ttaagaatct acttagaaag cgaacacgga    840
agtcccctga ccccgcgggt tggtatccct tcaggactag gtgcagaatg tccttcccag    900
ccacctctcc atgggattca tattgcagac aataacccct ttaacctgct aagaatacca    960
ggatcagtat cgagagaggc ttccggcctg cagaagggc gctttccacc cactcccccc    1020
ctgtttagtc caccaccgag acatcacttg gaccccacc gcatagagcg cctgggggcg    1080
gaagagatgg ccctggccac ccatcacccg agtgcctttg cagggtgct gcggttgaat    1140 ccaatggcta tggagcctcc cgccatggat ttctctagga gacttagaga gctggcaggg    1200
aacacgtcta gcccaccgct gtccccaggc cggcccagcc ctatgcaaag gttactgcaa    1260
ccattccagc caggtagcaa gccgcccttc ctggcgacgc ccccctccc tcctctgcaa    1320 tccgcccctc ctccctccca gccccggtc aagtccaagt catgcgagtt ctgcggcaag    1380
acgttcaaat ttcagagcaa cctggtggtg caccggcgca gccacacggg cgagaagccc    1440
tacaagtgca acctgtgcga ccacgcgtgc acccaggcca gcaagctgaa gcgccacatg    1500
aagacgcaca tgcacaaatc gtccccatg acggtcaagt ccgacgacgg tctctccacc    1560
gccagctccc cggaacccgg caccagcgac ttggtgggca cgccagcag cgcgctcaag    1620 tccgtggtgg ccaagttcaa gagcgagaac gaccccaacc tgatcccgga gaacggggac    1680
gaggaggaag aggaggacga cgaggaagag gaagaagagg aggaagagga ggaggaggag    1740
ctgacggaga gcgagagggt ggactacggc ttcgggctga gcctggaggc ggcgcgccac    1800
cacgagaaca gctcgcgggg cgcggtcgtg gcgtgggcg acgagagccg cgccctgccc    1860
gacgtcatgc agggcatggt gctcagctcc atgcagcact tcagcgaggc cttccaccag    1920
gtcctgggcg agaagcataa gcgcggccac ctggccgagg ccgagggcca cagggacact    1980
tgcgacgaag actcggtggc cggcgagtcg gaccgcatag acgatggcac tgttaatggc    2040
cgcggctgct ccccgggcga gtcggcctcg ggggcctgt ccaaaaagct gctgctgggc    2100
agccccagct cgctgagccc cttctctaag cgcatcaagc tcgagaagga gttcgacctg    2160 ccccccggccg cgatgcccaa cacggagaac gtgtactcgc agtggctcgc cggctacgcg    2220
gcctccaggc agctcaaaga tcccttcctt agcttcggag actccagaca atcgccttt    2280 gcctcctcgt cggagcactc ctcggagaac gggagtttgc gcttctccac accgcccggg    2340
gagctggacg gagggatctc ggggcgcagc ggcacgggaa gtgagggag cacgccccat    2400 attagtggtc cgggcccggg caggcccagc tcaaaagagg gcagacgcag cgacacttgt    2460
gagtactgtg ggaaagtctt caagaactgt agcaatctca ctgtccacag gagaagccac    2520
acgggcgaaa ggccttataa atgcgagctg tgcaactatg cctgtgccca gagtagcaag    2580
ctcaccaggc acatgaaaac gcatggccag gtggggaagg acgtttacaa atgtgaaatt    2640
tgtaagatgc ctttagcgt gtacagtacc ctggagaaac acatgaaaaa atggcacagt    2700
gatcgagtgt tgaataatga tataaaaact gaatagaggt atattaatac ccctccctca    2760
```

```
ctcccacctg acacccccctt tttcaccact cccccttcccc atcgccctcc agccccactc    2820
cctgtaggat tttttttctag tcccatgtga tttaaacaaa caaacaaaca aacagaagta    2880
acgaagctaa gaatatgaga gtgcttgtca ccagcacacc tgttttttttt cttttttcttt  2940 ttcttttttc ttttttcctttt tttttttttt tcctttatgt tctcaccgtt tgaatgcatg  3000
atctgtatgg ggcaatacta ttgcatttta cgcaaacttt gagcctttct cttgtgcaat    3060
aatttacatg ttgtgtatgt ttttttttaa acttagacag catgtatggt atgttatggc    3120
tattttaaat tgtccctaat tcgttgctga gcaaacatgt tgctgtttcc agttccgttc    3180
tgagagaaaa agagagagag agagaaaaag accatgctgc atacattctg taatacatat    3240
catgtacagt tttattttat aacgtgagga ggaaaaacag tctttggatt aaccctctat    3300
agacagaata gatagcactg aaaaaaaatc tctatgagct aaatgtctgt ctctaaaggg    3360
ttaaatgtat caattggaaa ggaagaaaaa aggccttgaa ttgacaaatt aacagaaaaa    3420
cagaacaagt ttattctatc atttggtttt aaaatatgag tgccttggat ctattaaaac    3480
cacatcgatg gttctttcta cttgttataa acttgtagct taattcagca ttgggtgagg    3540 taataaaccct taggaactag catataattc tatattgtat ttctcacaac aatggctacc    3600
taaaaagatg acccattatg tcctagttaa tcatcatttt tccctttagtt taattttata   3660 aacaaaactg attataccag tataaaagct actttgctcc tggtgagagc ttaaagaaaa    3720
tgggctgttt tgcccaaagt tttattttttt ttaaacaatg attaaattga atgtgtaatg   3780
tgcaaaagcc ctggaacgca attaaataca ctagtaagga gttcatttta tgaagatatt    3840
tgctttaata atgtcttttt aaaaatactg gcaccaaaag aaatagatcc agatctactt    3900
ggttgtcaag tggacaatca aatgataaac tttaagacct tgtataccat attgaaagga    3960
agaggctgac aataaggttt gacagagggg aacagaagaa aataatatga tttattagca    4020
caacgtggta ctatttgcca tttaaaacta gaacaggtat ataagctaat attgatacaa    4080
tgatgattaa ctatgaattc ttaagacttg catttaaatg tgacattctt aaaaaaagaa    4140
gagaaagaat tttaagagta gcagtatata tgtctgtgct ccctaaaagt tgtacttcat    4200
ttcttttcca tacactgtgt gctatttgtg ttaacatgga agaggattca ttgttttttat  4260 ttttattttt ttaattttttt cttttttatt aagctagcat ctgccccagt tggtgttcaa    4320
atagcacttg actctgcctg tgatatctgt atcttttctc taatcagaga tacagaggtt    4380
gagtataaaa taaacctgct cagataggac aattaagtgc actgtacaat tttcccagtt    4440
tacaggtcta tacttaaggg aaaagttgca agaatgctga aaaaaaattg aacacaatct    4500
cattgaggag cattttttaa aaactaaaaa aaaaaaaact ttgccagcca tttacttgac    4560
tattgagctt acttacttgg acgcaacatt gcaagcgctg tgaatggaaa cagaatacac    4620
ttaacataga aatgaatgat tgctttcgct tctacagtgc aaggattttt ttgtacaaaa    4680 ctttttaaa tataaatgtt aagaaaaatt ttttttaaaa aacacttcat tatgtttagg     4740
ggggaactgc attttagggt tccattgtct tggtggtgtt acaagacttg ttatccattt    4800
aaaaatggta gtggaaattc tatgccttgg atacacaccg ctcttcaggt tgtaaaaaaa    4860
aaaaacatac attggggaaa ggtttaagat tatatagtac ttaaatatag gaaaatgcac    4920
actcatgttg attcctatgc taaaatacat ttatggtctt ttttctgtat ttctagaatg    4980
gtatttgaat taaatgttca tctagtgtta ggcactatag tatttatatt gaagcttgta    5040 ttttaactg ttgcttgttc tcttaaaagg tatcaatgta cctttttttgg tagtggaaaa    5100
```

-continued

| | |
|---|---|
| aaaaaagaca ggctgccaca gtatattttt ttaatttggc aggataatat agtgcaaatt | 5160 |
| atttgtatgc ttcaaaaaaa aaaaaaagag agaaacaaaa aagtgtgaca ttacagatga | 5220 |
| gaagccatat aatggcggtt tgggggagcc tgctagaatg tcacatggat ggctgtcata | 5280 |
| ggggttgtac atatcctttt ttgttccttt tcctgctgc catactgtat gcagtactgc | 5340 |
| aagctaataa cgttggtttg ttatgtagtg tgcttttttgt ccctttcctt ctatcaccct | 5400 |
| acattccagc atcttacctt catatgcagt aaaagaaaga aagaaaaaaa aaggaaaaaa | 5460 |
| aaaaaaaaac caatgttttg cagttttttt cattgccaaa aactaaatgg tgctttatat | 5520 |
| ttagattgga aagaatttca tatgcaaagc atattaaaga gaaagcccgc tttagtcaat | 5580 |
| acttttttgt aaatggcaat gcagaatatt ttgttattgg cctttttctat tcctgtaatg | 5640 |
| aaagctgttt gtcgtaactt gaaattttat cttttactat gggagtcact atttattatt | 5700 |
| gcttatgtgc cctgttcaaa acagaggcac ttaatttgat cttttatttt tctttgtttt | 5760 |
| tatttttttt tttatttaga tgaccaaagg tcattacaac ctggcttttt attgtatttg | 5820 |
| tttctggtct ttgttaagtt ctattggaaa aaccactgtc tgtgtttttt tggcagttgt | 5880 |
| ctgcattaac ctgttcatac acccatttg tccctttatt gaaaaaataa aaaaaattaa | 5940 |
| agtaca | 5946 |

<210> SEQ ID NO 4
<211> LENGTH: 3958
<212> TYPE: DNA
<213> ORGANISM: Homo sapiens

<400> SEQUENCE: 4

| | |
|---|---|
| tttttttttt ttttttgctt aaaaaaaagc catgacggct ctcccacaat tcatcttccc | 60 |
| tgcgccatct ttgtattatt tctaatttat tttggatgtc aaaaggcact gatgaagata | 120 |
| ttttctctgg agtctccttc tttctaaccc ggctctcccg atgtgaaccg agccgtcgtc | 180 |
| cgcccgccgc cgccgccgcc gccgccgccg cccgccccgc agcccaccat gtctcgccgc | 240 |
| aagcaaggca accccagca cttaagcaaa cgggaattct cgcccgagcc tcttgaagcc | 300 |
| attcttacag atgatgaacc agaccacggc ccgttgggag ctccagaagg ggatcatgac | 360 |
| ctcctcacct gtgggcagtg ccagatgaac ttcccattgg gggacattct tatttttatc | 420 |
| gagcacaaac ggaaacaatg caatggcagc ctctgcttag aaaaagctgt ggataagcca | 480 |
| ccttccccctt caccaatcga gatgaaaaaa gcatccaatc ccgtggaggt tggcatccag | 540 |
| gtcacgccag aggatgacga ttgtttatca acgtcatcta gaggaatttg ccccaaacag | 600 |
| gaacacatag cagataaact tctgcactgg aggggcctct cctcccctcg ttctgcacat | 660 |
| ggagctctaa tccccacgcc tgggatgagt gcagaatatg ccccgcaggg tatttgtaaa | 720 |
| gatgagccca gcagctacac atgtacaact tgcaaacagc cattcaccag tgcatggttt | 780 |
| ctcttgcaac acgcacagaa cactcatgga ttaagaatct acttagaaag cgaacacgga | 840 |
| agtccctga ccccgcgggt tggtatccct tcaggactag gtgcagaatg tccttcccag | 900 |
| ccacctctcc atgggattca tattgcagac aataaccct ttaacctgct aagaatacca | 960 |
| ggatcagtat cgagagaggc ttccggcctg gcagaagggc gctttccacc cactccccc | 1020 |
| ctgtttagtc caccaccgag acatcacttg gaccccacc gcatagagcg cctggggggcg | 1080 |
| gaagagatgg ccctggccac ccatcacccg agtgcctttg acagggtgct gcggttgaat | 1140 |
| ccaatggcta tggagcctcc cgccatggat ttctctagga gacttagaga gctggcaggg | 1200 |
| aacacgtcta gcccaccgct gtccccaggc cggcccagcc ctatgcaaag gttactgcaa | 1260 |

-continued

```
ccattccagc caggtagcaa gccgcccttc ctggcgacgc ccccctccc tcctctgcaa    1320
tccgcccctc ctccctccca gccccggtc aagtccaagt catgcgagtt ctgcggcaag    1380
acgttcaaat ttcagagcaa cctggtggtg caccggcgca gccacacggg cgagaagccc    1440
tacaagtgca acctgtgcga ccacgcgtgc acccaggcca gcaagctgaa gcgccacatg    1500
aagacgcaca tgcacaaatc gtcccccatg acggtcaagt ccgacgacgg tctctccacc    1560
gccagctccc cggaacccgg caccagcgac ttggtgggca cgccagcag cgcgctcaag     1620
tccgtggtgg ccaagttcaa gagcgagaac gaccccaacc tgatcccgga aacggggac     1680
gaggaggaag aggaggacga cgaggaagag gaagaagagg aggaagagga ggaggaggag    1740
ctgacggaga gcgagagggt ggactacggc ttcgggctga gcctggaggc ggcgcgccac    1800
cacgagaaca gctcgcgggg cgcggtcgtg ggcgtgggcg acgagagccg cgccctgccc    1860
gacgtcatgc agggcatggt gctcagctcc atgcagcact tcagcgaggc cttccaccag    1920
gtcctgggcg agaagcataa gcgcggccac ctggccgagg ccgagggcca cagggacact    1980
tgcgacgaag actcggtggc cggcgagtcg gaccgcatag acgatggcac tgttaatggc    2040
cgcggctgct ccccgggcga gtcggcctcg ggggcctgt ccaaaaagct gctgctgggc     2100
agccccagct cgctgagccc cttctctaag cgcatcaagc tcgagaagga gttcgacctg    2160
cccccggccg cgatgcccaa cacggagaac gtgtactcgc agtggctcgc cggctacgcg    2220
gcctccaggc agctcaaaga tcccttcctt agcttcggag actccagaca tcgccttt     2280
gcctcctcgt cggagcactc ctcggagaac gggagtttgc gcttctccac accgcccggg    2340
gagctggacg gagggatctc ggggcgcagc ggcacgggaa gtggagggag cacgcccat    2400
attagtggtc cgggcccggg caggcccagc tcaaaagagg gcagacgcag cgacacttgt    2460
tcttcacaca ccccccattcg gcgtagtacc cagagagctc aagatgtgtg gcagttttcg    2520
gatgaagct cgagagccct taagttctga gaaaatttga agcccccagg ggtggggtgg     2580
acgcgtgccg cccagtcgac gtcagcgtgg tctgtcatcc tgctagtttg tgatgttttc    2640
tgacagtagc ctccaagaag ccgttgtgcg aagacagagt cctgcagagt ccttccagcc    2700
taggcctgca gcgccattt atttatattt tttaataaaa agtaaaaaca aaaaacaga     2760
cccacattgg aacagtgaat cagtcccata gagagggccc gtggaccatc gctgtcatga    2820
gtgatgccct ggcccttctg aaaccagcca acctaattac ctgtattgtg aaatgcgca    2880
tgagtcccca accccttgtt tctatacatt ctatgttgtc tttttaaaaag tgtgcttaac    2940
attgacacaa taaatgttgg agctttaggt ggtgtttgct tgttctttaa tttttaatgc    3000
ttataagaca atgaggctgc ttatgatttt gtacttctgt acctgtttcc tacagacacc    3060
catcgggtgg gtaggaggaa cagatttgag aaatgggcag gagatgtagg agggaacta     3120
ggttaccgct tatcagatgg cataaatttt caaggagaat caaaatgcaa aacttgggaa    3180
taaatcatag caatatcata attaatgtag tagtaatatt gctgtttatt aatgctgaag    3240
tgtggttttc ctaactgtct gacttataat ttgcatacca ttaaataatg cataatatgg    3300
cacgccgaat cctgtttttc aaatatatgc ttttggtggc taccatgcag gatttgaatt    3360
tgtcttttaa tttagcttag gaaagaacat cactgggcga gcggtaaatc ctaagaagg    3420
tgataaatgt cagtagtttc ttattaaata ttctaatttt aggttcccaa accttcagga    3480
aatatatctt aatgcagaca aacaaacata aacttctttt agtacttaca tcaggaaatt    3540
tggggcagat tttagagggg ggaaattata ggaggaaaga agttcacatc agaacagaca    3600
```

-continued

| | |
|---|---|
| atcacagcaa tgctctattc cttagaaatt agtgccacaa ataagttaca tctacaaaca | 3660 |
| ggtggtaaaa attcttttctg gcccagttaa tttgcacaga acttttctca gtttggtatt | 3720 |
| ttttactgct tggagatcca gaagagaatt agaaacaaca tagcaaatta aaataggttt | 3780 |
| gtcaataata gagctcagac acctgtgtgc tgtagattca catacaggcc gtgaacctaa | 3840 |
| gtggggaaaa tcctacctat ccaccttctg gctagattac ctagcttagt gaaaagatag | 3900 |
| ccaaataatt ggcatgtgaa ttatttcctg cttattcata ataaataatg actgtcta | 3958 |

<210> SEQ ID NO 5
<211> LENGTH: 2358
<212> TYPE: DNA
<213> ORGANISM: Homo sapiens

<400> SEQUENCE: 5

| | |
|---|---|
| ttttttttttt tttttttgctt aaaaaaaagc catgacggct ctcccacaat tcatcttccc | 60 |
| tgcgccatct ttgtattatt tctaatttat tttggatgtc aaaaggcact gatgaagata | 120 |
| ttttctctgg agtctccttc tttctaaccc ggctctcccg atgtgaaccg agccgtcgtc | 180 |
| cgcccgccgc cgccgccgcc gccgccgccg cccgccccgc agcccaccat gtctcgccgc | 240 |
| aagcaaggca aaccccagca cttaagcaaa cgggaattct cgcccgagcc tcttgaagcc | 300 |
| attcttacag atgatgaacc agaccacggc ccgttgggag ctccagaagg ggatcatgac | 360 |
| ctcctcacct gtgggcagtg ccagatgaac ttcccattgg gggacattct tatttttatc | 420 |
| gagcacaaac ggaaacaatg caatggcagc ctctgcttag aaaaagctgt ggataagcca | 480 |
| ccttcccctt caccaatcga gatgaaaaaa gcatccaatc ccgtggaggt tggcatccag | 540 |
| gtcacgccag aggatgacga ttgtttatca acgtcatcta gaggaatttg ccccaaacag | 600 |
| gaacacatag cagataaact tctgcactgg agggcctct cctcccctcg ttctgcacat | 660 |
| ggagctctaa tccccacgcc tgggatgagt gcagaatatg ccccgcaggg tatttgtaaa | 720 |
| gatgagccca gcagctacac atgtacaact tgcaaacagc cattcaccag tgcatggttt | 780 |
| ctcttgcaac acgcacagaa cactcatgga ttaagaatct acttagaaag cgaacacgga | 840 |
| agtcccctga ccccgcgggt tcttcacaca ccccccattcg gcgtagtacc cagagagctc | 900 |
| aagatgtgtg gcagttttcg gatggaagct cgagagccct taagttctga aaaatttga | 960 |
| agccccagg ggtggggtgg acgcgtgccg cccagtcgac gtcagcgtgg tctgtcatcc | 1020 |
| tgctagtttg tgatgttttc tgacagtagc ctccaagaag ccgttgtgcg aagacagagt | 1080 |
| cctgcagagt ccttccagcc taggcctgca gcgccatttt atttatattt tttaataaaa | 1140 |
| agtaaaaaca aaaaaacaga cccacattgg aacagtgaat cagtcccata gagagggccc | 1200 |
| gtggaccatc gctgtcatga gtgatgccct ggcccttctg aaaccagcca acctaattac | 1260 |
| ctgtattgtg gaaatgcgca tgagtcccca accccttgtt tctatacatt ctatgttgtc | 1320 |
| ttttaaaaag tgtgcttaac attgacacaa taaatgttgg agctttaggt ggtgtttgct | 1380 |
| tgttctttaa ttttaatgc ttataagaca atgaggctgc ttatgatttt gtacttctgt | 1440 |
| acctgttttcc tacagacacc catcgggtgg gtaggaggaa cagatttgag aaatgggcag | 1500 |
| gagatgtagg aggggaacta ggttaccgct tatcagatgg cataaatttt caaggagaat | 1560 |
| caaaatgcaa aacttgggaa taaatcatag caatatcata attaatgtag tagtaatatt | 1620 |
| gctgtttatt aatgctgaag tgtggttttc ctaactgtct gacttataat ttgcatacca | 1680 |
| ttaaataatg cataatatgg cacgccgaat cctgttttc aaatatatgc ttttggtggc | 1740 |
| taccatgcag gatttgaatt tgtctttaa tttagcttag gaaagaacat cactgggcga | 1800 |

-continued

```
gcggtaaatc ctaaagaagg tgataaatgt cagtagtttc ttattaaata ttctaatttt      1860
aggttcccaa accttcagga aatatatctt aatgcagaca aacaaacata aaacttcttt      1920
agtacttaca tcaggaaatt tggggcagat tttagagggg ggaaattata ggaggaaaga      1980
agttcacatc agaacagaca atcacagcaa tgctctattc cttagaaatt agtgccacaa      2040
ataagttaca tctacaaaca ggtggtaaaa attctttctg cccagttaa tttgcacaga       2100 acttttctca gtttggtatt ttttactgct tggagatcca aagagaatt agaaacaaca       2160 tagcaaatta aataggttt gtcaataata gagctcagac acctgtgtgc tgtagattca       2220
catacaggcc gtgaacctaa gtggggaaaa tcctacctat ccaccttctg gctagattac      2280
ctagcttagt gaaaagatag ccaaataatt ggcatgtgaa ttatttcctg cttattcata      2340
ataaataatg actgtcta                                                    2358
```

<210> SEQ ID NO 6
<211> LENGTH: 3425
<212> TYPE: DNA
<213> ORGANISM: Mus musculus

<400> SEQUENCE: 6

```
gacgttcaag ttcgcaggga cgtcacgtcc gcacttgaac ttgcagctca ggggggcttt        60
tgccattttt ttcatctctc tctctccctc tatccctctt ctctcttcct ctctctcttt      120
tttttcctta aaaaaaaaaa agccatgacg gctctcccac aattcatctt ccctgcgcca      180
tctttgtatt atttctaatt tattttggat gtcaaaaggc actgatgaag atattttctc      240
tggagtctcc ttctttctaa cccggctctc ccgatgtgaa ccgagccgtc gtccgcacgc      300
cgccgccgcc gccgccgccc gccccgcagc ccaccatgtc tcgccgcaag caaggcaaac      360
cccagcactt aagcaaacgg gaattctcgc ccgaacctct tgaagccatt cttacagatg      420
atgaaccaga ccatggcccg ttgggagctc agaaggggga ccacgacctt ctcacctgtg      480
ggcagtgcca gatgaatttc ccactggggg acattcttat ttttatcgag cacaaacgga      540
aacaatgcaa tggcagcctc tgcttagaaa aggtgtgga taagccgcct tcccttctc       600 ccatcgagat gaaaaaggca tccaatcctg tggaggttgg catccaggtc acgccagagg      660
atgacgattg tttatcaacg tcatctagag gaatttgccc caaacaggaa cacatagcag      720
ataaacttct gcactggagg ggcctgtcct ctcctcggtc tgcacacgga gctctaatcc      780
ccacgcccgg gatgagtgca gaatatgccc cgcagggtat ttgtaaagat gagcccagca      840
gctacacatg tacaacttgc aaacagccat tcaccagtgc atggtttctc ttgcaacacg      900
cacagaacac tcatggatta agaatctact tagaaagtga acacggaagt cccctgaccc      960
cgcgggttgg tatcccttca ggactaggtg cagaatgtcc ttcccagcca cctctccatg     1020
ggattcatat tgcagacaat aaccccttta acctgctaag aataccagga tcagtatcga     1080
gagaggcttc cggcctggca gaagggcgct ttccacccac tccccccctg tttagtccac     1140
caccgagaca tcacttggac ccccaccgca tagagcgcct gggggcggaa gagatggccc     1200
tggccaccca tcacccgagt gcctttgaca gggtgctgcg gttgaatcca atggctatgg     1260
agcctcccgc catggatttc tctaggagac ttagagagct ggcagggaac acgtctagtc     1320
caccgctgtc cccaggccgg cccagtccta tgcaaaggtt actgcaacca ttccagccag     1380
gtagcaagcc acccttcctg gcgacgcccc cctcccctcc tctgcaatcc gcccctcctc     1440
cctcccaacc cccggtcaag tccaagtcat gcgagttctg cggcaagacg ttcaaatttc     1500
```

| | |
|---|---|
| agagcaacttt ggtggttcac cgacgcagcc atactggtga gaagccctat aagtgcaacc | 1560 |
| tgtgcgacca cgcgtgcaca caggccagca agctgaagcg tcacatgaag acacacatgc | 1620 |
| acaaatcgtc ccccatgaca gtcaagtccg acgatggcct ctccacagcc agctccccgg | 1680 |
| aacctggtac cagcgacctg gtgggcagcg ccagcagtgc gctcaagtca gtggtggcca | 1740 |
| agttcaagag tgagaacgac cccaacttga tcccagagaa cggggatgag gaggaagagg | 1800 |
| aggacgacga ggaagaagaa gaagaggagg aagaggagga ggaggagctg acggagagcg | 1860 |
| agagggtgga ctacggcttc gggctgagcc tggaggctgc acgccaccat gagaacagct | 1920 |
| ctcggggcgc agtggtgggc gtgggcgacg agggccgcgc cctgcccgat gtcatgcagg | 1980 |
| gcatggtgct cagctccatg cagcacttca gcgaggcctt ccaccaggtc ctgggcgaaa | 2040 |
| agcataagcg tagccacctg gccgaggccg agggccatag ggacacttgt gatgaagact | 2100 |
| cggtggccgg tgagtcagac cgcatagacg atggcactgt taatggtcgt ggctgctccc | 2160 |
| ccggcgaatc ggcttcgggg ggtctgtcca aaaagctgct gctgggtagc cccagctcgc | 2220 |
| tgagccccttt ctccaagcgc atcaagctgg agaaggagtt tgacctgccc ccggccgcga | 2280 |
| tgcctaacac ggagaacgtg tattcgcagt ggctcgctgg ctatgcggcc tccaggcagc | 2340 |
| tcaaagatcc cttccttact ttcggagact ccagacaatc gccttttgcc tcctcatcag | 2400 |
| agcactcctc ggagaacggg agcttgcgct tctccacacc gcccggggag ctggacggag | 2460 |
| ggatctcagg gcgcagcggc acaggaagtg gagggagcac gccccatatt agtggtccgg | 2520 |
| gcccgggcag gcccagctca aaagagggca gacgcagcga cacttgtcct tcacacaccc | 2580 |
| ccgttcggcg tagtaccccg cgagctcaag atgtgtggca gttttcggat ggaagctcaa | 2640 |
| gaacccttaa gttctgagaa actttgaagc ccccaagggc ggggcggaca tgcgccgccc | 2700 |
| agccgacgtc aacgtgctcc gttatcctgc tagattgtga tgttttctga cagtagcctc | 2760 |
| caagaagaca agagtcctgc cgagtcctcc cagcctgggc ctgcagtgcc atttttattta | 2820 |
| tatttttttaa taaaacgtaa aaacaaaaaa aaccagaccc acattggaac agtgaacccg | 2880 |
| tcccatccag agggccctag gactgccgca gttggagcga cgtccaaccc ttttgaaacc | 2940 |
| agccaaccta attcccgta ctgtggaaat gagcatgacc cctgacccct tgtttctata | 3000 |
| cattctatgt tgtcttttaa aaagtgtgct taacattgac ataataaatg ttggagcttt | 3060 |
| aggcggtgtg tgcttgtttt ttaattttta atgctcgtaa acaatgtgg ctgcttcagg | 3120 |
| ctttatgtct gtgtactttt tttccttcag aagctcatag ggtgagcaga aggaccagac | 3180 |
| tcaagtgcca ggcaggagac ctagaaaagg aagtaggctt ttcagatggc atacattttc | 3240 |
| aaagaaaatc aaaatgcaaa gctaggggat aaatcatagt aatatcataa ttaatgtagt | 3300 |
| agtattgctg tttattaatg ctgacgtgtg ttttcctct ctgacttata atttgcatac | 3360 |
| cattaaataa tgcataaata tggcacactg aatccttttt caaatacacg cttttggtga | 3420 |
| ctacc | 3425 |

<210> SEQ ID NO 7
<211> LENGTH: 1825
<212> TYPE: DNA
<213> ORGANISM: Mus musculus

<400> SEQUENCE: 7

| | |
|---|---|
| gacgttcaag ttcgcaggga cgtcacgtcc gcacttgaac ttgcagctca gggggggcttt | 60 |
| tgccattttt ttcatctctc tctctcccctc tatccctctt ctctcttcct ctctctcttt | 120 |
| tttttcctta aaaaaaaaaa agccatgacg gctctcccac aattcatctt ccctgcgcca | 180 |

```
tctttgtatt atttctaatt tattttggat gtcaaaaggc actgatgaag atattttctc     240
tggagtctcc ttctttctaa cccggctctc ccgatgtgaa ccgagccgtc gtccgcacgc     300
cgccgccgcc gccgccgccc gccccgcagc ccaccatgtc tcgccgcaag caaggcaaac     360
cccagcactt aagcaaacgg gaattctcgc ccgaacctct tgaagccatt cttacagatg     420
atgaaccaga ccatggcccg ttgggagctc cagaagggga ccacgacctt ctcacctgtg     480
ggcagtgcca gatgaatttc ccactggggg acattcttat ttttatcgag cacaaacgga     540
aacaatgcaa tggcagcctc tgcttagaaa aaggtgtgga taagccgcct tcccttctc      600 ccatcgagat gaaaaaggca tccaatcctg tggaggttgg catccaggtc acgccagagg     660
atgacgattg tttatcaacg tcatctagag gaatttgccc caaacaggaa cacatagcag     720
ataaacttct gcactggagg ggcctgtcct ctcctcggtc tgcacacgga gctctaatcc     780
ccacgcccgg gatgagtgca gaatatgccc cgcagggtat ttgtaaagat gagcccagca     840
gctacacatg tacaacttgc aaacagccat tcaccagtgc atggtttctc ttgcaacacg     900
cacagaacac tcatggatta agaatctact tagaaagtga acacggaagt cccctgaccc     960
cgcgggtcct tcacacaccc ccgttcggcg tagtaccccg cgagctcaag atgtgtggca    1020
gttttcggat ggaagctcaa gaacccttaa gttctgagaa actttgaagc ccccaagggc    1080
ggggcggaca tgcgccgccc agccgacgtc aacgtgctcc gttatcctgc tagattgtga    1140
tgttttctga cagtagcctc caagaagaca agagtcctgc cgagtcctcc cagcctgggc    1200
ctgcagtgcc attttatttta tattttttaa taaaacgtaa aaacaaaaaa aaccagaccc    1260
acattggaac agtgaacccg tcccatccag agggccctag gactgccgca gttggagcga    1320
cgtccaaccc ttttgaaacc agccaaccta attacccgta ctgtggaaat gagcatgacc    1380 cctgaccct tgtttctata cattctatgt tgtcttttaa aaagtgtgct taacattgac     1440
ataataaatg ttggagcttt aggcggtgtg tgcttgtttt ttaattttta atgctcgtaa    1500
gacaatgtgg ctgcttcagg ctttatgtct gtgtacttt tttccttcag aagctcatag    1560
ggtgagcaga aggaccagac tcaagtgcca ggcaggagac ctagaaaagg aagtaggctt    1620
ttcagatggc atacattttc aaagaaaatc aaaatgcaaa gctaggggat aaatcatagt    1680
aatatcataa ttaatgtagt agtattgctg tttattaatg ctgacgtgtg ttttcctct    1740 ctgacttata atttgcatac cattaaataa tgcataaata tggcacactg aatccttttt    1800
caaatacacg cttttggtga ctacc                                          1825
```

<210> SEQ ID NO 8
<211> LENGTH: 1480
<212> TYPE: DNA
<213> ORGANISM: Mus musculus

<400> SEQUENCE: 8

```
agagcagacg cggcgcgcga cggtgtgaag ttacagcccg ccagccgaa cctcttgaag       60 ccattcttac agatgatgaa ccagaccatg gcccgttggg agctccagaa ggggaccacg     120
accttctcac ctgtgggcag tgccagatga atttcccact gggggacatt cttattttta    180
tcgagcacaa acggaaacaa tgcaatggca gcctctgctt agaaaaggt gtggataagc      240 cgccttcccc ttctcccatc gagatgaaaa aggcatccaa tcctgtggag gttggcatcc    300
aggtcacgcc agaggatgac gattgtttat caacgtcatc tagaggaatt tgccccaaac    360
aggaacacat agcagataaa cttctgcact ggaggggcct gtcctctcct cggtctgcac    420
```

```
acggagctct aatccccacg cccgggatga gtgcagaata tgccccgcag ggtatttgta      480
aagatgagcc cagcagctac acatgtacaa cttgcaaaca gccattcacc agtgcatggt      540
ttctcttgca acacgcacag aacactcatg gattaagaat ctacttagaa agtgaacacg      600
gaagtcccct gaccccgcgg gtccttcaca caccccgtt cggcgtagta ccccgcgagc       660
tcaagatgtg tggcagtttt cggatggaag ctcaagaacc cttaagttct gagaaacttt      720
gaagccccca agggcggggc ggacatgcgc cgcccagccg acgtcaacgt gctccgttat      780
cctgctagat tgtgatgttt tctgacagta gcctccaaga agacaagagt cctgccgagt      840
cctcccagcc tgggcctgca gtgccatttt atttatattt tttaataaaa cgtaaaaaca      900
aaaaaaacca gacccacatt ggaacagtga acccgtccca tccagagggc cctaggactg      960
ccgcagttgg agcgacgtcc aacccttttg aaaccagcca acctaattac ccgtactgtg     1020
gaaatgagca tgacccctga ccccttgttt ctatacattc tatgttgtct tttaaaaagt     1080
gtgcttaaca ttgacataat aaatgttgga gctttaggcg gtgtgtgctt gttttttaat     1140
ttttaatgct cgtaagacaa tgtggctgct tcaggcttta tgtctgtgta ctttttttcc     1200
ttcagaagct catagggtga gcagaaggac cagactcaag tgccaggcag gagacctaga     1260
aaaggaagta ggcttttcag atggcataca ttttcaaaga aaatcaaaat gcaaagctag     1320
gggataaatc atagtaatat cataattaat gtagtagtat tgctgtttat taatgctgac     1380
gtgtgttttt cctctctgac ttataatttg cataccatta aataatgcat aaatatggca     1440
cactgaatcc ttttttcaaat acacgctttt ggtgactacc                           1480
```

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
agugguggcg cuccgaaga                                                    19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ucuucggagc gccaccacu                                                    19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gccccuccac gugaagucu                                                    19

<210> SEQ ID NO 12
<211> LENGTH: 19
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 12
agacuucacg uggaggggc                                                    19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cgagacucug ggcgcauau                                                    19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
auaugcgccc agagucucg                                                    19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
uuuuggguuc ggaggauca                                                    19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ugauccuccg aacccaaaa                                                    19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ucggaggauc acucggguu                                                    19

<210> SEQ ID NO 18
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 18
aacccgagug auccuccga                                                        19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
uggcgcugca accggugua                                                        19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uacaccgguu gcagcgcca                                                        19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ccuccuuccu gaguuguuu                                                        19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
aaacaacuca ggaaggagg                                                        19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
aagcgaggcc gacguucgu                                                        19

<210> SEQ ID NO 24
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 24
acgaacgucg gccucgcuu                                                   19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
agcucugccc acgugcuuu                                                   19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
aaagcacgug ggcagagcu                                                   19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
gcccuggcac uuggacucu                                                   19

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
agaguccaag ugccagggc                                                   19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
uggcacuugg acucuccua                                                   19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 30
uaggagaguc caagugcca                                               19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ucuccuagug acuggggau                                               19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
auccccaguc acuaggaga                                               19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ugguuuuccc acgaaugga                                               19

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
uccauucgug ggaaaacca                                               19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uuucccacga auggacccu                                               19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36 agggguccauu cgugggaaa					19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
cuggacucgc guucccaaa					19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
uuugggaacg cgaguccag					19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
caaagaucca cccaaauau					19

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
auauuugggu ggaucuuug					19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
uaucaaacac ggacccaua					19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 42
uauggguccg uguuugaua                                              19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ucuuacggaa aauccgaca                                              19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ugucggauuu uccguaaga                                              19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
cuuacggaaa auccgacaa                                              19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
uugucggauu uccguaag                                               19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
cggaaaaucc gacaagccu                                              19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
```
aggcuugucg gauuuuccg                                        19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ggaaaauccg acaagccuu                                        19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
aaggcuuguc ggauuuucc                                        19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
gagaugucca aacugucgu                                        19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
acgacaguuu ggacaucuc                                        19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
auguccaaac ugucgugca                                        19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 54
ugcacgacag uuuggacau                                                19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uguccaaacu gucgugcaa                                                19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
uugcacgaca guuuggaca                                                19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
guccaaacug ucgugcaaa                                                19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
uuugcacgac aguuuggac                                                19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
aaacugucgu gcaaaccca                                                19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 60
uggguuugca cgacaguuu                                                19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
gugcaaaccc agugagaca                                                19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
ugucucacug gguuugcac                                                19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ugagacagac cgccaaaua                                                19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
uauuuggcgg ucugucuca                                                19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
gagacagacc gccaaauaa                                                19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 66
uuauuuggcg gucugucuc                                                    19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
agacagaccg ccaaauaaa                                                    19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
uuuauuuggc ggucugucu                                                    19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
agaccgccaa auaaacgga                                                    19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
uccguuuauu uggcggucu                                                    19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
cgccaaauaa acggacuca                                                    19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 72
ugaguccguu uauuuggcg                                              19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
aauaaacgga cucagugga                                              19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uccacugagu ccguuuauu                                              19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gacucagugg acacucaga                                              19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
ucugaguguc cacugaguc                                              19

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
cugggucuag aaagcggcu                                              19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 78
agccgcuuuc uagacccag                                                19

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gcuccugaag gucccuuau                                                19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
auaagggacc uucaggagc                                                19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
cuccugaagg ucccuuauu                                                19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
aauaagggac cuucaggag                                                19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
ccugaagguc ccuuauugu                                                19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 84
acaauaaggg accuucagg                                                   19

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
ucccuuauug uggcugauau u                                                21

<210> SEQ ID NO 86
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
aauaucagcc acaauaaggg acc                                              23

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
cccuuauugu ggcugauau                                                   19

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
auaucagcca caauaaggg                                                   19

<210> SEQ ID NO 89
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ccuuauugug gcugauauu                                                   19

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 90
aauaucagcc acauaagg                                                    19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
uguggcugau auuaacugu                                                   19

<210> SEQ ID NO 92
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
acaguuaaua ucagccaca                                                   19

<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
caaugguuau ggguccuau                                                   19

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
auaggaccca uaaccauug                                                   19

<210> SEQ ID NO 95
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
aaugguuaug gguccuaua                                                   19

<210> SEQ ID NO 96
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 96
uauaggaccc auaaccauu                                                    19

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97 augguaugg guccuauaa                                                     19

<210> SEQ ID NO 98
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
uuauaggacc cauaaccau                                                    19

<210> SEQ ID NO 99
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
ugguuauggg uccuauaaa                                                    19

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
uuuauaggac ccauaacca                                                    19

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
gguuaugggu ccuauaaaa                                                    19

<210> SEQ ID NO 102
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 102
uuuuauagga cccauaacc                                              19

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
gagcccucca agaaacuuu                                              19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
aaaguuucuu ggagggcuc                                              19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
gaaacuuucc uagccucau                                              19

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
augaggcuag gaaaguuuc                                              19

<210> SEQ ID NO 107
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
ccucauagcc caugaggca                                              19

<210> SEQ ID NO 108
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 108
ugccucaugg gcuaugagg                                                   19

<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
gcugagacug ucuuacccu                                                   19

<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
aggguaagac agucucagc                                                   19

<210> SEQ ID NO 111
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
gagacugucu uacccucca                                                   19

<210> SEQ ID NO 112
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
uggaggguaa gacagucuc                                                   19

<210> SEQ ID NO 113
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
gaggacuucc ucaaguggu                                                   19

<210> SEQ ID NO 114
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
accacuugag gaaguccuc					19

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
gucugaggag acgcaggau					19

<210> SEQ ID NO 116
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
auccugcguc uccucagac					19

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
cgucccauca cgugagucu					19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
agacucacgu gaugggacg					19

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
cccaucacgu gagucugaa					19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 120
uucagacuca cgugauggg                                                   19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
ccaucacgug agucugaaa                                                   19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
uuucagacuc acgugaugg                                                   19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
cugaaaucgg aggacccuu                                                   19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
aaggguccuc cgauuucag                                                   19

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
gaugagaggg acgugaccu                                                   19

<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 126
aggucacguc ccucucauc                                                  19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gcgugggacc cggaucuuu                                                  19

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
aaagauccgg gucccacgc                                                  19

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
cgugggaccc ggaucuuuu                                                  19

<210> SEQ ID NO 130
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
aaaagauccg ggucccacg                                                  19

<210> SEQ ID NO 131
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
cccggaucuu uuccuuaca                                                  19

<210> SEQ ID NO 132
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 132
uguaaggaaa agauccggg                                              19

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
ccggaucuuu uccuuacaa                                              19

<210> SEQ ID NO 134
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
uuguaaggaa aagauccgg                                              19

<210> SEQ ID NO 135
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
cggaucuuuu ccuuacaaa                                              19

<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
uuuguaagga aaagauccg                                              19

<210> SEQ ID NO 137
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
caaacuuucc agguuccga                                              19

<210> SEQ ID NO 138
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 138
ucggaaccug gaaaguuug					19

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
cuuuccaggu uccgagucu					19

<210> SEQ ID NO 140
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
agacucggaa ccuggaaag					19

<210> SEQ ID NO 141
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
ggccaguggc acaguucga					19

<210> SEQ ID NO 142
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
ucgaacugug ccacuggcc					19

<210> SEQ ID NO 143
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
cuuccuucuu gaauugucu					19

<210> SEQ ID NO 144
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
agacaauuca agaaggaag                                                    19

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
cagccggcga acuuuggca                                                    19

<210> SEQ ID NO 146
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
ugccaaaguu cgccggcug                                                    19

<210> SEQ ID NO 147
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
ggcgaacuuu ggcaccuaa                                                    19

<210> SEQ ID NO 148
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
uuaggugcca aaguucgcc                                                    19

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
cgaacuuugg caccuaaga                                                    19

<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 150
ucuuaggugc caaaguucg                                               19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gcucgcucag acgaacuga                                               19

<210> SEQ ID NO 152
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
ucaguucguc ugagcgagc                                               19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
gaagcacacu ggacaucgu                                               19

<210> SEQ ID NO 154
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
acgaugucca gugugcuuc                                               19

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
gccucugccc acgugcuuu                                               19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 156
aaagcacgug ggcagaggc        19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
cugaccacuu agcucugca        19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
ugcagagcua aguggucag        19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
cacuuagcuc ugcacauga        19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
ucaugugcag agcuaagug        19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
caaggacugg ggaugaaau        19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
auuucauccc caguccuug					19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163 cugggauga aauaagagu					19

<210> SEQ ID NO 164
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
acucuuauuu cauccccag					19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
ggaugaaaua agaguggau					19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
auccacucuu auuucaucc					19

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
guggauccaa ggaccguau					19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 168
auacgguccu uggauccac                                              19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
ccaaggaccg uaucccaaa                                              19

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
uuugggauac gguccuugg                                              19

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
ccaaaagaug ggccauuau                                              19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
auaauggccc aucuuuugg                                              19

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
gggccauuau auaguccua                                              19

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 174
uaggacuaua uaauggccc                                              19

<210> SEQ ID NO 175
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
cauuauauag uccuaccca                                              19

<210> SEQ ID NO 176
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
uggguaggac uauauaaug                                              19

<210> SEQ ID NO 177
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
cagaagacca uacaaagga                                              19

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
uccuuuguau ggucuucug                                              19

<210> SEQ ID NO 179
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
gagccuucag gacaaaccu                                              19

<210> SEQ ID NO 180
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
agguuugucc ugaaggcuc                                              19

<210> SEQ ID NO 181
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
caggacaaac cucacaugu                                              19

<210> SEQ ID NO 182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
acaugugagg uuuguccug                                              19

<210> SEQ ID NO 183
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
gacccagcaa uauagacca                                              19

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
uggucuauau ugcuggguc                                              19

<210> SEQ ID NO 185
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
caccagauaa aucaacuca                                              19

<210> SEQ ID NO 186
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
ugaguugauu uaucuggug                                                19

<210> SEQ ID NO 187
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
gauggacugg ggugagauu                                                19

<210> SEQ ID NO 188
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
aaucucaccc caguccauc                                                19

<210> SEQ ID NO 189
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
cccaucugcu aggauuguu                                                19

<210> SEQ ID NO 190
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
aacaauccua gcagauggg                                                19

<210> SEQ ID NO 191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
cugcuaggau uguugucgu                                                19

<210> SEQ ID NO 192
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
acgacaacaa uccuagcag                                                  19

<210> SEQ ID NO 193
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
ggauuguugu cguuacuau                                                  19

<210> SEQ ID NO 194
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
auaguaacga caacaaucc                                                  19

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
gauuguuguc guuacuaua                                                  19

<210> SEQ ID NO 196
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
uauaguaacg acaacaauc                                                  19

<210> SEQ ID NO 197
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
uucuuauuuu uaucgagca                                                  19

<210> SEQ ID NO 198
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
ugcucgauaa aaauaagaa                                              19

<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
uauuuuuauc gagcacaaa                                              19

<210> SEQ ID NO 200
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
uuugugcucg auaaaaaua                                              19

<210> SEQ ID NO 201
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
uuuaucgagc acaaacgga                                              19

<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
uccguuugug cucgauaaa                                              19

<210> SEQ ID NO 203
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
auggcagccu cugcuuaga                                              19

<210> SEQ ID NO 204
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
ucuaagcaga ggcugccau                                              19

<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
gcagccucug cuuagaaaa                                              19

<210> SEQ ID NO 206
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
uuuucuaagc agaggcugc                                              19

<210> SEQ ID NO 207
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
cagccucugc uuagaaaaa                                              19

<210> SEQ ID NO 208
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
uuuuucuaag cagaggcug                                              19

<210> SEQ ID NO 209
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
acgccagagg augacgauu                                              19

<210> SEQ ID NO 210
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
aaucgucauc cucuggcgu                                              19

<210> SEQ ID NO 211
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
gccagaggau gacgauugu                                              19

<210> SEQ ID NO 212
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
acaaucguca uccucuggc                                              19

<210> SEQ ID NO 213
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
ccagaggaug acgauuguu                                              19

<210> SEQ ID NO 214
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
aacaaucguc auccucugg                                              19

<210> SEQ ID NO 215
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
cagaggauga cgauuguuu                                              19

<210> SEQ ID NO 216
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
aaacaaucgu cauccucug                                                    19

<210> SEQ ID NO 217
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
agaggaugac gauuguuua                                                    19

<210> SEQ ID NO 218
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
uaaacaaucg ucauccucu                                                    19

<210> SEQ ID NO 219
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
gaggaugacg auuguuuau                                                    19

<210> SEQ ID NO 220
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
auaaacaauc gucauccuc                                                    19

<210> SEQ ID NO 221
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
ggaugacgau uguuuauca                                                    19

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 222
ugauaaacaa ucgucaucc                                              19

<210> SEQ ID NO 223
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
gacgauuguu uaucaacgu                                              19

<210> SEQ ID NO 224
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
acguugauaa acaaucguc                                              19

<210> SEQ ID NO 225
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
cgauuguuua ucaacguca                                              19

<210> SEQ ID NO 226
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
ugacguugau aaacaaucg                                              19

<210> SEQ ID NO 227
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
gauuguuuau caacgucau                                              19

<210> SEQ ID NO 228
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 228
augacguuga uaaacaauc                                                19

<210> SEQ ID NO 229
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
uuguuuauca acgucaucu                                                19

<210> SEQ ID NO 230
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
agaugacguu gauaaacaa                                                19

<210> SEQ ID NO 231
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
uguuuaucaa cgucaucua                                                19

<210> SEQ ID NO 232
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
uagaugacgu ugauaaaca                                                19

<210> SEQ ID NO 233
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
uuuaucaacg ucaucuaga                                                19

<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
ucuagaugac guugauaaa                                                19

<210> SEQ ID NO 235
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
aucaacguca ucuagagga                                                19

<210> SEQ ID NO 236
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
uccucuagau gacguugau                                                19

<210> SEQ ID NO 237
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
ucaacgucau cuagaggaa                                                19

<210> SEQ ID NO 238
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
uuccucuaga ugacguuga                                                19

<210> SEQ ID NO 239
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
acgucaucua gaggaauuu                                                19

<210> SEQ ID NO 240
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 240
aaauuccucu agaugacgu                                              19

<210> SEQ ID NO 241
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
caaacaggaa cacauagca                                              19

<210> SEQ ID NO 242
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
ugcuaugugu uccuguuug                                              19

<210> SEQ ID NO 243
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
caggaacaca uagcagaua                                              19

<210> SEQ ID NO 244
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
uaucugcuau guguuccug                                              19

<210> SEQ ID NO 245
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
aggaacacau agcagauaa                                              19

<210> SEQ ID NO 246
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 246
uuaucugcua uguguuccu                                              19

<210> SEQ ID NO 247
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
ggaacacaua gcagauaaa                                              19

<210> SEQ ID NO 248
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
uuuaucugcu auguguucc                                              19

<210> SEQ ID NO 249
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
acauagcaga uaaacuucu                                              19

<210> SEQ ID NO 250
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
agaaguuuau cugcuaugu                                              19

<210> SEQ ID NO 251
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
ugccccgcag gguauuugu                                              19

<210> SEQ ID NO 252
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 252
acaaauaccc ugcggggca                                              19

<210> SEQ ID NO 253
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
gccccgcagg guauuugua                                              19

<210> SEQ ID NO 254
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
uacaaauacc cugcggggc                                              19

<210> SEQ ID NO 255
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
ccccgcaggg uauuuguaa                                              19

<210> SEQ ID NO 256
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
uuacaaauac ccugcgggg                                              19

<210> SEQ ID NO 257
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
cccgcagggu auuuguaaa                                              19

<210> SEQ ID NO 258
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 258
uuuacaaaua cccugcggg                                                19

<210> SEQ ID NO 259
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259 cgcagggau uuguaaaga                                                 19

<210> SEQ ID NO 260
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
ucuuuacaaa uacccugcg                                                19

<210> SEQ ID NO 261
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
gcccagcagc uacacaugu                                                19

<210> SEQ ID NO 262
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
acauguguag cugcugggc                                                19

<210> SEQ ID NO 263
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
cccagcagcu acacaugua                                                19

<210> SEQ ID NO 264
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
uacaugugua gcugcuggg                                                    19

<210> SEQ ID NO 265
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
agcuacacau guacaacuu                                                    19

<210> SEQ ID NO 266
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
aaguuguaca uguguagcu                                                    19

<210> SEQ ID NO 267
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
uacacaugua caacuugca                                                    19

<210> SEQ ID NO 268
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
ugcaaguugu acaugugua                                                    19

<210> SEQ ID NO 269
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
acacauguac aacuugcaa                                                    19

<210> SEQ ID NO 270
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 270
uugcaaguug uacaugugu                                               19

<210> SEQ ID NO 271
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
uacaacuugc aaacagcca                                               19

<210> SEQ ID NO 272
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
uggcuguuug caaguugua                                               19

<210> SEQ ID NO 273
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
aacacgcaca gaacacuca                                               19

<210> SEQ ID NO 274
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
ugaguguucu gugcguguu                                               19

<210> SEQ ID NO 275
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
gcacagaaca cucauggau                                               19

<210> SEQ ID NO 276
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 276
auccaugagu guucugugc                                              19

<210> SEQ ID NO 277
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
cacagaacac ucauggauu                                              19

<210> SEQ ID NO 278
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
aauccaugag uguucugug                                              19

<210> SEQ ID NO 279
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
cagaacacuc auggauuaa                                              19

<210> SEQ ID NO 280
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
uuaauccaug aguguucug                                              19

<210> SEQ ID NO 281
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
gaacacucau ggauuaaga                                              19

<210> SEQ ID NO 282
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 282
ucuuaaucca ugaguguuc                                             19

<210> SEQ ID NO 283
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
aacacucaug gauuaagaa                                             19

<210> SEQ ID NO 284
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
uucuuaaucc augaguguu                                             19

<210> SEQ ID NO 285
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
acacucaugg auuaagaau                                             19

<210> SEQ ID NO 286
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
auucuuaauc caugagugu                                             19

<210> SEQ ID NO 287
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
acucauggau uaagaaucu                                             19

<210> SEQ ID NO 288
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 288
agauucuuaa uccaugagu                                                19

<210> SEQ ID NO 289
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
gauuaagaau cuacuuaga                                                19

<210> SEQ ID NO 290
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
ucuaaguaga uucuuaauc                                                19

<210> SEQ ID NO 291
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
auuaagaauc uacuuagaa                                                19

<210> SEQ ID NO 292
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
uucuaaguag auucuuaau                                                19

<210> SEQ ID NO 293
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 293
uuuaucgagc acaaacggat t                                             21

<210> SEQ ID NO 294
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                    oligonucleotide
<220> FEATURE:
<223> OTHER INFORMATION: Description of Combined DNA/RNA Molecule:
      Synthetic oligonucleotide

<400> SEQUENCE: 294 uccguugug cucgauaaat t                                          21

<210> SEQ ID NO 295
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 295
auggcagccu cugcuuagat t                                         21

<210> SEQ ID NO 296
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 296
ucuaagcaga ggcugccaut t                                         21

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 297
gcagccucug cuuagaaaat t                                         21

<210> SEQ ID NO 298
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 298
uuuucuaagc agaggcugct t                                         21

<210> SEQ ID NO 299
<211> LENGTH: 21
<212> TYPE: DNA
<213> ORGANISM: Artificial Sequence
<220> FEATURE:
```

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 299
cagccucugc uuagaaaaat t                                           21

<210> SEQ ID NO 300
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 300
uuuuucuaag cagaggcugt t                                           21

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 301
acgccagagg augacgauut t                                           21

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 302
aaucgucauc cucuggcgut t                                           21

<210> SEQ ID NO 303
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 303
gccagaggau gacgauugut t                                           21

<210> SEQ ID NO 304
<211> LENGTH: 21
<212> TYPE: DNA
<213> ORGANISM: Artificial Sequence -continued

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 304
acaaucguca uccucuggct t                                              21

<210> SEQ ID NO 305
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 305
ccagaggaug acgauuguut t                                              21

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 306
aacaaucguc aucccucuggt t                                             21

<210> SEQ ID NO 307
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 307
cagaggauga cgauuguuut t                                              21

<210> SEQ ID NO 308
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 308
aaacaaucgu cauccucugt t                                              21

<210> SEQ ID NO 309
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 309
agaggaugac gauuguuuat t                                           21

<210> SEQ ID NO 310
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 310
uaaacaaucg ucauccucut t                                           21

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 311
gaggaugacg auuguuuaut t                                           21

<210> SEQ ID NO 312
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 312
auaaacaauc gucauccuct t                                           21

<210> SEQ ID NO 313
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 313
ggaugacgau uguuuaucat t                                           21

<210> SEQ ID NO 314
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 314
ugauaaacaa ucgucaucct t                                                    21

<210> SEQ ID NO 315
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 315
gacgauuguu uaucaacgut t                                                    21

<210> SEQ ID NO 316
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 316
acguugauaa acaaucguct t                                                    21

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 317
cgauuguuua ucaacgucat t                                                    21

<210> SEQ ID NO 318
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 318
ugacguugau aaacaaucgt t                                                    21
```

<210> SEQ ID NO 319
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 319
gauuguuuau caacgucaut t                                              21

<210> SEQ ID NO 320
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 320
augacguuga uaaacaauct t                                              21

<210> SEQ ID NO 321
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 321
uguuuaucaa cgucaucuat t                                              21

<210> SEQ ID NO 322
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 322
uagaugacgu ugauaaacat t                                              21

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide -continued

<400> SEQUENCE: 323
uuuaucaacg ucaucuagat t                                              21

<210> SEQ ID NO 324
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 324
ucuagaugac guugauaaat t                                              21

<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 325
aucaacguca ucuagaggat t                                              21

<210> SEQ ID NO 326
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 326
uccucuagau gacguugaut t                                              21

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 327
ucaacgucau cuagaggaat t                                              21

<210> SEQ ID NO 328
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 328
uuccucuaga ugacguugat t                                              21

<210> SEQ ID NO 329
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 329
acgucaucua gaggaauuut t                                              21

<210> SEQ ID NO 330
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 330
aaauuccucu agaugacgut t                                              21

<210> SEQ ID NO 331
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 331
caaacaggaa cacauagcat t                                              21

<210> SEQ ID NO 332
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 332
ugcuaugugu uccuguuugt t                                              21

<210> SEQ ID NO 333
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: Description of Combined DNA/RNA Molecule:
      Synthetic oligonucleotide

<400> SEQUENCE: 333
caggaacaca uagcagauat t                                              21

<210> SEQ ID NO 334
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 334
uaucugcuau guguuccugt t                                              21

<210> SEQ ID NO 335
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 335
aggaacacau agcagauaat t                                              21

<210> SEQ ID NO 336
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 336
uuaucugcua uguguuccut t                                              21

<210> SEQ ID NO 337
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 337
ggaacacaua gcagauaaat t                                              21

<210> SEQ ID NO 338
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 338
uuuaucugcu auguguucct t                                              21

<210> SEQ ID NO 339
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 339
acauagcaga uaaacuucut t                                              21

<210> SEQ ID NO 340
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 340
agaaguuuau cugcuaugut t                                              21

<210> SEQ ID NO 341
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 341
ugccccgcag gguauuugut t                                              21

<210> SEQ ID NO 342
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 342
acaaauaccc ugcggggcat t                                              21

<210> SEQ ID NO 343
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 343
gccccgcagg guauuuguat t                                            21

<210> SEQ ID NO 344
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 344
uacaaauacc cugcggggct t                                            21

<210> SEQ ID NO 345
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 345
ccccgcaggg uauuuguaat t                                            21

<210> SEQ ID NO 346
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 346
uuacaaauac ccugcggggt t                                            21

<210> SEQ ID NO 347
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 347
cccgcagggu auuuguaaat t                                            21

<210> SEQ ID NO 348
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 348
uuuacaaaua cccugcgggt t                                              21

<210> SEQ ID NO 349
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 349
cgcaggguau uuguaaagat t                                              21

<210> SEQ ID NO 350
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 350
ucuuuacaaa uacccugcgt t                                              21

<210> SEQ ID NO 351
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 351
gcccagcagc uacacaugut t                                              21

<210> SEQ ID NO 352
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 352
acauguguag cugcugggct t                                              21
```

<210> SEQ ID NO 353
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 353
cccagcagcu acacauguat t                                               21

<210> SEQ ID NO 354
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 354
uacaugugua gcugcugggt t                                               21

<210> SEQ ID NO 355
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 355
agcuacacau guacaacuut t                                               21

<210> SEQ ID NO 356
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 356
aaguuguaca uguguagcut t                                               21

<210> SEQ ID NO 357
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 357
uacacaugua caacuugcat t                                              21

<210> SEQ ID NO 358
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 358
ugcaaguugu acauguguat t                                              21

<210> SEQ ID NO 359
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 359
acacauguac aacuugcaat t                                              21

<210> SEQ ID NO 360
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 360
uugcaaguug uacaugugut t                                              21

<210> SEQ ID NO 361
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 361
uacaacuugc aaacagccat t                                              21

<210> SEQ ID NO 362
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 362
uggcuguuug caaguuguat t                    21

<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 363
aacacgcaca gaacacucat t                    21

<210> SEQ ID NO 364
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 364
ugaguguucu gugcguguut t                    21

<210> SEQ ID NO 365
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 365
gcacagaaca cucauggaut t                    21

<210> SEQ ID NO 366
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 366
auccaugagu guucugugct t                    21

<210> SEQ ID NO 367
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 367
cacagaacac ucauggauut t                                              21

<210> SEQ ID NO 368
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 368
aauccaugag uguucugugt t                                              21

<210> SEQ ID NO 369
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 369
cagaacacuc auggauuaat t                                              21

<210> SEQ ID NO 370
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 370
uuaauccaug aguguucugt t                                              21

<210> SEQ ID NO 371
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 371
gaacacucau ggauuaagat t                                              21

<210> SEQ ID NO 372
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

<400> SEQUENCE: 372
ucuuaaucca ugaguguuct t                                    21

<210> SEQ ID NO 373
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 373
aacacucaug gauuaagaat t                                    21

<210> SEQ ID NO 374
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 374
uucuuaaucc augaguguut t                                    21

<210> SEQ ID NO 375
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 375
acacucaugg auuaagaaut t                                    21

<210> SEQ ID NO 376
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 376
auucuuaauc caugagugut t                                    21

<210> SEQ ID NO 377
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 377
acucauggau uaagaaucut t    21

<210> SEQ ID NO 378
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 378 agaucuuaa uccaugagut t    21

<210> SEQ ID NO 379
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 379
gauuaagaau cuacuuagat t    21

<210> SEQ ID NO 380
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 380
ucuaaguaga uucuuaauct t    21

<210> SEQ ID NO 381
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
ugguaucccu ucaggacua    19

<210> SEQ ID NO 382
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
uaguccugaa gggauacca    19

```
<210> SEQ ID NO 383
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
cuaggugcag aauguccuu                                                   19

<210> SEQ ID NO 384
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
aaggacauuc ugcaccuag                                                   19

<210> SEQ ID NO 385
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
gccaccucuc caugggauu                                                   19

<210> SEQ ID NO 386
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
aaucccaugg agagguggc                                                   19

<210> SEQ ID NO 387
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
ugcagacaau aaccccuuu                                                   19

<210> SEQ ID NO 388
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
aaagggguua uugucugca                                                   19
```

```
<210> SEQ ID NO 389
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
acaauaaccc cuuuaaccu                                                      19

<210> SEQ ID NO 390
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
agguuaaagg gguuauugu                                                      19

<210> SEQ ID NO 391
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
ccccuuuaac cugcuaaga                                                      19

<210> SEQ ID NO 392
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
ucuuagcagg uuaaagggg                                                      19

<210> SEQ ID NO 393
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
ccuuuaaccu gcuaagaau                                                      19

<210> SEQ ID NO 394
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
auucuuagca gguuaaagg                                                      19
```

```
<210> SEQ ID NO 395
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
agaauaccag gaucaguau                                                19

<210> SEQ ID NO 396
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
auacugaucc ugguauucu                                                19

<210> SEQ ID NO 397
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
auaccaggau caguaucga                                                19

<210> SEQ ID NO 398
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
ucgauacuga uccugguau                                                19

<210> SEQ ID NO 399
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
accaggauca guaucgaga                                                19

<210> SEQ ID NO 400
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
ucucgauacu gauccuggu                                                19

<210> SEQ ID NO 401
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
caccaccgag acaucacuu                                                 19

<210> SEQ ID NO 402
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
aagugauguc ucgguggug                                                 19

<210> SEQ ID NO 403
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
cagggugcug cgguugaau                                                 19

<210> SEQ ID NO 404
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
auucaaccgc agcacccug                                                 19

<210> SEQ ID NO 405
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
cgguugaauc caauggcua                                                 19

<210> SEQ ID NO 406
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
uagccauugg auucaaccg                                                 19

<210> SEQ ID NO 407
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
gagccucccg ccauggauu                                                    19

<210> SEQ ID NO 408
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
aauccauggc gggaggcuc                                                    19

<210> SEQ ID NO 409
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
agccucccgc cauggauuu                                                    19

<210> SEQ ID NO 410
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
aaauccaugg cgggaggcu                                                    19

<210> SEQ ID NO 411
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
ggauuucucu aggagacuu                                                    19

<210> SEQ ID NO 412
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
aagucuccua gagaaaucc                                                    19

<210> SEQ ID NO 413
<211> LENGTH: 19
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 413
ccagcccuau gcaaagguu                   19

<210> SEQ ID NO 414
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 414
aaccuuugca uagggcugg                   19

<210> SEQ ID NO 415
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 415
aaagguuacu gcaaccauu                   19

<210> SEQ ID NO 416
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 416
aaugguugca guaaccuuu                   19

<210> SEQ ID NO 417
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 417
aguccaaguc augcgaguu                   19

<210> SEQ ID NO 418
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 418
aacucgcaug acuuggacu                   19

<210> SEQ ID NO 419
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 419
cgccaccacg agaacagcu                                                    19

<210> SEQ ID NO 420
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
agcuguucuc gugguggcg                                                    19

<210> SEQ ID NO 421
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
guccugggcg agaagcaua                                                    19

<210> SEQ ID NO 422
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
uaugcuucuc gcccaggac                                                    19

<210> SEQ ID NO 423
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
uccugggcga gaagcauaa                                                    19

<210> SEQ ID NO 424
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
uuaugcuucu cgcccagga                                                    19

<210> SEQ ID NO 425
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 425
gacacuugcg acgaagacu                                                     19

<210> SEQ ID NO 426
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
agucuucguc gcaaguguc                                                     19

<210> SEQ ID NO 427
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
agucggaccg cauagacga                                                     19

<210> SEQ ID NO 428
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
ucgucuaugc gguccgacu                                                     19

<210> SEQ ID NO 429
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
gucggaccgc auagacgau                                                     19

<210> SEQ ID NO 430
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
aucgucuaug cgguccgac                                                     19

<210> SEQ ID NO 431
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 431
cgcugagccc cuucucuaa                                                  19

<210> SEQ ID NO 432
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
uuagagaagg ggcucagcg                                                  19

<210> SEQ ID NO 433
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
gccccuucuc uaagcgcau                                                  19

<210> SEQ ID NO 434
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
augcgcuuag agaaggggc                                                  19

<210> SEQ ID NO 435
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
cuccaggcag cucaaagau                                                  19

<210> SEQ ID NO 436
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
aucuuugagc ugccuggag                                                  19

<210> SEQ ID NO 437
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 437
aggcagcuca aagaucccu                                                  19

<210> SEQ ID NO 438
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
agggaucuuu gagcugccu                                                  19

<210> SEQ ID NO 439
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
ggcagcucaa agaucccuu                                                  19

<210> SEQ ID NO 440
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
aagggaucuu ugagcugcc                                                  19

<210> SEQ ID NO 441
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
cucaaagauc ccuuccuua                                                  19

<210> SEQ ID NO 442
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
uaaggaaggg aucuuugag                                                  19

<210> SEQ ID NO 443
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 443
acuccagaca aucgccuuu                                              19

<210> SEQ ID NO 444
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
aaaggcgauu gucuggagu                                              19

<210> SEQ ID NO 445
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
agggagcacg ccccauauu                                              19

<210> SEQ ID NO 446
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
aauauggggc gugcucccu                                              19

<210> SEQ ID NO 447
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
gggagcacgc cccauauua                                              19

<210> SEQ ID NO 448
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
uaauaugggg cgugcuccc                                              19

<210> SEQ ID NO 449
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
```

```
gagcacgccc cauauuagu                                              19

<210> SEQ ID NO 450
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
acuaauaugg ggcgugcuc                                              19

<210> SEQ ID NO 451
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
cacgccccau auuaguggu                                              19

<210> SEQ ID NO 452
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
accacuaaua uggggcgug                                              19

<210> SEQ ID NO 453
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 453
ugguaucccu ucaggacuat t                                           21

<210> SEQ ID NO 454
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 454
uaguccugaa gggauaccat t                                           21

<210> SEQ ID NO 455
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 455
cuaggugcag aauguccuut t                                              21

<210> SEQ ID NO 456
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 456
aaggacauuc ugcaccuagt t                                              21

<210> SEQ ID NO 457
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 457
gccaccucuc caugggauut t                                              21

<210> SEQ ID NO 458
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 458
aaucccaugg agaggugget t                                              21

<210> SEQ ID NO 459
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 459
ugcagacaau aaccccuuut t                                              21

<210> SEQ ID NO 460
<211> LENGTH: 21
<212> TYPE: DNA
```

<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 460
aaagggguua uugucugcat t          21

<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 461
acaauaaccc cuuuaaccut t          21

<210> SEQ ID NO 462
<211> LENGTH: 21
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 462
agguuaaagg gguuauugut t          21

<210> SEQ ID NO 463
<211> LENGTH: 21
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 463
ccccuuuaac cugcuaagat t          21

<210> SEQ ID NO 464
<211> LENGTH: 21
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 464
ucuuagcagg uuaaagggt t          21

<210> SEQ ID NO 465
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 465
ccuuuaaccu gcuaagaaut t                                              21

<210> SEQ ID NO 466
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 466
auucuuagca gguuaaaggt t                                              21

<210> SEQ ID NO 467
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 467
agaauaccag gaucaguaut t                                              21

<210> SEQ ID NO 468
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 468
auacugaucc ugguauucut t                                              21

<210> SEQ ID NO 469
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 469
auaccaggau caguaucgat t                                              21

<210> SEQ ID NO 470
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 470
ucgauacuga uccugguaut t                                              21

<210> SEQ ID NO 471
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 471
accaggauca guaucgagat t                                              21

<210> SEQ ID NO 472
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 472
ucucgauacu gauccuggut t                                              21

<210> SEQ ID NO 473
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 473
caccaccgag acaucacuut t                                              21

<210> SEQ ID NO 474
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 474
aagugauguc ucgguggugt t                                              21
```

<210> SEQ ID NO 475
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 475
cagggugcug cgguugaaut t                                        21

<210> SEQ ID NO 476
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 476
auucaaccgc agcacccugt t                                        21

<210> SEQ ID NO 477
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 477
cgguugaauc caauggcuat t                                        21

<210> SEQ ID NO 478
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 478
uagccauugg auucaaccgt t                                        21

<210> SEQ ID NO 479
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 479
gagccucccg ccauggauut t                                        21

<210> SEQ ID NO 480
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 480
aauccauggc gggaggcuct t                                               21

<210> SEQ ID NO 481
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 481
agccucccgc cauggauuut t                                               21

<210> SEQ ID NO 482
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 482
aaauccaugg cgggaggcut t                                               21

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 483
ggauuucucu aggagacuut t                                               21

<210> SEQ ID NO 484
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 484
aagucuccua gagaaaucct t                                               21

<210> SEQ ID NO 485
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 485
ccagcccuau gcaaagguut t                                             21

<210> SEQ ID NO 486
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 486
aaccuuugca uagggcuggt t                                             21

<210> SEQ ID NO 487
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 487
aaagguuacu gcaaccauut t                                             21

<210> SEQ ID NO 488
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 488
aaugguugca guaaccuuut t                                             21

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 489
aguccaaguc augcgaguut t					21

<210> SEQ ID NO 490
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 490
aacucgcaug acuuggacut t					21

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 491
cgccaccacg agaacagcut t					21

<210> SEQ ID NO 492
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 492
agcuguucuc gugguggcgt t					21

<210> SEQ ID NO 493
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 493
guccugggcg agaagcauat t					21

<210> SEQ ID NO 494
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 494
uaugcuucuc gcccaggact t         21

<210> SEQ ID NO 495
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 495
uccugggcga gaagcauaat t         21

<210> SEQ ID NO 496
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 496
uuaugcuucu cgcccaggat t         21

<210> SEQ ID NO 497
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 497
gacacuugcg acgaagacut t         21

<210> SEQ ID NO 498
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 498
agucuucguc gcaaguguct t         21

<210> SEQ ID NO 499
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 499
agucggaccg cauagacgat t                                              21

<210> SEQ ID NO 500
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 500
ucgucuaugc gguccgacut t                                              21

<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 501
gucggaccgc auagacgaut t                                              21

<210> SEQ ID NO 502
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 502
aucgucuaug cgguccgact t                                              21

<210> SEQ ID NO 503
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 503
cgcugagccc cuucucuaat t                                              21

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 504
uuagagaagg ggcucagcgt t                                              21

<210> SEQ ID NO 505
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 505
gccccuucuc uaagcgcaut t                                              21

<210> SEQ ID NO 506
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 506
augcgcuuag agaaggggct t                                              21

<210> SEQ ID NO 507
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 507
cuccaggcag cucaaagaut t                                              21

<210> SEQ ID NO 508
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 508
aucuuugagc ugccuggagt t                                              21

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 509
aggcagcuca aagaucccut t                                          21

<210> SEQ ID NO 510
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 510
agggaucuuu gagcugccut t                                          21

<210> SEQ ID NO 511
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 511
ggcagcucaa agaucccuut t                                          21

<210> SEQ ID NO 512
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 512
aagggaucuu ugagcugcct t                                          21

<210> SEQ ID NO 513
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 513
cucaaagauc ccuuccuuat t                                          21

<210> SEQ ID NO 514
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 514
uaaggaaggg aucuuugagt t                                              21

<210> SEQ ID NO 515
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 515
acuccagaca aucgccuuut t                                              21

<210> SEQ ID NO 516
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 516
aaaggcgauu gucuggagut t                                              21

<210> SEQ ID NO 517
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 517
agggagcacg ccccauauut t                                              21

<210> SEQ ID NO 518
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 518 aauaugggge gugcucccut t                                              21

<210> SEQ ID NO 519
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 519
gggagcacgc cccauauuat t                                              21

<210> SEQ ID NO 520
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 520
uaauaugggg cgugcuccct t                                              21

<210> SEQ ID NO 521
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 521
gagcacgccc cauauuagut t                                              21

<210> SEQ ID NO 522
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 522
acuaauaugg ggcgugcuct t                                              21

<210> SEQ ID NO 523
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 523
cacgccccau auuaguggut t                                              21

<210> SEQ ID NO 524
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<223> OTHER INFORMATION: Description of Combined DNA/RNA Molecule:
      Synthetic oligonucleotide

<400> SEQUENCE: 524
accacuaaua uggggcgugt t                                              21

<210> SEQ ID NO 525
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
tattgctgaa gagcttgg                                                  18

<210> SEQ ID NO 526
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
gtcaagaagg cgatagaa                                                  18

<210> SEQ ID NO 527
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
taaagcacga ggaagcgg                                                  18

<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 528
aaacugucgu gcaaacccat t                                              21

<210> SEQ ID NO 529
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 529
uggguuugca cgacaguuut t                                              21
```

<210> SEQ ID NO 530
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 530
aagcgaggcc gacguucgut t                                              21

<210> SEQ ID NO 531
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 531
acgaacgucg gccucgcuut t                                              21

<210> SEQ ID NO 532
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 532
aauaaacgga cucaguggat t                                              21

<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 533
uccacugagu ccguuuauut t                                              21

<210> SEQ ID NO 534
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 534

```
aaugguuaug gguccuauat t                                             21
```

<210> SEQ ID NO 535
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 535

```
uauaggaccc auaaccauut t                                             21
```

<210> SEQ ID NO 536
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 536

```
agacagaccg ccaauaaat t                                              21
```

<210> SEQ ID NO 537
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 537

```
uuuauuuggc ggucugucut t                                             21
```

<210> SEQ ID NO 538
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 538

```
agaccgccaa auaaacggat t                                             21
```

<210> SEQ ID NO 539
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 539
uccguuuauu uggcggucut t                                             21

<210> SEQ ID NO 540
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 540
agcucugccc acgugcuuut t                                             21

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541
aaagcacgug ggcagagcut t                                             21

<210> SEQ ID NO 542
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 542
agugguggcg cuccgaagat t                                             21

<210> SEQ ID NO 543
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 543
ucuucggagc gccaccacut t                                             21

<210> SEQ ID NO 544
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 544
augguuaugg guccuauaat t                                              21

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 545
uuauaggacc cauaaccaut t                                              21

<210> SEQ ID NO 546
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 546
auguccaaac ugucgugcat t                                              21

<210> SEQ ID NO 547
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 547
ugcacgacag uuuggacaut t                                              21

<210> SEQ ID NO 548
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 548
caaagaucca cccaaauaut t                                              21

<210> SEQ ID NO 549
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 549
auauuugggu ggaucuuugt t                                               21

<210> SEQ ID NO 550
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 550
caaugguuau ggguccuaut t                                               21

<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 551
auaggaccca uaaccauugt t                                               21

<210> SEQ ID NO 552
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 552
cccuuauugu ggcugauaut t                                               21

<210> SEQ ID NO 553
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 553
auaucagcca caauaagggt t                                               21

<210> SEQ ID NO 554
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

```
                       Synthetic oligonucleotide

<400> SEQUENCE: 554
ccuccuuccu gaguuguuut t                                              21

<210> SEQ ID NO 555
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 555
aaacaacuca ggaaggaggt t                                              21

<210> SEQ ID NO 556
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 556
ccugaagguc ccuuauugut t                                              21

<210> SEQ ID NO 557
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 557
acaauaaggg accuucaggt t                                              21

<210> SEQ ID NO 558
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 558
ccuuauugug gcugauauut t                                              21

<210> SEQ ID NO 559
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
      Synthetic oligonucleotide

<400> SEQUENCE: 559
aauaucagcc acaauaaggt t                                              21

<210> SEQ ID NO 560
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 560
ccuuauugug gcugauauut t                                              21

<210> SEQ ID NO 561
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 561
aauaucagcc acaauaaggt t                                              21

<210> SEQ ID NO 562
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 562
cgagacucug ggcgcauaut t                                              21

<210> SEQ ID NO 563
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 563
auaugcgccc agagucucgt t                                              21

<210> SEQ ID NO 564
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 564
cgccaaauaa acggacucat t                                              21

<210> SEQ ID NO 565
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 565
ugaguccguu uauuuggcgt t                                              21

<210> SEQ ID NO 566
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 566
cggaaaaucc gacaagccut t                                              21

<210> SEQ ID NO 567
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 567
aggcuugucg gauuuuccgt t                                              21

<210> SEQ ID NO 568
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 568
cuccugaagg ucccuuauut t                                              21

<210> SEQ ID NO 569
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
Synthetic oligonucleotide

<400> SEQUENCE: 569
aauaagggac cuucaggagt t                                          21

<210> SEQ ID NO 570
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
Synthetic oligonucleotide

<400> SEQUENCE: 570
cuggacucgc guucccaaat t                                          21

<210> SEQ ID NO 571
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
Synthetic oligonucleotide

<400> SEQUENCE: 571
uuugggaacg cgaguccagt t                                          21

<210> SEQ ID NO 572
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
Synthetic oligonucleotide

<400> SEQUENCE: 572
cugggucuag aaagcggcut t                                          21

<210> SEQ ID NO 573
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
Synthetic oligonucleotide

<400> SEQUENCE: 573
agccgcuuuc uagacccagt t                                          21

<210> SEQ ID NO 574
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 574
cuuacggaaa auccgacaat t                                               21

<210> SEQ ID NO 575
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 575
uugucggauu uuccguaagt t                                               21

<210> SEQ ID NO 576
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 576
gacucagugg acacucagat t                                               21

<210> SEQ ID NO 577
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 577
ucugaguguc cacugaguct t                                               21

<210> SEQ ID NO 578
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 578
gagacagacc gccaaauaat t                                               21

<210> SEQ ID NO 579
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 579
uuauuuggcg gucugucuct t                                              21

<210> SEQ ID NO 580
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 580
gagaugucca aacugucgut t                                              21

<210> SEQ ID NO 581
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 581
acgacaguuu ggacaucuct t                                              21

<210> SEQ ID NO 582
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 582
gccccuccac gugaagucut t                                              21

<210> SEQ ID NO 583
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 583
agacuucacg uggaggggct t                                              21

<210> SEQ ID NO 584
<211> LENGTH: 21
<212> TYPE: DNA
```

-continued

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 584
gcccuggcac uuggacucut t          21

<210> SEQ ID NO 585
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 585
agaguccaag ugccagggct t          21

<210> SEQ ID NO 586
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 586
gcuccugaag gucccuuaut t          21

<210> SEQ ID NO 587
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 587
auaagggacc uucaggagct t          21

<210> SEQ ID NO 588
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 588
ggaaaauccg acaagccuut t          21

<210> SEQ ID NO 589
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 589
aaggcuuguc ggauuuucct t                                             21

<210> SEQ ID NO 590
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 590
guccaaacug ucgugcaaat t                                             21

<210> SEQ ID NO 591
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 591
uuugcacgac aguuuggact t                                             21

<210> SEQ ID NO 592
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 592
gugcaaaccc agugagacat t                                             21

<210> SEQ ID NO 593
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 593
ugucucacug gguuugcact t                                             21

<210> SEQ ID NO 594
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 594
uaucaaacac ggacccauau t                                            21

<210> SEQ ID NO 595
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 595
uauggguccg uguuugauat t                                            21

<210> SEQ ID NO 596
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 596
ucccuuauug uggcugauat t                                            21

<210> SEQ ID NO 597
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 597
uaucagccac aauaagggat t                                            21

<210> SEQ ID NO 598
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598
ucccuuauug uggcugauau u                                            21

<210> SEQ ID NO 599
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 599
aauaucagcc acaauaaggg acc                                            23

<210> SEQ ID NO 600
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 600
ucuccuagug acugggaut t                                               21

<210> SEQ ID NO 601
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 601
auccccaguc acuaggagat t                                              21

<210> SEQ ID NO 602
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 602
ucuuacggaa aauccgacat t                                              21

<210> SEQ ID NO 603
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 603
ugucggauuu uccguaagat t                                              21

<210> SEQ ID NO 604
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 604
ugagacagac cgccaaauat t                                               21

<210> SEQ ID NO 605
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 605
uauuuggcgg ucugucucat t                                               21

<210> SEQ ID NO 606
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 606
uggcacuugg acucuccuat t                                               21

<210> SEQ ID NO 607
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 607
uaggagaguc caagugccat t                                               21

<210> SEQ ID NO 608
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 608
uggcgcugca accgguguat t                                               21

<210> SEQ ID NO 609
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 609
uacaccgguu gcagcgccat t                                              21

<210> SEQ ID NO 610
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 610
ugguuauggg uccuauaaat t                                              21

<210> SEQ ID NO 611
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 611
uuuauaggac ccauaaccat t                                              21

<210> SEQ ID NO 612
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 612
ugguuuuccc acgaauggat t                                              21

<210> SEQ ID NO 613
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 613
uccauucgug ggaaaaccat t                                              21

<210> SEQ ID NO 614
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 614
uguccaaacu gucgugcaat t                                                    21

<210> SEQ ID NO 615
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 615
uugcacgaca guuuggacat t                                                    21

<210> SEQ ID NO 616
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 616
uguggcugau auuaacugut t                                                    21

<210> SEQ ID NO 617
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 617
acaguuaaua ucagccacat t                                                    21

<210> SEQ ID NO 618
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 618
uuucccacga auggacccut t                                                    21

<210> SEQ ID NO 619
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 619
aggguccauu cgugggaaat t                                              21

<210> SEQ ID NO 620
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 620
uuuuggguuc ggaggaucat t                                              21

<210> SEQ ID NO 621
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 621
ugauccuccg aacccaaaat t                                              21

<210> SEQ ID NO 622
<211> LENGTH: 29
<212> TYPE: PRT
<213> ORGANISM: Homo sapiens

<400> SEQUENCE: 622

Glu Tyr Cys Gly Lys Val Phe Lys Asn Cys Ser Asn Leu Thr Val His
1               5                   10                  15

Arg Arg Ser His Thr Gly Glu Arg Pro Tyr Lys Cys Glu
            20                  25

<210> SEQ ID NO 623
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

Ser Ser His Thr Pro Ile Arg Arg Ser Thr Gln Arg Ala Gln Asp Val
1               5                   10                  15

Trp Gln Phe Ser Asp Gly Ser Ser Arg Ala Leu Lys Phe
            20                  25

<210> SEQ ID NO 624
<211> LENGTH: 32
```

```
<212> TYPE: PRT
<213> ORGANISM: Homo sapiens

<400> SEQUENCE: 624

Gly Ile Pro Ser Gly Leu Gly Ala Glu Cys Pro Ser Gln Pro Pro Leu
1               5                   10                  15

His Gly Ile His Ile Ala Asp Asn Asn Pro Phe Asn Leu Leu Arg Ile
            20                  25                  30

<210> SEQ ID NO 625
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 625

Leu His Thr Pro Pro Phe Gly Val Val Pro Arg Glu Leu Lys Met Cys
1               5                   10                  15

Gly Ser Phe Arg Met Glu Ala Arg Glu Pro Leu Ser Ser Glu Lys Ile
            20                  25                  30

<210> SEQ ID NO 626
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 626
uuuaucgagc acaaacggat t                                           21

<210> SEQ ID NO 627
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 627
uccguuugug cucgauaaat t                                           21

<210> SEQ ID NO 628
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 628
uuuuuaucga gcacaaacgg a                                           21

<210> SEQ ID NO 629
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 629
uccguuugug cucgauaaaa aua                                              23

<210> SEQ ID NO 630
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 630
uuuuuaucga gcacaaacgg a                                                21

<210> SEQ ID NO 631
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 631
uccguuugug cucgauaaaa aua                                              23

<210> SEQ ID NO 632
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 632
uuuuuaucga gcacaaacgg a                                                21

<210> SEQ ID NO 633
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 633
uccguuugug cucgauaaaa aua                                              23

<210> SEQ ID NO 634
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 634
uuuuuaucga gcacaaacgg a                                                21

<210> SEQ ID NO 635
<211> LENGTH: 23
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 635
uccguuugug cucgauaaaa aua					23

<210> SEQ ID NO 636
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 636
uuuuuaucga gcacaaacgg a					21

<210> SEQ ID NO 637
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 637
uccguuugug cucgauaaaa aua					23

<210> SEQ ID NO 638
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 638
uuuuuaucga gcacaaacgg a					21

<210> SEQ ID NO 639
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 639
uccguuugug cucgauaaaa aua					23

<210> SEQ ID NO 640
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 640
uuuuuaucga gcacaaacgg a					21

<210> SEQ ID NO 641
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 641
uccguuugug cucgauaaaa aua                23

<210> SEQ ID NO 642
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 642
uuuuuaucga gcacaaacgg a                21

<210> SEQ ID NO 643
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 643
uccguuugug cucgauaaaa aua                23

<210> SEQ ID NO 644
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 644
uuuuuaucga gcacaaacgg a                21

<210> SEQ ID NO 645
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 645
uccguuugug cucgauaaaa aua                23

<210> SEQ ID NO 646
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 646
uuuuuaucga gcacaaacgg a                21

<210> SEQ ID NO 647
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 647
uccguuugug cucgauaaaa aua                                              23

<210> SEQ ID NO 648
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 648
uuuuuaucga gcacaaacgg a                                                21

<210> SEQ ID NO 649
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 649
uccguuugug cucgauaaaa aua                                              23

<210> SEQ ID NO 650
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 650
uuuuuaucga gcacaaacgg a                                                21

<210> SEQ ID NO 651
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 651
uccguuugug cucgauaaaa aua                                              23

<210> SEQ ID NO 652
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 652
uuuuuaucga gcacaaacgg a                                                21

<210> SEQ ID NO 653
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 653
```
uccguuugug cucgauaaaa aua                                              23

<210> SEQ ID NO 654
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 654
uuuuuaucga gcacaaacgg a                                                21

<210> SEQ ID NO 655
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 655
uccguuugug cucgauaaaa aua                                              23

<210> SEQ ID NO 656
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 656
uuuuuaucga gcacaaacgg a                                                21

<210> SEQ ID NO 657
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 657
uccguuugug cucgauaaaa aua                                              23

<210> SEQ ID NO 658
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 658
uuuuuaucga gcacaaacgg a                                                21

<210> SEQ ID NO 659
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 659

-continued uccguuugug cucgauaaaa aua                                                    23

<210> SEQ ID NO 660
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 660
uuuuuaucga gcacaaacgg a                                                      21

<210> SEQ ID NO 661
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 661
uccguuugug cucgauaaaa aua                                                    23

<210> SEQ ID NO 662
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 662
uuuuuaucga gcacaaacgg a                                                      21

<210> SEQ ID NO 663
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 663
uccguuugug cucgauaaaa aua                                                    23

<210> SEQ ID NO 664
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 664
uuuuuaucga gcacaaacgg a                                                      21

<210> SEQ ID NO 665
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 665
uccguuugug cucgauaaaa aua                                                    23

<210> SEQ ID NO 666
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 666
uuuaucgagc acaaacgga                                                  19

<210> SEQ ID NO 667
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 667
uccguuugug cucgauaaa                                                  19

<210> SEQ ID NO 668
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 668
uuuuuaucga gcacaaacgg a                                               21

<210> SEQ ID NO 669
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 669
uccguuugug cucgauaaaa aua                                             23

<210> SEQ ID NO 670
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 670
uuuuuaucga gcacaaacgg a                                               21

<210> SEQ ID NO 671
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 671
uccguuugug cucgauaaaa aua                                             23

<210> SEQ ID NO 672
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 672
uuuuuaucga gcacaaacgg a                                              21

<210> SEQ ID NO 673
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 673
uccguuugug cucgauaaaa aua                                            23

<210> SEQ ID NO 674
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 674
uuuuuaucga gcacaaacgg a                                              21

<210> SEQ ID NO 675
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 675
uccguuugug cucgauaaaa aua                                            23

<210> SEQ ID NO 676
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 676
uuuuuaucga gcacaaacgg a                                              21

<210> SEQ ID NO 677

<400> SEQUENCE: 677

000

<210> SEQ ID NO 678
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 678
uccguuugug cucgauaaaa aua                                              23

<210> SEQ ID NO 679
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 679
uuuuuaucga gcacaaacgg a                                                21

<210> SEQ ID NO 680
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 680
uccguuugug cucgauaaaa aua                                              23

<210> SEQ ID NO 681
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 681
uuuuuaucga gcacaaacgg a                                                21

<210> SEQ ID NO 682
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 682
uccguuugug cucgauaaaa aua                                              23

<210> SEQ ID NO 683
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 683
uuuuuaucga gcacaaacgg a                                                21

<210> SEQ ID NO 684
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 684
uccguuugug cucgauaaaa aua                                               23

<210> SEQ ID NO 685
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 685
uuuuuaucga gcacaaacgg a                                                 21

<210> SEQ ID NO 686
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 686
uccguuugug cucgauaaaa aua                                               23

<210> SEQ ID NO 687
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 687
uuuuuaucga gcacaaacgg a                                                 21

<210> SEQ ID NO 688
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 688
uccguuugug cucgauaaaa aua                                               23

<210> SEQ ID NO 689
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 689
uuuuuaucga gcacaaacgg a                                                 21

<210> SEQ ID NO 690
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 690
uccguuugug cucgauaaaa aua                                           23

<210> SEQ ID NO 691
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 691
uuuuuaucga gcacaaacgg a                                             21

<210> SEQ ID NO 692
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 692
uccguuugug cucgauaaaa aua                                           23

<210> SEQ ID NO 693
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 693
uuuuuaucga gcacaaacgg a                                             21

<210> SEQ ID NO 694
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 694
uccguuugug cucgauaaaa aua                                           23

<210> SEQ ID NO 695
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 695
uuuuuaucga gcacaaacgg a                                             21

<210> SEQ ID NO 696
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 696
```
uccguuugug cucgauaaaa aua                                                    23

<210> SEQ ID NO 697
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 697
uuuuuaucga gcacaaacgg a                                                      21

<210> SEQ ID NO 698
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 698
uccguuugug cucgauaaaa aua                                                    23

<210> SEQ ID NO 699
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 699
uuuuuaucga gcacaaacgg a                                                      21

<210> SEQ ID NO 700
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 700
uccguuugug cucgauaaaa aua                                                    23

<210> SEQ ID NO 701
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 701
uuuuuaucga gcacaaacgg a                                                      21

<210> SEQ ID NO 702
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 702

-continued uccguuugug cucgauaaaa aua                                           23

<210> SEQ ID NO 703
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 703
uuuuuaucga gcacaaacgg a                                             21

<210> SEQ ID NO 704
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 704
uccguuugug cucgauaaaa aua                                           23

<210> SEQ ID NO 705
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 705
uuuuuaucga gcacaaacgg a                                             21

<210> SEQ ID NO 706
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 706
uccguuugug cucgauaaaa aua                                           23

<210> SEQ ID NO 707
<211> LENGTH: 16
<212> TYPE: PRT
<213> ORGANISM: Unknown
<220> FEATURE:
<223> OTHER INFORMATION: Description of Unknown: Exemplary hydrophobic
      membrane translocations sequence peptide

<400> SEQUENCE: 707

Ala Ala Val Ala Leu Leu Pro Ala Val Leu Leu Ala Leu Leu Ala Pro
1               5                   10                  15

<210> SEQ ID NO 708
<211> LENGTH: 11
<212> TYPE: PRT
<213> ORGANISM: Unknown
<220> FEATURE:
<223> OTHER INFORMATION: Description of Unknown: RFGF analogue peptide

<400> SEQUENCE: 708

Ala Ala Leu Leu Pro Val Leu Leu Ala Ala Pro

-continued

```
<210> SEQ ID NO 709
<211> LENGTH: 13
<212> TYPE: PRT
<213> ORGANISM: Human immunodeficiency virus

<400> SEQUENCE: 709

Gly Arg Lys Lys Arg Arg Gln Arg Arg Arg Pro Pro Gln
1               5                   10

<210> SEQ ID NO 710
<211> LENGTH: 16
<212> TYPE: PRT
<213> ORGANISM: Drosophila sp.

<400> SEQUENCE: 710

Arg Gln Ile Lys Ile Trp Phe Gln Asn Arg Arg Met Lys Trp Lys Lys
1               5                   10                  15

<210> SEQ ID NO 711
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 711
ucccuuauug uggcugauau u                                              21

<210> SEQ ID NO 712
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 712
aauaucagcc acaauaaggg acc                                            23

<210> SEQ ID NO 713
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 713
ucccuuauug uggcugauau u                                              21

<210> SEQ ID NO 714
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 714
aauaucagcc acaauaaggg acc                                            23

<210> SEQ ID NO 715
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 715
ucccuuauug uggcugauau u                                              21

<210> SEQ ID NO 716
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 716
aauaucagcc acaauaaggg acc                                            23

<210> SEQ ID NO 717
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 717
ucccuuauug uggcugauau u                                              21

<210> SEQ ID NO 718
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 718
aauaucagcc acaauaaggg acc                                            23

<210> SEQ ID NO 719
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 719
ucccuuauug uggcugauau u                                              21

<210> SEQ ID NO 720
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 720
aauaucagcc acaauaaggg acc                                            23

<210> SEQ ID NO 721
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 721
ucccuuauug uggcugauau u                                             21

<210> SEQ ID NO 722
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 722
aauaucagcc acaauaaggg acc                                           23

<210> SEQ ID NO 723
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 723
ucccuuauug uggcugauau u                                             21

<210> SEQ ID NO 724
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 724
aauaucagcc acaauaaggg acc                                           23

<210> SEQ ID NO 725
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 725
ucccuuauug uggcugauau u                                             21

<210> SEQ ID NO 726
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 726
aauaucagcc acaauaaggg acc                                           23

<210> SEQ ID NO 727
<211> LENGTH: 21
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 727
ucccuuauug uggcugauau u                                              21

<210> SEQ ID NO 728
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 728
aauaucagcc acaauaaggg acc                                            23

<210> SEQ ID NO 729
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 729
ucccuuauug uggcugauau u                                              21

<210> SEQ ID NO 730
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 730
aauaucagcc acaauaaggg acc                                            23

<210> SEQ ID NO 731
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 731
ucccuuauug uggcugauau u                                              21

<210> SEQ ID NO 732
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 732
aauaucagcc acaauaaggg acc                                            23

<210> SEQ ID NO 733
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 733
ucccuuauug uggcugauau u                                            21

<210> SEQ ID NO 734
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 734
aauaucagcc acaauaaggg acc                                          23

<210> SEQ ID NO 735
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 735
ucccuuauug uggcugauau u                                            21

<210> SEQ ID NO 736
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 736
aauaucagcc acaauaaggg acc                                          23

<210> SEQ ID NO 737
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 737
ucccuuauug uggcugauau u                                            21

<210> SEQ ID NO 738
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 738
aauaucagcc acaauaaggg acc                                          23

<210> SEQ ID NO 739
<211> LENGTH: 21
<212> TYPE: RNA
<213> ORGANISM: Artificial Sequence
<220> FEATURE:
<223> OTHER INFORMATION: Description of Artificial Sequence: Synthetic -continued

```
      oligonucleotide

<400> SEQUENCE: 739
ucccuuauug uggcugauau u                                              21

<210> SEQ ID NO 740
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 740
aauaucagcc acaauaaggg acc                                            23

<210> SEQ ID NO 741
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 741
ucccuuauug uggcugauau u                                              21

<210> SEQ ID NO 742
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 742
aauaucagcc acaauaaggg acc                                            23

<210> SEQ ID NO 743
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 743
ucccuuauug uggcugauau u                                              21

<210> SEQ ID NO 744
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 744
aauaucagcc acaauaaggg acc                                            23

<210> SEQ ID NO 745
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 745
ucccuuauug uggcugauau u                                              21

<210> SEQ ID NO 746
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 746
aauaucagcc acaauaaggg acc                                            23

<210> SEQ ID NO 747
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 747
ucccuuauug uggcugauau u                                              21

<210> SEQ ID NO 748
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 748
aauaucagcc acaauaaggg acc                                            23

<210> SEQ ID NO 749
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 749
ucggaggauc acucggguut t                                              21

<210> SEQ ID NO 750
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 750
aacccgagug auccuccgat t                                              21

<210> SEQ ID NO 751
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 751
uauuuuuauc gagcacaaat t                                              21

<210> SEQ ID NO 752
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 752
uuugugcucg auaaaaauat t                                              21

<210> SEQ ID NO 753
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 753
cuuuccaggu uccgagucut t                                              21

<210> SEQ ID NO 754
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 754
agacucggaa ccuggaaagt t                                              21
```